(12) United States Patent
Gasparavicius et al.

(10) Patent No.: US 11,958,947 B2
(45) Date of Patent: Apr. 16, 2024

(54) CORE-SHELL MICROCAPSULES, MANUFACTURING PROCESSES AND USES

(71) Applicant: DROPLET GENOMICS, UAB, Vilnius (LT)

(72) Inventors: Jonas Gasparavicius, Vilnius (LT); Vaidotas Kiseliovas, Vilnius (LT); Karolis Leonavicius, Vilnius (LT); Linas Mazutis, Vilnius (LT); Juozas Nainys, Vilnius (LT); Andrius Sinkunas, Vilnius (LT); Giedrius Zolubas, Vilnius (LT); Rapolas Zilionis, Vilnius (LT); Vaida Kurmauskaite, Vilnius (LT); Greta Ruksnaityte, Moletu raj (LT); Ignas Ragaisis, Vilnius (LT); Duygucan Gul, Vilnius (LT)

(73) Assignee: DROPLET GENOMICS, UAB, Vilnius (LT)

(*) Notice: Subject to any disclaimer, the term of this patent is extended or adjusted under 35 U.S.C. 154(b) by 0 days.

(21) Appl. No.: 18/159,317

(22) Filed: Jan. 25, 2023

(65) Prior Publication Data
US 2023/0340210 A1    Oct. 26, 2023

Related U.S. Application Data

(63) Continuation of application No. PCT/EP2022/083932, filed on Nov. 30, 2022.
(60) Provisional application No. 63/284,770, filed on Dec. 1, 2021.

(51) Int. Cl.
| | | |
|---|---|---|
| C08J 3/075 | (2006.01) | |
| B01J 13/16 | (2006.01) | |
| C08J 3/12 | (2006.01) | |
| C12Q 1/6806 | (2018.01) | |
| C12Q 1/6816 | (2018.01) | |

(52) U.S. Cl.
CPC ............... *C08J 3/126* (2013.01); *B01J 13/16* (2013.01); *C08J 3/075* (2013.01); *C08J 2301/02* (2013.01); *C08J 2305/02* (2013.01); *C12Q 1/6806* (2013.01); *C12Q 1/6816* (2013.01)

(58) Field of Classification Search
CPC ........ C08J 3/126; C08J 3/075; C08J 2305/02; C12Q 1/6806; C12Q 1/6816; B01J 13/16
USPC ...................................................... 523/201
See application file for complete search history.

(56) References Cited

U.S. PATENT DOCUMENTS

| | | | |
|---|---|---|---|
| 5,084,350 A | 1/1992 | Chang et al. | |
| 5,700,848 A * | 12/1997 | Soon-Shiong | .......... C08B 37/00 522/74 |
| 7,179,660 B1 * | 2/2007 | Kirakossian | ......... G01N 33/548 435/969 |
| 11,166,457 B1 | 11/2021 | Zou et al. | |
| 2015/0157576 A1 | 6/2015 | Shum et al. | |
| 2017/0095514 A1 | 4/2017 | Ma et al. | |
| 2017/0189282 A1 * | 7/2017 | Malle | ..................... A61Q 13/00 |
| 2018/0001291 A1 * | 1/2018 | Nussinovitch | ........... B01J 13/14 |
| 2018/0105808 A1 * | 4/2018 | Mikkelsen | ........... C12N 5/0602 |
| 2019/0297937 A1 * | 10/2019 | Guyard | ..................... A24D 1/20 |
| 2020/0232979 A1 | 7/2020 | Revzin et al. | |
| 2020/0400538 A1 | 12/2020 | Mazutis et al. | |
| 2021/0017348 A1 * | 1/2021 | Lee | ........................ A61K 47/61 |
| 2021/0077394 A1 | 3/2021 | Moaseri | |

FOREIGN PATENT DOCUMENTS

| | | |
|---|---|---|
| CN | 101817998 A | 9/2010 |
| EP | 3782613 A1 | 2/2021 |
| KR | 100395633 B1 | 8/2003 |
| WO | 2001067105 A1 | 9/2001 |
| WO | 2016108234 A1 | 7/2016 |
| WO | 2019/028166 A1 | 2/2019 |
| WO | 2020152222 A1 | 7/2020 |

OTHER PUBLICATIONS

Callewaert et al.(2009) "Serum albumin-alginate coated microspheres: Role of the iner gel in binding and release of the KRFK peptide" International Journal of Pharmaceuticals 366(1-2):103-110. Jan. 21, 2009.
Oh et al. (2009) "Biopolymer-based microgels/nanogels for drug delivery applications" Progress in Polymer Science, Pergamon Press, Oxford, GB 34(12):1261-1282 Dec. 2009.
Sabhachandani et al. (2016) "Generation and functional assessment of 3D multicellular spheroids in droplet-based microfluidics platform" Lab on a Chip 16(3):497-505 Jan. 1, 2016.
Vijayakumar et al (2010) Rapid cellextraction in aqueous two-phase microdroplet systems. Chem. Sci., 2010,1, 447-452.
Yanasigawa et al. (2014) Multiple patterns of polymer gels in microspheres due to the interplay among phase separation, wetting, and gelation. PNAS 111(45):15894-15899.
Domejean et al. (2016) Controlled production of sub-millimeter liquid core hydrogel capsules for parallelized 3D cell culture. Lab Chip, 2017, 17, 110-119.
Niepa et al. (2016) Microbial Nanoculture as an Artificial Microniche. Sci. Rep. 6, 30578.
Li et al. (2017) Continuous and scalable polymer capsule processing for inertial fusion energy target shell fabrication using droplet microfluidics. Scientific Reports 7: 6302.
Mytnyk et al. (2017) Microcapsules with a permeable hydrogel shell and an aqueous core continuously produced in a 3D microdevice by all-aqueous microfluidics. RSC Adv., 2017, 7, 11331.
Werner et al. (2018) Hydrogel Microcapsules with Dynamic pH-Responsive Properties from Methacrylic Anhydride. Macromolecules 2018, 51, 15, 5798-5805.

(Continued)

*Primary Examiner* — Hannah J Pak
(74) *Attorney, Agent, or Firm* — Garrett H. Anderson

(57) ABSTRACT

Provided herein are core-shell microcapsules useful for compartmentalizing biological molecules in solution. Also provided are processes for manufacturing core-shell microcapsules and methods for using core-shell microcapsules to compartmentalize and optionally process biological entities and molecules.

27 Claims, 47 Drawing Sheets

Specification includes a Sequence Listing.

(56) References Cited

OTHER PUBLICATIONS

Werner et al. (2018) Dynamic Microcapsules with Rapid and Reversible Permeability Switching. Adv. Funct. Mater. 2018, 1803385.
Watanabe et al. (2019) Microfluidic Formation of Hydrogel Microcapsules with a Single Aqueous Core by Spontaneous Cross-Linking in Aqueous Two-Phase System Droplets. Langmuir 2019, 35, 6, 2358-2367.
Song et al. (2019) Soft Bacterial Cellulose Microcapsules with Adaptable Shapes. Biomacromolecules 2019, 20, 12, 4437-4446.
Leonaviciene et al. (2020) Multi-step processing of single cells using semi-permeable capsules. Lab Chip, 2020,20, 4052-4062.
Dinh et al. (2020) Functional reservoir microcapsules generated via microfluidic fabrication for long-term cardiovascular therapeutics. Lab Chip, 2020,20, 2756-2764.
Lee et al. (2021) Designing Semipermeable Hydrogel Shells with Controlled Thickness through Internal Osmosis in Triple-Emulsion Droplets. Designing Semipermeable Hydrogel shells. AFM 31:42 2105477.
Xu et al. (2021) Deformable and Robust Core-Shell Protein Microcapsules Templated by Liquid-Liquid Phase-Separated Microdroplets. Adv. Mater. Interfaces 2021, 8, 2101071.
Tang et al. (2021) Hydrogel-Based Biocontainment of Bacteria for Continuous Sensing and Computation. Nat Chem Biol. Jun. 2021 ; 17(6): 724-731.
De Rutte et al. (2021) Massively parallel encapsulation of single cells with structured microparticles and secretion-based flow sorting. bioRxiv preprint doi: https://doi.org/10.1101/2020.03.09. 984245; this version posted Sep. 18, 2021.
De Rutte et al. (2022) Sorting single-cell microcarriers using commercial flow cytometers. SLAS Technology 27 150-159. Epub Oct. 25, 2021.

* cited by examiner

Percentage of unrecoverably lost unique
transcripts after 3 rounds of barcode addition

*Efficiency of single barcode addition, %*

| Number of PCR cycles prior to barcoding | 10 | 20 | 30 | 40 | 50 | 60 | 70 | 80 | 90 | 95 |
|---|---|---|---|---|---|---|---|---|---|---|
| 0 | 99.9 | 99.2 | 97.3 | 93.6 | 87.5 | 78.4 | 65.7 | 48.8 | 27.1 | 14.3 |
| 1 | 99.8 | 98.4 | 94.7 | 87.6 | 76.6 | 61.5 | 43.2 | 23.8 | 7.3 | 2 |
| 2 | 99.6 | 96.8 | 89.6 | 76.8 | 58.6 | 37.8 | 18.6 | 5.7 | 0.5 | 0 |
| 3 | 99.2 | 93.8 | 80.3 | 58.9 | 34.4 | 14.3 | 3.5 | 0.3 | 0 | 0 |
| 4 | 98.4 | 87.9 | 64.5 | 34.7 | 11.8 | 2 | 0.1 | 0 | 0 | 0 |
| 5 | 96.8 | 77.3 | 41.6 | 12 | 1.4 | 0 | 0 | 0 | 0 | 0 |
| 6 | 93.8 | 59.8 | 17.3 | 1.5 | 0 | 0 | 0 | 0 | 0 | 0 |
| 7 | 88 | 35.8 | 3 | 0 | 0 | 0 | 0 | 0 | 0 | 0 |
| 8 | 77.4 | 12.8 | 0.1 | 0 | 0 | 0 | 0 | 0 | 0 | 0 |
| 9 | 59.9 | 1.6 | 0 | 0 | 0 | 0 | 0 | 0 | 0 | 0 |
| 10 | 35.9 | 0 | 0 | 0 | 0 | 0 | 0 | 0 | 0 | 0 |

Fig. 7

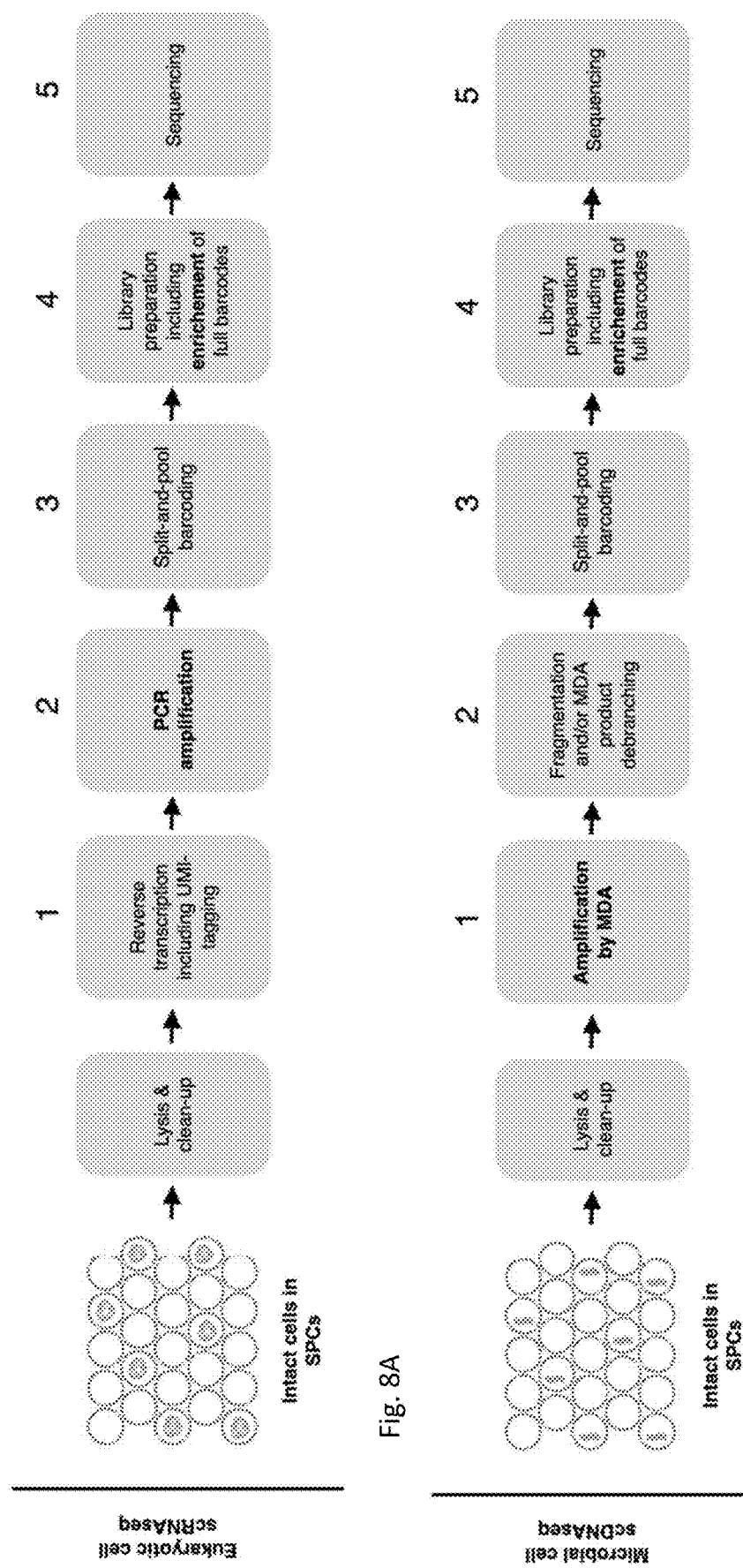

Simulation 1:
- 100 cells
- 20 genomic targets
- 20-unit concatemers
- 5 cycles of PCR1
  (=20x2^5 = 640
  unique molecules)
- 10k sequencing reads

Simulation 2:
- 100 cells
- 20 genomic targets
- 20-unit concatemers
- 10 cycles of PCR1
  (=20x2^10 = 20,480
  unique molecules)
- 10k sequencing reads

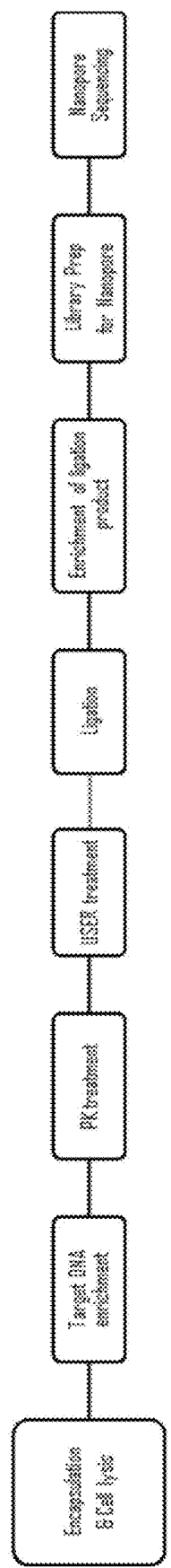
Fig. 28
5'-[16s_fw]-[16S]-AATGAGT-3'       5'-AATGAGU-[AmpR]-3'      5'-ACAAGGU-[GFP]-[GFP_rev]-3'
3'-[16s_fw]-[16S]-UTACTCA-5'      3'-TTACTCA-[AmpR]-5'      3'-TGTTCCA-[GFP]-[GFP_rev]-5'
 USER
5'-[16s_fw]-[16S]-AATGAGT-3'      5'-[AmpR]-ACAAGGT-3'      5'-[GFP]-[GFP_rev]-3'
3'-[16s_fw]-[16S]-5'      3'-TTACTCA-[AmpR]-5'      3'-TGTTCCA-[GFP]-[GFP_rev]-5'
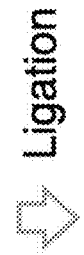 Ligation
5'-[16s_fw]-[16S]-AATGAGT-[AmpR]-ACAAGGT-[GFP]-[GFP_rev]-3'
3'-[16s_fw]-[16S]-TTACTCA-[AmpR]-TGTTCCA-[GFP]-[GFP_rev]-5'
Fig. 29

| | |
|---|---|
| Number of Reads | 672786 |
| Reads With Valid Barcodes | 0.91821 |
| Sequencing Saturation | 0.0238098 |
| Q30 Bases in CB+UMI | 0.91175 |
| Q30 Bases in RNA read | 0.856627 |
| Reads Mapped to Genome: Unique+Multiple | 0.804479 |
| Reads Mapped to Genome: Unique | 0.739995 |
| Reads Mapped to Gene: Unique+Multiple Gene | NoMulti |
| Reads Mapped to Gene: Unique Gene | 0.497412 |
| Estimated Number of Cells | 1173 |
| Unique Reads in Cells Mapped to Gene | 294320 |
| Fraction of Unique Reads in Cells | 0.879481 |
| Mean Reads per Cell | 250 |
| Median Reads per Cell | 197 |
| UMIs in Cells | 286619 |
| Mean UMI per Cell | 244 |
| Median UMI per Cell | 194 |
| Mean Gene per Cell | 204 |
| Median Gene per Cell | 167 |
| Total Gene Detected | 16244 |

Fig. 32

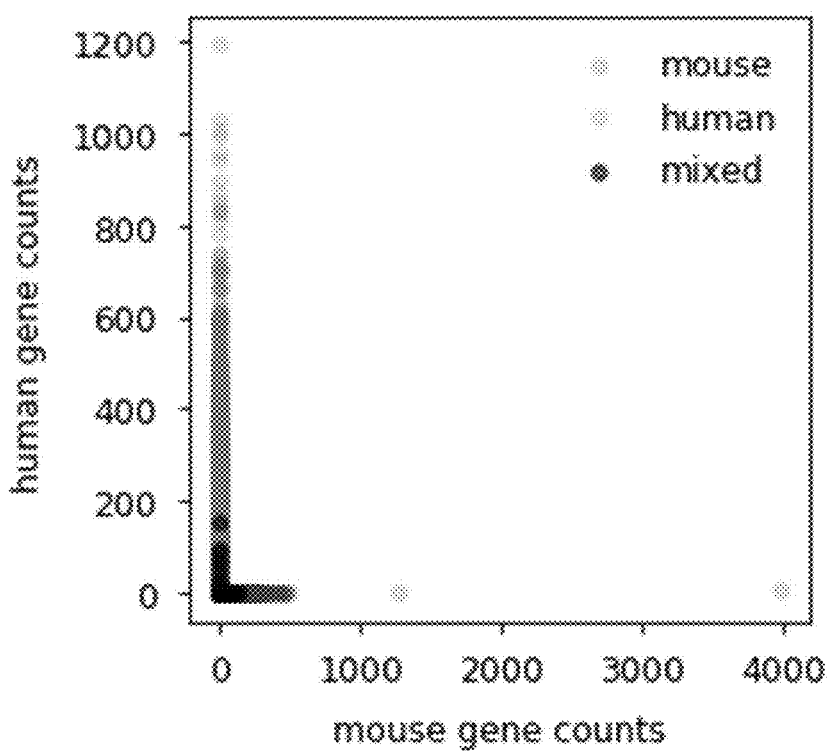

Fig. 33

| Cellulase digestion | No cellulase | 50 ul SPCs + 5 ul cellulase + 5 ul 1 M HCl. Overnight at room temp. |
|---|---|---|
| Appearance of SPC solution in the tube | Cloudy suspension at the bottom of the tube typical to intact SPCs | Clear solution, indicative of SPC dissolution, >90% volume loss. |

| Dextran (core polymer) average MW | 10,000 Da | 100,000 Da | 2,000,000 Da |
|---|---|---|---|
| Concentration in Working Core Solution | 25% w/w | 20% w/w | 7.5% w/w |

CORE-SHELL MICROCAPSULES, MANUFACTURING PROCESSES AND USES

RELATED APPLICATIONS

This application is a US National Phase entry of PCT Application No. PCT/EP2022/083932, and claims the benefit of priority to U.S. Provisional Application Ser. No. 63/284,770, filed Dec. 1, 2021, the contents of which are hereby incorporated by reference in their entirety.

SEQUENCE LISTING

The instant application contains a Sequence Listing which has been submitted electronically in XML file format and is hereby incorporated by reference in its entirety. Said XML copy, created on May 19, 2023, is named DRG_003US_SL.xml and is 202,731 bytes in size.

FIELD

The technology relates in part to core-shell microcapsules useful for compartmentalizing biological molecules in solution. The technology relates in part to processes for manufacturing core-shell microcapsules and methods for using core-shell microcapsules to compartmentalize and optionally process biological entities and molecules.

BACKGROUND

Core-shell microcapsules include a core surrounded by a shell and can serve as micro-compartments in a liquid environment for containing biological entities and biological molecules. The shell can be a hydrogel, and typically is permeable to biological molecules that are relatively small, such as peptides, proteins, enzymes, nucleotides, and shorter oligonucleotides (e.g., less 50 consecutive nucleotides in length), for example. The core typically is liquid or semi-liquid and can retain larger biological entities, such as eukaryotic or prokaryotic cells for example, and/or larger biological molecules, such as nucleic acid (e.g., greater than 100 consecutive nucleotides in length) for example. Core-shell microcapsules are structurally distinguished from other types of micro-compartments. For example, core-shell microcapsules are different than hydrogel beads as the latter do not have a liquid or semi-liquid core surrounded by a permeable shell. Also, for example, core-shell microcapsules are different than droplets as the latter have no shell.

SUMMARY

Provided are core-shell microcapsules containing a shell polymer that includes a polysaccharide modified by cross-linking moieties and optionally modified by hydrophilicity/hydrophobicity-modifying moieties, and a core polymer that includes a polysaccharide not modified by the cross-linking moieties and the hydrophilicity/hydrophobicity-modifying moieties that modify the first polymer. Such core-shell microcapsules are useful for encapsulating, and thereby compartmentalizing, biological entities and biological molecules in a liquid environment, and are particularly useful for processing encapsulated biological molecules. Such core-shell microcapsules also are degradable under relatively mild degradation conditions, which maintains the integrity of encapsulated contents during degradation. Degradation is accomplished through contacting to an enzyme such as a glycosylase or through contacting to thermal or mechanical degradation conditions, such as heat, sonication or shearing. Encapsulated contents, such as biological entities and biological molecules, for example, are at risk of being degraded under the more disruptive microcapsule degradation conditions required by degradation of microcapsule shells and/or cores used in the art herein. Core-shell microcapsules also are referred to as "microcapsules" herein. Similarly provided herein are methods for degrading core-shell microcapsules, such as those described herein or otherwise known in the art, such that the core-shell microcapsule contents are not negatively impacted. Degradation is often effected by an enzyme, such as an enzyme that degrades a monomer precursor or other constituent of a core-shell microcapsule, so as to degrade the core-shell microcapsule under biologically relevant or biologically suitable conditions. An example of such an enzyme described herein is a glycosidase, which degrades microcapsules as described above without chemically impacting the composition of the reaction products that they harbored.

Provided also herein are methods for processing nucleic acid in intact core-shell microcapsules. Some such methods allow iterative reactions to be performed upon microcapsule contents. In exemplary embodiments, successive reactions are mutually incompatible with one another, but are nonetheless accomplished without substantial dilution of the microcapsule contents. This is accomplished through the replacement of incompatible reaction reagents and/or buffers by washing or allowing them to diffuse out of the microcapsules. In contrast, iterative reactions in emulsions are accomplished largely through serial dilution, such as of a first reaction droplet with a second, substantially larger volume droplet so as to dilute the contents of the first reaction. This process in emulsions is difficult to serially repeat for more than a second reaction as the volumes necessary to dilute incompatible reaction conditions become difficult to manipulate and deliver. Using the methods and compositions disclosed herein, multiple iterative reactions, such as incompatible reactions, may be performed upon a single microcapsule's contents without successive order-of-magnitude increases in volume. The products may then be readily released from the microcapsule so as to facilitate downstream analysis.

Provided also herein are compositions for making microcapsules, and for concurrently embedding a reaction product precursor or analyte target into microcapsules so as to facilitate downstream iterative reactions, such as incompatible reactions, and subsequent biocompatible release. Compositions comprise a polymerization monomer such as those described above or elsewhere herein or known in the art, distributed in one or both of an aqueous shell phase. The compositions are mixed in emulsified droplets, and form microcapsules having a uniform exterior hydrogel and an aqueous interior. The interior may harbor an analyte or reaction product, while the uniform exterior hydrogel facilitates regular, predicable timing of reagent replacement. This predictable timing of reagent replacement allows one to more confidently and efficiently replace one buffer, reagent or set of reaction conditions with a second set of buffer, reagent or set of reaction conditions, such as one incompatible with the first set. Variability in shell thickness may lead to variability in reagent set replacement efficiency, which would negatively impact reaction efficiency particularly when subsequent reactions are incompatible.

Certain implementations are described further in the following description, examples and claims, and in the drawings. Figures set forth herein illustrate certain implementations of the technology and are not limiting. For clarity and ease of illustration, the figures are not made to scale and, in some instances, various aspects may be shown exaggerated or enlarged to facilitate an understanding of particular implementations. In the figures, "NA" refers to nucleic acid and "SPC" refers to microcapsules.

BRIEF DESCRIPTION OF THE DRAWINGS

FIG. 2A is a schematic of a microcapsule generation device. FIG. 2B presents emulsification of microcapsule precursor reagents. FIG. 2C presents mixed microcapsule precursors in which hydrogel shells have not yet formed. FIG. 2D presents a population of microcapsules, with hydrogel exterior layers present. FIG. 2E shows an individual microcapsule having visually distinct hydrogel shell and aqueous core.

FIG. 7 shows barcode addition efficiency for a range of single barcode efficiency rates (x-axis) and a number of PCR cycles performed prior to barcoding (y-axis) after three rounds of barcode addition, indicating a very high rate of barcode success and a very low percentage of unrecoverably lost unique transcripts.

FIG. 8A shows a Eukaryotic cell scRNAseq workflow comprising a series of mutually incompatible reaction steps performed on the contents of a single microcapsule.

FIG. 8B shows a microbial cell scDNAseq workflow comprising a series of mutually incompatible reaction steps performed on the contents of a single microcapsule.

FIG. 28 shows a workflow for USER-mediated concatenation of bacterial amplicons.

FIG. 29 shows a more detailed implementation of the workflow in FIG. 28.

FIG. 32 presents successful results obtained from use of the approach of FIGS. 8A, 11, 12.

FIG. 33 presents a graphic display of results from the approach of FIGS. 8A, 11, 12.

DETAILED DESCRIPTION

Figure 1:
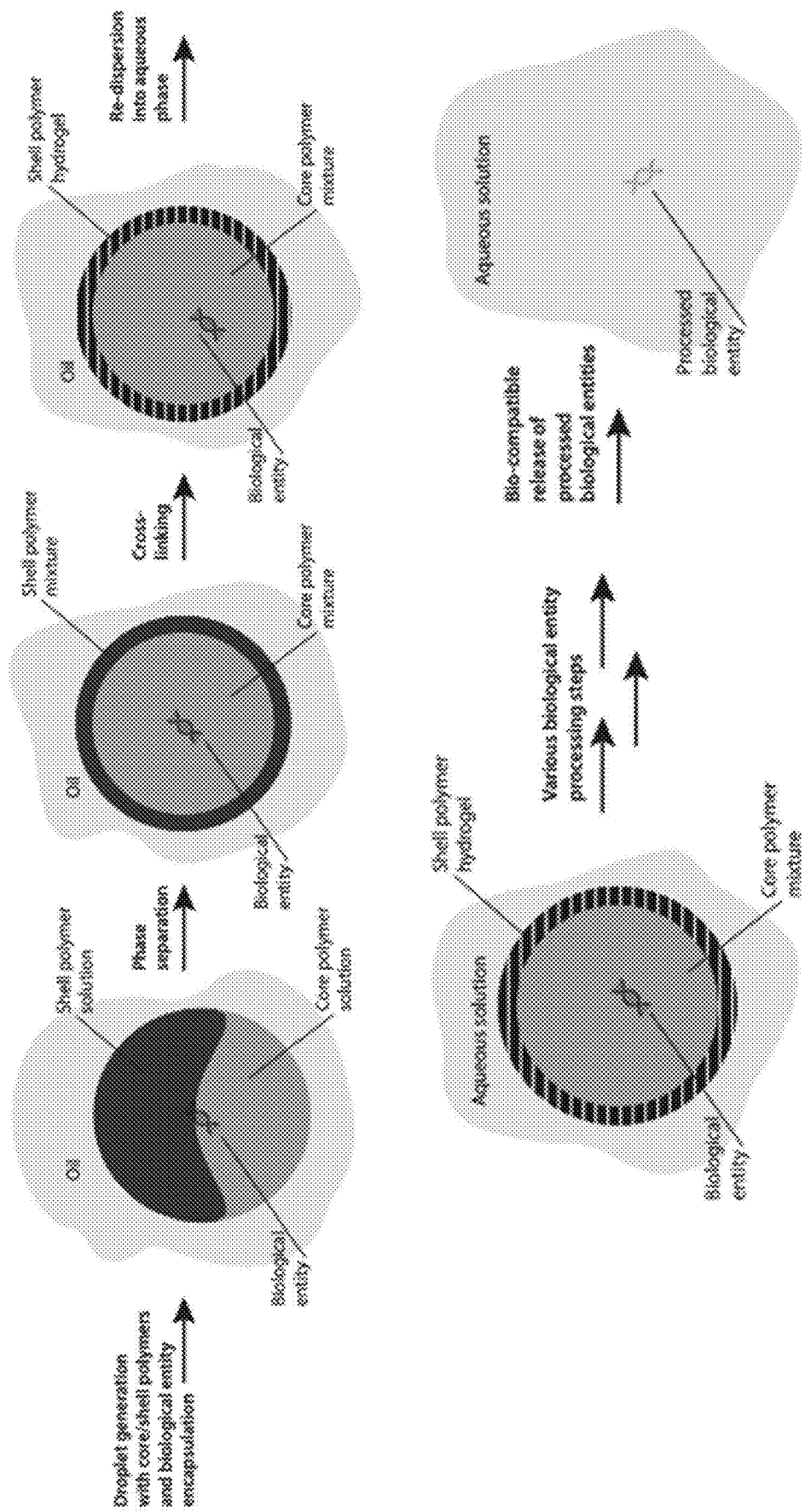
FIG. 1 presents a schematic of a workflow herein, from microparticle assembly containing an analyte to serial reaction performance to analyte product release.

Describe hereafter are core-shell microcapsules and processes for manufacturing them, such as processes for manufacturing core-shell microcapsules containing encapsulated biological entities and/or molecules. Also described are methods for using core-shell microcapsules (e.g., those described herein), such as (i) methods in which core-shell microcapsules described herein are degraded under biocompatible conditions, such as enzymatic degradation by an enzyme such as glycosidase (see, e.g., Examples 4-10, 12, 19); (ii) methods in which encapsulated nucleic acid from a biological entity is concatenated in intact microcapsules and then released (see, e.g., Examples 7-9); (iii) methods in which encapsulated nucleic acid from a biological entity is amplified and then barcoded in intact microcapsules, and then released (see, e.g., Examples 9, 10, and 12); and (iv) methods in which microcapsules containing encapsulated nucleic acid from a biological entity are combined with particles to which barcode polynucleotides are attached in droplets, and nucleic acid barcoding in the droplets (see, e.g., Example 10). The term "nucleic acid" generally refers to nucleic acid molecules.

Compositions and methods disclosed herein allow for an analyte to be contained in a core-shell microparticle. Once contained, the analyte, such as a cell, protein, nucleic acid or other biomolecule or non-biomolecule can be subjected to mutually incompatible reactions in series without serially diluting each prior reaction condition or environment in a reaction volume. Thus, for example, a cell may be lysed, the lysate protease treated and DNase treated, followed by reverse transcription, RNase treatment, barcoding or other oligo adapter addition and then PCR amplification, delivery of the microcapsule to a location on a reaction surface, and then the microcapsule may be lysed to locally release the PCR products. This series of reactions are in some case mutually incompatible (protease treatment is incompatible with later enzymatic manipulations, while DNase treatment is incompatible with later DNA synthesis steps, for example). Using emulsion-based approaches, successive reactions are accomplished by serially diluting a prior reaction environment with a substantial excess of a successive reaction environment (such as, say, a volume of 10×) so as to dilute the reagent detrimental to subsequent reactions. Such as approach limits the efficacy of downstream reactions and limits the number of subsequent reactions that may be performed, both through the failure to clear prior reagents and buffers, and due to the necessary substantial increase in emulsion droplet volume required for each successive step. Using the approaches herein, in contrast, reagents and buffers are allowed to diffuse out of a microcapsule, to be replaced by buffer and reagents necessary for a subsequent manipulation, without adding a substantial excess volume to the microcapsule. This is accomplished by manipulating the aqueous environment in which microcapsules are successively incubated, so as to effectively replace one reaction environment with another without dilution and without loss of analyte or reaction products. Microcapsules are in some cases generated to have uniform hydrogel exteriors, such that the time to completion of reagent exchange is uniform throughout a population. Once reactions are completed, products are readily released under biological conditions, so as to minimize harm to the reaction products and to maximize compatibility with reagents or materials in the environment where the release occurs. Consequently, a substantially larger spectrum of manipulations may be performed through practice of the disclosure herein relative to that of the current technology.

Core-Shell Microcapsules

Provided are core-shell microcapsules suitable for harboring a series of in some cases mutually incompatible reactions to be performed on a contained analyte. The microcapsules are often of uniform shell thickness, such that reagents are exchanged with an aqueous carrier environment at a predicable rate. The microcapsules are readily degraded, such as under biological conditions, so as to release reaction products without further reactions and without harm to the environment in which release occurs.

In one exemplary set of embodiments, microcapsules contain a shell polymer that includes a polysaccharide modified by cross-linking moieties (see, e.g., Examples 1, 4, 14-23, 27, 28).

Microcapsules in some cases comprise crosslinking moieties or polysaccharides that are modified by hydrophilicity/hydrophobicity-modifying moieties, and a core polymer that includes a polysaccharide not modified by the cross-linking moieties and the hydrophilicity/hydrophobicity-modifying moieties that modify the first polymer. Such core-shell microcapsules are useful for encapsulating, and thereby compartmentalizing, biological entities and biologic molecules in a liquid environment, and are particularly useful for processing encapsulated biological molecules.

The shell of core-shell microcapsules described herein generally are porous and semi-permeable. The shell of intact microcapsules generally permits reagents, such as nucleic acid primers, nucleotides, buffers and enzymes, for example, to pass through, but prevents nucleic acid (e.g., released from an encapsulated biological entity), and nucleic acid processed therefrom (e.g., processed nucleic acid transcribed and/or amplified from the released nucleic acid), escaping the intact microcapsules (see, e.g., Examples 3, 24, 25). The porous, semi-permeable shell generally remains intact when exposed to nucleic acid release conditions that release nucleic acid from biological entities within the microcapsules. The porous, semi-permeable shell also generally remains intact when exposed to nucleic acid processing conditions, such as, for example, (i) strand displacement conditions, (ii) ligation conditions, (iii) oligonucleotide annealing conditions, (iv) conditions that disrupt double-stranded nucleic acid structure, (v) RNA reverse transcription conditions, (vi) isothermal amplification conditions, (vii) thermocycle amplification conditions (e.g., polymerase chain reaction conditions), and (viii) nucleic acid fragmentation conditions (e.g., in which microcapsules are exposed to a nuclease). The porous, semi-permeable shell generally remains intact under nucleic conditions that release nucleic acids from an encapsulated cell, and nucleic acid processing conditions until microcapsules are exposed to reagent release conditions (see, e.g., Examples 6, 8, 9, 10, 12). An example of reagent release conditions that are biologically compatible includes contacting the microcapsules to an enzyme (a hexose or pentose sugar degrading enzyme such as a glycosidase (see, e.g., Examples 4, 19), for example) under degradation conditions, which typically are specific and relatively mild in comparison to certain nucleic acid release conditions and nucleic acid processing conditions. The aqueous core or microcapsules generally permits a biological entity and/or nucleic acid contained therein to interact with agents introduced outside the shell and that diffuse into the core. An aqueous core sometimes is liquid or semi-liquid, and in certain implementations is more viscous than water.

FIG. 1 illustrates a particular implementation for forming a semi-permeable compartment with encapsulated biological entities, processing of the biological entities and eventual biocompatible release. The semi-synthetic shell material can be based on a polysaccharide backbone, which can be bio-compatibly dissolved to release live cells, double-stranded DNA or other biological entities. Polysaccharide modifications allow for cross-linking the shell into a hydrogel and tuning the phase separation of core/shell polymer solutions during microcapsule formation. The microcapsules are subjected to a series of biochemical entity processing steps to form a reaction product from an encapsulated analyte. The processing steps may be mutually incompatible if practiced concurrently on a single microcapsule. Finally, the analyte reaction product is released into aqueous solution so as to be available for downstream reactions, such as nucleic acid sequencing.

Figures 2A, 2B, 2C, 2D, 2E:
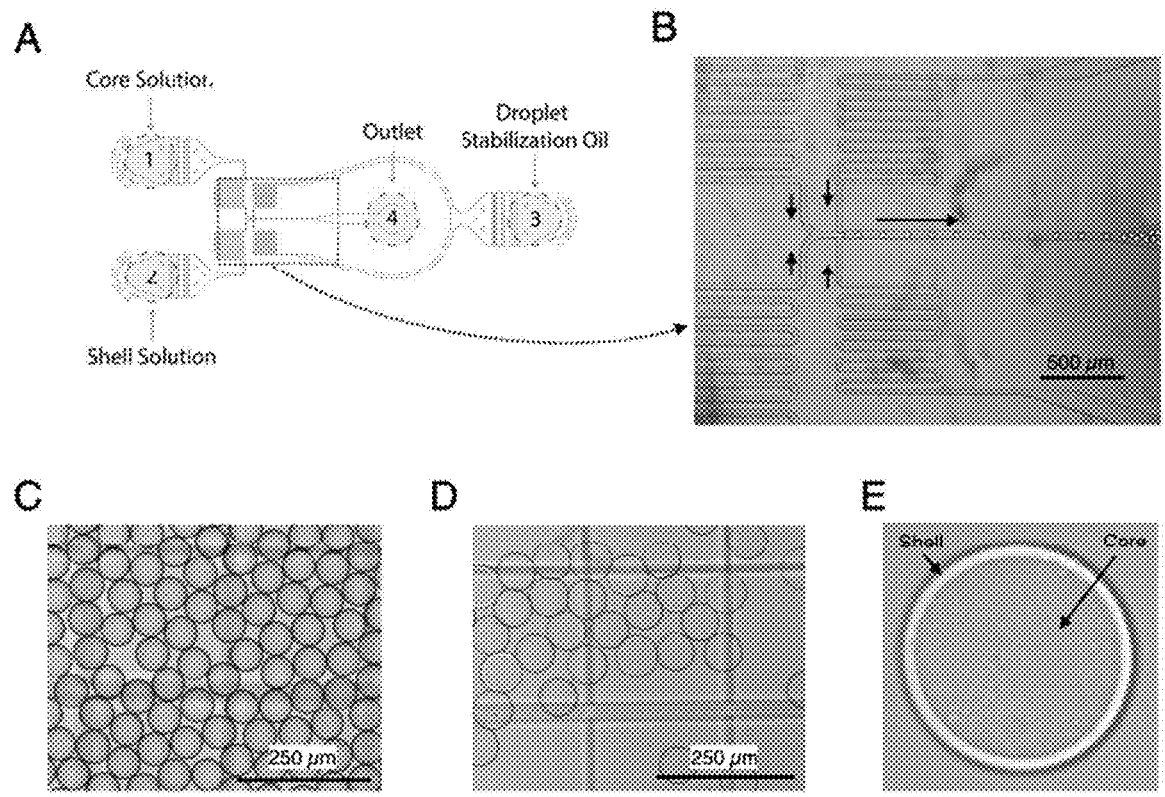
FIG. 2A-2E depict microcapsule formation.

FIG. 2A-E show actual images of the microcapsule generation process. An emulsion generator microfluidics device generates droplets having a mixture of core and hydrogel shell precursor reagents, as seen in FIG. 2A and FIG. 2B, and detailed in Example 2. The result is an unpolymerized emulsion population FIG. 2C, which is allowed to polymerize to from microparticles, FIG. 2D. A close-up of a microparticle clearly shows that the shell has uniform thickness and is distinguished from the aqueous core.

Core-shell microcapsules can include a hydrogel shell that generally is semi-permeable in a size-selective manner. Pores present in a shell can be characterized by the size of the macromolecules that the microcapsules are able to retain. For example, microcapsules described herein can retain double-stranded DNA that is 100 or 500 or 1000 or more consecutive nucleotides in length.

A number of approaches for modulating microcapsule porosity are disclosed herein. Some approaches comprise one or more of changing shell thickness, changing the level of substitution with the crosslinking moiety, and changing the backbone polysaccharide that forms the shell (see, e.g., Example 4). Alternately or in combination, microcapsule porosity may be modulated by the ionic strength of the solution capsules are in, as ionic strength may cause microcapsule hydrogels to either swell of shrink, impacting porosity. Similarly, selective degradation of a constituent of hydrogels, such as via enzymatic treatment to digest a part of the shell, e.g., if a shell composed of a blend of dextran and cellulose-based polymers, is subjected to digestion of the dextran only, one may impact porosity of the hydrogel as a whole so as to increase permeability while maintaining the capsules. Similarly, microcapsules comprising nanoparticles in their hydrogel may be subjected to partial or total selective nanoparticle degradation, so as to change microcapsule permeability.

Alternately, microcapsule surface charge, or reactions that change the surface charge of microcapsules may also impact permeability, particularly of molecules having a charge similar to that of the surface charge. For example, alkaline treatment used for cell lysis hydrolyses the ester bond by which the cross-linking moieties are attached to dextran in the shell polymer of some hydrogel microcapsules. Interestingly, the capsule integrity is maintained. Under the close-to-neutral pH that is typically used, the resulting —COOH groups formed after ester hydrolysis are —COO—, resulting in a negatively charged capsule. The presence of this charge may affect the permeability of the shell to negatively charged molecules such as nucleic acids.

While the semi-permeable nature of the microcapsules is similar to hydrogel beads, an advantage of capsules is that they comprise a liquid or semi-liquid core. A liquid or semi-liquid core allows for containment of an analyte in an aqueous liquid environment wholly within a microparticle. At the same time, the hydrogel shell allows for retention of the analyte or a reaction product thereof while the reaction buffer and reagents within the microcapsule are changed through incubation or washing of the microcapsule in an aqueous environment comprising a new reaction buffer and new reagents. In addition to retaining the analyte or analyte reaction product while exchanging the reaction environment, this process allows iterative, in some case incompatible reactions to be performed on a common analyte without iteratively diluting a completed reaction environment with a new reaction environment, via droplet merger or other approach known in the art, leading to substantial volume increase with each new reaction step. These volume increases in the approaches in the art can approach 5× to 10× or more per reaction, and pose challenges to the fluidic droplet manipulation. Using the semi-permeable nature and the aqueous liquid core volume of the microcapsules as disclosed herein, one can perform a substantially larger number of successive reactions without having a substantial impact on the volume of the reaction site.

In addition, molecular biology reactions are often executed more efficiently in an aqueous liquid environment than in a solid or semisolid hydrogel bead. Reagents and analytes freely diffuse within the aqueous environment, allowing faster, more efficient reactions. For example, nucleic acid processing is much more efficient in a liquid environment such as that disclosed herein, as nucleic acids are otherwise entangled within the bulk of hydrogel beads, and interact with one another only slowly if at all. In particular, reactions progress much faster in aqueous environment relative to hydrogel environments. This timing has a practical impact, as reagents may diffuse across the hydrogel shell of the microcapsules.

Using the microcapsules herein, diffusion within the aqueous core is faster and favored over diffusion across the hydrogel shell. As a result, the rate of analyte loss is low relative to the rate of reaction in the microcapsules disclosed herein. In contrast, hydrogel beads' diffusion rates within the bead core is comparable to the rate of loss of analytes from the bead to the environment. This further hampers one's ability to perform reactions in series in hydrogel beads relative to the microcapsules disclosed herein. Furthermore, as reagents such as buffers and enzymes are generally smaller than are nucleic acids, such as nucleic acids of 100-500 bases or greater, and are often neutral or positively charged, reagents are likely to diffuse into and out of the microcapsules at a rate higher than that of nucleic acid analytes.

Often, diffusion across microcapsule membranes by reagents, below the size of target analytes such as nucleic acids of 100-500 bases or more is sufficiently efficient that encapsulated analytes in microcapsules may be processed using protocols and timing parameters designed or optimized for unpartitioned analytes in solution. That is, no additional time need be added to incubation or wash steps to allow reagent diffusion across microcapsule shells.

Additionally, liquid or semi-liquid core also allows for the culturing of viable, intact cells within the core, which is yet another advantage over hydrogel beads or water in oil emulsions.

Core-shell microcapsules can be generated by forming water-in-oil droplets containing aqueous solutions of two immiscible polymers forming an aqueous two-phase system (ATPS). Biological entities (e.g., molecules, cells, viral particles) can be placed within microcapsules during droplet generation and polymer phase separation into core and shell layers. A shell polymer can be converted into a hydrogel by crosslinking it or by allowing it to solidify. Upon shell polymerization, microcapsules can be released from the water-in-oil emulsion and further handled as water-in-water microcapsule "droplets" and used for cell or molecule compartmentalization.

An advantage of microcapsules is that they can allow for multi-step workflows: components of an earlier reaction can be washed out of the microcapsule interior before continuing with a subsequent reaction. This feature is in contrast with regular water-in-oil droplets from which molecules cannot be removed without losing compartmentalization and adding reagents requires challenging droplet manipulation.

A similar advantage of microcapsules as disclosed herein is that the exchange of reagent buffers is often rapid. Consequently, analytes encapsulated within microcapsules may be subjected to molecular biological protocols under conditions and parameters comparable to those of analytes in free solution. That is, reactions in some cases do not need to be delayed or incubation steps extended so as to accommodate for diffusion steps.

Certain features and advantages of particular core-shell microcapsule implementations are described hereafter.

1. The shell polymer can be a semi-synthetic polysaccharide sometimes including a natural polysaccharide backbone with backbone groups (e.g., hydroxyl groups, and/or amino groups and/or carboxyl groups when applicable) modified by conjugating chemical groups providing additional functionality (see, e.g., Examples 1, 14, 16, 18, 20, 22, 27).

2. The polysaccharide backbone sometimes is a charge-neutral non-ionic backbone. This feature is in contrast to ionic (charge-bearing) polymers or polyampholytes (charge-bearing but with an overall charge that can be neutral). Shell polymer neutrality can minimize binding of polyelectrolytes such as nucleic acids or proteins having a net surface charge. Not binding encapsulated entities and molecules allows for encapsulated entities to freely move within the core and freely interact with external reagents that enter the microcapsules (e.g., for nucleic acid processing). Alternately, modifying the microcapsule surface charge may impact effective porosity of the hydrogel, so as to limit the diffusion of commonly charged molecules across the hydrogel. For example, modifying a hydrogel so as to apply a negative charge may impede diffusion of negative molecules such as nucleic acids across the hydrogel, effectively decreasing the microcapsule porosity as to nucleic acids while allowing more efficient transfer of neutral or positively charged reagents.

3. Cross-linking moieties in the shell polymer (e.g., acryloyl- or methacryloyl-groups) enable cross-linking of the shell polymer and formation of a semi-porous hydrogel shell in the microcapsules (FIG. 1), permitting external reagents to enter the microcapsules and concomitantly retaining biological entities and molecules, thereby permitting processing of the biological entities and molecules, for example.

4. The degree of polysaccharide modification with cross-linking moieties is controlled by adjusting the stoichiometry of the polysaccharide functionalization reaction (see, e.g., Example 4). Higher degrees of substitution lead to more cross-linking and reduced microcapsule shell permeability.

Starting with a naturally-occurring polysaccharide and modifying it chemically enables fine-tuning of shell permeability, hydrogel stiffness (e.g., deformable microcapsules), and shell resistance to elevated temperatures and extreme pH (e.g., shell compositions that survive thermal cycling). The ability to fine-tune shell permeability is useful. Different shell polymers can be utilized that form microcapsules retaining DNA having a length greater than 100, 200, 500, or 1000 consecutive nucleotides, for example. Microcapsules containing other types of polymer backbones do not readily permit fine-tuning of the degree of modification with cross-linking moieties and other substituents.

For example, PEG diacrylate (PEGDA) used as a shell polymer cannot be easily modified with functional groups throughout its length due to its inert chemical composition. It is difficult to tune pore size or add additional desired functionality, like fluorescence or protein binding. The control of shell permeability when using PEGDA has not been demonstrated. Additional PEGDA allows only pore size reduction and not pore size enhancement.

5. Hydrophilicity/hydrophobicity-modifying agents, when modifying a polysaccharide in a shell polymer, can facilitate aqueous-two phase system (ATPS) formation with core polymer and facilitate core/shell separation within a droplet to form the microcapsules. For example, methacryloyl-modified dextran with less than a 20% degree of modification does not form an ATPS with naturally-occurring dextran. However, when naturally-occurring dextran is additionally modified with butyryl moieties (which are inert in cross-linking), even a 2% methacryloyl substitution is sufficient for the double-modified polysaccharide to form an ATPS as well as cross-linked into a hydrogel (see, e.g., Example 4).

6. Modification of a naturally occurring polysaccharide, for example, expands the choice of microcapsule shell and core polymer pairs that phase separate. For example, dextran modified with methacryloyl and/or butyryl forms an ATPS with unmodified dextran.

7. Additional functional groups can be introduced that serve a different primary function than ATPS formation or cross-linking. For example, a fluorescent dye can be introduced into the shell polymer to enable fluorescent microcapsule detection. Similarly, biotin can be introduced to immobilize proteins bearing an avidin tag (see, e.g., Examples 16, 17).

8. The cross-linked shell hydrogel can be degraded, for example hydrolyzed enzymatically, such as using backbone polysaccharide-specific hydrolases under relatively mild conditions (e.g., pH 6-8; temperature less than 40 degrees Celsius). For example, microcapsules containing dextran-based core and shell polymers can be degraded by dextranase under relatively mild enzymatic conditions that do not degrade encapsulated biological entities and/or molecules released from the microcapsules upon microcapsule degradation (see, e.g., Example 4). Similarly, microcapsules may be subjected to sonication or shearing. In some cases this allows reaction products to be released without harm to the products or to the environment to which they are delivered (see, e.g., Example 13). In contrast, degradation of microcapsules containing PEGDA shells requires extreme pH and elevated temperature. Specifically, a 10-minute treatment with 1M NaOH at 50 degrees Celsius sometimes is required release PCR amplicons from microcapsules containing PEGDA shells. Such a relatively harsh treatment prevents the release of viable cells from microcapsules containing PEGDA shells without killing the cells. When working with RNA, such alkaline conditions would lead to RNA degradation by hydrolysis. Such conditions would also denature double-stranded DNA (dsDNA) to single-stranded DNA (ssDNA), which is undesirable for most workflows involving DNA manipulation within microcapsules.

9. The microcapsules allow diffusion of reagents through the hydrogel shell while maintaining analytes in their aqueous liquid core. This allows reaction buffers and reagents to be washed in and out by incubating microcapsules in one or another reaction mix, while preserving a favorable reaction environment in the interior and without iteratively diluting reaction buffers. Accordingly, multiple mutually incompatible reactions may be performed in an analyte in series without the need to iteratively dilute the reaction volume.

10. Microcapsules exhibit uniform minimum thickness. As a result, diffusion times for buffers or reaction reagents are predictable, while analytes are less likely to 'leak out' through local thin points in shells.

Consistent with microcapsules possessing one or more of the above-mentioned improvements, disclosed herein are compositions, methods of use, compositions that are beneficially or exclusively made through use of disclosure herein, methods of making, systems for making, and compositions for making said microcapsules.

In certain aspects, provided herein is a composition that includes a plurality of microcapsules each comprising a core surrounded by a shell. The shell can be a hydrogel that includes a first polymer. The first polymer can include a polysaccharide modified with a conjugated cross-linking moiety and optionally modified with a conjugated hydrophilicity/hydrophobicity-modifying moiety. Molecules of the cross-liking moiety of the first polymer often are cross linked in the hydrogel. The core can be a liquid or semi-liquid core. The core can include a second polymer that contains a polysaccharide that does not include the cross-linking moiety and does not include the hydrophilicity/hydrophobicity-modifying moiety.

A polysaccharide generally is a polymer that includes multiple saccharide monomers or saccharide units (e.g., disaccharide units) covalently linked. A polysaccharide may be linear or branched. A polysaccharide (i) can include saccharide monomers linked by a glycosidic bond; (ii) can be a glucan; (iii) can include pentose and/or hexose monomers (see, e.g., Examples 14, 15); (iv) can include glucose monomers; (v) can include fructose monomers (see, e.g., Example 4); or (vi) a combination of two or more of (i), (ii), (iii), (iv) and (v). Non-limiting examples of polysaccharides include glucans, dextran (see, e.g., Example 1), alginate, hyaluronic acid, glycogen, starch (e.g., amylose, amylopectin), agarose, agar-agar, heparin, pectin, cellulose and modified celluloses (e.g., methyl-, ethyl-, hydroxyethyl-, hydroxypropyl-modified celluloses; Examples 18, 19), hemicelluloses (e.g., xyloglucans, xylans, mannans and glucomannans, and beta-(1→3,1→4)-glucans), chitosan, chitin, xanthan gum, arabic gum, galactomannan and pectin. A polysaccharide can be naturally occurring (e.g., dextran, cellulose) or can be a non-naturally occurring polysaccharide or synthetic polysaccharide (e.g., ficoll and modified celluloses (e.g., methyl-, ethyl-, hydroxyethyl-, hydroxypropyl-modified celluloses). A polysaccharide sometimes is a charge-neutral non-ionic polysaccharide, non-limiting examples of which include glucans, dextran, starch, agarose, galactomannan, hemicelluloses, cellulose and modified celluloses (methyl-, ethyl-, hydroxyethyl-, hydroxypropyl-modified celluloses) and chitin, and a polysaccharide sometimes is charge-neutral and non-ionic at pH 7. A polysaccharide sometimes is an ionic polysaccharide (e.g., pectin, alginate, chitosan). A polysaccharide can be of any suitable molecular mass for forming microcapsules, including without limitation a molecular mass of about 5,000 g/mole to about 50,000,000 g/mole, or a molecular mass of about 50,000 g/mole to about 2,000,000 g/mole, or a molecular mass of about 500,000 g/mole (see, e.g., Examples 1, 14, 18, 32).

A microcapsule as disclosed herein exhibits an often uniform hydrogel shell thickness. Shells in some cases exhibit a thickness of about, at least or no more than 1 um, 2 um, 3 um, 4 um, 5 um, 6 um, 7 um, 8 um, 9 um, 10 um, 11 um, 12 um, 13 um, 14 um, 15 um, 16 um, 17 um, 18 um, 19 um, 20 um, 25 um, 30 um, 40 um, or 50 um. Often, shell thicknesses vary by no more than 50% within populations or microparticles. Exemplary shell thicknesses are in some cases from 1-6 um, 10-20 um, or 15-30 um. Some microcapsules exhibit shell thicknesses of about 3 um or 3 um plus or minus 50%. Alternate shell thickness observed are about 14 um, or 14 um plus or minus 50%.

A microcapsule or portion thereof is often degradable, for example under chemical or biological conditions. Some microcapsules are degradable at a pH range of 3-11, 4-10, 5-9, 6-8, or a comparable range having a low endpoint as listed previously in combination with a high endpoint as listed previously. Similarly, some microcapsules are degradable at a temperature in Celsius of about, at least or at most 10, 15, 20, 25, 30, 35, 40, 45, 50, 55, 60, 65, 70, or 75 C (see, e.g., Examples 4, 19).

Some microcapsules are degradable under mechanical conditions, such as shearing or sonication. Sonication at levels below that sufficient to shear nucleic acids is sufficient to break the hydrogel microcapsule shells. In particular, mechanical degradation such as sonication is suitable when analytes are predicted to be of no greater than 1 kb, for example no greater than 900, no greater than 800, no greater than 700, no greater than 600, no greater than 500, or less than 500 pb. Alternately, under analysis conditions where some breakage of analyte or reaction product is tolerated, analytes of up to greater than 1 kb may be released through mechanical degradation such as shearing or sonication (see, e.g., Example 13).

Some microcapsules are degradable under thermal conditions, such as by heating. Hydrogels generally exhibit a melting point below the temperature at which analyte or reaction products contained within a microcapsule degrade. Heating variously comprises a single incubation at a melting temperature, or alternately iterative thermocycling to a melting temperature. Some compositions of hydrogel disclosed herein or contemplated in the art are resistant to thermocycling, such that polymerase chain reactions may be performed upon the microcapsules, for example so as to amplify contents of a particular microcapsule. Other compositions, in contrast, are vulnerable to higher temperatures of some thermocycling reactions, such that analytes or reaction contents are released at higher temperatures. Various compositions disclosed herein or contemplated in the art are vulnerable to degradation at temperatures of at least 65, 70, 75, 80, 85, 90, 95, 100 or greater than 100° C. Alternately, other compositions disclosed herein or contemplated in the art are resistant to degradation at temperatures of at least 65, 70, 75, 80, 85, 90, 95, 100 or greater than 100° C. (see, e.g., Examples 3, 4).

Biological degradation is often effected through enzymatic treatment, such as using an enzyme that degrades a monomer or polymerized monomer constituent of a hydrogel polymer. Exemplary targets are hexose or pentose sugar monomer or polymer constituents, but any constituent for which a degrading enzyme is available may be used as a target.

Microcapsules are glycosidase degradable in certain implementations (see, e.g., Examples 4, 19). In certain instances (i) the first polymer is glycosidase degradable, or (ii) the second polymer is glycosidase degradable; or (iii) the first polymer and the second polymer each is glycosidase degradable. A microcapsule is glycosidase degradable in instances where the microcapsule or portion thereof is degradable under enzymatic conditions that permit a glycosidase enzyme to degrade the microcapsule. A microcapsule described herein can be degraded by a glycosidase under relatively mild conditions to release encapsulated biological entities (e.g., cells, molecules) that may be contained in the microcapsules. The degree of degradation can be determined by light microscopy or by the presence or amount of entities released from the microcapsules (e.g., dye-labeled particles, fluorescent-labeled particles, nucleic acid) as determined by a suitable method (e.g., microscopy, electrophoresis), for example. Microcapsule degradation conditions generally are enzymatic microcapsule degradation conditions under which polymer in the shell and sometimes in the core is degraded enzymatically by one glycosidase type or two or more types of glycosidases. Microcapsule degradation conditions can include contacting microcapsules with a glycosidase at a pH of about 3 to about 11 at a temperature of about 80 degrees Celsius or less, and in certain instances can include contacting microcapsules with a glycosidase at a pH of about 6 to about 8 at a temperature of about 40 degrees or less. Glycosidase degradation conditions can include any suitable glycosidase, including without limitation a glycosidase that degrades a polysaccharide described herein, such as dextranase (e.g., suitable for degradation of dextran; Example 4), agarase (e.g., suitable for degradation of agarose), amylase (e.g., suitable for degradation of starch), and cellulase (e.g., suitable for degradation of cellulose; Example 19), for example. Glycosidase degradation conditions can include any suitable amount of a glycosidase that degrades microcapsules in a reasonable amount of time (e.g., within one hour; within 30 minutes; within 15 minutes, or any of no more than 1 hour, 45 minutes, 30 minutes, 20 minutes 15 minutes, 10 minutes, 5 minutes, 2, minutes, 1 minute, 30 seconds) and does not significantly degrade biological entity contents within the microcapsules. A microcapsule is glycosidase degradable in some cases when nucleic acid encapsulated in the microcapsule core is released after 15 minutes or less, as determined by electrophoresis of the solution containing the microcapsule, by contacting microcapsules with 200 glycosidase enzyme units (U; micromoles/minute) per 1 gram of shell polymer biological conditions comprising in this case pH 7.0 and at a temperature of 25 degrees Celsius. Certain microcapsules, such as microcapsules containing a cross-linked polyethylene glycol shell or polyacrylamide shell, are not glycosidase degradable under such conditions.

A shell and core of a microcapsule can be degraded under glycosidase degradation conditions where the glycosidase(s) utilized degrade(s) a polysaccharide that is the major component of the shell and a polysaccharide that is the major component of the core, for example, where the polysaccharide in the core and the shell is the same. The shell but not the core of a microcapsule can be degraded under glycosidase degradation conditions where a polysaccharide in the core is not the same as the polysaccharide in the shell and where a glycosidase utilized degrades the polysaccharide that is the major component of the shell but not the polysaccharide that is the major component of the core. The core but not the shell of a microcapsule can be degraded under glycosidase degradation conditions where the polysaccharide in the core is not the same as the polysaccharide in the shell and where the glycosidase utilized does not degrade the polysaccharide that is the major component of the shell but does degrade the polysaccharide that is the major component of the core (see, e.g., Example 4).

In certain implementations, a microcapsule or portion thereof is enzyme degradable, such as glycosidase degradable. This degradation is effected at a pH between about 3 and about 11 and at a temperature of about 80 degrees Celsius or less. A microcapsule or portion thereof sometimes is enzyme such as glycosidase degradable at a pH between about 6 and about 8 and at a temperature of about 40 degrees Celsius or less. An enzyme such as glycosidase utilized for degradation conditions sometimes is chosen from dextranase and cellulase (see, e.g., Examples 4, 19). A degree of microcapsule degradation can be determined by the amount of entities released from the core of microcapsules and/or retained within the core of microcapsules (e.g., dye-labeled particles, dye-labeled nucleic acid) as determined by a suitable method (e.g., light and/or fluorescence microscopy, electrophoresis).

Glycosidase is but one example of enzymatic degradation of microcapsules under biological conditions. Degradation under biological conditions allows for reaction products to be gently released from microcapsules even after multiple reaction processes in series, without harm to the reaction products or to the local environment into which the reaction products are released. Microcapsule compositions often comprise a first polymer and a second polymer. In certain implementations, the first polymer is a major component of the shell and the second polymer is a major component of the core. In certain instances (i) that the amount of the first polymer in the microcapsule is enriched in the shell and the amount of the second polymer in the microcapsule is enriched in the core, (ii) the ratio of the amount of the first polymer to the amount of the second polymer is significant higher in the shell relative to the ratio in the core, (iii) the ratio of the amount of the second polymer to the amount of the first polymer is significantly higher in the core relative to the ratio in the shell, (iv) enrichment of the first polymer in the shell and the second polymer in the core results from separation of an aqueous two-phase system in a droplet, where the aqueous two-phase system includes a solution including the first polymer as a first aqueous phase and a solution including the second polymer as a second aqueous phase, and where the droplet containing the two-phase aqueous system is in an oil environment (e.g., an oil composition); (v) the first polymer is greater than 50% of the dry shell mass and the second polymer is greater than 50% of the dry core mass; or (vi) combination of two or more of (i), (ii), (iii), (iv) and (v).

The first polymer and the second polymer sometimes include a different polysaccharide, and in certain instances the first polymer and the second polymer include the same polysaccharide. In certain implementations the first polymer, or the first polymer and the second polymer, contains a charge-neutral non-ionic polysaccharide. In certain implementations, the first polymer and/or the second polymer includes a polysaccharide that contains monomers linked by a glycosidic bond. The first polymer and/or the second polymer sometimes includes a glucan polysaccharide, and/or sometimes includes a polysaccharide that includes pentose and/or hexose monomers, and/or sometimes includes a polysaccharide that includes glucose and/or fructose monomers. The first polymer and/or the second polymer sometimes includes a naturally occurring polysaccharide, and sometimes the first polymer and/or the second polymer includes a polysaccharide chosen from dextran and cellulose. The first polymer and/or the second polymer sometimes includes a polysaccharide that is not naturally occurring, and the first polymer and/or the second polymer sometimes includes ficoll. The first polymer and/or the second polymer sometimes includes a polysaccharide having a molecular mass of about 5,000 g/mole to about 50,000,000 g/mole, or having a molecular mass of about 50,000 g/mole to about 2,000,000 g/mole, or having a molecular mass of about 500,000 g/mole (see, e.g., Examples 4, 19, 32).

A first polymer sometimes includes one type of cross-linking moiety, and in certain instances includes two or more types of cross-linking moieties (see, e.g., Examples 1, 20, 33). Any suitable cross-linking moiety can be chosen for modification in a first polymer, and a cross-linking moiety or moieties included in a first polymer sometimes are chosen from light-activated, chemically-activated or thermally-activated cross-linking moieties (see, e.g., Examples 2 and 11). Non-limiting examples of cross-linking moieties include thiomers (e.g., thiolated polysaccharides that are cross-linked via their thiol substructures (e.g., Summonte et al., J. Controlled Release 330:470-482 (2021)); acryloyl or substitute acryloyl groups; copper catalyzed azide/alkyne cycloaddition (CuAAC) groups and other "click chemistry" groups (e.g., see Elchinger et al., Polymers 3(4):1607-1651 (2011)). In certain implementations, a cross-linking moiety or moieties in a first polymer independently are chosen from an acryloyl group or a substituted acryloyl group, and sometimes a cross-linking moiety or moieties in a first polymer independently are selected from acryloyl, or methacryloyl, or acryloyl and methacryloyl groups (see, e.g., Examples 1, 20, 33). Changing the cross-linker moiety density, type, and/or monomer amount in a first polymer can permit tuning of mechanical properties (e.g., elasticity, porosity) of microcapsules (see, e.g., Example 4). A second polymer sometimes includes no cross-linking moiety, and in certain instances a second polymer is not cross linked.

A first polymer in certain instances includes a hydrophilicity/hydrophobicity modifying moiety, and often a hydrophilicity/hydrophobicity modifying moiety modifies water solubility of a first polymer relative to the first polymer not containing the hydrophilicity/hydrophobicity-modifying moiety (see, e.g., Example 1, 4, 27). A hydrophilicity/hydrophobicity-modifying moiety generally modifies a hydrophobic property and/or hydrophilic property of the first polymer relative to the first polymer not containing the hydrophilicity/hydrophobicity-modifying moiety. Without being limited by theory, inclusion of a hydrophilicity/hydrophobicity-modifying moiety in the first polymer facilitates liquid-liquid phase separation of the first polymer with the second polymer relative to first polymer not containing a hydrophilicity/hydrophobicity-modifying moiety. Any suitable hydrophilicity/hydrophobicity-modifying moiety may be chosen for modification in a first polymer, including without limitation a fatty acid acyl group, such as a C2-C8 fatty acid acyl group (e.g., acetyl (see, e.g., Example 27), propionyl, butyryl (see, e.g., Example 1), isobutyryl, valeryl, isovaleryl, caproyl, heptanoyl, octanoyl group). A first polymer can include one type of the hydrophilicity/hydrophobicity-modifying moiety, and in certain instances can include two or more types of a hydrophilicity/hydrophobicity-modifying moiety. The cross-linking moiety can act as a hydrophilicity/hydrophobicity-modifying moiety. In certain implementations, a second polymer includes no hydrophilicity/hydrophobicity-modifying moiety, and in certain instances a second polymer includes no hydrophilicity/hydrophobicity-modifying moiety that modifies the first polymer (when the first polymer includes a hydrophilicity/hydrophobicity-modifying moiety).

A polysaccharide in a first polymer can be modified with a cross-linking moiety and/or a hydrophilicity/hydrophobicity-modifying moiety by any suitable conjugation. A cross-linking moiety and/or a hydrophilicity/hydrophobicity-modifying moiety often is covalently linked (i.e., covalently bound) to a polysaccharide and can by covalently linked to a primary hydroxyl and/or secondary hydroxyl group of a polysaccharide backbone, especially in the case of polysaccharides having a charge-neutral non-ionic backbone (see, e.g., Examples 1, 14, 16, 18, 20, 27). In the case of dextran, for example, a cross-linking moiety and/or a hydrophilicity/hydrophobicity-modifying moiety can be covalently linked via a secondary hydroxyl group of the polysaccharide backbone as glucose monomers in the polysaccharide backbone are linked by primary hydroxyl groups. In an implementation for which a polysaccharide backbone is ionic, a cross-linking moiety and/or a hydrophilicity/hydrophobicity-modifying moiety can be covalently linked via a hydroxyl group, an amino group or acid group (e.g., carboxylic acid group).

In certain implementations, a polysaccharide of a first polymer contains monomers (e.g., pentose and/or hexose monomers), and a molar ratio of (i) cross-linking moiety to (ii) monomer is about 0.01 to about 2.0, or about 0.01 or greater, or about 0.20 or less, or about 0.01 to about 0.20 (e.g., a ratio of about 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 1.1, 1.2, 1.3, 1.4, 1.5, 1.6, 1.7, 1.8, 1.9 or 2.0; see e.g., Example 4). In certain implementations, a polysaccharide of a first polymer contains monomers (e.g., pentose and/or hexose monomers), and a molar ratio of (i) hydrophilicity/hydrophobicity-modifying moiety to (ii) monomer is about 0.05 to about 1.0, or about 0.10 or greater, or about 0.80 or less, or about 0.20 to about 0.80 or about 0.25 to about 0.65 (e.g., a ratio of about 0.05, 0.06, 0.07, 0.08, 0.09, 0.10, 0.20, 0.30, 0.40, 0.50, 0.60, 0.70, 0.80, 0.90, 1.0). In certain implementations, a polysaccharide of the first polymer is modified by a cross-linking moiety and is modified by a hydrophilicity/hydrophobicity-modifying moiety, the cross-linking moiety is methacryloyl, and the hydrophilicity/hydrophobicity-modifying moiety is butyryl, and in certain instances the molar ratio of (i) methacryloyl moieties to (ii) first monomer is a ratio or in a ratio range stated above and the molar ratio of (i) butyryl moieties to monomer is a ratio or in a ratio range stated above (see, e.g., Example 1, 4).

In certain instances, a first polymer and/or a second polymer includes a detectable label (see, e.g., Example 17). Any suitable detectable label can be utilized, non-limiting examples of which include fluorescent labels such as organic fluorophores, lanthanide fluorophores (chelated lanthanides; dipicolinate-based Terbium (III) chelators), transition metal-ligand complex fluorophores (e.g., complexes of Ruthenium, Rhenium or Osmium); quantum dot fluorophores, isothiocyanate fluorophore derivatives (e.g., FITC, TRITC), succinimidyl ester fluorophores (e.g., NHS-fluorescein), maleimide-activated fluorophores (e.g., fluorescein-5-maleimide), and amidite fluorophores (e.g., 6-FAM phosphoramidite); radioactive isotopes (e.g., 1-125, 1-131, S-35, P-31, P-32, C-14, H-3, Be-7, Mg-28, Co-57, Zn-65, Cu-67, Ge-68, Sr-82, Rb-83, Tc-95m, Tc-96, Pd-103, Cd-109, and Xe-127); light scattering or light diffracting labels (e.g., light scattering gold nanorods, resonance light scattering particles); an enzymic or protein label (e.g., green fluorescence protein (GFP), peroxidase); or other chromogenic label or dye (e.g., cyanine). Non-limiting examples of organic fluorophores include xanthene derivatives (e.g., fluorescein, rhodamine, Oregon green, eosin, Texas red); cyanine derivatives (e.g., cyanine, indocarbocyanine, oxacarbocyanine, thiacarbocyanine, merocyanine); naphthalene derivatives (dansyl, prodan derivatives); coumarin derivatives; oxadiazole derivatives (e.g., pyridyloxazole, nitrobenzoxadiazole, benzoxadiazole); pyrene derivatives (e.g., cascade blue); oxazine derivatives (e.g., Nile red, Nile blue, cresyl violet, oxazine 170); acridine derivatives (e.g., proflavin, acridine orange, acridine yellow); arylmethine derivatives (e.g., auramine, crystal violet, malachite green); and tetrapyrrole derivatives (e.g., porphin, phtalocyanine, bilirubin). A detectable label sometimes includes a fluorophore or a dye.

In certain implementations, a first polymer and/or a second polymer includes a binding partner moiety to which a binding partner counterpart moiety can bind (see, e.g., Examples 16, 17). Non-limiting examples of binding partner/binding partner counterpart pairs include antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, nucleic acid/complementary nucleic acid (e.g., DNA, RNA, PNA) and the like. In certain implementations, the binding partner moiety is biotin and the binding partner counterpart moiety is avidin, or the binding partner counterpart moiety is biotin and the binding partner moiety is avidin (see, e.g., Examples 16, 17).

A detectable label and/or binding partner moiety, when included, often are conjugated to a polymer backbone, sometimes directly and sometimes via an intermediate moiety. In certain instances, a detectable label and/or a binding partner moiety are covalently attached to a polymer (e.g., covalently attached to a polysaccharide of a polymer (e.g., covalently attached to a polysaccharide backbone of a polymer)).

In certain implementations, microcapsules remain intact (i) under a pH in a pH range of about pH 2 to about pH 12 at 37 degrees Celsius for 2 hours or more, and/or (ii) under polymerase chain reaction thermocycle conditions. Polymerase chain reaction (PCR) thermocycle conditions are known and sometimes include denaturation conditions at about 95 degrees Celsius for about one minute, annealing conditions at about 55 degrees Celsius for about two minutes and extension conditions at about 70 to about 75 degrees Celsius for about three minutes, for example (see, e.g., Example 3).

Microcapsules are microspheroids in certain implementations. Microcapsules sometimes are defined by a diameter of about 1 micrometer to about 10,000 micrometers, or sometimes by a diameter of about 10 micrometers to about 100 micrometers (e.g., a diameter of about 10, 20, 30, 40, 50, 60, 70, 80, 90 or 100 micrometers; Examples 2, 29, 30). Microcapsules in a composition often are generally uniform and often are monodisperse, and microcapsules in a composition generally have high circularity and high concentricity. Circularity and concentricity are determined at the individual microcapsule level, and their average can be reported at the microcapsule population level. Microcapsules in a composition generally have an average radius, R, where R is (square root over (S/π)), and S is the equatorial transverse surface of the capsule. In certain instances, a diameter of microcapsules in a composition varies by a coefficient of variation of about 30% or less (e.g., a diameter of microcapsules varies by a coefficient of variation of about 25% or less, 20% or less, 15% or less, 10% or less or 5% or less). Circularity, C, is a ratio of the minor axis (R min) over the major axis (R max) of the ellipse adjusted to the external edge of the projected equatorial section. In certain implementations, C is about 0.8 to about 1.0 (e.g., C is about 0.85 or more, 0.90 or more, 0.95 or more, 0.99 or more or 1.0) for microcapsules in a composition. Concentricity, O, of microcapsules in a composition generally is equal to (Wmin/Wmax)*100%, where Wmin is the thinnest part of the shell and Wmax is the thickest part of the shell. In certain implementations, O is greater than or equal to 75% for microcapsules in a composition.

microparticle morphology, particularly of the hydrogel shell, allows for exquisite control over reagent exchange without analyte leakage from the aqueous liquid core. Having a uniform microparticle shell minimum thickness allows one to accurately calculate and execute incubation times necessary to clear reagent buffers, such as incompatible reagent buffers for reactions performed consecutively on an analyte harbored within a microcapsule.

Microparticles are durable, such that changes in ionic strength or composition of successive buffers may cause some expansion or contraction of microparticle overall volume, of, variously, no more than 1%, 2%, 3%, 4%, 5%, 10%, 15%, 20%, or even 25%. However, this buffer dependent expansion or contraction is very modest compared to the 2×, 3, 5×, or even 10× dilution which is often required when delivering a diluting buffer to a droplet for which an incompatible reaction has previously occurred. Furthermore, the buffer-driven volume fluctuations in microparticles herein are not additive from one reaction to another in a reaction series, while buffer dilutions delivered to droplets in emulsions lead invariable to droplet volume increases that are proportional to the volume being diluted. That is, droplet volume increase is exponential, and unlikely to be manageable over more than one or two reaction condition sets.

Furthermore, reagent delivery is easily effected by washing microcapsules in an aqueous carrier of the new reaction buffer. At the completion of each reaction, microcapsules are washed into the upcoming reaction buffer, which then diffuses across the hydrogel shell into the aqueous interior to 'swap out' prior buffer conditions. This process is relatively easy and does not require complex microfluidic manipulation. In contrast, reactions in emulsions requires that new reaction buffers be merged into emulsion droplets, and in a volume sufficient to dilute the prior reaction conditions. This often requires finely tuned droplet merger and results in droplets of substantially greater size, thus complicating microfluidic manipulations.

Microcapsules generated through the disclosure herein may have a broad range of volumes. Volume variation may be observed from microcapsule to microcapsule in some cases, but is often largely uniform for a given population of microcapsules. Microcapsule volume is often governed by the fluidics of the emulsion process and the relative proportion of shell and core constituents in the emulsion process leading to microcapsule generation. In some cases microcapsules of a given population differ in volume from one another by no more than 2×, 3×, 4×, 5×, 6×, or 10×.

Alternately, microcapsules of a given population differ in volume by no more than 50%, 25%, 10%, 5% or less than 5%.

A wide range of microcapsule volumes are consistent with the disclosure herein. Some microcapsule populations exhibit mean, median, maximum or minimum volumes of no more than, no less than or about 1 pL, 2 pL, 5 pL 10 pL, 20 pL, 50 pL, 100 pL, 200 pL, 500 pL, 1 nL, 2 nL, 5 nL, 10 nL, 20 nL, 50 nL, 100 nL, 200 nL, or 500 nL volumes. Similarly, some individual microcapsules exhibit volumes of no more than, no less than or about 1 pL, 2 pL, 5 pL 10 pL, 20 pL, 50 pL, 100 pL, 200 pL, 500 pL, 1 nL, 2 nL, 5 nL, 10 nL, 20 nL, 50 nL, 100 nL, 200 nL, or 500 nL volumes. In some cases microcapsule populations exhibit a range of sizes, with a low endpoint of the range selected from a first volume as previously listed and a high endpoint of the range selected from a second, larger volume as previously listed. Microcapsule volumes are in some cases selected to accommodate particular analytes or reaction products, or to facilitate particular reaction times or to accommodate particular reaction constituents. A shell of microcapsules in a composition sometimes includes pores and the microcapsules retain nucleic acid of a size of about 100 base pairs or greater, or of a size of about 500 base pairs or greater, or of a size of about 1,000 base pairs or greater (see, e.g., Examples 3, 4, 24). A shell of microcapsules in a composition sometimes includes pores of about 0.1 nanometers to about 500 nanometers or of about 10 nanometers to about 50 nanometers. A shell of microcapsules in a composition can have pores of about 0.1 nm, 0.5 nm, 1 nm, 2 nm, 3 nm, 5 nm, 7 nm, 10 nm, 15 nm, 20 nm, 30 nm, 40 nm, 50 nm, 60 nm, 70 nm, 80 nm, 90 nm, 100 nm, 150 nm or 200 nm, where "nm" is nanometers. In some cases, a microcapsule may have pores at least about 0.1 nm, 0.5 nm, 1 nm, 2 nm, 3 nm, 5 nm, 7 nm, 10 nm, 15 nm, 20 nm, 30 nm, 40 nm, 50 nm, 60 nm, 70 nm, 80 nm, 90 nm, 100 nm, 150 nm or 200 nm. In some cases, the pores may vary in size and be in range of about 0.1-1 nm, 0.1-10 nm, 1-10 nm, 0.1-100 nm, 1-100 nm, 10-100 nm, 0.1-200 nm, 1-200 nm, 10-200 nm.

In certain instances, (i) microcapsules in a composition contain no intermediate layer between the shell and the core; (ii) there is no intermediate layer, containing a polymer different than the first polymer and the second polymer, between the shell and the core in microcapsules in a composition; (iii) there is no layer on the exterior of the shell of microcapsules in a composition; (iv) microcapsules in a composition are lipid-free and organic solvent-free; (v) polymers of microcapsules in a composition consist of the first polymer and the second polymer; (vi), microcapsules in the composition consist of the core and the shell; (vii) microcapsules in the composition include no polyethylene glycol polymer or modified polyethylene glycol polymer; or (viii) a combination of two or more of (i), (ii), (iii), (iv), (v), (vi) and (vii).

In certain implementations, a composition containing microcapsules is a liquid composition (e.g., an aqueous liquid composition). In certain instances, a composition containing microcapsules is a solid composition, where the solid composition sometimes includes a hydrogel.

In certain implementations, microcapsules in a composition include a biological entity encapsulated within the core of a portion or all of the microcapsules. Any suitable biological entity may be encapsulated within a microcapsule. A biological entity sometimes is a molecule or reagent, non-limiting examples of which include a buffer, organic molecule, biological molecule, nucleotide, oligonucleotide, nucleic acid, detectable agent, amino acid, enzyme (e.g., ligase, polymerase, transposase) and protein (e.g., antibody, biotin, avidin, streptavidin). A biological entity sometimes is a nucleic acid-containing entity, non-limiting examples of which include a unicellular organism, multi-cellular organism, a cell from a multi-cellular organism, eukaryotic cell, prokaryotic cell, microorganism, bacterium, archaeon, fungus, plant, virus, organelle (e.g., mitochondria or chloroplast), liposomal vector and extracellular vesicle. Eukaryotic cells sometimes are from a unicellular organism or multi-cellular organism, and sometimes are from a human subject or non-human subject. A non-human subject sometimes is a mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman, a pregnant woman). A subject may be any age (e.g., an embryo, a fetus, infant, child, adult).

The disclosure herein allows iterative or successive reactions to be performed on an analyte encapsulated in a microcapsule. In some cases two or more of these reactions are mutually incompatible, such that they could not be concurrently executed in a common volume, or such that one would interfere or inhibit the second. Nonetheless, through the technology disclosed herein a first reaction may be performed and then its reaction conditions replaced with those of a second reaction without substantial volume increase or dilution, such that successive incompatible reactions may be performed in a common microcapsule.

Examples of mutually incompatible reaction include the following: 1) A first reaction proteinase treatment, followed by any enzymatic second reaction for which the enzyme is vulnerable to the protease; 2) a first reaction primary antibody staining, followed by a second reaction—secondary antibody staining—If primary antibody excess not washed out, secondary antibody binding occurs but leads to unspecific signal and suboptimal staining; 3) a first reaction comprising RNase treatment, followed by a second reaction comprising RNA synthesis—the synthesized RNA would be immediately degraded if the RNase is not cleared from the reaction volume. In each of these cases, retention of the first reaction conditions above a threshold inhibits a second reaction. Additional incompatible scenarios are readily contemplated by one of skill in the art.

In certain aspects, provided is a method that includes degrading the microcapsules. Degradation is accomplished through subjecting microcapsules to degradations conditions or through contacting the microcapsules to a degradation reagent. Exemplary degradation reagents catalyze microcapsule degradation. In some cases, the catalyst comprises a degradation enzyme, such as a glycosidase or other carbohydrate degrading enzyme, under enzymatic microcapsule degradation conditions. Enzymatic microcapsule degradation conditions generally hydrolyze microcapsules (e.g., hydrolyze all or a portion of a microcapsule shell). Microcapsule degradation conditions may degrade all or a portion of microcapsules in the composition and can include one or more types of glycosidase enzyme. A glycosidase, in certain implementations, is capable of enzymatic degradation of a polysaccharide in the first polymer and a polysaccharide in the second polymer of the microcapsules. A polysaccharide in the first polymer is the same as the polysaccharide in the second polymer in certain instances. Under glycosidase degradation conditions, at least the shell of the majority of the microcapsules often is degraded enzymatically by the glycosidase. In certain implementations, enzymatic microcapsule degradation conditions include a pH of about pH 3 to about pH 11 and are at a temperature of about 80 degrees Celsius or less, or include a pH of about pH 6 to about pH 8 and are at a temperature of about 40 degrees Celsius or less. Microcapsule degradation conditions sometimes include a glycosidase chosen from a dextranase and or a cellulase (see, e.g., Examples 4, 19).

In certain aspects, provided is a method that includes exposing a composition that contains microcapsules described herein to wash conditions. Wash conditions can change the composition of the solution microcapsules are suspended in, and often change the composition or reaction buffer environment of the core and the shell. Wash conditions often comprise exposing a microcapsule population to a solution comprising buffer and in some cases reagents suitable for a reaction to be performed on microcapsule contents, such as an analyte or product of a prior reaction step. For example, washes can change the pH, salinity, and reagent concentration in the microcapsule suspension. Wash conditions can (i) reduce the concentration of a component and/or remove a component present in the microcapsules, and/or (ii) increase the concentration of a component present in the solution used for washes. Often, wash conditions can replace a first set of buffer conditions compatible with a first reaction, with reaction conditions and reagents compatible with a second reaction, which is in some cases incompatible with the first reaction or first reaction buffer conditions. Washing a microcapsule population so as to replace one set of reaction conditions and reagents with a second, in some cases incompatible set of reaction conditions and reagents, allows one to perform mutually incompatible reactions in a microcapsule population. In various cases, microcapsules are subjected to 1, 2, 3, 4, 5, 6, 7, 8, 9, 10 or more than 10 changes in wash conditions, so as to facilitate performing reactions in series on an analyte or reaction product contained in a microcapsule (see, e.g., Examples 6, 8, 9, 10, 12).

Without being limited by theory, a component can move in and out of the microcapsule interior through a pore of a microcapsule shell when microcapsules are exposed to wash conditions. In certain implementations, microcapsules containing nucleic acid can be exposed to wash conditions after the microcapsules have been exposed to nucleic acid processing conditions (e.g., cell lysis conditions, nucleic acid fragmentation conditions, reverse transcription conditions, ligation conditions, MIP incorporation conditions, amplification conditions, barcode incorporation conditions, sequencing adapter incorporation conditions, and the like), where processed nucleic acid generally is retained within the microcapsules and other molecules (e.g., reagents) move out of the microcapsule interior. Microcapsules can be exposed to washing conditions for implementation of a subsequent processing step. In non-limiting examples, microcapsules can be exposed to wash conditions after lysis (e.g., to remove certain lysate components), after amplification (e.g., to remove excess primers and change the buffer), after barcode attachment (e.g., to remove unattached barcodes), after fragmentation (e.g., to change the buffer), and after multiple steps of nucleic acid library preparation for sequencing (see, e.g., Examples 6, 8, 9, 10, 12).

Wash conditions enable one to replace a microcapsule buffer environment without diluting the contents or conditions of a prior reaction, or otherwise substantially diluting the microcapsule core volume. Accordingly, wash condition changes allow one to change a reaction buffer environment without substantially changing the microcapsule core reaction volume. In some cases, changes to core reaction volume occur, such as those resulting from changes in osmotic pressure on microcapsule hydrogel shell. These changes are likely to be no more than 20%, 15%, 10%, 5% or less than 5%.

These changes stand in sharp contrast to the changes in volume resulting from reaction condition dilution through droplet merger in emulsion droplet populations, where the change in volume is substantial and may be 5×, 10× or more. Changes in volume of this magnitude may create challenges for microfluidic manipulation, and the droplet merger which effects them is technically challenging. In contrast, through the technology herein, reagent buffers and reagents are exchanged in some cases through simple but technically elegant incubation of microcapsules in an excess of new reagent buffer.

Reagent buffer exchange is in some cases direct, that is of one buffer by another. Alternately, in some cases reagent buffer exchange is effected through incubation in an intermediary buffer, such as PBS or water, so as to minimize the prior or first reaction conditions and buffer contamination of the second reaction conditions and buffer. Alternately, in some cases direct exchange of a first reaction buffer with a second reaction buffer is not impacted by contacting of the first reaction buffer to the second reaction buffer, for example in conditions where the second reaction buffer is provided in sufficient excess so as to dilute out any impact of the first reaction buffer on subsequent reaction conditions.

In certain aspects, provided is a process for manufacturing a composition including a plurality of microcapsules, where the process includes: (a) emulsifying in a droplet generation device (i) a first aqueous solution including a first polymer, and (ii) a second aqueous solution including a second polymer, in an oil, where: the first polymer includes a polysaccharide modified with a conjugated cross-linking moiety and optionally modified with a conjugated hydrophilicity/hydrophobicity-modifying moiety; the second polymer includes a polysaccharide that does not include the cross-linking moiety and does not include the hydrophilicity/hydrophobicity-modifying moiety of the first polymer; the first aqueous solution and/or the second aqueous solution comprises a biological entity; monodisperse water-in-oil droplets containing the first polymer, the second polymer and the biological entity are generated; and an aqueous two-phase system is formed inside the water-in-oil droplets in which a liquid core is completely surrounded by a liquid shell and the biological species is preferentially distributed in the liquid core; and (b) exposing the microcapsules to cross-linking conditions that conjugate cross-linking moieties in the first polymer, thereby forming a hydrogel shell surrounding a core in a plurality of microcapsules (see, e.g., Example 2, as well as most of the other examples). Without being limited by theory, microcapsules, including a core surrounded by a shell, form in the droplets as a result of separation of a first phase that includes the first polymer and a second phase that includes the second polymer. In certain implementations, a polysaccharide of the second polymer contains no cross-linking moiety and no hydrophilicity/hydrophobicity-modifying moiety, and sometimes the second polymer is an unmodified polysaccharide. In certain implementations, the first polymer is a modified polysaccharide and the second polymer is an unmodified polysaccharide, and in certain instances, the polysaccharide backbone of the first polymer and the second polymer is the same (e.g., the first polymer is a modified dextran and the second polymer is an unmodified dextran).

In certain implementations, the contacting in part (a) includes contacting the first aqueous solution and the second aqueous solution with a third aqueous solution, where the third aqueous solution is contained in the water-in-oil droplet (see, e.g., Example 31). Without being limited by theory, the third aqueous solution in the water-in-oil droplets (i) separates the first aqueous solution and the second aqueous solution, (ii) mixes with the first aqueous solution and/or the second aqueous solution, (iii) forms a core within a core, (iv) forms a shell outside a shell, or (v) a combination of two or more of (i), (ii), (iii) and (iv). In certain instances, the first aqueous solution, the second aqueous solution, the third aqueous solution, or combination of two or three thereof, independently includes a biological entity.

The contacting in part (a) can be implemented by injecting, infusing, delivering and/or loading the first aqueous solution and the second aqueous solution, and optionally the third aqueous solution, in a device that combines the two solutions, such as a droplet forming device for example (see, e.g., Example 2, 31). In certain implementations, the water-in-oil droplets are generated by a microfluidic device. A microfluidic device often includes channels, which sometimes are in a capillary assembly, where channels in the capillary assembly have any suitable cross-sectional geometry (e.g., ovoid, circular, quadrilateral, rectangular, square). Channels in a microfluidic device sometimes have a cross-sectional width of about 1 micrometer to about 10,000 micrometers, about 10 micrometers to about 1000 micrometers, or about 20 micrometers to about 100 micrometers. A microfluidic device sometimes is a microfluidic chip. In certain implementations, a fluidic device includes a flow-focusing junction (e.g., a nozzle), and sometimes the water-in-oil droplets are generated by infusing the first aqueous solution, the second aqueous solution, optionally the third aqueous solution, and the oil through the flow-focusing junction. In certain instances, the water-in-oil droplets and the microcapsules are not sprayed.

An oil can be considered a carrier oil in a process described herein.

Oils as used herein are often hydrophobic, so as to render energetically favorable the accumulation of microcapsule hydrogel constituents at the microdroplet perimeter.

Any suitable oil can be utilized, non-limiting examples of which include a fluorinated oil (fluid) such as FC40 oil (3M®), FC43 (3M®), FC77 oil (3M®), FC72 (3M®), FC84 (3M®), FC70 (3M®), HFE-7500 (3M®), HFE-7100 (3M®), perfluorohexane, perfluorooctane, perfluorodecane, Galden-HT135 oil (Solvay Solexis), Galden-HT170 oil (Solvay Solexis), Galden-HT110 oil (Solvay Solexis), Galden-HT90 oil (Solvay Solexis), Galden-HT70 oil (Solvay Solexis), Galden PFPE liquids, Galden® SV Fluids or H-Galden® ZV Fluids; and hydrocarbon oils such as Mineral oils, Light mineral oil, Adepsine oil, Albolene, Cable oil, Baby Oil, Drakeol, Electrical Insulating Oil, Heat-treating oil, Hydraulic oil, Lignite oil, Liquid paraffin, Mineral Seal Oil, Paraffin oil, Petroleum, Technical oil, White oil, Silicone oils or Vegetable oils. An oil may include a surfactant in certain implementations. A surfactant can be a stabilizing surfactant, which without being limited by theory, can stabilize water-in-oil droplets formed in a process described herein. Any suitable surfactant may be utilized and a surfactant can be present in a carrier oil at a concentration ranging from about 0.05% to about 10% (w/w), about 0.1% to about 5% (w/w), or about 0.25% to about 2% (w/w). Non-limiting examples of surfactants include emulsifying surfactants, non-ionic surfactants (e.g., Triton X-100, Pluronic F127), anionic surfactants, hydrocarbon surfactants and fluoro-surfactants (e.g., perfluoropolyether-polyethylene glycol-perfluoropolyether (PFPE-PEG-PFPE) tri-block copolymer; polyethylene glycol-perfluoropolyether (PEG-PFPE) di-block copolymer). In certain instances, an oil includes a fluorinated fluid and a fluoro-surfactant, and in certain implementations, an oil comprises HFE-7500 fluid and a PFPE-PEG-PFPE) tri-block copolymer or PEG-PFPE di-block copolymer fluoro-surfactant. In certain instances, an oil (e.g., carrier oil) comprises a surfactant, and sometimes an oil (e.g., carrier oil) comprises a fluorinated fluid and a fluorosurfactant.

In certain implementations, water-in-oil droplets are collected in the form of an emulsion, and sometimes an emulsion is collected outside of a microfluidic device. In certain instances, after part (a) or after part (b), a process includes separating microcapsules from the oil into an aqueous solution, and the separating sometimes includes de-emulsification. De-emulsification generally is a process during which water-in-oil droplets are broken by chemical or physical means. A non-limiting example of a chemical form or de-emulsification includes bursting water-in-oil droplets with perfluorooctanol.

In microcapsules formed by a process described herein, the first polymer often is a major component of the shell and the second polymer often is a major component of the core. A major component is a component having a dry weight greater than 50% of the total dry microcapsule weight in a microcapsule-containing composition.

In certain aspects, provided herein is a process for manufacturing a composition including a plurality of microcapsules, that includes: (a) contacting (i) a first aqueous solution comprising a first polymer, (ii) a second aqueous solution comprising a second polymer, and (iii) an oil, under droplet-forming conditions, where: the first polymer includes a polysaccharide modified with a conjugated cross-linking moiety and optionally modified with a hydrophilicity/hydrophobicity-modifying moiety; the core includes a second polymer comprising a polysaccharide that does not include the cross-linking moiety and does not include the hydrophilicity/hydrophobicity-modifying moiety of the first polymer; monodisperse water-in-oil droplets containing the first polymer and the second polymer are generated; and an aqueous two-phase system is formed inside the water-in-oil droplets in which a liquid core is completely surrounded by a liquid shell; and (b) cross-linking the cross-linking moieties in the first polymer, thereby forming a hydrogel shell surrounding the core in a plurality of microcapsules encapsulating the biological entity; and (c) breaking the water-in-oil droplets and releasing the microcapsules encapsulating the biological entity into an aqueous solution (see, e.g., Examples 2, 31).

In certain aspects, provided herein is a composition that includes a plurality of microcapsules, obtainable by a process described herein.

Concatenation Methods

Provided are methods in which encapsulated nucleic acid from a biological entity is concatenated in intact microcapsules and then released. Concatenation allows, for example, for nucleic acids from a common source to be linked by a common phosphodiester bond, so as to facilitate identification of their common origin. Coupled with long-read sequencing technologies nucleic acid concatenation within microcapsules opens the possibility for single-cell sequencing without additional cellular barcode use. Non-limiting examples of long-read sequencing technologies include nanopore sequencing and real-time DNA sequencing from single polymerase molecules.

High-throughput methods for single-cell nucleic acid (NA) analysis often rely on a "1 barcode=1 cell" paradigm: all nucleic acids of interest from a given cell are tagged with the same barcode, which is different between cells. The barcoding step needs to happen with NAs from individual cells being in separate compartments (e.g., wells, drops, fixed cell or nuclei scaffolds). After barcoding nucleic acids from multiple cells are pooled and sequenced as a single sequencing library. Reads sharing the same barcode are considered to originate from the same cell.

Here, two different principles are provided for single-cell sequencing: "1 read=1 cell" (see, e.g., Examples 6, 8) and "1 unique molecule index (UMI) set=1 cell" (see, e.g., Example 7). The "1 read=1 cell" principle is based in part on an approach that nucleic acids of interest from individual cells in separate microcapsule compartments can be concatenated into long concatemers (as shown in one example in FIG. 5). Next, concatemers from individual cells can be pooled and sequenced using long read sequencing (LRS; e.g., Oxford Nanopore, PacBio sequencing apparatus) as a single library. Information from a single read originates from the same cell. Such a method can be used for BCR heavy- and light-chain pair sequencing, which is an example of coupling two targets by concatenation (see, e.g., Example 6). The "1 read=1 cell" principle is useful for simultaneous studies of less than 10 genomic/transcriptomic targets of similar abundance.

Figure 5:
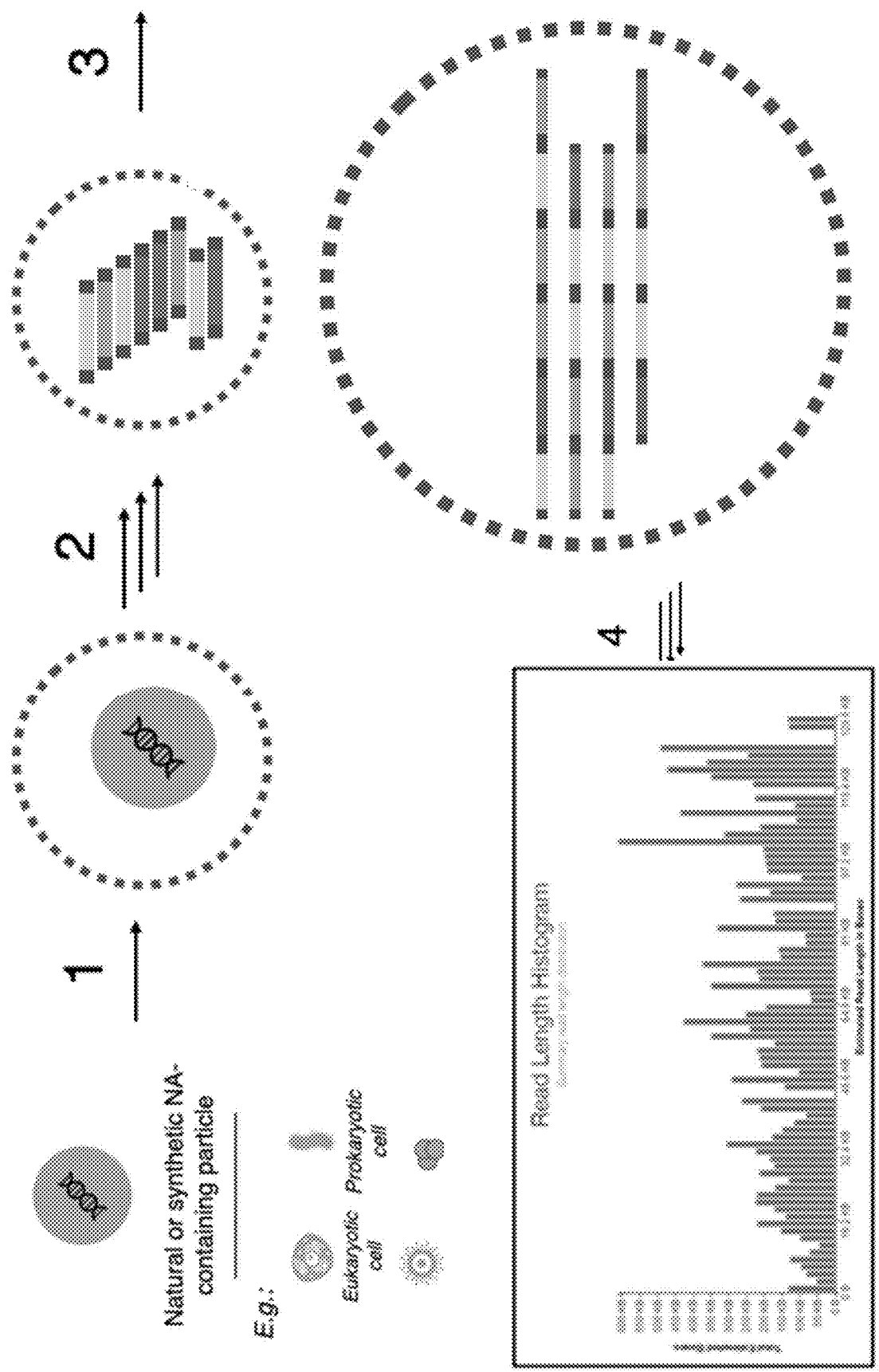
FIG. 5 depicts a microcapsule nucleic acid concatenation workflow that yields concatenated nucleic acids from a common source.

The "1 UMI set=1 cell" principle is an extension of the "1 read=1 cell" principle (see, e.g., Example 7). For the "1 UMI set=1 cell" principle, targets from a single cell can be tagged with a unique set of UMIs (i.e., 1 UMI per target). The unique set of UMIs often is composed of random sequences sampled from a pool of poly-N oligos (FIG. 5). Given a large enough pool of poly-N oligos, each sample of UMIs is essentially unique and is equivalent to a molecular "barcode." Next, the UMI-tagged targets can be amplified (e.g., by PCR) and then concatenated in microcapsules. Concatemer reads originating from the same cell share one or more UMIs, while information from one given read is from the same cell. The "1 UMI set=1 cell" principle can be useful for a number of targets in the thousands of targets range.

Droplet-based approaches have been demonstrated to address more than a million cells in a single experiment. Droplet-based approaches, however, are expensive and technically complex for the purpose of studying less than 1000, and especially less than 10, targets per cell. Droplet-based methods typically rely on the "1 barcode=1 cell" principle, with a notable exception of a few demonstrations of two target pairing by emulsion overlap-extension RT-PCR for BCR sequencing. Certain droplet-based methods rely on the delivery of cellular barcodes attached to beads (e.g., 10× Genomics' solution, inDrops, DropSeq). The production of such beads is technically challenging and expensive, and the coupling of cells with beads requires advanced microfluidic manipulation. Droplet-based approaches also typically rely on water-in-oil droplets, in which reagents cannot be fully removed, and for which multi-step processing is impossible without loss of compartmentalization. Due to this limitation, concatenation-based methodology described herein are not readily applied to droplets, and instead typically are carried out in core-shell microcapsules. Water-in-oil droplet-based approaches for single-cell sequencing rely on early barcoding and permit limited nucleic acid preprocessing before barcoding. Because multi-step processing is not possible in such compartments, only a limited number of preprocessing steps can be performed on nucleic acids from individual cells before the barcode is introduced. For example, widespread droplet-based single cell RNA sequencing (scR-NAseq) methods often rely on cell lysis (i.e., making RNA accessible) and barcoding by reverse transcription happening as one step in the same droplet. The breadth of applications is restrained, however, when nucleic acid preprocessing is not decoupled from the barcoding step. For example, harsh lysis necessary to make microbe nucleic acids accessible cannot be combined with enzymatic barcoding. Core-shell microcapsule-based multi-step approaches do not suffer from this limitation (see, e.g., Example 8).

Certain core-shell microcapsule concatemer methodology described herein is based in part on the "1 read=1 cell" and "1 UMI set=1 cell" principles, described herein, and benefit from at least the following advantages. Core-shell microcapsules benefit from the high-throughput nature of droplet microfluidics. Contrary to water-in-oil droplets, microcapsules enable true multi-step nucleic acid processing, including uncompromised lysis, nucleic acid amplification and concatenation, without loss of compartmentalization. The methodology is relatively simple, as it avoids the use of large numbers of wells or advanced microfluidic manipulations (e.g., cell and barcoding bead co-encapsulation). Cells often are encapsulated into microcapsules using a basic microfluidic water-in-oil droplet formation, followed by shell polymerization and emulsion breaking to transfer microcapsules into an aqueous solution. Once this is done, all steps generally are performed as a single-tube reaction on up to millions of microcapsules in parallel, with no split-and-pool steps and no steps required for re-encapsulation into droplets, for example. The core-shell microcapsule concatemer methodology described herein generally implements microcapsule-enabled multi-step processing of nucleic acids derived from individual cells, and long-read sequencing technologies enabling sufficient read lengths (up to megabases, with 10 thousand and 100 thousand consecutive nucleotides routinely sequence in a read).

FIG. 5, shown below, illustrates the "1 read=1 cell" principle. The schematic shows a 3-target case but larger numbers of targets can also be studied this way. DNA containing entities (e.g., eukaryotic cells, prokaryotic cells, viruses, liposomal vectors, extracellular vesicles, organelles (e.g., mitochondria, chloroplasts)) are encapsulated into microcapsules (1), followed by cell lysis and molecular biology reactions to obtain amplicons of DNA or RNA targets of interest. Next, amplicons are concatenated within microcapsules (3). The concatenated DNA is further prepared for Nanopore sequencing (4). Amplicons on the same concatemer, and therefore the same read, originate from the same cell.

The "1 read=1 cell" principle of core-shell microcapsule-based concatemer methodology described herein is applicable in particular to B-cell receptor (BCR) sequencing, as a non-limiting application (see, e.g., Example 6). BCR sequencing is relevant to antibody-based drug screening among other applications. BCR sequencing is not straightforward as it requires uncovering the sequencing of both the heavy-chain and light-chain subunits of the antibody, and performing this at the single-cell level to know which heavy- and light-chains pairs form a functional antibody. Microcapsules together with a long-read sequencing (LRS) readout enable the sequencing of BCR heavy- and light-chain pairs originating from the same cell. This sequencing is achieved by concatenating within the microcapsule heavy and light chain cDNA molecules originating from the same B cell. After concatenation, concatemers (joined single cDNA molecules) from individual microcapsules can be pooled together into bulk solution after microcapsule shell dissolution. Information from the same long read, and therefore the same concatemer, originates from the same cell. The workflow is detailed in FIG. 5 and FIG. 20 above.

The workflow described above and in FIG. 5 is generalizable to any two or more target DNA or RNA molecules that can be concatenated by ligation or Gibson assembly (e.g., about 10 target molecules). Multiple gene targets can be sequenced at the single-cell level using their concatenation within microcapsules. Long read sequencing can be utilized to sequence and identify concatemers generated in the same microcapsule and for one cell.

Figure 27A:
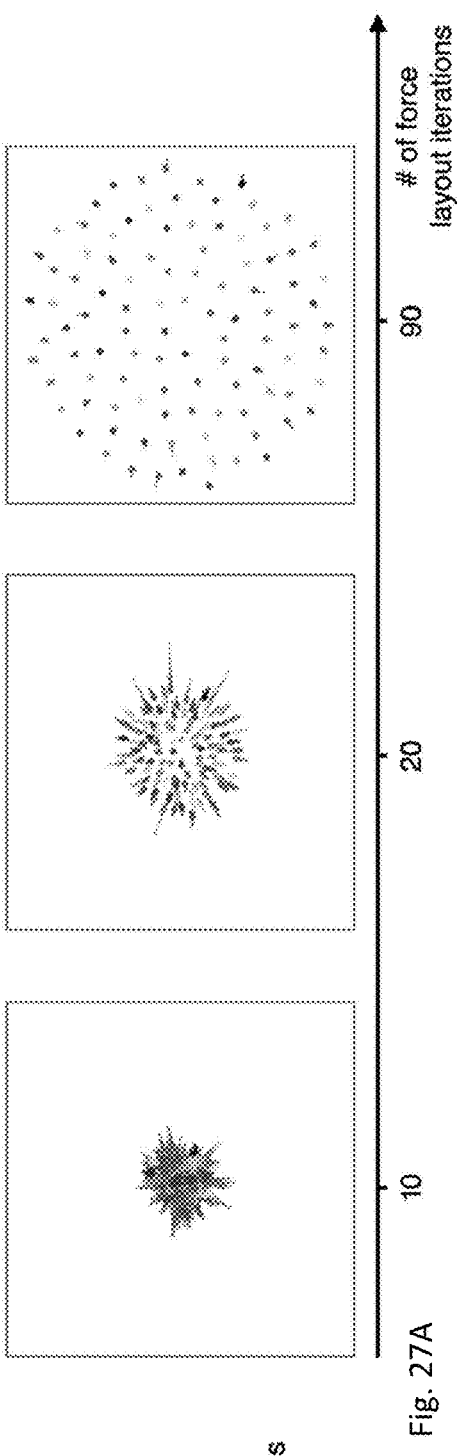
FIGS. 27A-27B provide anticipated results based on two in silico simulations of the workflow and the "1 UMI set=1 cell" principle.
Figure 27B:
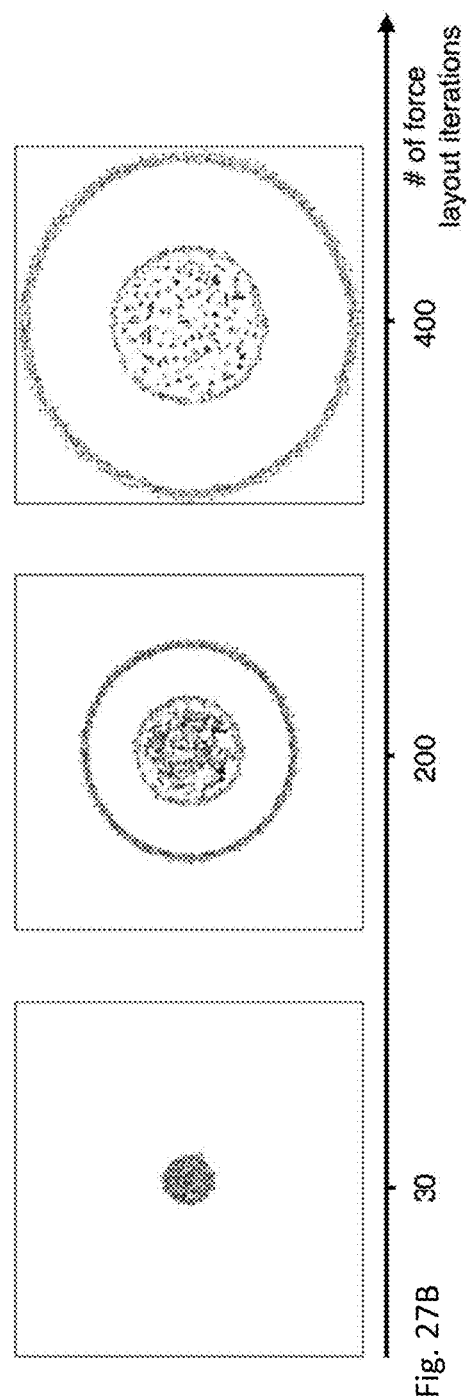

For the "1 UMI set=1 cell" principle, nucleic acids within individual microcapsules can be tagged with unique molecular identifiers (UMIs), e.g., by ligation. Next, UMI-tagged NAs can be amplified and concatenated within microcapsules. Then concatemers containing UMIs can be pooled in bulk solution, prepared for sequencing and sequenced using standard protocols. The resulting reads can be demultiplexed by shared UMI information within the long reads. FIG. 27A and FIG. 27B provided hereafter illustrate a specific example for demultiplexing long reads using the "1 UMI set=1 cell" principle.

Thus, in certain aspects, provided is a method for preparing a plurality of nucleic acids for sequencing, the method including: (a) generating a plurality of microcapsules comprising biological entities, where: the microcapsules are suspended in an aqueous environment; and each of the biological entities comprises at least one nucleic acid molecule; (b) after part (a), contacting intact microcapsules with releasing conditions that release nucleic acid from the biological entities within intact microcapsules; (c) after part (b), exposing the intact microcapsules to nucleic acid amplification conditions that generate amplicons corresponding to target portions of the nucleic acid released in the intact microcapsules; and (d) after part (c), exposing the intact microcapsules to concatenation conditions that join a plurality of the amplicons end to end within the intact microcapsules, thereby generating one or more concatemers within particular intact microcapsules. Amplicons generally are multiple copies of a portion of the encapsulated nucleic acid that sometimes include target portions.

In certain implementations, (i) each of the microcapsules include a shell surrounding a core, (ii) each of the microcapsules include a cross-linked, porous and semi-permeable shell surrounding a liquid or semi-liquid core; (iii) the microcapsule shell sometimes includes a polysaccharide and is glycosidase degradable; (iv) the shell permits primers, enzymes and assay reagents to pass through, and prevents the nucleic acids released from the biological entity escaping the microcapsule; or (v) a combination of two or more of (i), (ii), (iii) and (iv). Microcapsules generated in part (a) sometimes are microcapsules described herein that include a core surrounded by a shell, where: the shell is a hydrogel comprising a first polymer; the first polymer includes a polysaccharide modified with a conjugated cross-linking moiety and optionally modified with a conjugated hydrophilicity/hydrophobicity-modifying moiety; molecules of the cross-liking moiety of the first polymer are cross linked in the hydrogel; and the core comprises a second polymer comprising a polysaccharide that does not include the cross-linking moiety and does not include the hydrophilicity/hydrophobicity-modifying moiety of the first polymer.

In certain implementations, the plurality of microcapsules generated in part (a) include microcapsules containing no biological entity and microcapsules containing a biological entity. Of the microcapsules containing a biological entity, a majority of the microcapsules generally contain a single biological entity. Of total microcapsules in a population, sometimes about 1% to about 37% contain a single biological entity, and in certain instances about 10% to about 30% include a single biological entity. Of microcapsules in a population containing a biological entity, sometimes about 58% to about 99.5% of the microcapsules contain a single biological entity and in certain instances about 77% to about 95% of the microcapsules contain a single biological entity.

In certain instances, a method includes, after part (d), a part (e) that includes exposing the intact microcapsules to microcapsule degradation conditions that release the concatemers from the microcapsules. In certain instances, parts (b), (c) and (d) are performed in a single container, or parts (b), (c), (d) and (e) are performed in a single container. Sometimes, one or more of parts (b), (c), (d) and (e) sometimes are performed in different containers In certain implementations, a method includes sequencing the concatemers, or portion thereof, or processed product of concatemers or portion thereof. A sequencing device can be a component separate from a sequencing instrument that sequences the concatemers, or portion thereof or processed product of concatemers or portion thereof, or can be the sequencing instrument. In certain instances, a method includes placing the microcapsules or a portion thereof in a sequencing device and then releasing the concatemers from microcapsules in the sequencing device. In certain instances, a method includes releasing the concatemers from microcapsules and then placing the concatemers or a portion thereof, or processed product of concatemers or portion thereof, in a sequencing device. Processed products of concatemers can result from implementing part (c) and other steps. For example, concatemers released from microcapsules can be exposed to further amplification conditions, and optionally purification conditions implemented prior to and/or after implementing the further amplification conditions, prior to the resulting processed concatemers or portion thereof being placed in a sequencing device. A method sometimes includes contacting nucleic acid with library preparation conditions. Any suitable library preparation conditions can be utilized, including those that include contacting nucleic acid with an adapter under adapter incorporation conditions. An adapter sometimes includes a tether, a motor or a hairpin. In certain implementations, the sequencing generates reads greater than 50 base pairs in length, or reads greater than 100 base pairs in length, or reads greater than 500 base pairs in length, or reads greater than 2,000 base pairs in length, or reads greater than 3,000 base pairs in length, or reads greater than 4,000 base pairs in length, or reads greater than 5,000 base pairs in length. Each read generally corresponds to nucleic acid from a single biological entity.

Nucleic acid released from the biological entities in microcapsules can include RNA, and the RNA can be reverse transcribed, by reverse transcription conditions known in the art, into complementary DNA (cDNA). The resulting cDNA sometimes is amplified prior to part (c). In certain implementations, a method includes amplifying and/or reverse transcribing, after part (b) and prior to part (c), nucleic acid released from biological entities within the intact microcapsules. A method sometimes includes, prior to part (c), tagging nucleic acid released in part (b), or tagging nucleic acid amplified and/or reversed transcribed from nucleic acid released in part (b), with molecular index polynucleotides (MIPs) from a plurality of different MIPs, where the concatemers in one microcapsule include a set of MIPs different than the set of MIPs in other microcapsules. In certain instances, the amplification conditions of part (c) incorporate a molecular index polynucleotide (MIP) from a plurality of different MIPs into each amplicon, where the amplicons in one microcapsule include a set of MIPs that is different from the set of MIPs in other microcapsules.

A MIP sometimes is referred to as a unique molecular index (UMI). A MIP incorporated into a nucleic acid often is from a plurality of MIPs contacted with the intact microcapsules. MIPs in a plurality of MIPs often are random polynucleotides that sometimes are about 4 consecutive nucleotides to about 50 consecutive nucleotides in length. Tagging a nucleic acid with a MIP generally results in covalently attaching a MIP to a nucleic acid contained in an intact microcapsule. Nucleic acid within a microcapsule can be tagged with a MIP in certain implementations by exposing nucleic acid in the intact microcapsules to a plurality of MIPs under ligation, primer extension by DNA or RNA polymerases, Gibson assembly, and/or template-switching conditions, for example, that result in a MIP being linked to nucleic acid in the intact microcapsules. MIPs can be incorporated into individual cDNAs prior to part (c), or MIPs can be incorporated into amplicons in part (c). Tagging of n nucleic acid molecules per cell in m cells sometimes is performed using a pool of at least $10*n*m$ unique MIPs and sometimes is performed with a pool of at least $100*n*m$ unique MIPs. Sequencing can generate reads each containing one or more MIPs and part of the genome sequence, where individual reads sharing one or more MIPs are considered to originate from a single biological entity.

In certain implementations, biological entities in the plurality of microcapsules are from a group of about 10 million or fewer biological entities, about 100,000 or fewer biological entities, or about 1,000 or fewer biological entities. Each biological entity can contain about 300,000 transcripts (RNA molecules) or about 1,000 DNA molecules (e.g., representative of 48 chromosomes and tens or several hundreds of mitochondria DNA in the instance of human cells, for example). A biological entity sometimes is a nucleic acid-containing entity, non-limiting examples of which include a unicellular organism, multi-cellular organism, a cell from a multi-cellular organism, eukaryotic cell, prokaryotic cell, microorganism, alga, protozoon, bacterium, archaeon, fungus, plant, virus, organelle (e.g., mitochondria or chloroplast), liposomal vectors and extracellular vesicle. A biological entity sometimes is an antibody-producing cell (e.g., B-cell or hybridoma), and sometimes the target portions of the nucleic acid released in the intact microcapsules in part (c) are heavy chain variable (VH) domain and light chain variable (VL) domain target portions (see, e.g., Example 6). Sometimes a biological entity is a prokaryotic cell (e.g., a Gram-positive bacterium, a Gram-negative bacterium, an archaeon; Example 8), and sometimes is a yeast cell.

A method in certain instances includes, after part (b), exposing the intact microcapsules to wash conditions. Wash conditions can include contacting intact microcapsules with an aqueous solution that alters the internal composition of the microcapsules. Wash conditions sometimes include contacting the intact microcapsules with an aqueous solution that removes, or reduces, an amount of an inhibitor of the amplification conditions present in the microcapsules. In certain instances, the aqueous solution includes a buffer.

In certain implementations, a method includes, after part (b) and prior to part (c), purifying one or more of: (i) nucleic acid released into the intact microcapsules, (ii) nucleic acid amplified prior to part (c), and (iii) amplicons generated in part (c). In certain instances, the amplification conditions of part (c) or other amplification performed include contacting nucleic acid with a DNA polymerase, RNA polymerase or combination thereof.

In certain implementations, (i) a particle that includes a barcode nucleic acid is not contacted with a microcapsule as part of a concatenation method described herein; (ii) the biological entity and nucleic acid of the biological entity is not fixed to a solid support or in a matrix, and is not contacted with a barcode polynucleotide, as part of a concatenation method described herein; and (iii) nucleic acid is not exposed to precipitation conditions that generate precipitated nucleic acid as part of a concatenation method described herein; (iv) nucleic acid is not exposed to rehydration conditions that rehydrate precipitated nucleic acid as part of a concatenation method described herein; or (v) combination of two or more of (i), (ii), (iii) and (iv).

Microcapsule Barcoding Methods

Provided are methods in which encapsulated nucleic acid from a biological entity is amplified and then barcoded in intact microcapsules, and then released (see, e.g., Examples 9, 12). In methods described herein, after encapsulation into microcapsules, biological entities such as cells generally are lysed to release nucleic acids (NAs) into the core of the microcapsule. The volume of the core often is in the 0.25-250 pL range. Nucleic acids homogenously dissolve within this volume and barcode assembly reactions using split-and-pool can happen in a homogenous 0.25-250 pL solution, as opposed to on a surface, leading to enhanced barcoding efficiency.

In methods described herein, NAs within microcapsules generally are amplified prior to split-and-pool barcoding. After amplification, inefficiencies of the barcoding steps can be tolerated: losing some of NAs due to incomplete barcoding can be tolerated, because most NAs have copies after amplification. By contrast, when using other methods based on NAs being entrapped in a fixed cell scaffold, for example, there is no pre-amplification step because it is generally no possible due to the amplified material diffusing out of the cell scaffold.

The aforementioned advantages of the microcapsule-based methods provided herein enable more efficient whole genome single cell DNA sequencing. This advantage is especially evident for de novo genome assembly, where high coverage of the genome from a single-cell is a prerequisite. For single-cell RNA sequencing (scRNAseq), the preamplification of cDNA using methods provided herein can result in dramatically increased transcriptome capture rates, which is a performance indicator for scRNAseq protocols.

Methods described herein solve problems associated with other barcoding methods. One problem stems from the requirement of other methods to fix cells or nuclei prior to split-and-pool barcoding. Without being limited by theory, the homogenous reactions afforded by the present methods, that do not require fixing of cells or other biological entities prior to split-and-pool barcoding, are more efficient than those involving substrates being attached to a surface. Another problem is the inevitable inefficiency of enzymatic reactions that propagate through multiple barcoding steps in a multiplicative manner. For example, during barcoding-in-droplet approaches, as part of barcode synthesis hydrogel beads with DNA barcodes undergo a clean-up step to eliminate barcoding oligonucleotides with incomplete barcodes. Such incomplete oligonucleotides can constitute greater than 50% of the oligonucleotides on the beads. However, with direct split-and-pool barcoding of fixed cell or nuclei, incomplete barcode assembly remains on the target molecules. In practice, if considering mRNA sequencing as an example, a large fraction of unique transcripts never receives a full barcode and therefore they are lost in the final sequencing data. Losses due to split-and-pool barcode assembly inefficiencies can lead to failed studies and can prevent certain applications, such as single organism whole genome sequencing.

Figure 19:
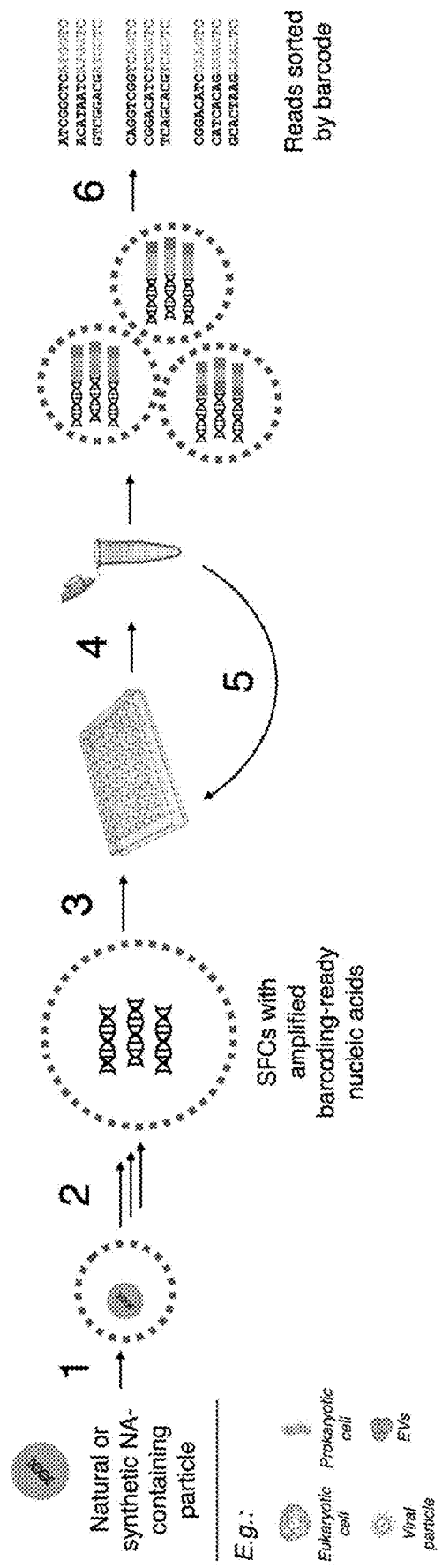
FIG. 19 and FIG. 20 illustrate workflows compatible with the technology herein.

FIG. 19 illustrates a particular implementation of methods described herein that permit split-and-pool barcoding of nucleic acids within microcapsules. Eukaryotic or prokaryotic cells are encapsulated (1) in semi-permeable droplets (microcapsules) such that on average there are one or fewer cells per microcapsule. Next, the cells are lysed and nucleic acid (DNA or RNA) undergo multi-step processing (2), such as one or more of, for example, a buffer exchange to remove undesired lysate components, fragmentation, A-tailing, adapter ligation, removal of undesired nucleic acid species by DNase or RNase treatment, reverse-transcription and template switching. Nucleic acid pre-processing generally includes amplification, which compensates for inefficiencies during subsequent split-and-pool barcode synthesis. For copy counting applications, such as RNAseq, target molecules often are tagged with UMIs prior to amplification. Steps 1 and 2 are generalizable to other nucleic-acid-containing particles, such as but not limited to viruses, organelles, extracellular vesicles (EVs), or liposomal vectors. The barcoding-ready amplified nucleic acids undergo split (3) and pool (4) barcode addition in microwell plates. At least two split-and-pool cycles generally are performed (5). After barcodes are incorporated, at least some nucleic acids within a given microcapsule have the same barcode, and that barcode is different than the barcodes attached to nucleic acid in at least some other microcapsules. Upon sequencing (6), the barcode sequence is used to sort reads by microcapsule of origin.

Barcode technologies as disclosed herein in some cases exhibit remarkably high efficiency of incorporation. For example, after three rounds of barcode addition, technologies disclosed herein exhibit a rate of unrecoverably lost target molecules of no more than 50%, 40%, 30%, 20%, 10%, or less than 10%. As seen in FIG. 7, in many cases the percentage of unrecoverably lost unique transcripts is in some cases no greater than 3.5%, 2%, 1.5%, 0.3%, 0.2%, or in many cases less than 0.1%.

Similarly, barcoding technologies disclosed herein facilitate nucleic acid sorting and in some cases substantial genome coverage for genomes sequenced from homogeneous or heterogeneous samples. Barcoding of partitioned nucleic acids in heterogeneous samples in some cases result in no more than 10% mixed sample read, such as 10, 9, 8, 7, 6, 5, 4, 3, or less than 3% mixed samples. In some cases substantial sorted genome coverage is accomplished on genomes extracted from partitioned cells in homogeneous or heterogeneous samples, such as at least 50%, 60%, 70%, 75% or up to about 80% of genome coverage.

Thus, in certain aspects, provided is a method for preparing a plurality of nucleic acids for sequencing (see, e.g., Examples 9 and 12), comprising: (a) generating a plurality of microcapsules comprising biological entities, where: the microcapsules are in an aqueous environment; the plurality of microcapsules include on average no more than one of the biological entities per microcapsule; and each of the biological entities carries at least one nucleic acid molecule; (b) after part (a), contacting intact microcapsules with releasing conditions that release nucleic acid from the biological entity within intact microcapsules; (c) after part (b), exposing the intact microcapsules to amplification conditions that generate amplicons of the nucleic acid in the intact microcapsules; (d) after part (c), (i) splitting the intact microcapsules into separate compartments, wherein each of the compartment contains more than one of the intact microcapsules, (ii) exposing the intact microcapsules in each compartment to barcode polynucleotide linkage conditions that attach a barcode polynucleotide species to nucleic acids in the microcapsule, wherein the barcode polynucleotide species attached to nucleic acids in each of the microcapsules in a particular compartment is different than the barcode polynucleotide species attached to nucleic acids in the microcapsules within other compartments; and (iii) pooling the intact microcapsules from the compartments; and (e) repeating (d) at least one time, thereby generating barcoded nucleic acid in the intact microcapsules. After pooling in part (iii), microcapsules often are exposed to washing conditions that remove unincorporated barcoding oligonucleotides, and sometimes the washing conditions inhibit further enzymatic addition of barcoding oligonucleotides (e.g., a washing buffer can include EDTA).

In certain implementations, (i) each of the microcapsules include a shell surrounding a core, (ii) each of the microcapsules include a cross-linked, porous and semi-permeable shell surrounding a liquid or semi-liquid core; (iii) the microcapsule shell sometimes includes a polysaccharide and is glycosidase degradable; (iv) the shell permits primers, enzymes and assay reagents to pass through, and prevents the nucleic acids released from the biological entity escaping the microcapsule; or (v) a combination of two or more of (i), (ii), (iii) and (iv). Microcapsules generated in part (a) sometimes are microcapsules described herein that include a core surrounded by a shell, where: the shell is a hydrogel comprising a first polymer; the first polymer includes a polysaccharide modified with a conjugated cross-linking moiety and optionally modified with a conjugated hydrophilicity/hydrophobicity-modifying moiety; molecules of the cross-liking moiety of the first polymer are cross-linked in the hydrogel; and the core comprises a second polymer comprising a polysaccharide that does not include the cross-linking moiety and does not include the hydrophilicity/hydrophobicity-modifying moiety of the first polymer.

In certain implementations, the plurality of microcapsules generated in part (a) include microcapsules containing no biological entity and microcapsules containing a biological entity. Of the microcapsules containing a biological entity, a majority of the microcapsules generally contain a single biological entity. Of total microcapsules in a population, sometimes about 1% to about 37% contain a single biological entity, and in certain instances about 10% to about 30% include a single biological entity. Of microcapsules in a population containing a biological entity, sometimes about 58% to about 99.5% of the microcapsules contain a single biological entity and in certain instances about 77% to about 95% of the microcapsules contain a single biological entity.

In certain instances, part (d) is repeated in part (e) a number of times until a predetermined number of the barcode polynucleotide species is attached to nucleic acid in the microcapsules. A predetermined number of barcode species added sometimes is about 1 to about 6 barcode species added to nucleic acid in the microcapsules, and sometimes is about 2 to about 5 barcode species added to nucleic acid in the microcapsules.

A method in certain implementations includes, after part (b), exposing the intact microcapsules to wash conditions. Wash conditions can include contacting intact microcapsules with an aqueous solution that alters the internal composition of the microcapsules. Wash conditions sometimes include contacting the intact microcapsules with an aqueous solution that removes, or reduces, an amount of an inhibitor of the amplification conditions present in the microcapsules. In certain instances, the aqueous solution includes a buffer.

A method in certain implementations includes, after part (b) but prior to part (c), tagging nucleic acid in intact microcapsules with a molecular index polynucleotide (MIP). See, e.g., Example 9. A MIP is about 4 consecutive nucleotides to about 50 consecutive nucleotides in length.

A method in certain instances includes, prior to part (c) or after part (c), exposing nucleic acid in intact microcapsules to fragmentation conditions. Fragmentation conditions sometimes result in nucleic acid fragments of about 100 base pairs (bp) to about 100 kilobase pairs (kbp) in length, or about 100 bp to about 10 kbp in length. Fragmentation conditions sometimes include exposing nucleic acid in intact microcapsules to a nuclease, a chemical agent that generates hydroxy radicals, and/or ultrasound.

In certain implementations, amplification conditions comprise contacting the intact microcapsules with DNA polymerase, RNA polymerase, or combination thereof. A method in certain instances includes, prior to part (c), exposing nucleic acid released in part (b) to reverse transcription conditions. Reverse transcription conditions often include contacting nucleic acid with reverse transcriptase.

In certain implementations, microcapsules in part (d) are distributed in wells of a plate. A plate sometimes includes 96 wells plate or 384 wells. Each well often contains a different barcode polynucleotide, and barcode polynucleotides in each well often are about 4 consecutive nucleotides to about 100 consecutive nucleotides in length, or about 6 consecutive nucleotides to about 18 consecutive nucleotides in length, or about 6 consecutive nucleotides to about 12 consecutive nucleotides in length. Each barcode polynucleotide sometimes includes a molecular identifier polynucleotide (MIP), and sometimes each barcode polynucleotide includes a polymerase chain reaction (PCR) adapter polynucleotide.

Barcode polynucleotide linkage conditions sometimes are the same as MIP linkage conditions, and barcode polynucleotide linkage conditions sometimes include exposing nucleic acid in the intact microcapsules to a plurality of barcode polynucleotides under ligation, primer extension by DNA or RNA polymerases, Gibson assembly, and/or template-switching conditions.

A method in certain implementations includes, after part (e), exposing intact microcapsules to microcapsule degradation conditions that release barcoded nucleic acid, thereby generating released barcoded nucleic acid. Microcapsule degradation conditions often include a glycosidase, as described herein.

In certain instances, a method includes exposing released barcoded nucleic acid to purification conditions, thereby generating purified barcoded nucleic acid. Purification conditions sometimes are or include phase extraction purification processes, including without limitation, magnetic bead purification (e.g., AMPure purification) or spin-column purification. If using magnetic bead purification, 0.4×, 0.5×, 0.6×, 0.7×, 0.8×, 0.9×, or 1× AMPure XP bead purification may be selected, for example. Purification conditions sometimes are or include chemical purification processes, including without limitation, ethanol precipitation and/or phenol-chloroform extraction, for example. A method in certain implementations includes contacting nucleic acid with library preparation conditions. Library preparation conditions sometimes include contacting nucleic acid with an adapter under adapter incorporation conditions. A method in certain instances includes sequencing the released barcoded nucleic acid and/or the purified barcoded nucleic acid.

In certain instances, in part (d), the nucleic acid encapsulated by the microcapsules is not fixed. The nucleic acid often is not fixed to a solid support, often is not fixed to the microcapsule; and often is not fixed to any other matrix. In certain implementations fixed biological entities (e.g., cells fixed with cross-linking fixatives such as formaldehyde or coagulants such as methanol and ethanol) can be encapsulated in microcapsules, rehydrated (e.g., applicable to MeOH fixation) or have the cross-linking reversed (e.g., applicable to formaldehyde fixation), lysed and then nucleic acid that is no longer fixed can be processed according to methods described herein.

Figure 6:
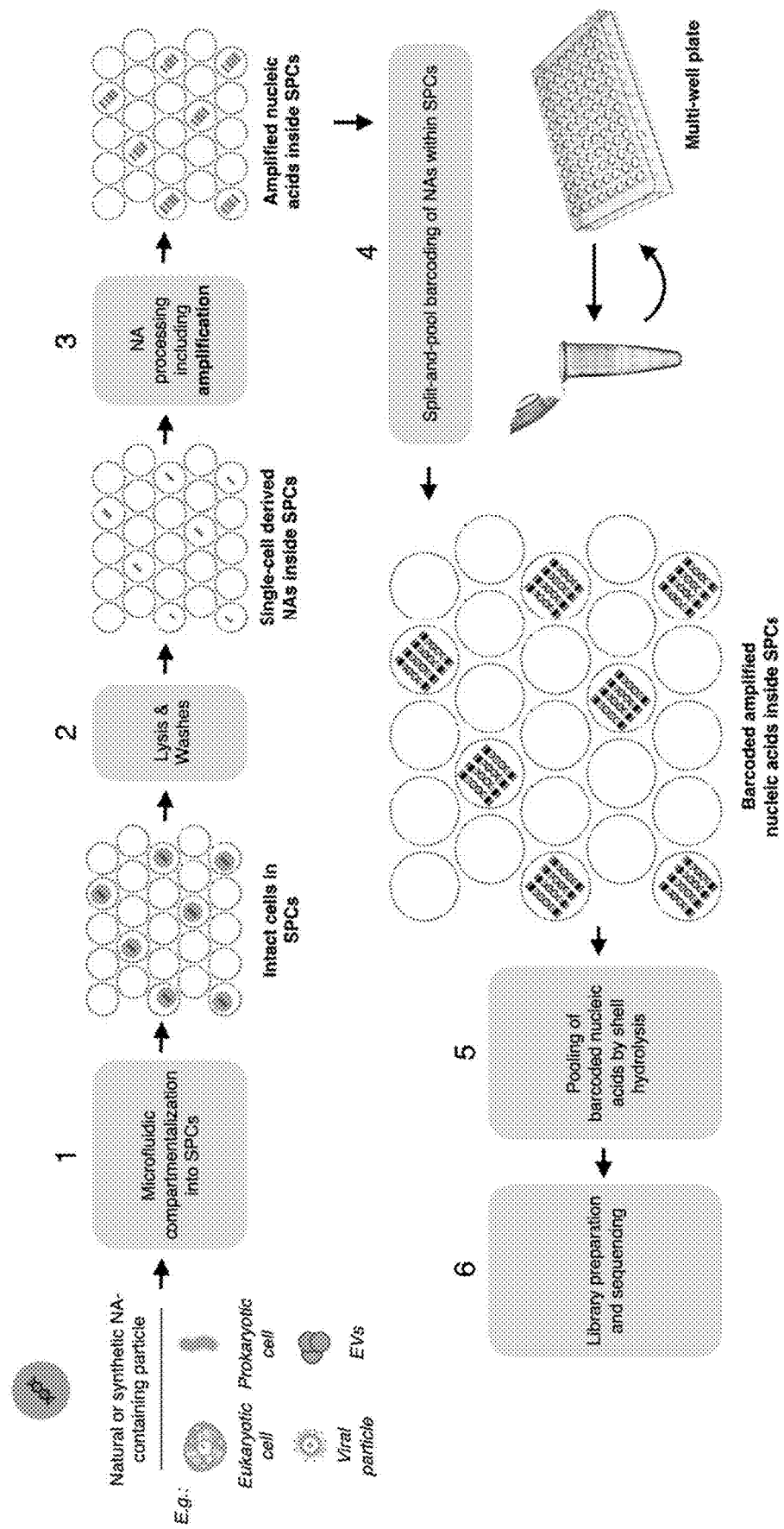
FIG. 6 shows a split-pool nucleic acid barcoding workflow ending in release of barcoded nucleic acids for bulk sequencing.

FIG. 6 illustrates an example of split-and-pool barcoding methodology applicable to nucleic acid within microcapsules. Biological entities, such as eukaryotic or prokaryotic cells, are encapsulated in semi-permeable compartments (i.e., microcapsules) such that the majority of microcapsules contain one or zero cells (#1). Next, the cells are lysed (#2) and nucleic acid (DNA or RNA) undergo multi-step processing, such as buffer exchange to remove undesired lysate components, fragmentation, A-tailing, adapter ligation, removal of undesired nucleic acid species by DNase or RNase treatment, reverse-transcription, and template switching. A central nucleic acid processing step prior to barcoding is amplification (#3), which compensates for inefficiencies during subsequent split-and-pool barcode synthesis. For copy counting applications, such as RNAseq, target molecules are tagged with unique molecular identifiers (UMIs) prior to amplification. Steps 1 and 2 are generalizable to other nucleic acid-containing particles, such as viruses, organelles, extracellular vesicles (EVs), or liposomal vectors, for example. The barcoding-ready amplified nucleic acids undergo split-and-pool barcode addition in microwell plates (#4). After barcoding, all nucleic acids within a given microcapsule have the same barcode, the barcode attached to nucleic acid in one microcapsule is different than the barcode attached to nucleic acid in other microcapsules. The barcoded material is pooled by enzymatic microcapsule shell hydrolysis (#5) before continuing with further sequencing library preparation (#6).

As addressed above, a central step for the methodology illustrated in FIG. 6 is amplification of nucleic acid within microcapsules prior to split-and-pool barcoding. Without amplification, each molecule that fails to have the full barcode assembled is unrecoverably lost. FIG. 7 illustrates how the percentage of unrecoverably lost molecules in a 3-step barcode assembly depends on the efficiency of barcode addition, and how amplification mitigates the loss.

FIG. 7 shows the percentage of unrecoverably lost unique transcripts after 3 rounds of barcode extension. Percentages below 5% are highlighted in a darker shade of gray. The first row ("0") represents the scenario where transcripts are not amplified prior to barcoding. Given a relatively high efficiency of 95% for each barcoding step, without amplification prior to barcoding ~86% of transcripts have the full barcode but 14% are lost (top-right corner of the table). If the efficiency of each barcoding step is 50%, only 12.5% of transcripts have the full barcode, and 87.5% of unique transcripts are lost. Amplification significantly mitigates unrecoverable loss of unique transcripts. If a given unique transcript is amplified prior to barcoding, some (or even the majority) of its copies can be lost due to incomplete barcoding but as long as at least one copy has the full barcode, the unique transcript is not lost. For example, with a relatively low 30% efficiency of each barcoding step and 7 PCR pre-amplification cycles, the percentage of unrecoverably lost unique transcripts is 3%, while without amplification it would be 97.3%.

Microcapsule split-and-pool barcoding can be used for eukaryotic cell single-cell RNAseq (scRNAseq; Example 9) or microbial cell scDNAseq in certain applications (see, e.g., Example 12). In the case of scRNAseq, UMI-tagging prior to amplification is required to obtain quantitative gene expression data, and amplification is performed using PCR. A specific workflow for scRNAseq is illustrated in FIG. 8A and a specific workflow for scDNAseq is illustrated in FIG. 8B. For the microbial scDNAseq workflow illustrated in FIG. 8B, no UMI-tagging is performed and multiple displacement amplification (MDA) is used for DNA amplification.

FIGS. 8A and 8B illustrate a comparison of specific microcapsule split-and-pool barcoding workflows for eukaryotic cell single-cell RNAseq (scRNAseq) (FIG. 8A) and for microbial cell single-cell DNAseq (scDNAseq) (FIG. 8B). FIG. 8A shows nucleic acid modified by UMIs prior to amplification, which is a requirement for quantitative scRNAseq. UMIs are introduced during the reverse transcription (RT) step (#1). RT can be performed as a single-tube reaction (no barcoding). Alternatively, during RT, in addition to the UMI, the first cellular barcode can be introduced, in which case RT is performed with microcapsules split into the wells of a multi-well plate. The resulting UMI-tagged cDNA is then amplified by PCR (#2), and the cellular barcode is assembled on the transcript by split-and-pool barcoding (#3). An essential step of further library preparation (#4) for sequencing (#5) is the enrichment of fully assembled barcodes by PCR with one of the primers targeting a primer-annealing site only present on molecules that successfully are modified by the last barcode. FIG. 8B illustrates that in the case of microbial DNA sequencing, UMIs are not used, and whole cellular DNA is amplified by multiple displacement amplification (MDA) (#1), resulting in a hyper-branched product that is fragmented and/or de-branched (#2) prior to split-and-pool barcoding (#3). Further steps (#4 and #5) are analogous to steps shown in FIG. 8A.

Figures 9A, 9B:
FIG. 9A shows a sequencing library consistent with the disclosure herein. Figure discloses SEQ ID NOS 31-32, respectively, in order of appearance.
FIG. 9B shows a sequencing library consistent with the disclosure herein. Figure discloses SEQ ID NOS 33 and 32, respectively, in order of appearance.

FIGS. 9A and 9B illustrate examples of final Illumina sequencing library structures, obtained after microcapsule split-and-pool barcoding of eukaryotic cell whole transcriptomes (FIG. 9A, see e.g., Example 9) and MDA-amplified whole cellular DNA (FIG. 9B, see, e.g., Example 12). "SPASp5" refers to Illumina sequencing primer annealing site at the p5 end and "SPASp7" refers to Illumina sequencing primer annealing site at the p7 end. The p5, p7, SPASp7, and SPASp5 sequences are based on the Illumina TruSeq library design. W, X, Y, and Z are for cellular barcodes introduced during the $1^{st}$, $2^{nd}$, $3^{rd}$ and $4^{th}$ round of split-and-pool, respectively. FIG. 9A illustrates, as in the case of mRNA barcoding requiring UMI-tagging prior to amplification, a PCR adapter is introduced between the UMI and the cellular barcode. To avoid wasting sequencing cycles on the adapter sequence, the sequence between the cellular barcode and the UMI is used as SPASp7 (which itself is not sequenced during an Illumina instrument run). The Index 1 read is set to be 20 cycles and reveals the cellular barcode parts X, Y, Z. If a cellular barcode (W) is also introduced during RT, it is revealed by Read 2 together with the UMI. The transcript sequencing is revealed by Read 1. FIG. 9B illustrates, as in the case of MDA-amplified whole cellular DNA sequencing, UMI-tagging is not performed, and Read 2 is used to reveal the full cellular barcode (parts W, X, Y, Z).

Figure 10:
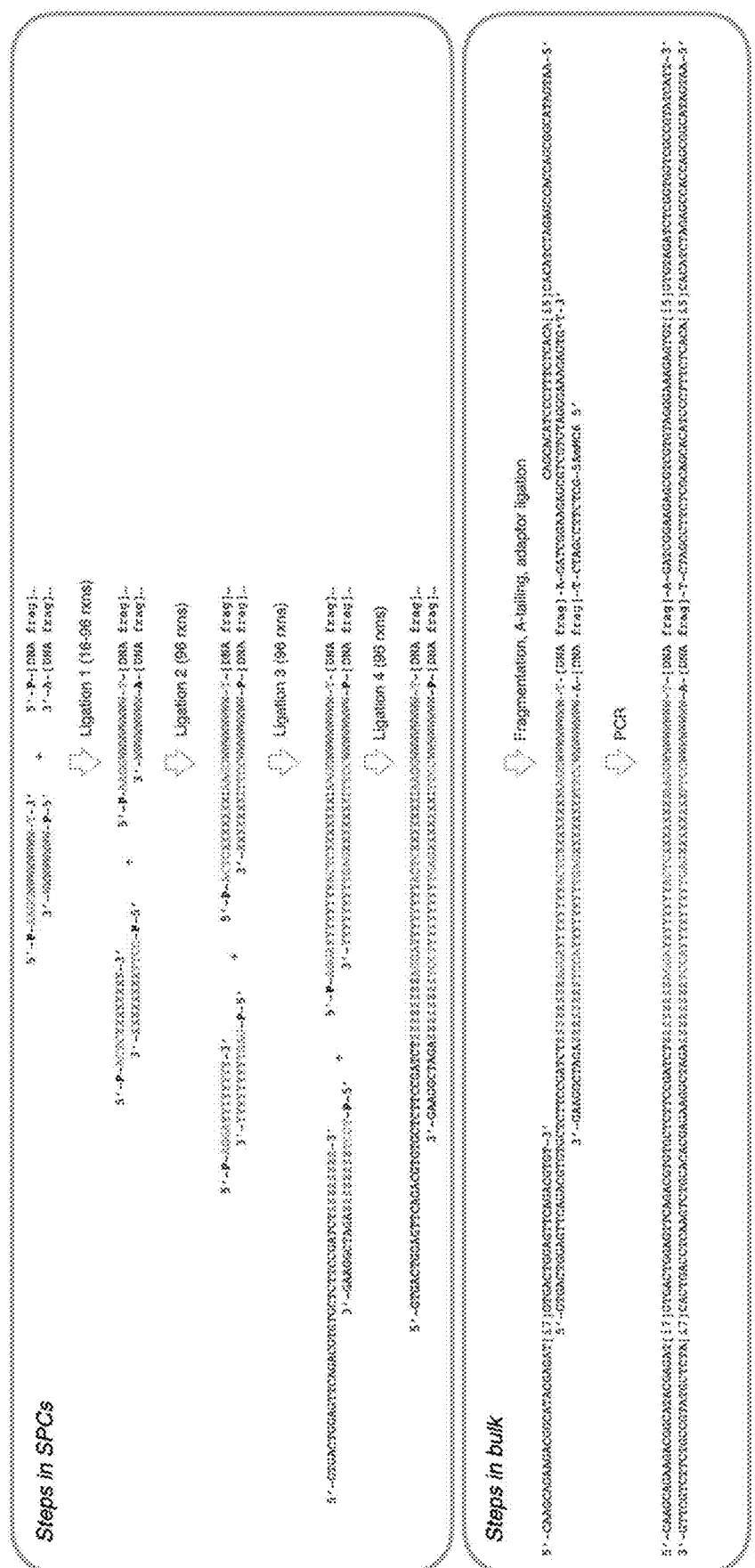
FIG. 10 shows a library assembly for single-cell DNA sequencing, focusing on steps from A-tailed amplified DNA fragment barcoding in microcapsules to barcoded material release to final library construction as a bulk reaction. Figure discloses SEQ ID NOS 34-36, 38-41, 38, 42-44, 31, 45-47, respectively, in order of appearance.

FIG. 10 shows a schematic for oligonucleotide sequencing detailing the assembly of barcodes when performing cellular DNA amplification by MDA followed by split-and-pool barcoding within microcapsules. Post-barcoding PCR is performed to enrich DNA fragments that have the last barcode (Z) successfully added, and to introduce adapter for sequencing on Illumina instruments.

Figure 11:
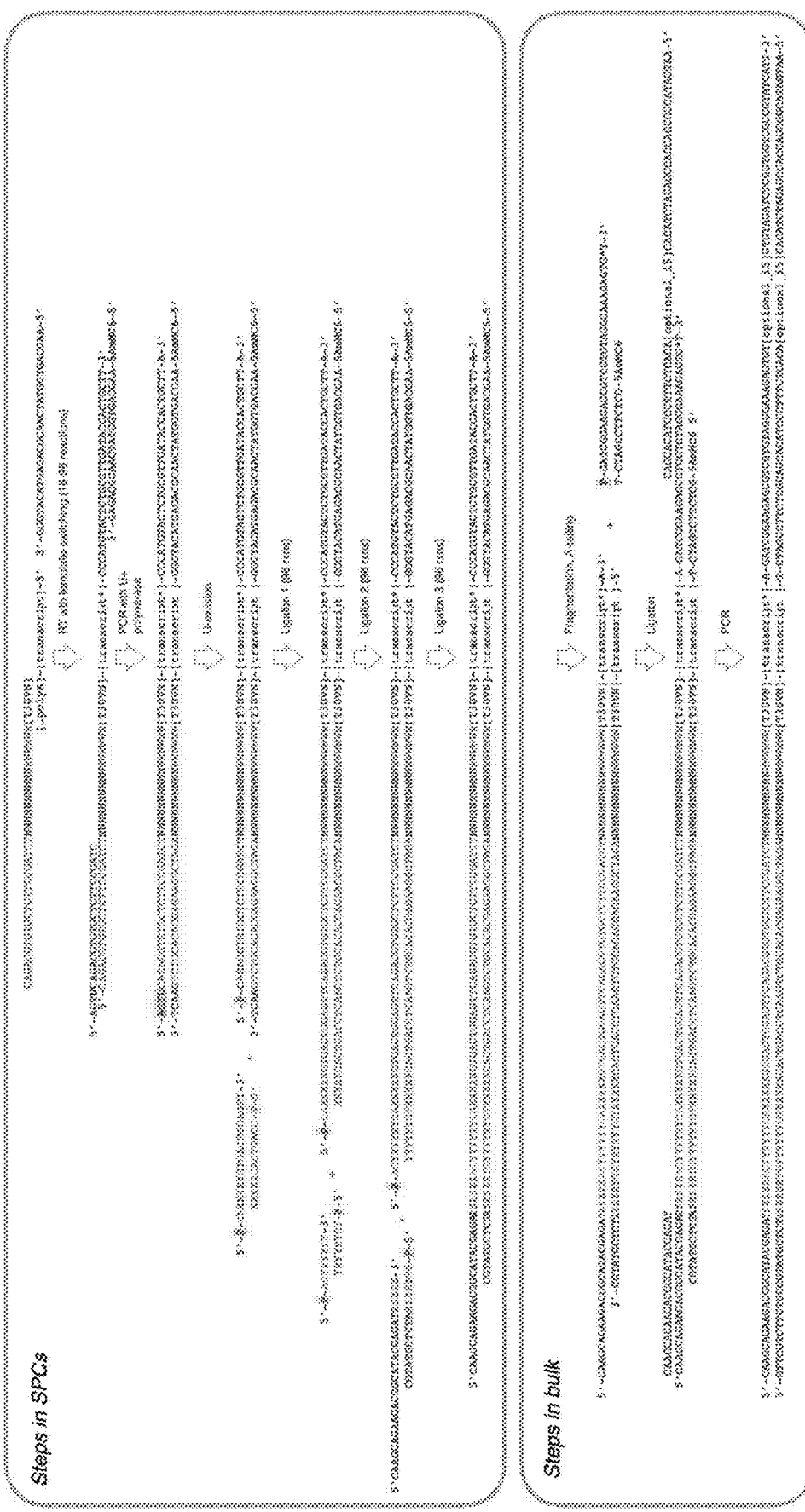
FIG. 11 shows a library assembly for single-cell sequencing of eukaryotic mRNA, including a series of steps involved in library preparation, including RT, PCR with U+polymerase, U excision, and barcode Ligation (x3) performed in microcapsules, followed by release of the reaction products and fragmentation, A-tailing, ligation and PCR performed on bulk reaction products. Figure discloses SEQ ID NOS 48-50, 48, 51-58, 54-56, 59, 54, 60, 56, 61-62, 54, 63-64, 56, 33, 54, 65, 56, 33, 66-67, 44, 69-70, 33, 71-72, 44, 33, 32, and 73-74, respectively, in order of appearance.

FIG. 11 shows a schematic for oligonucleotide sequencing detailing the assembly of barcodes when performing cDNA amplification followed by split-and-pool barcoding within microcapsules. The adapter for pre-barcoding PCR is introduced during reverse transcription upstream of the UMI. Post-barcoding PCR is performed to enrich DNA fragments that have the last barcode (Z) successfully added, and to introduce adapter for sequencing on Illumina instruments. The workflow detailed here is for 3'-biased scRNAseq. For 5'-biased scRNAseq, the assembly is analogous, except that the PCR1 adapter, UMI, and the optional barcode W are introduced with the TSO, not with the RT primer. Barcodes Z and X, are 5-mer, whereas barcodes Y and W are 6-mers (FIG. 11). Including the 2-nucleotide linkers between barcodes, the combined barcode ZYX is 20 nt long, which is the longest index read allowed by all Illumina sequencing platforms. Exploiting the index read to reveal the barcode structure enables more cycle-efficient sequencing, as sequencing cycles are not wasted on the adaptor sequence between barcode X and W (FIG. 9B). The 5-mers (barcodes Z and X) are selected to satisfy the following criteria: i) 40%<=% GC<=60%; ii) no palindromic barcodes, i.e. sequences that are the reverse complement of themselves; iii) minimum pairwise hamming distance of 2 between any pair of barcodes X (or Z). The 6-mers (barcodes Y and W) are selected to satisfy the following criteria: i) % GC=50%; ii) no palindromic barcodes, i.e. sequences that are the reverse complement of themselves; iii) minimum pairwise hamming distance of 2 between any pair of barcodes Y (or W); iv) for barcode Y, the melting temperature (Tm) close or higher to that of barcode "CGGTTA", which is a low-Tm barcode confirmed to be suitable for barcode applications in a small sample barcode sample. The specific barcode sequences used in Example 9 are the following. Barcode W:

```
AGTGTG, ATGCAC, ATACGC, CGATCA, GCGATA, ATTGCC,

GTTTGC, ATGCTG, CACGTA, TCGATG, CGACAT, TGTCGT, TCAGCT, CGCATT,

GCAGAT, TGATGC.

Barcode X:
CCATA, AGATC, TTCGT, TGGTA, ATCTG, TCAAC,

ATGGC, CTGAT, AGGAG, GGAGT, GAAAC, CAGTA, GTTAG, ACTAG, AAGCA, CTACT,

AGACT, GAAGG, GCTTC, TGACG, CTATC, GTGCA, TACGG, AAGAC, ACATG, CAACA,

CTCAG, TAGTC, ACTCA, AGCGT, GGCTA, GATCG, CAAGT, ACCTA, TCTCG, CAATG,

CGTTA, TCCCA, CATGA, TTTCC, TTGGG, AGTAC, GCGTT, GACCA, ACAGT, CAGAG,

TGGAT, AACTC, TTGAC, TAACC, CTGTG, CCAAT, GGTCA, GCTCT, AGTCG, TCGAG,

AACGA, TGTTC, ACACC, CCTAA, GACTT, GAACT, TGTGA, ATGCT, CACAA, CTAGG,

CATTC, TCACT, CGGTT, TAGCT, CGTCT, TCCTG, GTGTC, CGAAC, GCAGA, GTCGA,

TCGGT, TTCTC, TCCAT, GGCAT, ATACG, GTGGT, TTCCG, AACAG, GCCAA, AGAGG,

CACCT, GAGTG, CCTTG, GATGT, AAGGG, CTTCA, GTATG, GAGAT, TGCAG, AATCC.

Barcode Y:
AGTGTG, ATGCAC, ATACGC, TCGGAA, CGATCA, GCCAAT, GCGATA,

GCAAGA, ATTGCC, CCACAA, GTTTGC, CACAAC, AAGCCA, ATGCTG, AACACC,

CCAACA, CACGTA, TCGATG, CGACAT, TGTCGT, CGCTAA, TCAGCT, CGCATT,

GCAGAT, TGATGC, ATCAGC, GCATTG, AAGGCT, ACGGTT, CGTCAA, TGCTGA,

TCGAAC, AGGTGT, ATCGCT, CAACCA, TCAACG, TCGACA, GGTTGT, GCTTCA,

TAACCG, ACCCAT, TGCAAG, TGTGGA, TTGCAG, ACCGTA, TTGCTC, AACGGT,

CATTGC, AACGAC, ACGACT, TCGTTC, AAGTGC, TTGGCA, TGCGTA, TTCCCA,

CGATGT, GAAGCT, TCTCGA, CATTCG, AGCAGA, TCGTGT, TGTTCG, ACGTAC,

AAAGCG, ATCCGA, CTGTGT, TACGTC, ATTCGG, TTGTGC, TTGTCG, ACTTCG, TCGCTT,

TCCGTT, ACAGCA, AGCATC, ACAGTG, AGCGAA, GCTGAA, GTCGAT, GCAACT,

AGGCAA, ATCACG, ACTGCT, CAGCTT, AGCTCA, ACGATC, AAGCTC, TGACAC,

AGGCTT, TGCACA, TAGCGT, ACCACA, ACTTGC, TCTGCA, CATGCA, ACTCGT.

Barcode Z:
CCATA, AGATC, TTCGT, TGGTA, TCAAC, ATGGC, CTGAT, AGGAG, GGAGT, GAAAC,
```

-continued

```
CAGTA, GTTAG, ACTAG, AAGCA, CTACT, AGACT, GAAGG, GCTTC, TGACG, CTATC,

GTGCA, TACGG, AAGAC, ACATG, CAACA, TAGTC, ACTCA, AGCGT, GGCTA, GATCG,

CAAGT, ACCTA, TCTCG, CAATG, CGTTA, TCCCA, CATGA, TTTCC, TTGGG, AGTAC,

GCGTT, GACCA, ACAGT, CAGAG, TGGAT, AACTC, TTGAC, TAACC, CTGTG, CCAAT,

GGTCA, GCTCT, AGTCG, TCGAG, AACGA, TACAC, TGTTC, ACACC, CCTAA, GACTT,

GAACT, TGTGA, ATGCT, CACAA, CTAGG, CATTC, TCACT, CGGTT, TAGCT, CGTCT,

TCCTG, GTGTC, CGAAC, GCAGA, GTCGA, TCGGT, TTCTC, CTGGA, TCCAT, ATACG,

GTGGT, TTCCG, AACAG, GCCAA, AGAGG, CACCT, GAGTG, CCTTG, GTCAC, GATGT,

AAGGG, CTTCA, GTATG, GAGAT, TGCAG, AATCC.
```

Droplet Barcoding Methods

Provided are methods in which microcapsules containing encapsulated nucleic acid from a biological entity are combined in droplets with particles to which barcode polynucleotides are attached, and barcoding nucleic acid from the microcapsules in the droplets (see, e.g., Example 10).

An advantage of core-shell microcapsule-based methods described herein is the ability to utilize a wide variety of biological entity and biological molecule processing steps, some of which are incompatible with other types of methods. For example, the possibility of using "no-compromise" lysis conditions is an advantage over droplet-based methods. In droplet-based methods, generally mild lysis conditions are used as lysis and enzymatic reactions occur together, and workarounds involve complex droplet merging techniques that are not readily adaptable. In the case of split-and-pool barcoding protocols, cells serve as compartments and need to be permeabilized prior to barcoding. Different permeabilization approaches have been described for different cell types, and it is not clear whether a universal approach is possible. Microcapsules enable the use of virtually any chemical cell lysis approach, including proteases, high concentrations of detergents such as SDS and alkaline pH. Heat and/or sonication may be utilized (microcapsules survive thermal cycling during PCR). Lysis can be performed in one step, or as a series of independent steps. Also, the ability to amplify nucleic acid released from a biological entity prior to barcoding significantly reduces the effects of target sequence loss that deleteriously affect other methods.

Figure 13A:
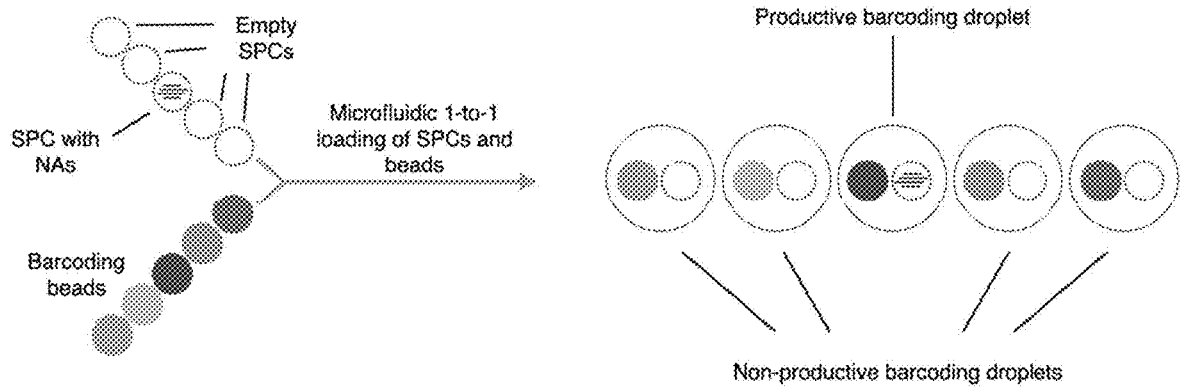
FIG. 13A depicts delivery of barcodes to microcapsules having a low analyte loading rate (of 1 in 5) via a 1-to-1 loading of microcapsules with barcoding beads followed by introduction of the barcodes into microcapsule interiors.
Figure 13B:
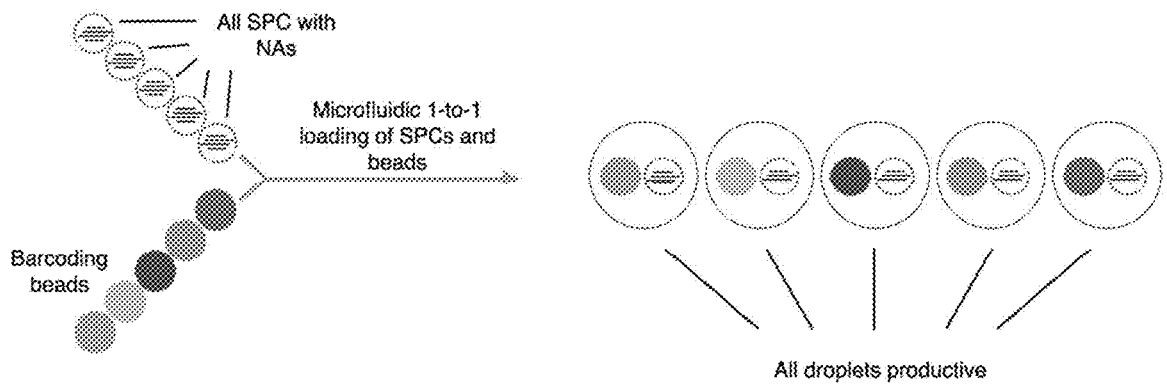
FIG. 13B depicts delivery of barcodes to pre-sorted microcapsules having a high analyte loading rate (of 5 in 5) via a 1-to-1 loading of microcapsules with barcoding beads followed by introduction of the barcodes into microcapsule interiors.

Another advantage of core-shell microcapsule-based methods described herein over conventional cell barcoding-in-droplets is that microcapsule loading into droplets can be synchronized with droplet generation, such that every droplet is loaded with a microcapsule. Microcapsule and barcoding particle loading can be synchronized such that every droplet contains one microcapsule and one barcoding bead (FIG. 13A-FIG. 13B). While a fraction of the microcapsules contain nucleic acid (FIG. 13A), the empty-microcapsule problem can be overcome by sorting-out only nucleic acid-containing microcapsules (i.e., productive microcapsules). Microcapsules are flow cytometry-compatible, for example, and productive microcapsules can be fluorescently labeled with DNA-staining dyes, which allows flow cytometry enrichment of productive microcapsules. When using a microcapsule suspension depleted of empty non-productive microcapsules for barcoding-in-droplets, all or most of the droplets are productive (FIG. 13B). Considering that a typical regime for cell barcoding in droplets results in 90% of droplets without a cell, the pre-sorting of core-shell microcapsules enables a 10-fold higher barcoding throughput for a given duration and amount of reagents. As empty non-productive microcapsules also can lead to different types of background (e.g., primer-derived by-products; in scRNAseq applications, by-products derived from ambient RNA present in all droplets), background signals that can confound sequencing analyses also can be reduced 10-fold by depleting empty non-productive microcapsules.

FIG. 13A and FIG. 13B illustrate an enhancement over Poisson cell barcoding with depletion of empty microcapsules. FIG. 13A illustrates barcoding of non-sorted microcapsules. Microcapsules behave similarly to hydrogel beads in microfluidic channels and loading of microcapsules into droplets can be synchronized with droplet-generation speed. As a result, 1-to-1 loading of barcoding particles and microcapsules can be achieved. However, encapsulation of cells into microcapsules is a random process governed by the Poisson distribution. A typical approach is to ensure less than 5% of non-empty microcapsules have two or more cells (in other words, P(X>1)/P(X>0) is less than or equal to 5%; where X is the number of cells in a microcapsule). When working under this approach, about 90% of the microcapsules typically are empty, and therefore 90% of the barcoding droplets are non-productive. FIG. 13B illustrates barcoding of sorted microcapsules.

Figure 14A:
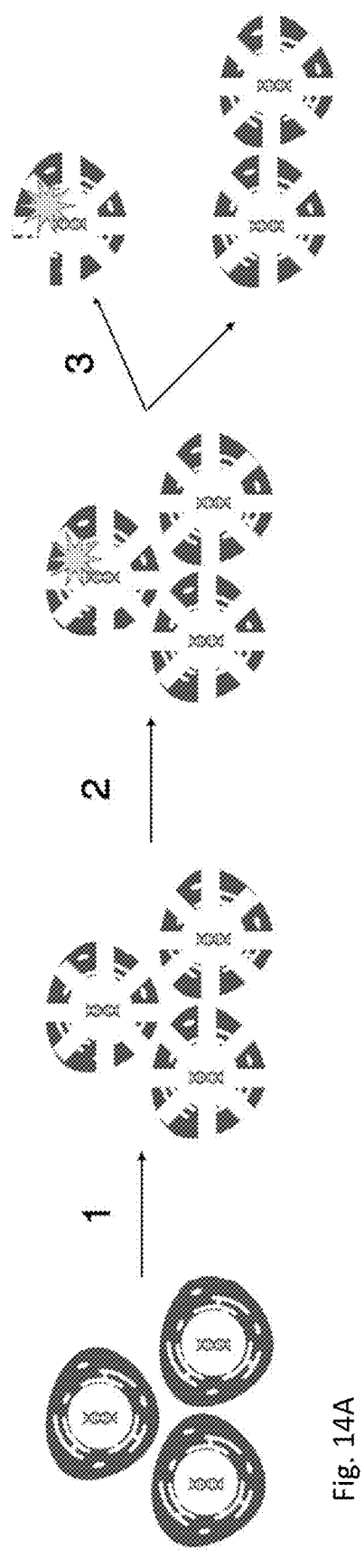
FIG. 14A depicts cell lysis fixation and permeabilization for nucleic acid labeling.
Figure 14B:
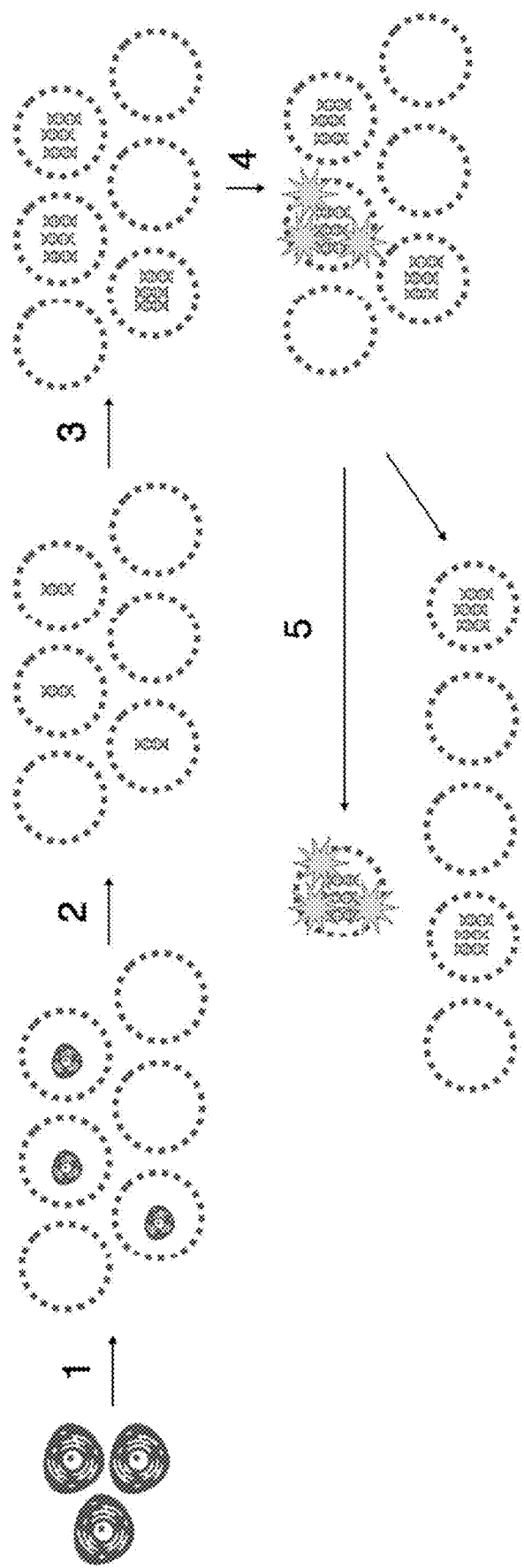
FIG. 14B depicts cell lysis and nucleic acid labeling of cells partitioned into microcapsules in which cell lysates are subjected to nucleic acid amplification prior to labeling, and for which the microcapsules prevent intermingling of amplified nucleic acids, such that the number of target nucleic acids, and target-bound signal, are amplified in the microcapsule.

FIGS. 14A and 14B compare non-limiting examples of methods that include pre-sorting based on the presence of target nucleic acid sequences. For comparison, FIG. 14A illustrates a strategy using cell fixation and permeabilization without utilizing microcapsules. Cells are fixed and permeabilized (1), followed by annealing of fluorescent probes complementary to a target sequence of interest and washing of unannealed probe (2). Next, fluorescent cells are enriched for using flow cytometry. FIG. 14B illustrates a microcapsule-based method. Cells are encapsulated into microcapsules (1), followed by cell lysis (2), and an optional amplification of the genetic material (3), which concomitantly translates to fluorescent signal amplification after probe annealing in the next step. Next, probes against target sequences of interest are annealed (4) and fluorescent microcapsules are selected for using flow cytometry.

Core-shell microcapsule-based barcoding methods are particularly useful for single-cell microbial genome sequencing. While droplet-based high-throughput single-cell RNA and DNA sequencing can be applied to animal cells, they generally have not been applied to single-microbe DNA or RNA sequencing. A technical limitation is the need to apply harsh lysis conditions (protease, detergents, alkaline pH treatment), which prevent subsequent molecular biology steps in the same droplet. While a few droplet-based single-microbe sequencing methods have been demonstrated, they rely on technically challenging advanced droplet manipulation. In such manipulations reagents are added by droplet merging, which inherently limits the choice of lysis strategies that can be used. Alternatively, an approach using agarose hydrogels has also been shown and is used in single-microbe sequencing methods. Microbes are embedded into agarose hydrogels, which allows multi-step processing by replacing the buffer hydrogels are in. However, when using hydrogel beads more than half of the genomic material from single bacterial cells is lost, most likely due to bacteria positioning close to the edge of the hydrogel during its formation. Also, the workflow generally relies on dispensing single-hydrogel into multi-well plates, which requires special cell sorting instrumentation, is more complex and is low-throughput.

Core-shell microcapsule-based methods enable efficient retention of nucleic acids from single-microbes within microcapsules, for example.

Thus, provided in certain aspects is a method for preparing a plurality of nucleic acids for sequencing, comprising: (a) generating a plurality of microcapsules comprising biological entities, where: the microcapsules are in an aqueous environment; the plurality of microcapsules comprises on average no more than one of the biological entities per microcapsule; and each of the biological entities carries at least one nucleic acid molecule; (b) after part (a), contacting intact microcapsules with releasing conditions that release nucleic acid from the biological entity within intact microcapsules; (c) after part (b), exposing the intact microcapsules to nucleic acid processing conditions that generate processed nucleic acid in the intact microcapsules; (d) after part (c), combining the intact microcapsules with microparticles comprising barcode polynucleotide species under droplet forming conditions that combine an individual intact microcapsule with a microparticle comprising a barcode polynucleotide species in a droplet, wherein the barcode polynucleotide species in each droplet is different than the barcode polynucleotide species in the other droplets; (e) optionally exposing, after or during part (d), the droplets to microcapsule degradation conditions that release the nucleic acid contained within the microcapsules into the interior of the droplets; and (f) exposing, after part (d) or after part (e), the droplets to barcode polynucleotide incorporation conditions that link barcode polynucleotides to nucleic acid in the droplets, thereby generating barcoded nucleic acid in the droplets. In part (f), barcode polynucleotides sometimes are linked to nucleic acid in the microcapsules if part (e) is not performed prior to part (f) or barcode polynucleotides sometimes are linked to nucleic acid in the droplets if part (e) is performed prior to part (f).

In certain implementations, a method includes exposing nucleic acid released from the biological entity after part (b) to nucleic acid processing conditions. Any suitable nucleic acid processing conditions can be utilized, and in certain instances, nucleic acid processing conditions include exposing nucleic acid to reverse-transcription conditions and/or amplification conditions that generate amplicons of the nucleic acid. Nucleic acid processing conditions sometimes include exposing nucleic acid to oligonucleotide probe annealing conditions that anneal one or more oligonucleotide probes to nucleic acid.

Certain implementations include, prior to part (d), exposing microcapsules to selection conditions that select microcapsules containing released nucleic acid and/or processed nucleic acid. Certain microcapsules may not contain processed nucleic acid because the microcapsules never were loaded with a biological entity (i.e., certain microcapsules did not encapsulate a biological entity). Any suitable selection conditions can be utilized, and selection conditions can include in certain implementations (i) fluorescently-activated microcapsule sorting, in which nucleic acid within microcapsules are stained with a non-specific DNA dye or sequence-specific probes, and stained microcapsules can be sorted by flow cytometry techniques, and (ii) electrophoretic separation of nucleic acid-containing microcapsules.

In certain implementations, (i) each of the microcapsules include a shell surrounding a core, (ii) each of the microcapsules include a cross-linked, porous and semi-permeable shell surrounding a liquid or semi-liquid core; (iii) the microcapsule shell sometimes includes a polysaccharide and is glycosidase degradable; (iv) the shell permits primers, enzymes and assay reagents to pass through, and prevents the nucleic acids released from the biological entity escaping the microcapsule; or (v) a combination of two or more of (i), (ii), (iii) and (iv). Microcapsules generated in part (a) sometimes are microcapsules described herein that include a core surrounded by a shell, where: the shell is a hydrogel comprising a first polymer; the first polymer includes a polysaccharide modified with a conjugated cross-linking moiety and optionally modified with a conjugated hydrophilicity/hydrophobicity-modifying moiety; molecules of the cross-liking moiety of the first polymer are cross linked in the hydrogel; and the core comprises a second polymer comprising a polysaccharide that does not include the cross-linking moiety and does not include the hydrophilicity/hydrophobicity-modifying moiety of the first polymer.

In certain implementations, the plurality of microcapsules generated in part (a) include microcapsules containing no biological entity and microcapsules containing a biological entity. Of the microcapsules containing a biological entity, a majority of the microcapsules generally contain a single biological entity. Of total microcapsules in a population, sometimes about 1% to about 37% contain a single biological entity, and in certain instances about 10% to about 30% include a single biological entity. Of microcapsules in a population containing a biological entity, sometimes about 58% to about 99.5% of the microcapsules contain a single biological entity and in certain instances about 77% to about 95% of the microcapsules contain a single biological entity.

In certain instances, barcode polynucleotide species attached to nucleic acid in part (f) are about 10 consecutive nucleotides to about 100 consecutive nucleotides in length, or about 16 consecutive nucleotides to about 90 consecutive nucleotides in length. In certain implementations, part (f) is repeated a number of times until a predetermined number of the barcode polynucleotide species is attached to nucleic acid in the droplets.

Part (f) sometimes is repeated about 1 to about 5 times, and part (f) sometimes is repeated about 1 to about 3 times. When part (f) is repeated, barcode polynucleotides added each time sometimes are about 4 consecutive nucleotides to about 100 consecutive nucleotides in length, or about 6 consecutive nucleotides to about 18 consecutive nucleotides in length, or about 6 consecutive nucleotides to about 12 consecutive nucleotides in length. The final length of the barcode polynucleotide species attached to the nucleic acid after the barcode-additive repetitions sometimes is about 10 consecutive nucleotides to about 100 consecutive nucleotides in length, or about 16 consecutive nucleotides to about 90 consecutive nucleotides in length.

Barcode polynucleotide linkage conditions sometimes are the same as the MIP linkage conditions (i.e., ligation, primer extension by DNA or RNA polymerases, Gibson assembly and/or template-switching conditions). After a single-step barcode polynucleotide addition, or after a barcoding-additive repetition, each barcode polynucleotide species attached to nucleic acid sometimes includes a molecular identifier polynucleotide (MIP), and sometimes each barcode polynucleotide species attached to nucleic acid includes a polymerase chain reaction (PCR) adapter polynucleotide. Certain implementations include exposing, after part (b), intact microcapsules to wash conditions. Wash conditions can include contacting intact microcapsules with an aqueous solution that alters the internal composition of the microcapsules. Wash conditions sometimes include contacting intact microcapsules with an aqueous solution that removes, or reduces, an amount of an inhibitor of the amplification conditions present in the microcapsules. In certain instances, the aqueous solution includes a buffer.

Certain implementations include tagging, after part (b), prior to part (c) and/or as part of part (c), nucleic acid in the intact microcapsules with a molecular index polynucleotide (MIP). A MIP sometimes is about 4 consecutive nucleotides to about 50 consecutive nucleotides in length.

In certain instances, a method includes exposing, prior to part (c), as part of part (c) and/or after part (c), nucleic acid in intact microcapsules to fragmentation conditions. Fragmentation conditions sometimes result in nucleic acid fragments of about 100 base pairs (bp) to about 100 kilobase pairs (kbp) in length, or about 100 bp to about 10 kbp in length. Fragmentation conditions sometimes include exposing nucleic acid in intact microcapsules to a nuclease, a chemical agent that generates hydroxy radicals, and/or ultrasound.

In certain implementations, amplification conditions include contacting intact microcapsules with DNA polymerase, RNA polymerase, or a combination thereof. A method in certain instances includes exposing nucleic acid released in part (b) to reverse transcription conditions. Reverse transcription conditions generally include contacting nucleic acid with reverse transcriptase.

In certain implementations, part (e) is not performed, and a method includes, after part (f), exposing intact microcapsules to microcapsule degradation conditions that release barcoded nucleic acid, thereby generating released barcoded nucleic acid. Microcapsule degradation conditions often include a glycosidase, as described herein.

In certain implementations, microcapsules are hydrolyzed within droplets and the content of the hydrolyzed microcapsules is release into the droplet interior. In such implementations, nucleic acid contents can be barcoded within the droplets. After barcoding, the droplets can be coalesced, and nucleic acid can be processed for sequencing (e.g., subject to library preparation), starting with purification (addressed hereafter), for example.

In certain implementations, microcapsules are not hydrolyzed within droplets and remain intact within droplets. In such implementations, encapsulated nucleic acid can be barcoded within the core of microcapsules by barcoding oligonucleotides that diffuse freely through the shell. After barcoding, the droplets can be coalesced, after which microcapsules are in the same suspension (e.g., aqueous suspension). Thereafter, nucleic acid can be processed for sequencing (e.g., subject to library preparation), starting with purification (addressed hereafter), for example, with or without release of the nucleic acid from microcapsules (i.e., with or without microcapsule hydrolysis).

In certain instances, a method includes exposing barcoded nucleic acid to purification conditions, thereby generating purified barcoded nucleic acid. Purification conditions sometimes are or include phase extraction purification processes, including without limitation, magnetic bead purification (e.g., AMPure purification) or spin-column purification. If using magnetic bead purification, 0.4×, 0.5×, 0.6×, 0.7×, 0.8×, 0.9×, or 1× AMPure XP bead purification may be selected, for example. Purification conditions sometimes are or include chemical purification processes, including without limitation, ethanol precipitation and/or phenol-chloroform extraction, for example.

A method in certain implementations includes exposing nucleic acid to library preparation conditions. Library preparation conditions sometimes include contacting nucleic acid with an adapter under adapter incorporation conditions. A method in certain instances includes sequencing the released barcoded nucleic acid and/or the purified barcoded nucleic acid.

In certain implementations, the droplet generation conditions include: an inlet for a continuous phase; an inlet for a first aqueous fluid comprising the first polymer; an inlet for a second aqueous fluid comprising the second polymer; a microchannel where the first aqueous fluid and the second aqueous fluid are combined; a flow focusing junction where continuous phase meets the first aqueous fluid, or the second aqueous fluid, or the first aqueous fluid and the second aqueous fluid; a channel where droplet generation occurs; and a water-in-oil droplet collection outlet. In certain instances, the continuous phase is a carrier oil. Droplet generation conditions sometimes are provided in part by a fluidic device as described herein.

Kits

Provided in certain aspects is a kit that includes a first polymer and a second polymer described herein. A kit can include any suitable number of separate containers, and in certain implementations, the first polymer and the second polymer each are in separate containers. The first polymer and the second polymer each independently is in liquid form or solid form (e.g., hydrogel form, dry powder).

A kit optionally includes a microfluidic device. A kit may include a carrier oil with or without a surfactant. A kit may include additional reagents such as one or more of a buffer-containing solution for washing (rinsing) microcapsules, a cross-linking initiator that conjugates cross-linking moieties in the first polymer, and a de-emulsification agent (e.g., perfluorooctanol). A kit may include additional consumables, for example, microfluidics consumables such as tubing, syringes, needles and the like. A kit may or may not include additional devices, for example, a light emitting device for photo-illumination and initiation of conjugation of the cross-linker moieties in the first polymer.

A kit may include one or more of an RNA or DNA amplifying enzyme (e.g., reverse transcriptase, and polymerase chain reaction enzymes), nucleoside triphosphates or their analogues, primers, buffers, and the like. A kit can include molecular index polynucleotides (MIPs) in any suitable form (e.g., dry, liquid, or attached to a substrate). A kit may comprise a microcapsule degrading reagent such as an enzyme that degrades microcapsule shells, such as a glycosylase.

A kit can include instructions for carrying out a manufacturing process or method of using a microcapsule as described herein. A kit can include instructions for generating microcapsules described herein (e.g., instructions for generating water-in-oil droplets containing the first polymer and the second polymer), and may include instructions for using microcapsules for amplifying contained nucleic acid. Instructions and/or descriptions may be in tangible form (e.g., paper and the like) or electronic form (e.g., computer readable file on a tangle medium (e.g., compact disc) and the like) and may be included in a kit insert. A kit also may include a written description of an internet location that provides such instructions or descriptions.

Consistent with the above disclosure, a kit may comprise reagents for microcapsule assembly, microcapsule reagent release, sequential reactions to be performed on the contents of a microcapsule, concatenation, barcoding, or other microcapsule reagents.

Thus, provided is a kit that includes a first polymer and a second polymer, wherein: the first polymer comprises a polysaccharide modified with a conjugated cross-linking moiety and optionally modified with a conjugated hydrophilicity/hydrophobicity-modifying moiety, and the second polymer comprises a polysaccharide that does not include the cross-linking moiety and does not include the hydrophilicity/hydrophobicity-modifying moiety of the first polymer. A kit can include instructions for using the first polymer and the second polymer. The instructions sometimes are for manufacturing microcapsules according to the process described herein, and sometimes the instructions are for manufacturing microcapsules in a composition described herein. The instructions sometimes are for using microcapsules according to a method described herein. In certain implementations, provided is a kit that includes reagents, and optionally microcapsules, for conducting a method described herein, where the kit can include instructions for conducting a method described herein.

Consistent with the disclosure herein, kits relating to the synthesis or use of any of the compositions disclosed herein or practice of any of the methods herein are included as part of the present disclosure.

FIGURE OVERVIEW

Turning to the figures, one sees the following.

At FIG. 1. One sees a schematic of a microcapsule generation and analysis workflow. Droplet generation begins with core/shell polymers and biological entity encapsulation in an oil emulsion. The shell polymer accumulates at the edge of the droplet, while the core polymer mixture and the encapsulated biological entity such as an analyte accumulates in the center. Without being bound by theory, the shell and core polymers, will undergo liquid-liquid phase separation. In an oil carrier, the more hydrophobic shell polymer is drawn to the exterior of the emulsion droplet. The droplet is then crosslinked, causing the shell polymer to from a shell hydrogel. Polymerized microparticles are redistributed into aqueous solution, which facilitates buffer and reagent swapping necessary for the practice of various biological entity processing steps, which in some cases are mutually incompatible. Following analyte processing, biocompatible release of the biological entity or analyte reaction product is effected without damage to the microcapsule contents, facilitating downstream analysis.

At FIG. 2A-E, one sees a diagram depicting microcapsule encapsulation of a biological entity. Droplet generation begins with a mixture of core and shell polymers and a biological entity as an aqueous droplet in an oil, as seen in FIG. 2A and FIG. 2B. Phase separation results in the droplet configured in the oil as an exterior shell polymer mixture encasing a core polymer mixture and a biological entity in a population of droplets, at FIG. 2C. Polymerization of the shell polymer mixture forms an exterior shell hydrogel, as seen in FIG. 2D, E. Once the shell has polymerized, the microcapsules may be removed from their oil carrier and redistributed into an aqueous solution, for example to facilitate reagent delivery and removal from the microcapsule core. At FIG. 2E one sees a close-up view of a microcapsule, demonstrating uniform shell thickness that facilitates reagent exchange.

Figure 3:
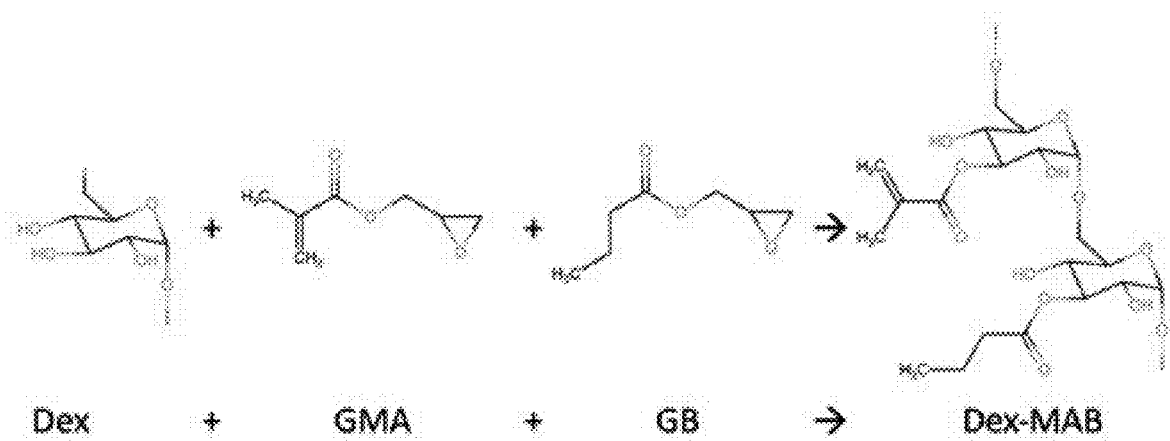
FIG. 3 depicts a chemical synthesis for microcapsule precursor Dex-MAB.

At FIG. 3, one sees a chemical synthesis scheme for Dex-MAB. Methacryloyl (MA) and butyryl (B) are added to the Dextran (Dex) scaffold in proportion to their initial concentrations. GMA-glycidyl methacrylate, GB-glycidyl butyrate.

Figure 4:
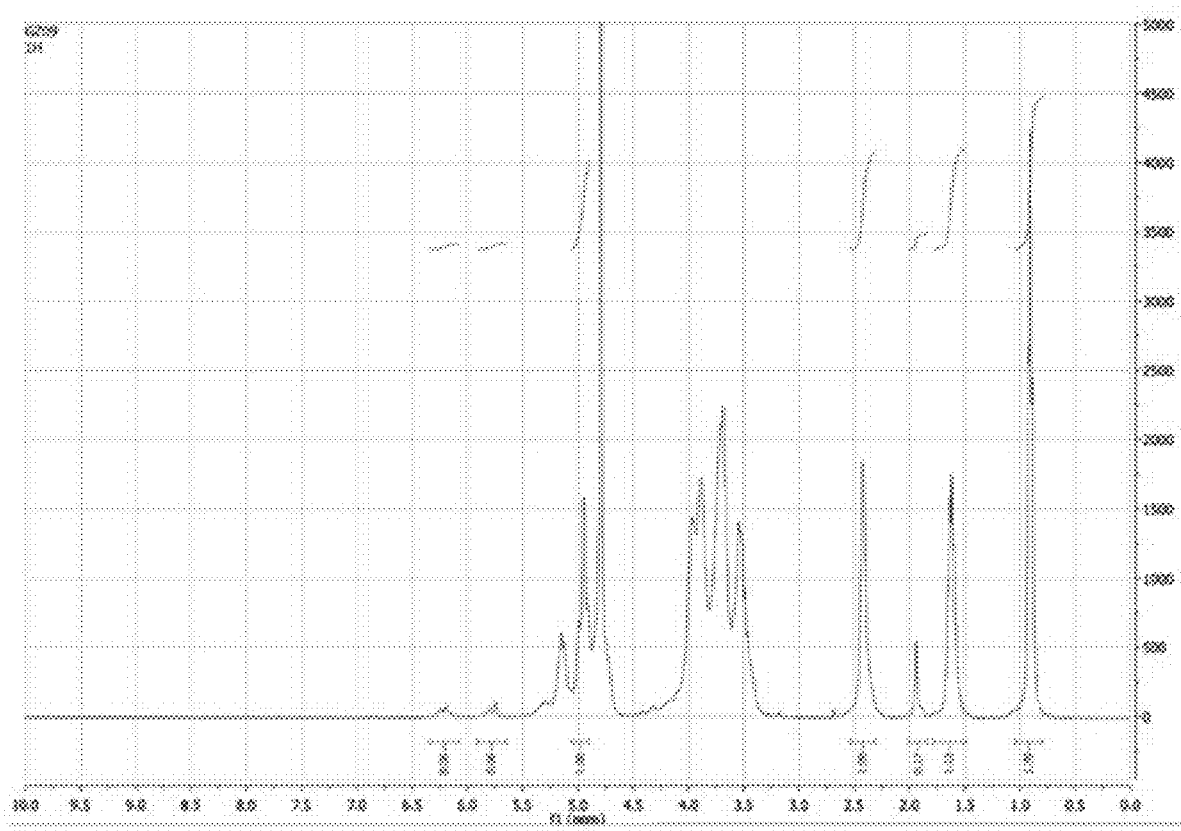
FIG. 4 shows 1H-NMR analysis indicating successful Dex-MAB synthesis.

At FIG. 4, one sees an INMR analysis of a synthesis product of the synthesis pathway of FIG. 3.

At FIG. 5, one sees a workflow facilitated by the microcapsule technology herein. Biological entities such as cells, organelles, viral particles, or other discrete units, or even free-floating nucleic acids, are compartmentalized. Samples are then subjected to a series of processing steps, some of which may be mutually incompatible if practiced concurrently on a sample (such as lysis, DNase treatment, reverse transcription, ligation and end-tagging, for example). Individual nucleic acids are then concatenated, which preserves information regarding common biological entity of origin for co-concatenated molecules upon release of microcapsule contents into an aqueous environment. Concatenated nucleic acid products are sequenced, such that reads from a single molecule can be correlated to a single biological entity of origin. This process relies upon the ability to wash out mutually incompatible reagents and buffers, so as to facilitate iterative reactions in a single microcapsule, while preserving the nucleic acids of interest within the core of the microcapsule. Microcapsules are subjected to shell hydrolysis, and the released contents are subjected to library preparation and sequencing.

At FIG. 6, one sees a split and pool workflow facilitated by the microcapsule technology herein. Biological entities such as cells, organelles, viral particles, or other discrete units, or even free-floating nucleic acids, are compartmentalized. Samples are then subjected to a series of processing steps, such as lysis, wash, nucleic acid processing, and split and pool barcoding of nucleic acids within SPCs. Importantly, nucleic acids can be amplified without loss of compartmentalization prior to barcoding. Such amplification mitigates barcoding inefficiencies. This process relies upon the ability to wash out mutually incompatible reagents and buffers, so as to facilitate iterative reactions in a single microcapsule. Microcapsules are subjected to shell hydrolysis, and the released contents are subjected to library preparation and sequencing.

FIG. 7 illustrates a model for the efficiency of the labeling process practiced using the technology herein. Compartmentalized samples are subjected to 0-10 PCR cycles prior to barcoding by barcodes having an efficiency of addition of from 10-95%. The model assumes a PCR efficiency of 100%, i.e., the input is doubled at every cycle. After three rounds of addition, the percentage of unrecoverably lost unique transcripts was calculated. One sees that for a highly efficient barcode addition, the majority of transcripts are recoverable even without PCR amplification prior to barcoding, as evidenced by the low percentage of unrecoverably lost transcripts at the upper right of the figure. For less efficient barcode addition, performing a modest number of PCR cycles prior to barcoding achieves a barcoding high success rate, as evidenced by the low percentage of unrecoverably lost transcripts at the lower left of the figure. This figure demonstrates that the number of unrecoverably lost unique transcripts can be minimized for a broad range of barcodes and PCR amplification regimens using the microcapsule technology disclosed herein.

FIG. 8A and FIG. 8B show workflows for eukaryotic cell scRNAseq and microbial cell scDNAseq, respectively. Both workflows include a nucleic acid amplification step prior to barcoding. In FIG. 8A, lysis and clean up are followed by reverse transcription including UMI tagging, followed by PCR amplification, split and pool barcoding, library preparation, and sequencing. In FIG. 8B, lysis and clean up are followed by MDA amplification, fragmentation and/or MDA product debranching, split and pool barcoding, library preparation including enrichment of full barcodes, and sequencing. Both of these workflows, and variants on either workflow, rely upon the ability to efficiently wash out or replace reaction conditions so as to perform iterative reactions on common microcapsules, as well as the ability to efficiently and gently release microcapsule contents so as to allow downstream sequencing.

FIG. 9A and FIG. 9B present exemplary Illumina library configurations. SPASp5 and SPASp7 stand for sequencing primer annealing at the p5 and the p7 end, respectively. In the case of scDNAseq (FIG. 9A), a conventional paired-end sequencing regime is need, and Illumina indices can be optionally used. In the case of scRNAseq (FIG. 9B), one of the index reads (i7 read, 20 bases long) is used to reveal part of the cell barcode sequence.

FIG. 10 presents exemplary barcoding steps, nucleotide sequences, and reagents for scDNAseq applications. Barcoding has to be performed with the single-cell compartmentalization retained within SPCs. Library preparation steps downstream of barcoding can be performed as a bulk reaction following the release of encapsulated nucleic acids from SPCs.

FIG. 11 presents exemplary barcoding steps, nucleotide sequences, and reagents for scRNAseq applications. Barcoding has to be performed with the single-cell compartmentalization retained within SPCs. Library preparation steps downstream of barcoding can be performed as a bulk reaction following the release of encapsulated nucleic acids from SPCs.

Figure 12:
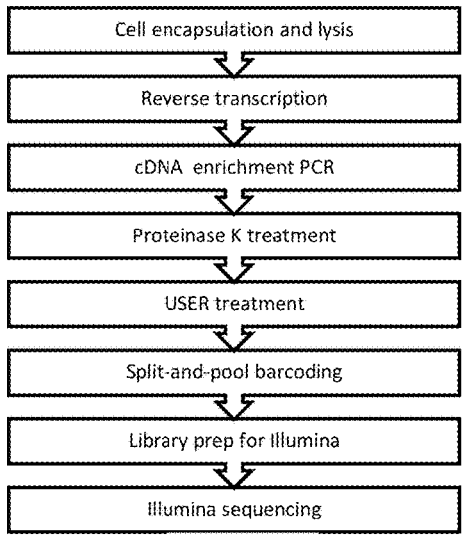
FIG. 12 shows a microcapsule workflow for scRNAseq comprising mutually incompatible reactions performed in series within single microcapsule volumes, including the steps of cell encapsulation and lysis, reverse transcription, cDNA enrichment PCR, proteinase K treatment, USER treatment, split-and-pool barcoding, library preparation and sequencing.

FIG. 12 lists a series of steps for scRNAseq applications, including mutually incompatible steps, including cell encapsulation, lysis, reverse transcription, cDNA enrichment PCR, Proteinase K treatment, USER treatment, split and pool barcoding, library preparation and sequencing, performed in some workflows as disclosed herein or facilitated by the technology herein. Library prep and sequencing are in some cases performed after biocompatible release of microcapsule contents.

FIG. 13A and FIG. 13B show loading of SPCs and barcoding beads into compartments for barcoding of microcapsule/SPC enclosed nucleic acids. Barcoding beads may be iteratively removed and replaced, facilitating multiple rounds of barcoding and increasing the microcapsule-specific distinctiveness of an eventual nucleic acid barcoding pattern for a particular set of microcapsule contents. For single-cell sequencing applications, cells are encapsulated into SPCs using a typical microfluidic regime which, to avoid multiple cells entering the same SPC, requires most SPCs to be cell-free, and only some SPCs (typically <10%) to contain a cell. During barcoding in droplets with barcoding beads, most of the droplets are non-productive as they contain an empty SPC (FIG. 13A). This inefficiency can be overcome by pre-sorting SPCs containing desired cells at any step between SPC generation and barcoding (FIG. 13B).

FIG. 14A and FIG. 14B show alternative approaches for nucleic acid detection. At FIG. 14A, cells are permeabilized and subjected to nuclei acid detection. The signal is a function of the number of nucleic acid copies in the original cell. In FIG. 14B, cells are compartmentalized, lysed and subjected to nucleic acid amplification prior to detection, such that the nucleic acids available for detection and the subsequent signal are substantially amplified relative to the signal arising from the original cell's nucleic acid population. This facilitates isolation of cell contents of cells harboring target nucleic acids.

Figure 15A:
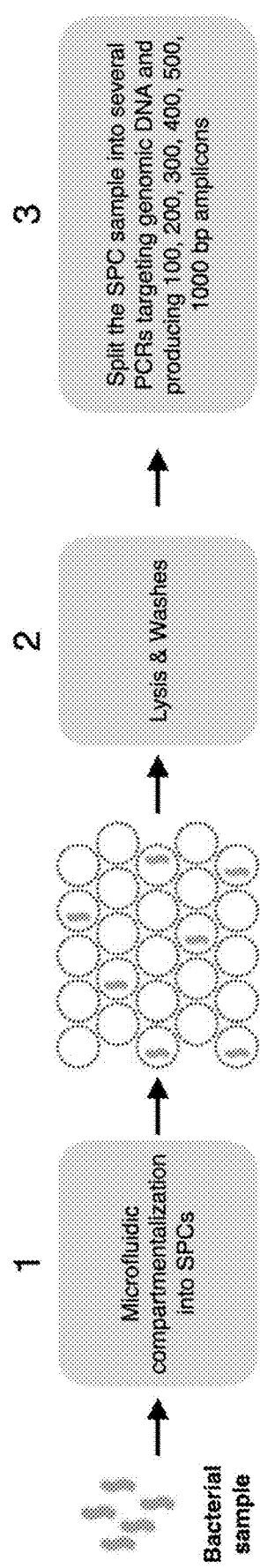
FIG. 15A and FIG. 15B demonstrate a protocol and results for determination of microcapsule nucleic acid size retention.
Figure 15B:
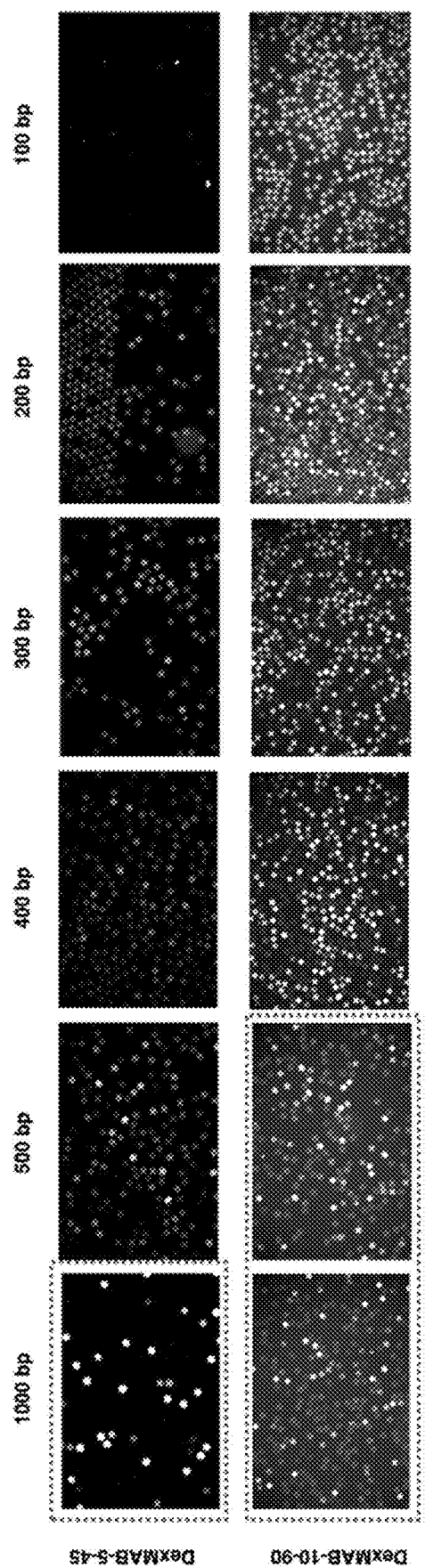

FIG. 15A and FIG. 15B demonstrate a protocol and results for determination of microcapsule nucleic acid size retention for compositions DexMAB 5-45 and DexMAB 10-90. The results indicate that multiple compositions are suitable for microcapsule formation, and that nucleic acid size retention thresholds may be modulated by selecting suitable microcapsule shell compositions.

Figure 16:
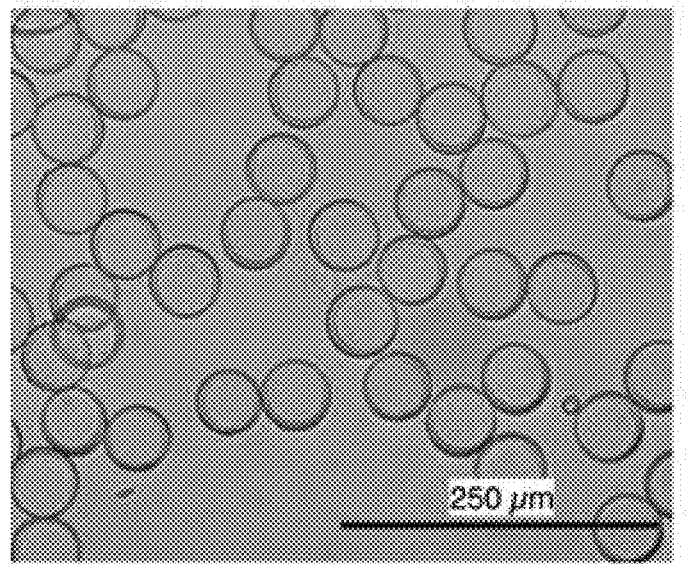
FIG. 16 and FIG. 17 demonstrate microcapsule populations with Ficoll-based shells before and after dextranase treatment of core polymers.
Figure 17:
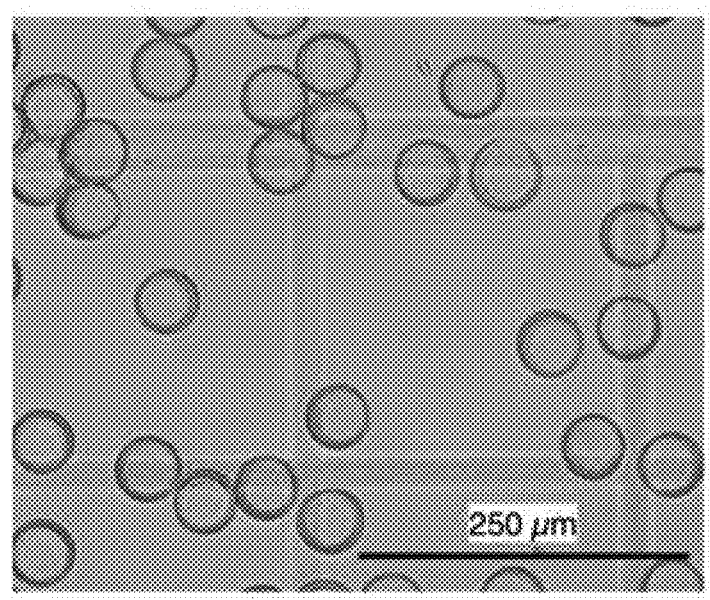

FIG. 16 and FIG. 17 demonstrate microcapsule populations before and after dextranase treatment of core polymers. The backbone polymer of the shell is ficoll, which is resistant to dextranase. Hydrogel shell and microcapsule size is particularly uniform for the populations presented, but approximately 15% smaller subsequent to treatment.

Figure 18:
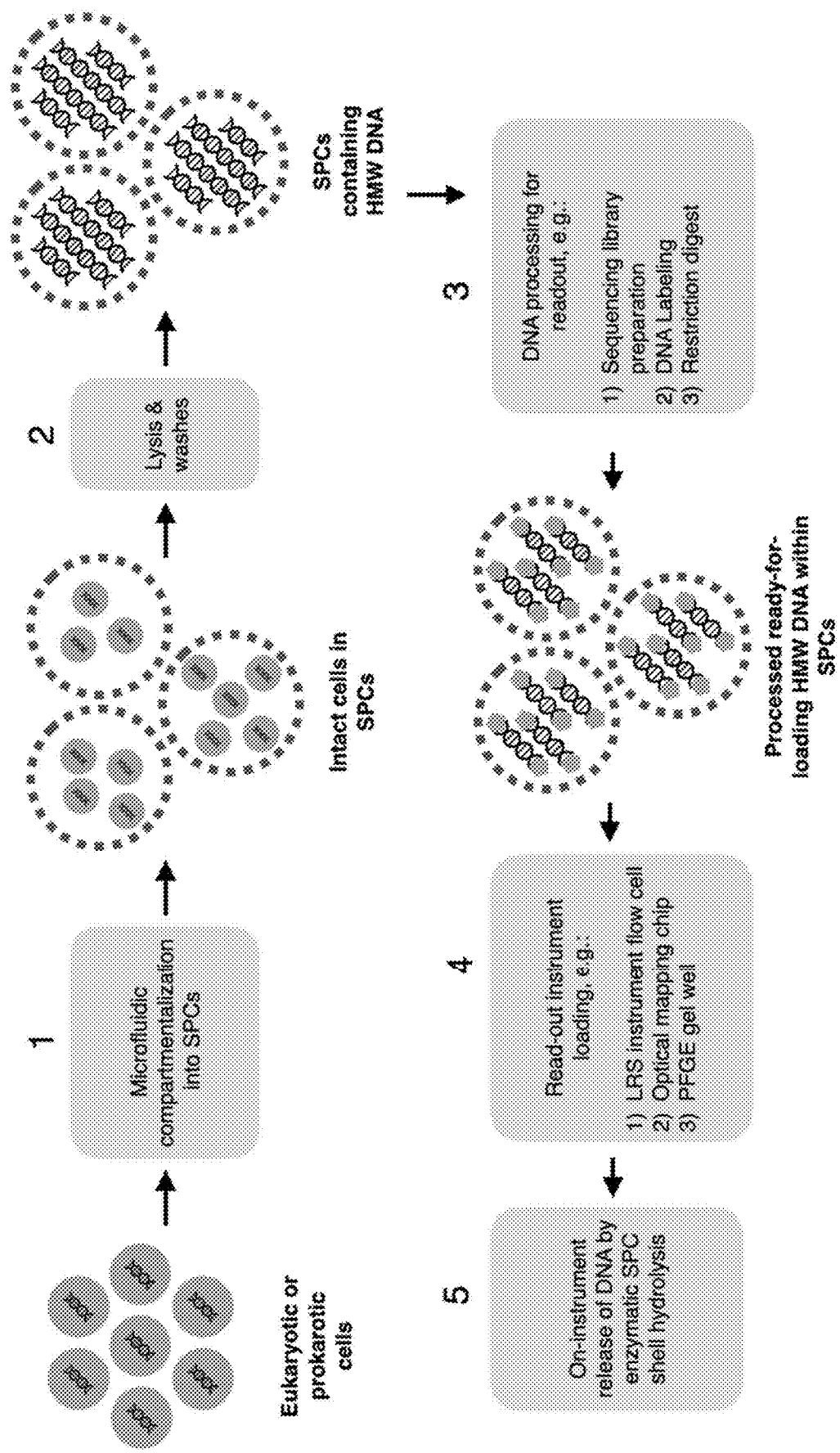
FIG. 18 presents a workflow for preparing nucleic acids for sequencing.

FIG. 18 presents a workflow for preparing nucleic acids for sequencing. Cells are compartmentalized, lysed and washed, and processed from readout, for example subjecting them to sequencing library preparation, DNA labeling or restriction endonuclease treatment in capsules, followed by loading the microcapsules onto a sequencing instrument such as a flow cell and releasing microcapsule contents onto the instrument. The position on the instrument may be used to reflect the microcapsule of origin. High-molecular-weight (HMW) DNA preparation for analysis benefits from the protection that microcapsules offer against mechanical fragmentation during handling.

Figure 20:
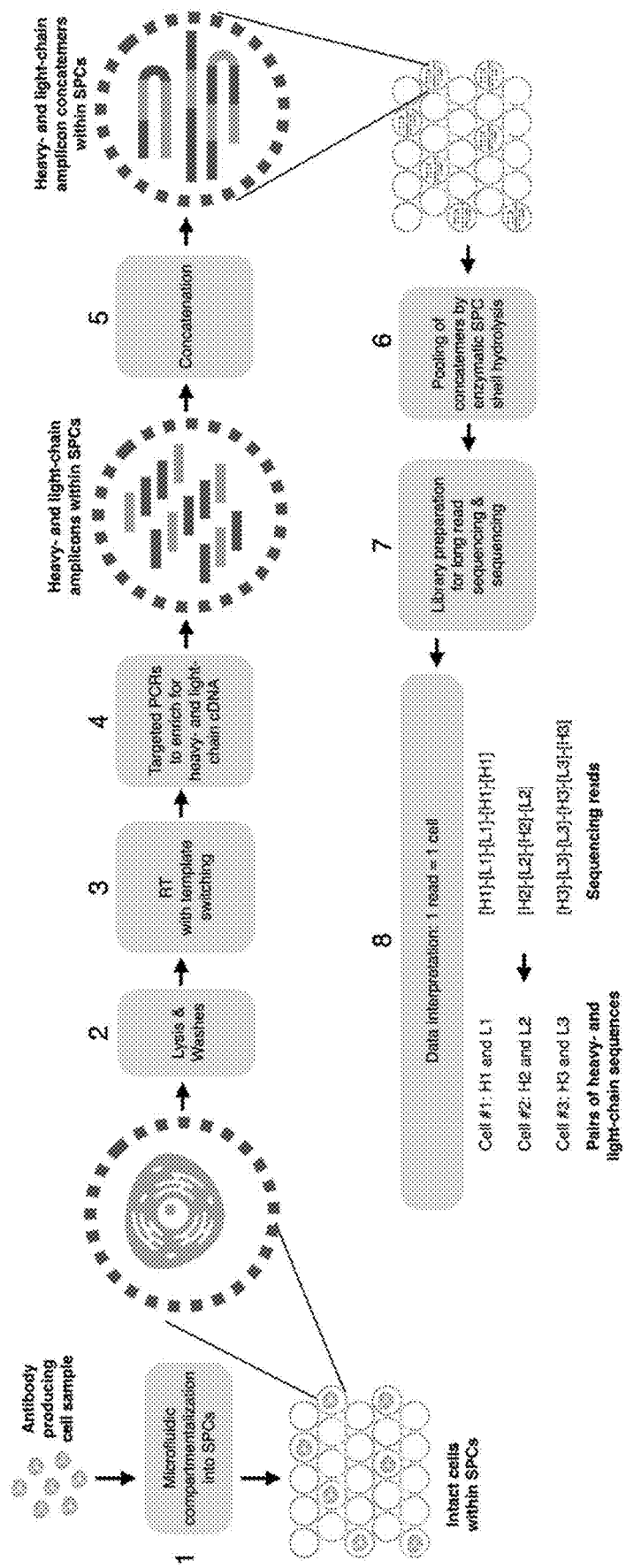

FIGS. 19-20 illustrate workflows compatible with the technology herein. Included are workflows for concatenation, barcoding, and heavy and light chain amplicon concatemer sequencing and isolation.

Figure 21:
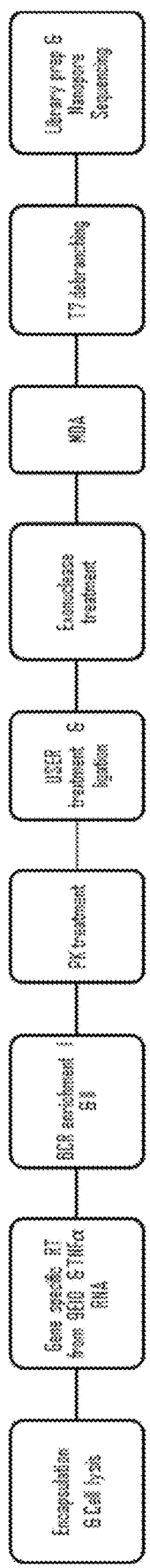
FIG. 21 presents a schematic for long read sequencing library preparation of B cell receptor heavy and light chain concatemers formed within microcapsules. Figure discloses SEQ ID NOS 75-81, 37 and 68, respectively, in order of appearance.

FIG. 21 presents a schematic for long-read sequencing library preparation of concatemers formed within microcapsules. Cells are compartmentalized and lysed, subjected to targeted reverse transcription and BCR enrichment, followed by USER treatment, ligation and exonuclease treatment. Concatenated molecules were subjected to MDA, T7 debranching, followed by library prep and nanopore sequencing. This workflow involves multiple mutually incompatible reaction steps which are efficiently performed due to the ability to wash out and replace reaction environments in microcapsules, and to efficiently recover reaction products for downstream processing such as nanopore sequencing.

Figure 22:
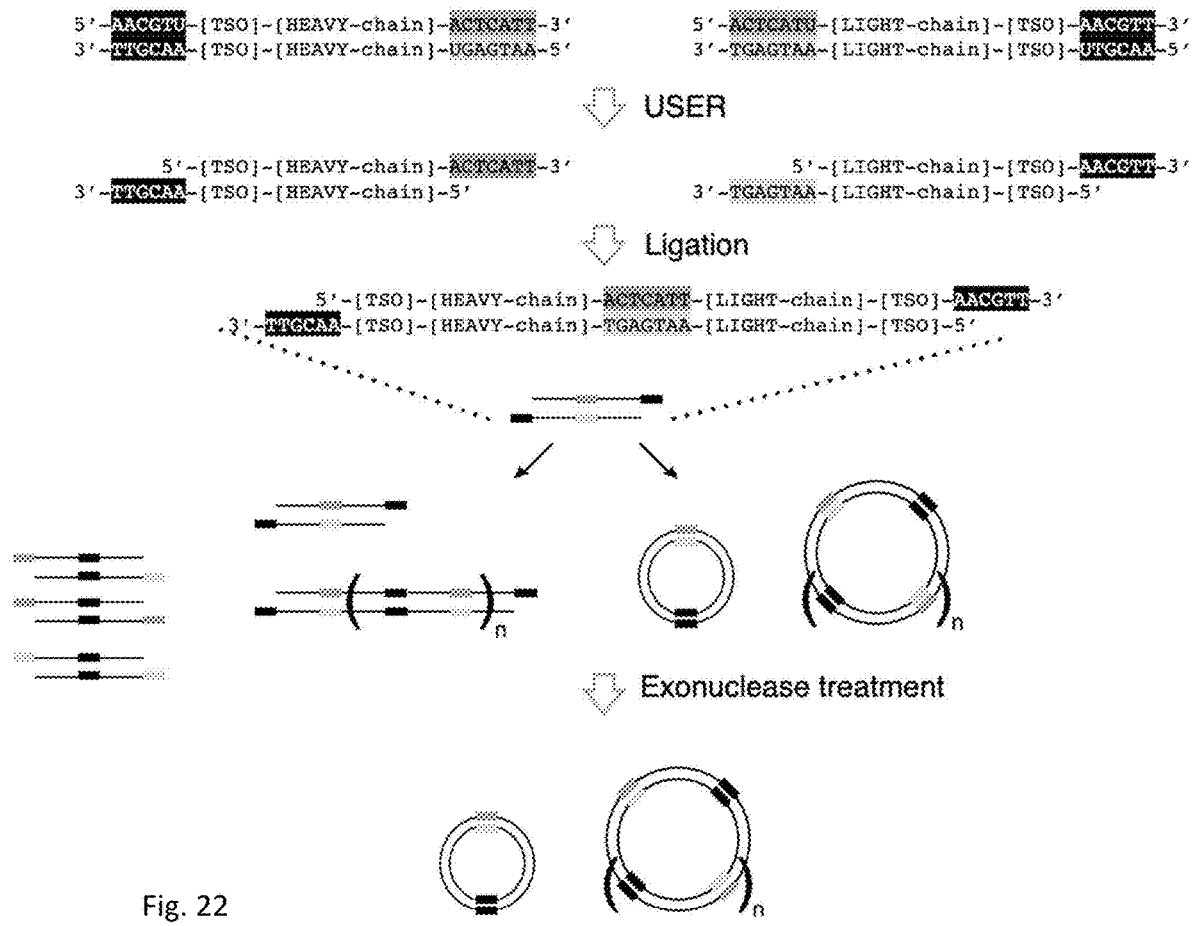
FIG. 22 shows a workflow and specific nucleotide sequences for heavy chain and light chain concatenation and sequencing.

FIG. 22 shows a workflow and specific nucleotide sequences for heavy chain and light chain concatenation via addition of Uracil bases and USER treatment to generate sticky ends for ligation. Concatenated chains may then be sequenced so as to determine the heavy/light chain combinations for a given cell of origin.

Figure 23:
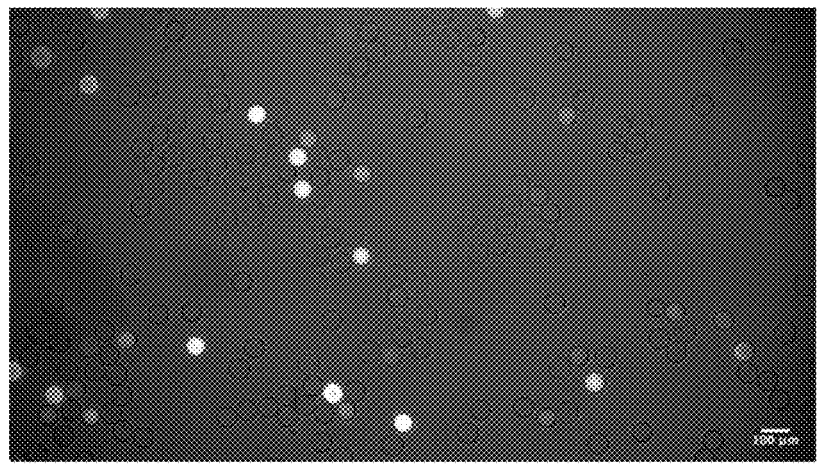
FIG. 23 shows detection of MDA amplified nucleic acids as evidenced by fluorescence in DNA containing microcapsules.

In FIG. 23, one sees detection of MDA amplified nucleic acids as evidenced by fluorescence in DNA containing microcapsules.

Figure 24:
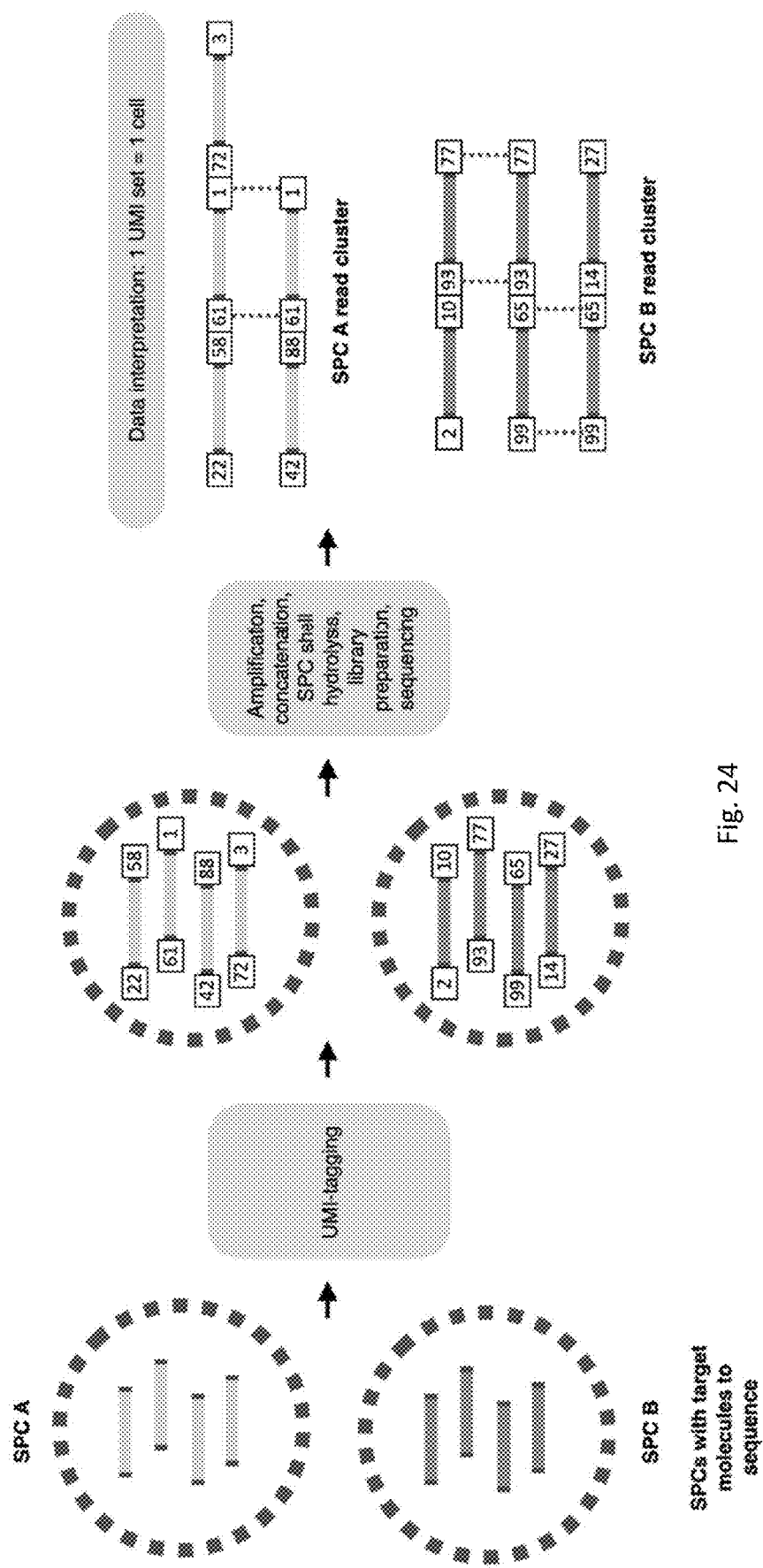
FIG. 24 presents a UMI/concatenation workflow, and the "1 UMI set=1 cell" principle.

FIG. 24 presents a UMI/concatenation workflow, and the "1 UMI set=1 cell" principle. Samples are compartmentalized in microcapsules, UMI-tagged, and subjected to amplification, concatenation, SPC shell hydrolysis, library preparation and sequencing. Reads sharing common UMIs are confidently assigned to a common microcapsule of origin.

Figure 25:
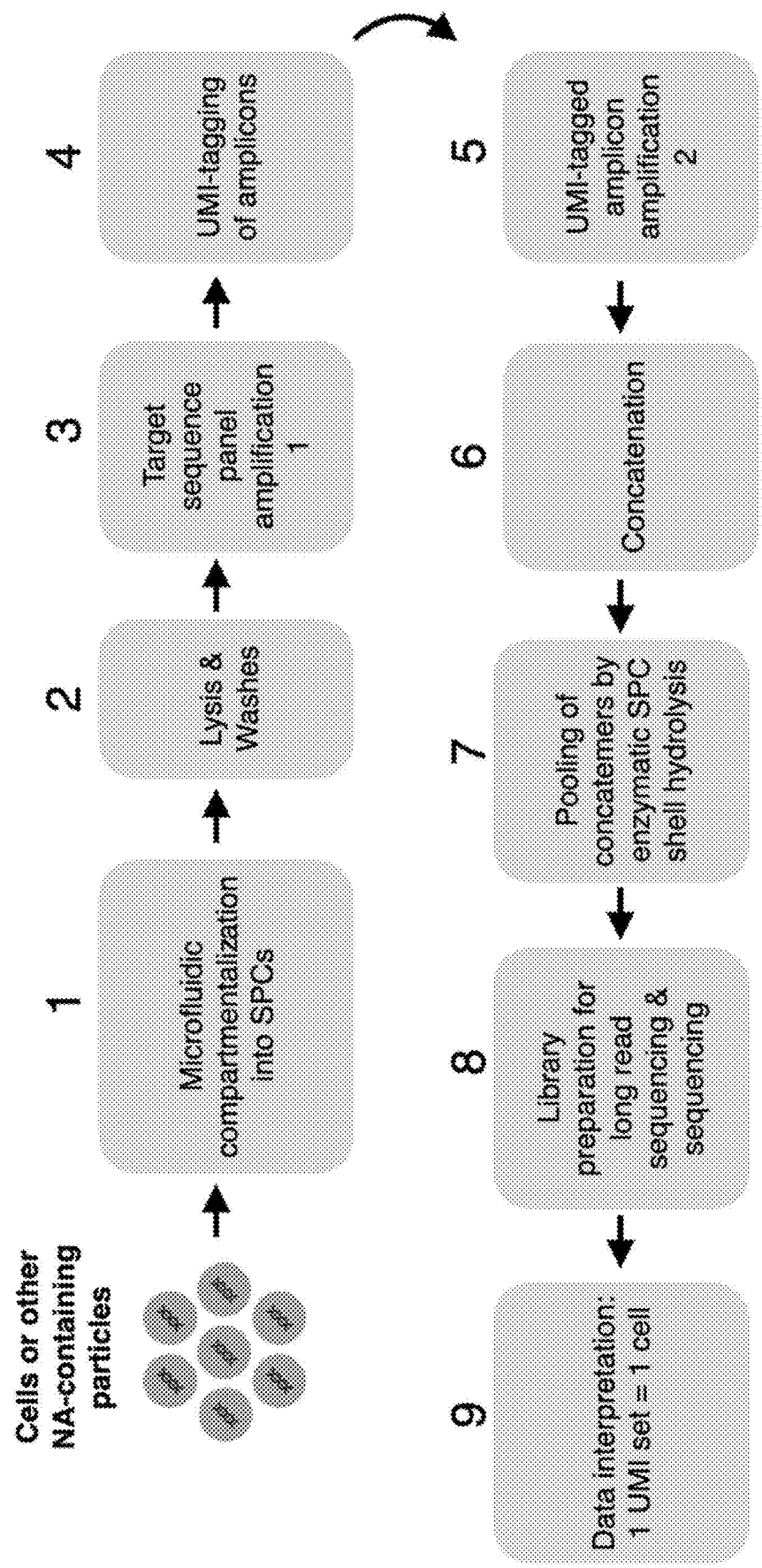
FIG. 25 presents a tagging workflow consistent with the technology herein.

FIG. 25 presents a tagging workflow consistent with the technology herein. Cells or other nucleic acid containing microparticles are compartmentalized, lysed and washed, and subjected to target panel amplification and UMI tagging. UMI tagged amplicons are concatenated and then the microcapsules are hydrolyzed to release the contents, which may be subjected to library prep and then long read sequenced.

Figure 26:
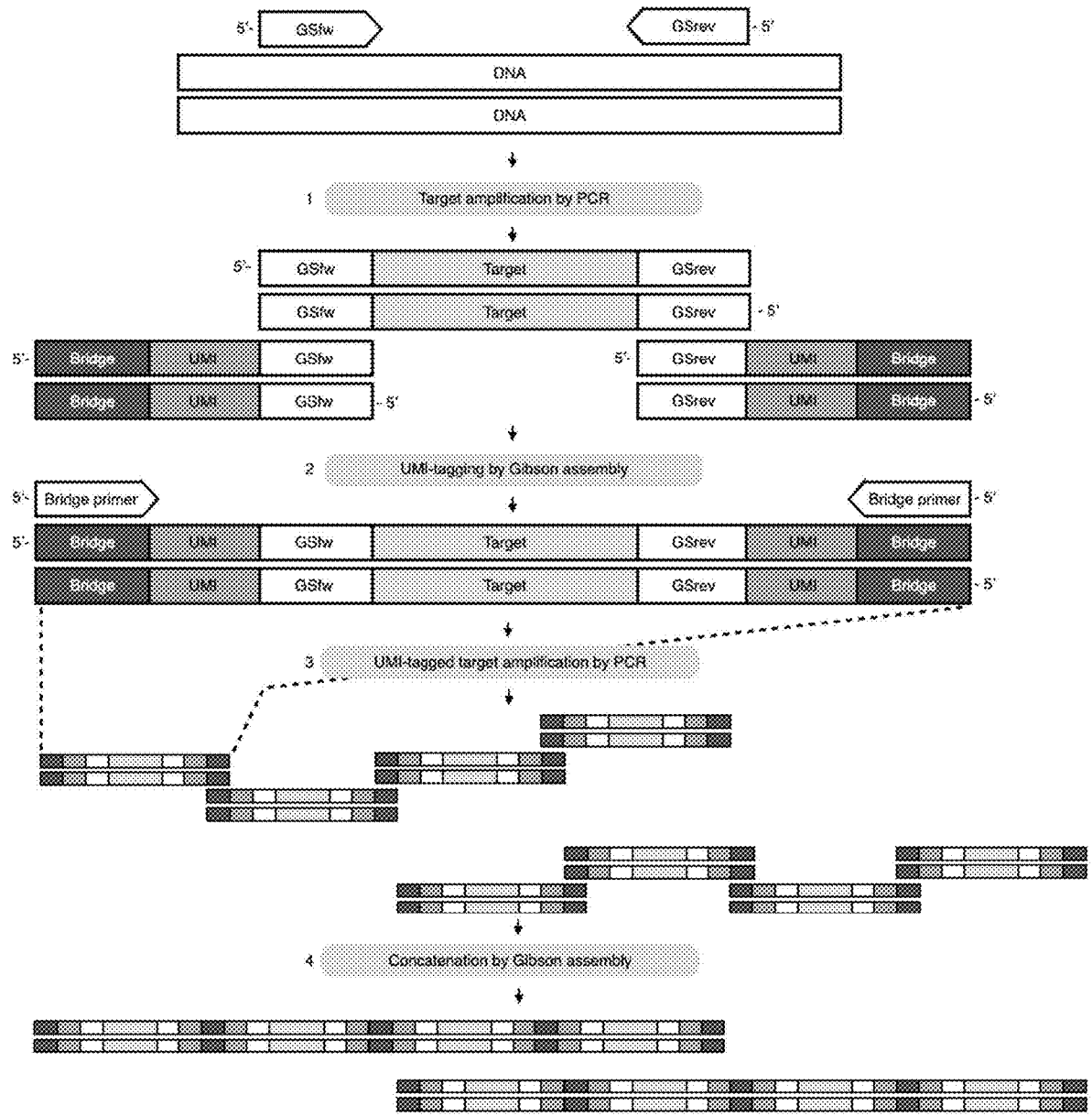
FIG. 26 provides a schematic of an example workflow for target amplification, UMI-tagging, and concatenation.

FIG. 26 provides a schematic of an example workflow for target amplification, UMI-tagging, and concatenation. DNA contained multiple targets of interest are amplified using a panel of primers for multiplex PCR (#1). The number of cycles is 2-10. The resulting amplicons are tagged with UMIs (#2) using Gibson assembly and duplex DNA oligonucleotides having the structure Bridge-UMI-GSfw or Bridge-UMI-GSrev, where "GSfw" and "GSrev" are the PCR1 primer sequences and "Bridge" serves as an adapter for the single-primer PCR2 (#3), and as the overlapping sequence between amplicons to be concatenated in the subsequent step (#4). "GSfw" refers to gene-specific forward primer, and "GSrev" refers to gene-specific reverse primer.

FIGS. 27A-27B provide anticipated results based on two in silico simulations of the workflow and the "1 UMI set=1 cell" principle described in FIGS. 24-26. To enable a successful graph-based read demultiplexing by shared UMIs as shown in FIG. 27A, the number of reads and/or the concatemer length must be sufficient for the chosen number of cells, genomic targets, and PCR1 amplification cycles. For example, increasing the number of PCR1 cycles from 5 (FIG. 27A) to 10 (FIG. 27B), while keeping the other parameters constant, leads to incomplete demultiplexing of the data and the presence of "orphan" reads that do not share UMIs with any other read. Simulations like these can be used to decide in advance on the sequencing depth needed for the "1 UMI set=1 cell" principle to work successfully and prevent "orphan" reads.

FIG. 28 shows a workflow for USER-mediated concatenation of bacterial amplicons.

At FIG. 29, one sees a more detailed implementation of the workflow in FIG. 28, which results in the targeted concatenation of AmpR, 16S and GFP loci from a single source. The choice of loci for amplification is arbitrary, such that the approach may be used to concatenate a broad number of target loci from a single source.

Figure 30:
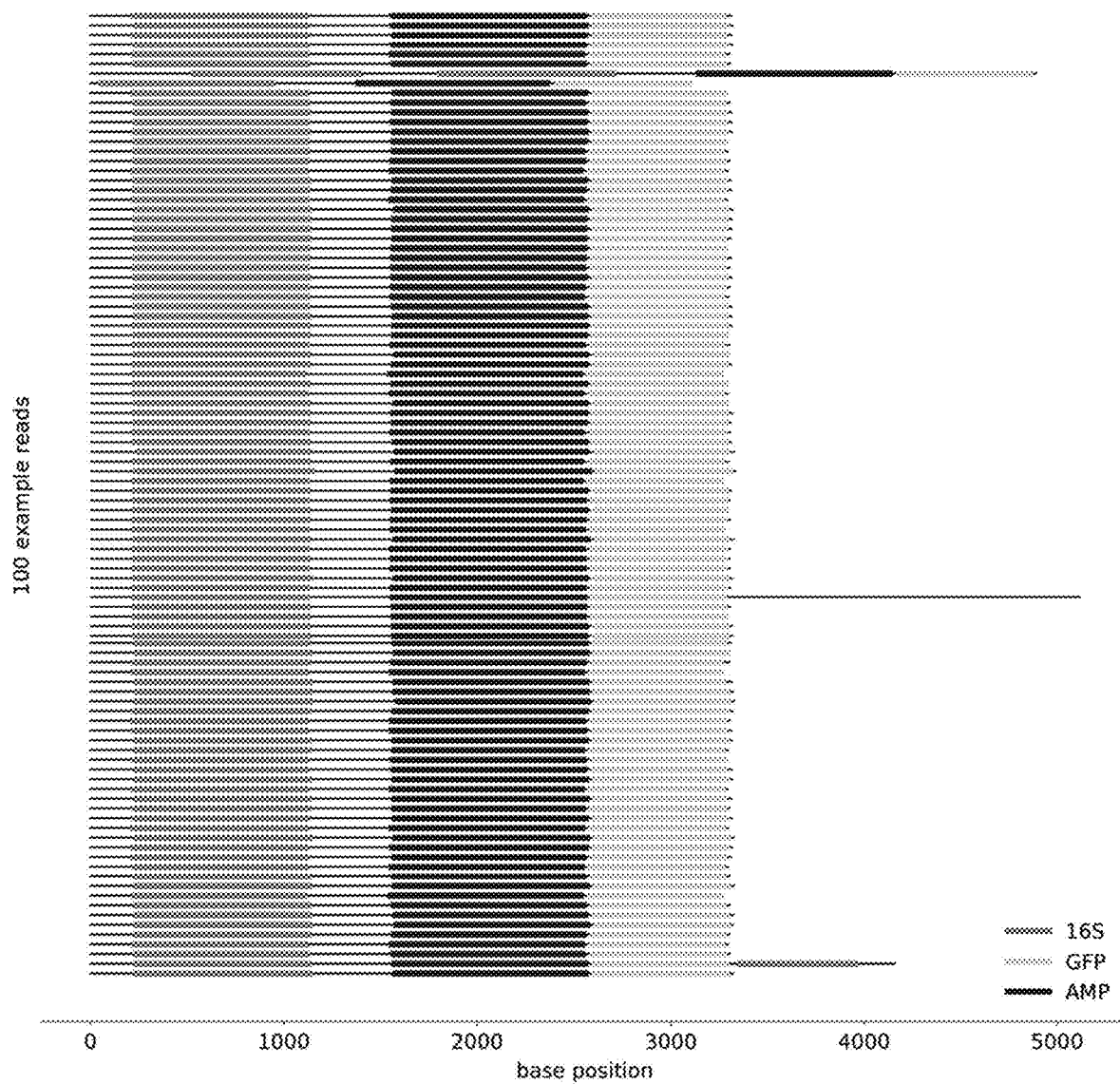
FIG. 30 shows coverage for a sample of 100 reads identified to contain all 3 of the loci identified in FIG. 29.

FIG. 30 shows coverage for a sample of 100 reads identified to contain all 3 of the loci identified in FIG. 29. This figure demonstrates that the anticipated concatemers in the desired order are efficiently obtained using the approach elucidated in FIGS. 28 and 29.

Figure 31:
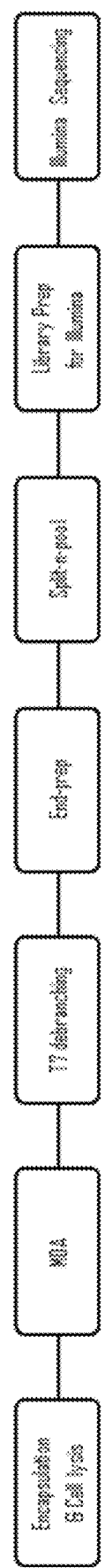
FIG. 31 shows a split pool synthesis workflow for scDNAseq.

FIG. 31 shows a split pool synthesis workflow for scDNAseq, comprising encapsulation and lysis, MDA, T7 debranching, end prep, split and pool labeling, followed by release, library prep and sequencing. This approach relies upon the ability to efficiently replace reagents and buffer conditions so as to perform mutually incompatible reactions on common microcapsule volumes.

FIG. 32 presents successful results obtained from use of the approach of FIGS. 8A, 11, 12. The table is generated as part of the STARsolo pipeline for scRNAseq read mapping and demultiplexing.

FIG. 33 presents a graphic display of results from the approach of FIG. 8A, 11, 12, illustrating the ability to separate read results in pooled sequencing reactions. Human gene counts are presented on the Y-axis, labeled from 0 to 1200 in intervals of 200, while mouse gene counts are presented on the X-axis from 0 to 4000 in intervals of 1000. Each dot represents a barcode, and therefore a cell. Cell barcodes comprising both human and mouse counts would be presented off-axis. Reads associated with a given barcode exclusively map the either mouse or human genome, as evidenced by their position on the X or Y axis, respectively. The few instances of mixed-species mouse and human barcodes are shown in black and map near the origin, indicating that they are relatively rare.

Figure 34:
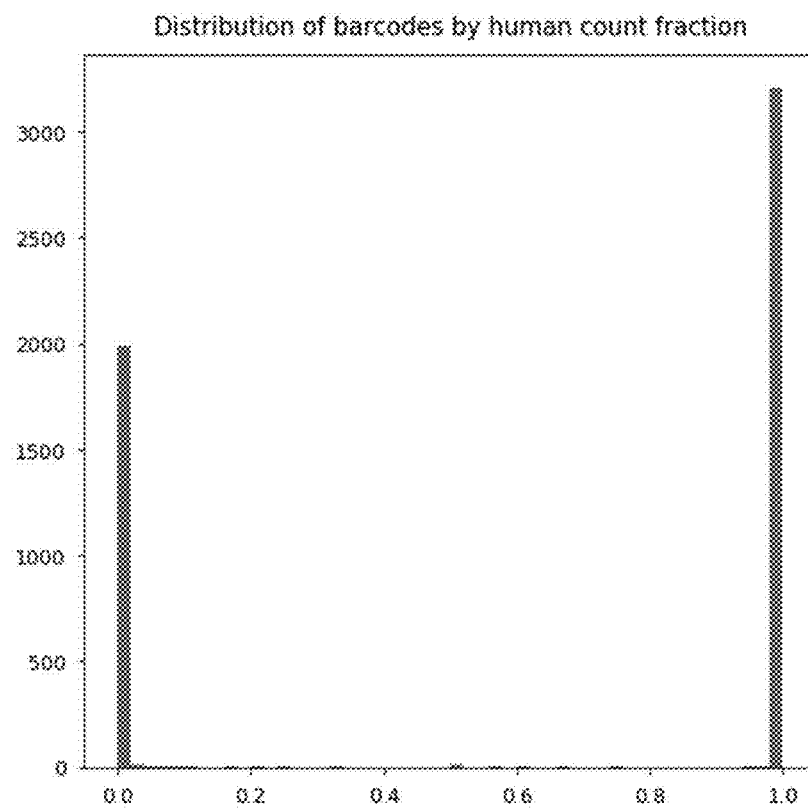
FIG. 34 presents a separate graphic display of the success of the approach of FIGS. 8A, 11, 12.

FIG. 34 presents a separate graphic display of the success of the approach of 8A, 11, 12. The data is presented as a barcode histogram, where barcodes are binned by the fraction of reads mapping to the human genome out of all reads mapping to a mixed human-mouse reference genome. Barcode count is presented on the y-axis, ranging from 0 to 3000 in intervals of 500, and the human count fraction from 0 to 1 on the x-axis. One sees that the vast majority of barcodes were either 0% or 100% human count reads.

Figure 35:
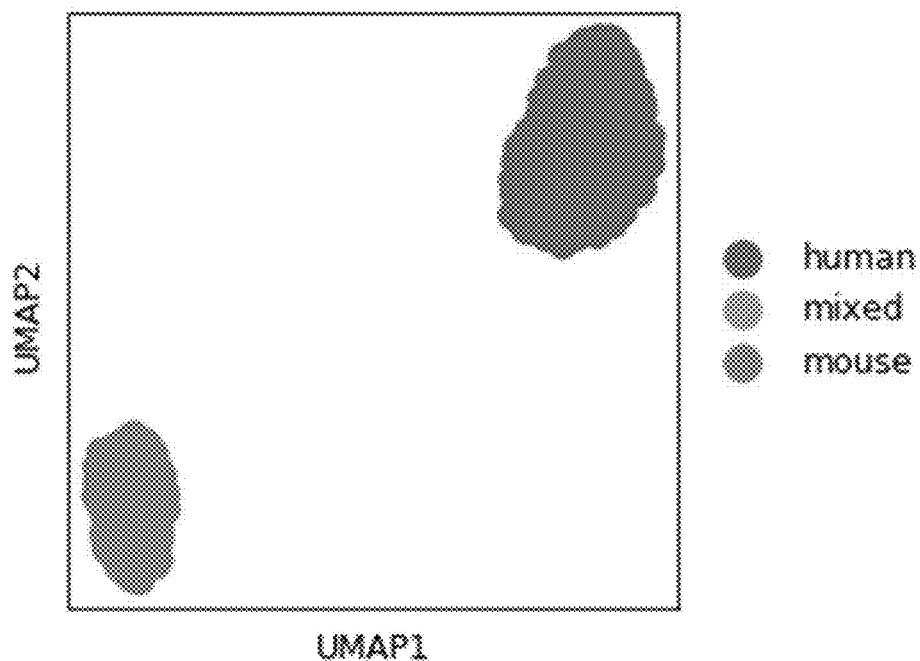
FIG. 35 presents a separate graphic display of the success of the approach FIGS. 8A, 11, 12.

FIG. 35 presents a separate graphic display of the success of the approach FIGS. 8A, 11, 12. An unbiased two-dimensional representation of the high-dimensional scRNAseq data was obtained using UMAP (Uniform Manifold Approximation and Projection for Dimension Reduction). UMAP1 and UMAP2 are arbitrary axis names. Barcodes comprising only human counts group to the upper right, while mouse count barcodes group to the lower left. Mixed barcodes are not seen in the data.

Figure 36:
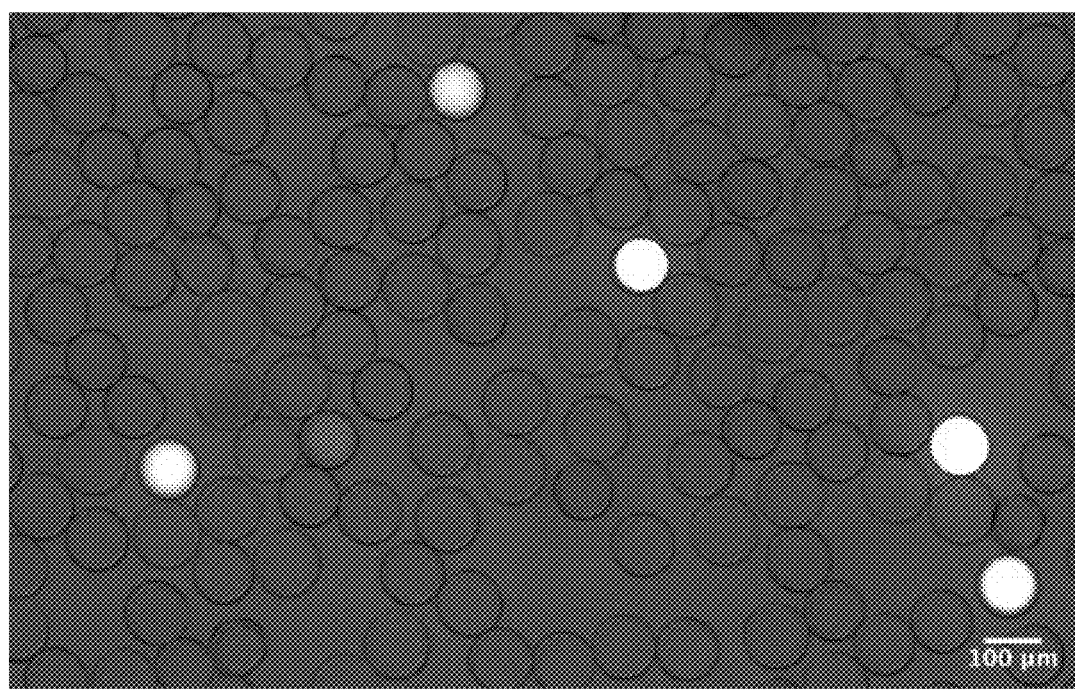
FIG. 36 is a DNA-stained image of genome-amplified DNA encapsulated in microcapsules.

FIG. 36 is a DNA-stained image of genome-amplified DNA encapsulated in microcapsules, and intermediate control of the approach of FIG. 31.

Figure 37:
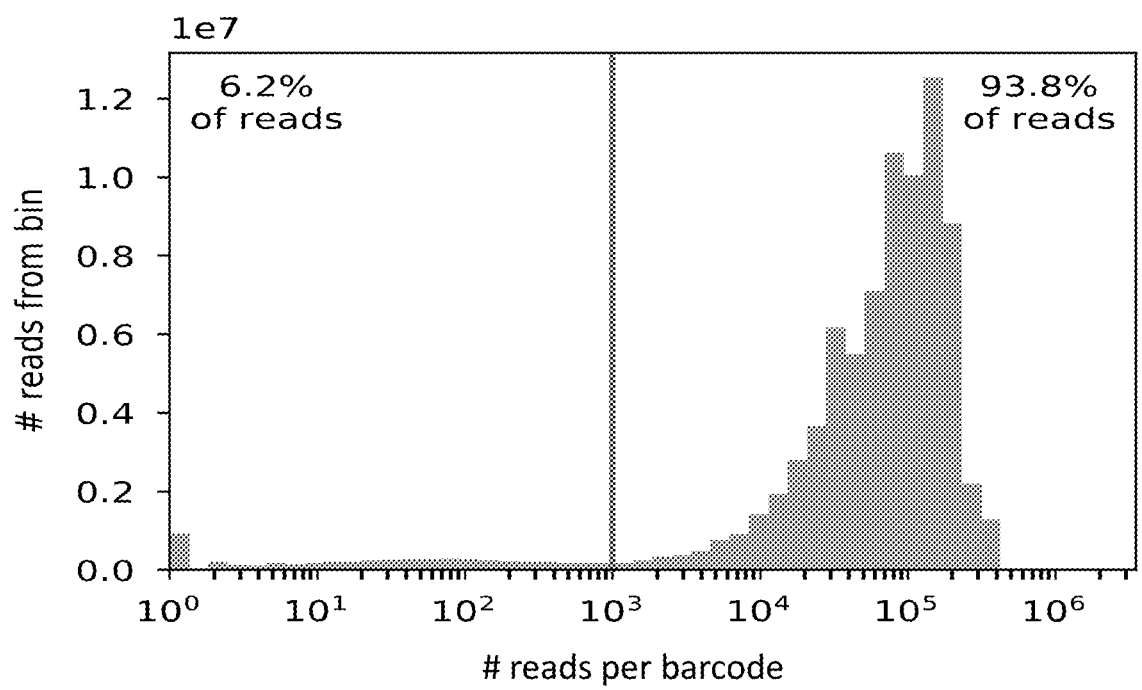
FIG. 37 depicts barcoding specificity for encapsulated nucleic acids of the approach of FIG. 31.

FIG. 37 depicts barcoding specificity for encapsulated nucleic acids of the approach of FIG. 31. Almost 94% of the reads mapped to highly abundant. which represent cell-containing microcapsules.

Figure 38:
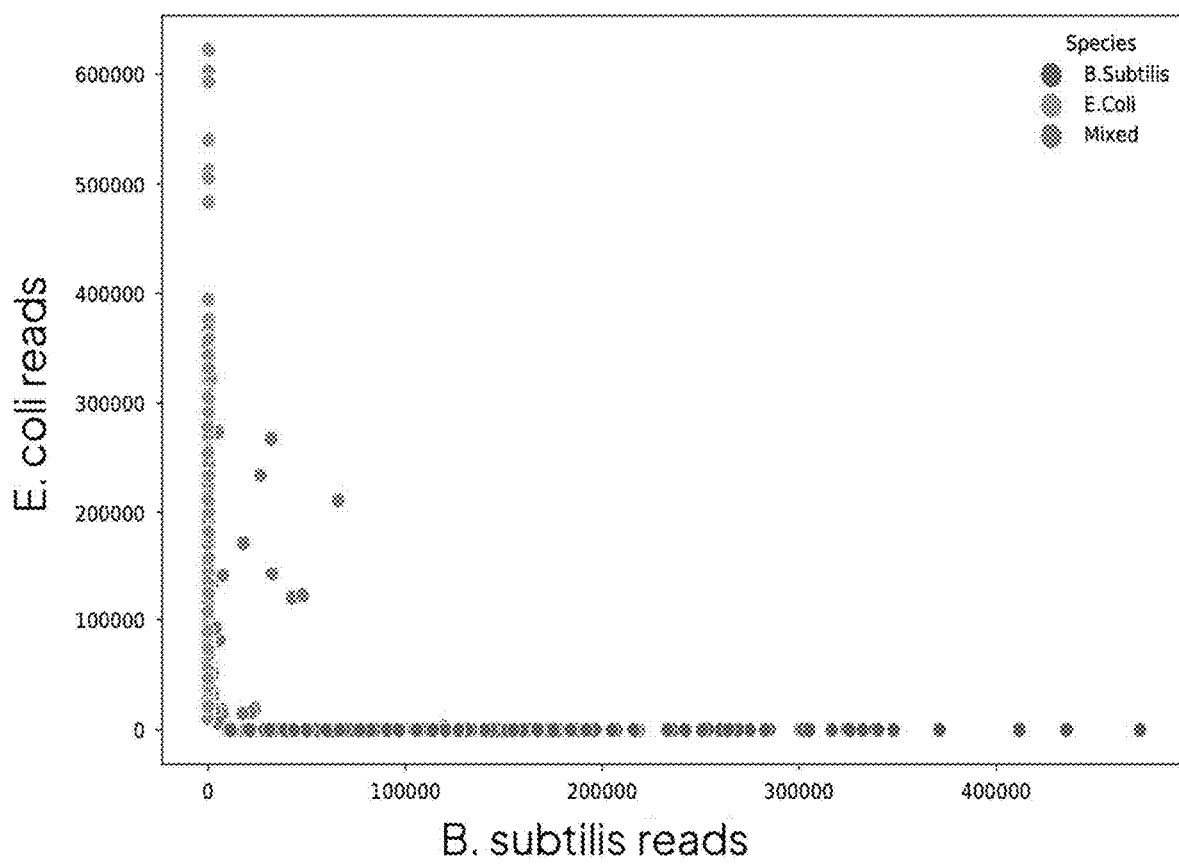
FIG. 38 presents results from a species-mixing experiment using the approach of FIG. 31.

FIG. 38 presents results from a species-mixing experiment using the approach of FIG. 31. E. coli read count is shown in the y-axis, ranging from 0 to 600,000 in intervals of 100,000. B. subtilis read count is presented in the x-axis, ranging from 0 to 400,000 in intervals of 100,000. In this plot, every dot is a barcode, and its position on the x- and y-axis depends on the number of reads harboring that barcode and uniquely mapping to B. subtilis or E. coli reference genomes, respectively. One sees that the vast majority of barcodes have reads assigned to one or the other of the bacterial genomes exclusively. Off-axis mixed-species barcodes are relatively rare, indicating that no cross-contamination of microcapsule-entrapped nucleic acids occurs, and that the barcoding approach efficiently allows one to map a barcoded read to its compartmentalized cell of origin.

Figure 39:
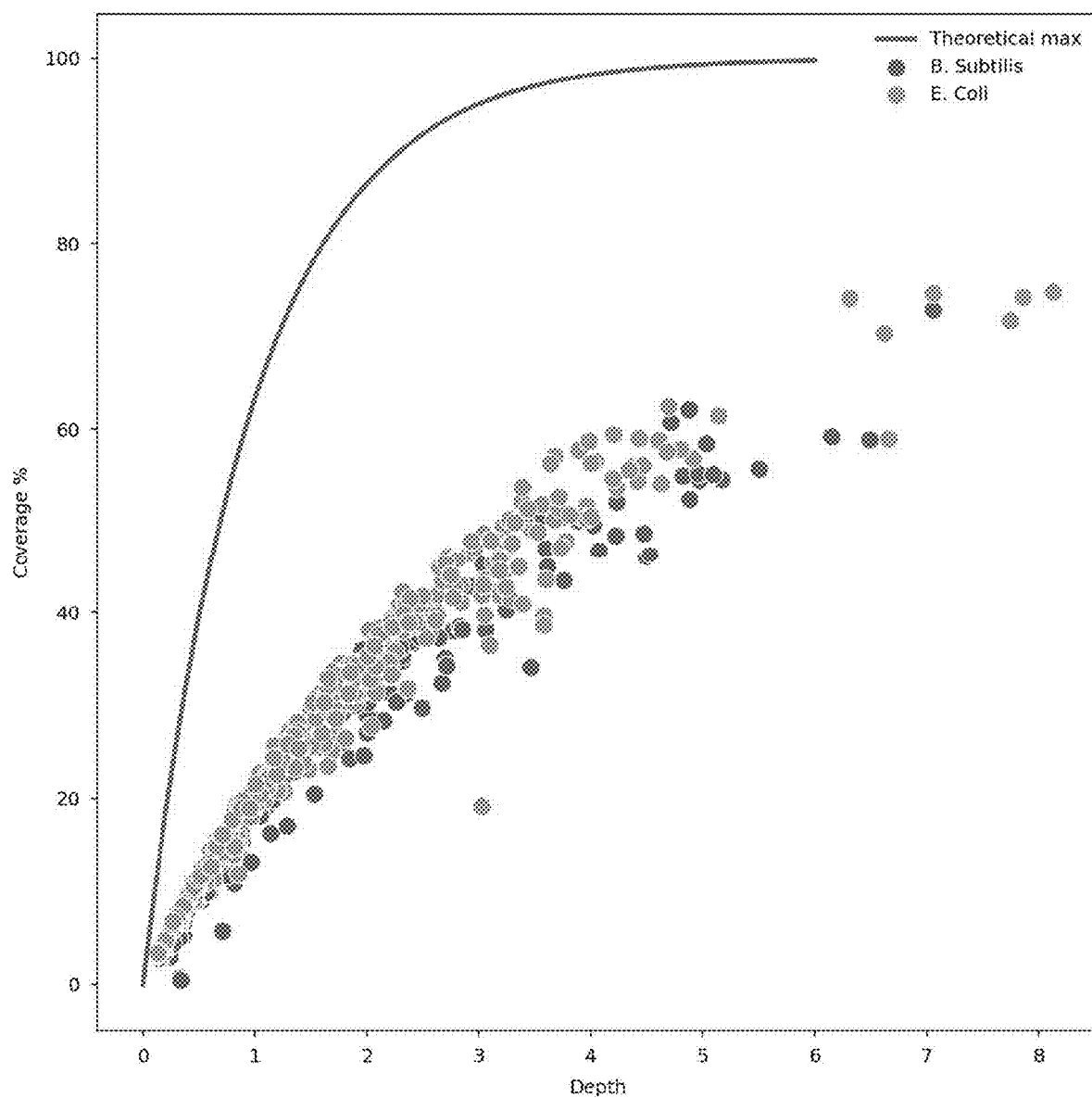
FIG. 39 shows the scatter of barcodes from the approach of FIG. 31 on a percent coverage vs depth plot.

FIG. 39 shows the scatter of barcodes from the approach of FIG. 31 on a percent coverage vs depth plot. Coverage is defined as the percentage of the reference genome covered at least once. Depth is defined as the average number of bases in the sequencing data per base in the reference genome. Percent coverage is presented on the y axis, from 0 to 100% in 20% intervals. The x-axis presents depth of coverage from 0 to 8. This graph indicates that for both E. coli and B. subtilis genomes, high coverage for a given depth is achieved using the approach demonstrated previously to accurately sort these genomes by their microcapsule of origin (FIG. 38).

Figure 40:
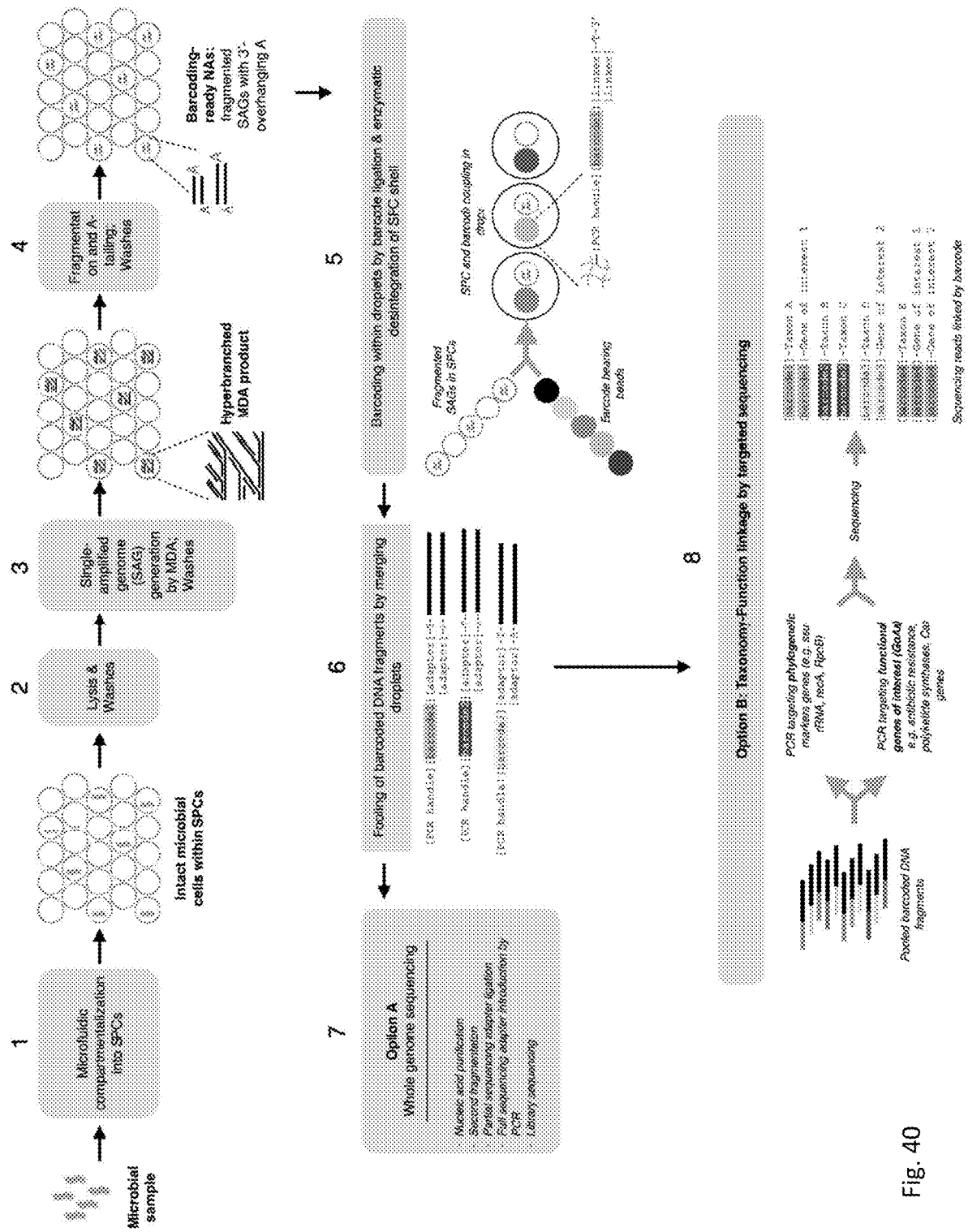
FIG. 40 presents a workflow for efficient genome amplification and barcoding in droplets using barcoding beads, followed by either whole genome or targeted sequencing.

FIG. 40 presents a workflow for efficient genome amplification and barcoding in droplets using barcoding beads, followed by either whole genome or targeted sequencing.

Figure 41A:
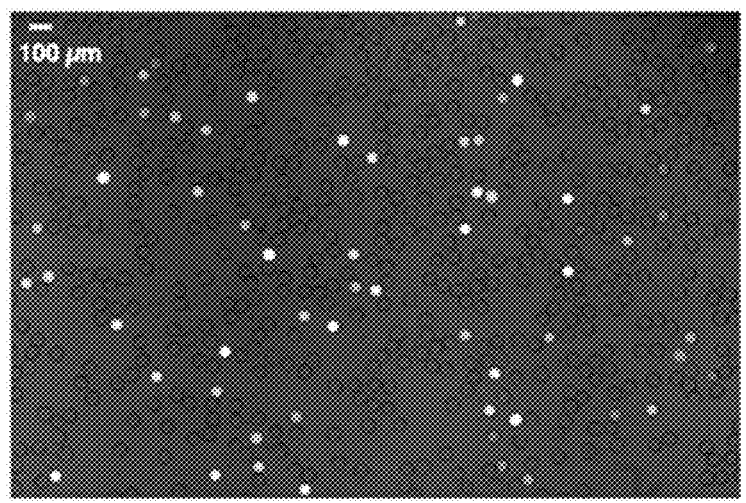
FIGS. 41A-41E show experimental results from applying the approach detailed in FIG. 40 for whole microbial genome sequencing.
Figure 41B:
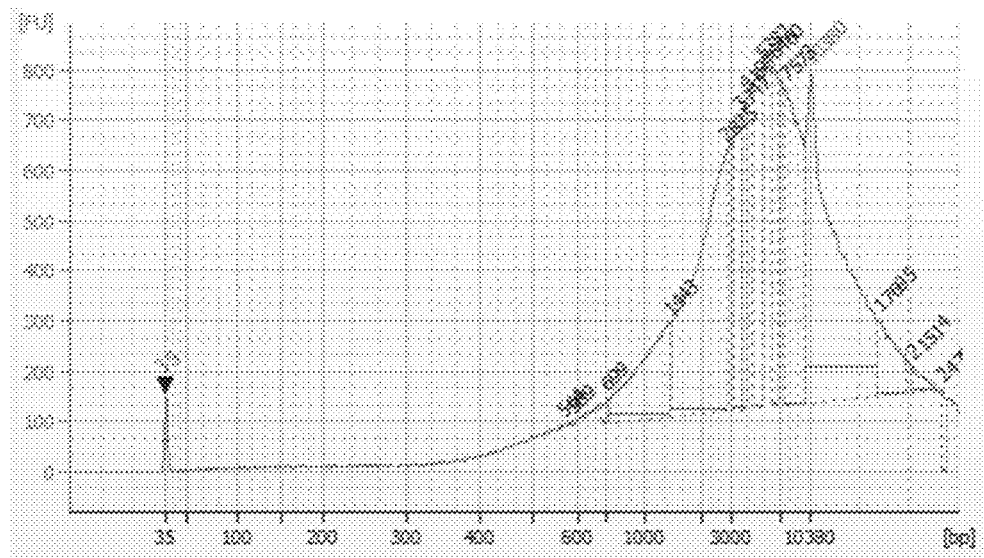
Figure 41C:
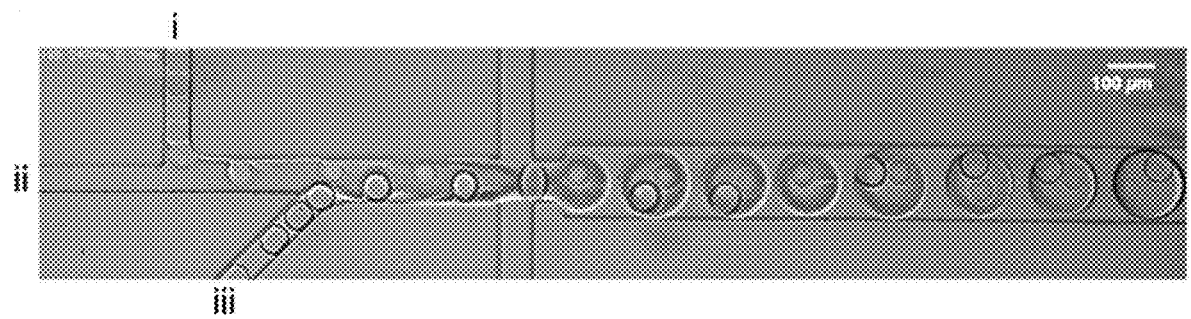
Figure 41D:
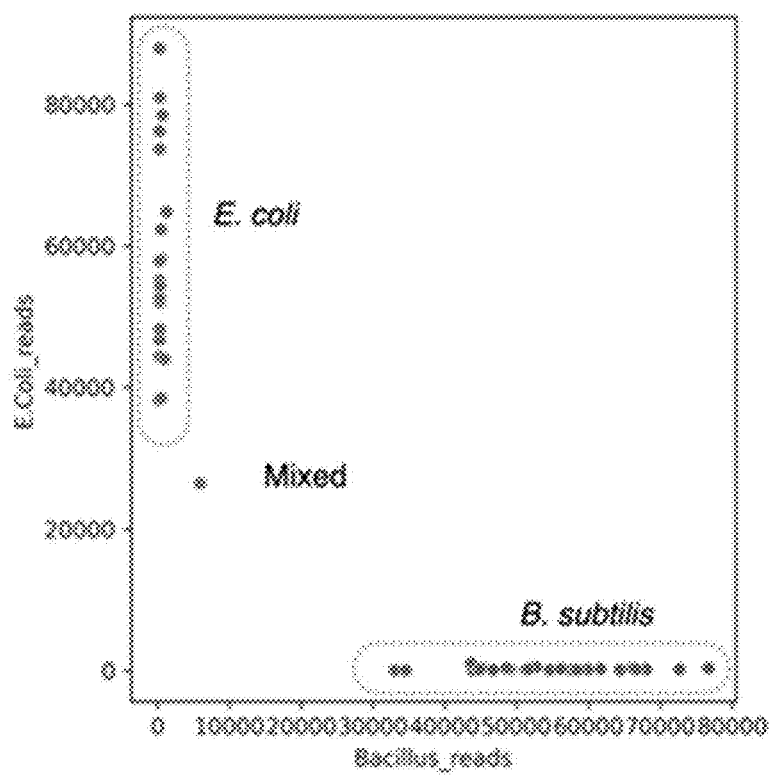
Figure 41E:
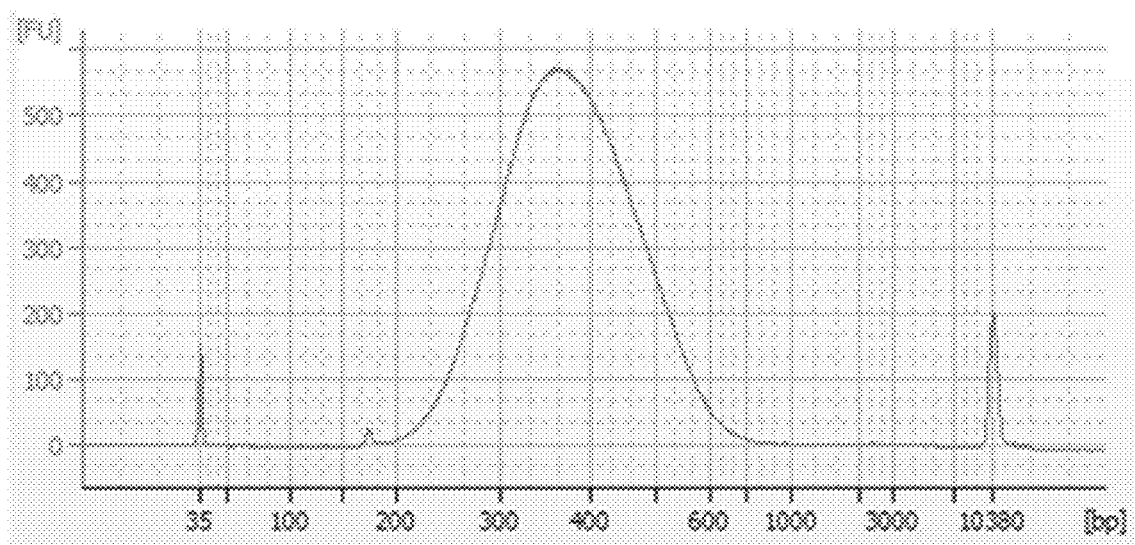

FIGS. 41A-41E show experimental results from applying the approach detailed in FIG. 40 for whole microbial genome sequencing. FIG. 41A shows single amplified genomes (SAGs) stained with a DNA-binding fluorescent dye (Cyto 9). FIG. 41B shows an electropherogram of fragmented SAG DNA prior to barcoding. FIG. 41C shows fragmented SAG-containing microcapsule co-encapsulation with barcoding beads. Barcoding beads were delivered through (i), ligation reagents through (ii), and microcapsules through (iii). FIG. 41D shows an electropherogram of final DNA libraries loaded onto an Illumina MiSeq sequencer. FIG. 41E shows the number of reads mapping to *E. coli* and *B. subtilis* genomes for each barcode. *E. coli* and *B. subtilis* SAG-bearing microcapsules were mixed at approximately equal ratios prior to barcoding.

FIGS. 42A-42D show bacterial lysis optimization results. Dots in the scatter plots represent individual barcodes (e.g., cells). Breadth is defined as the percentage of the reference *E. coli* genome covered at least once. Depth is defined as the average number of bases in the sequencing data per base in the reference genome. Both measures were obtained from BAM files after aligning the sequencing data to the *E. coli* reference genome using STARsolo. The solid line represents the maximum expected breadth for a given depth. The experimental procedure was as described below with MDA performed for 1 h, and modifications to the lysis conditions.

Figure 43:
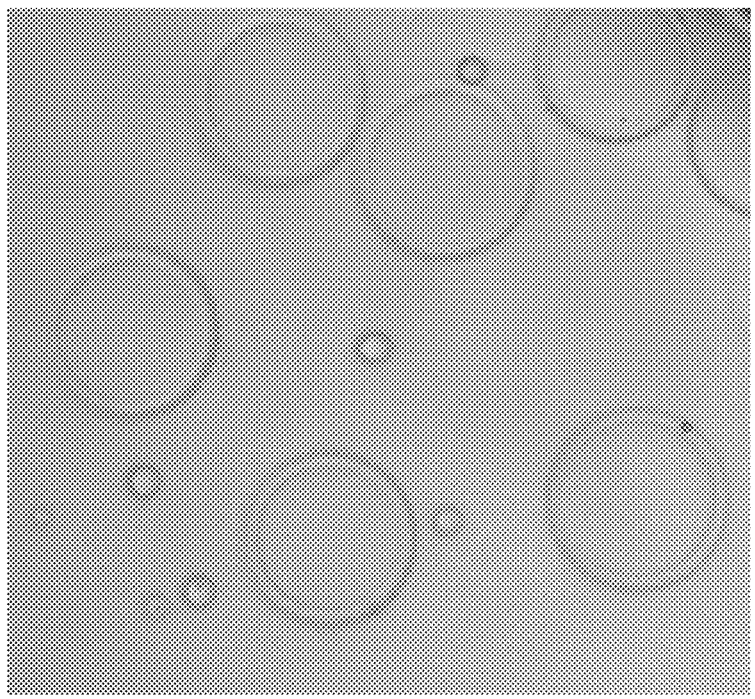
FIG. 43 depicts the results as a bright-light microscopy image of SPC suspension in aqueous buffer after chemically-induced shell polymerization.

FIG. 43 depicts the results as a bright-light microscopy image of SPC suspension in aqueous buffer after polymerization. Formulation 4 was used (5% TEMED in core phase, 5% APS in shell phase; as detailed in Example 11).

Figure 44:
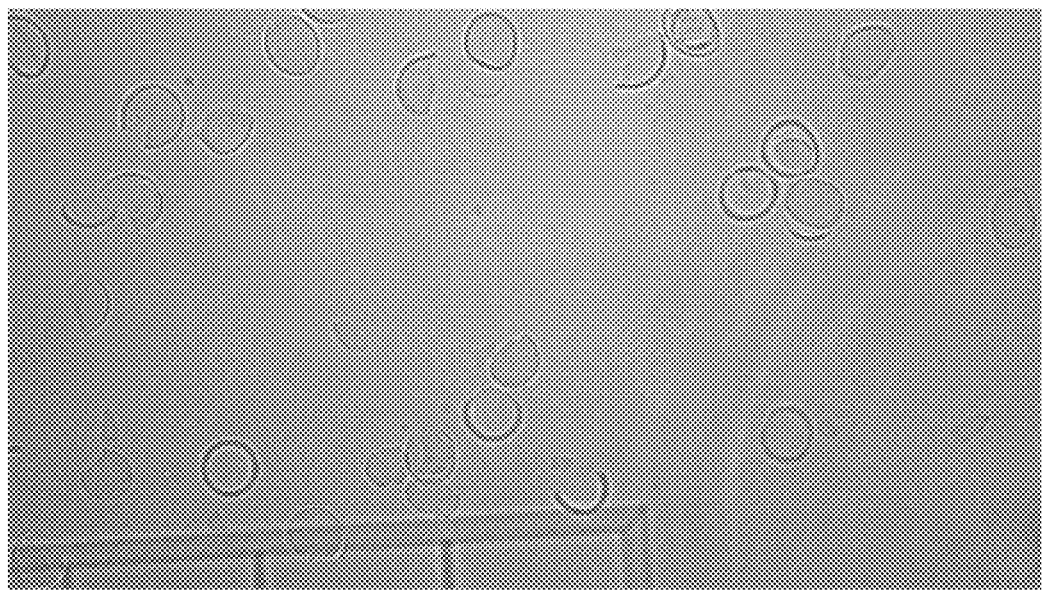
FIG. 44 shows the result of sonication on microcapsules under a first treatment regimen.

FIG. 44 shows the result of sonication on microcapsules. Some intact microcapsules and large debris is observed after 20% amplitude sonication. Reaction products are available for downstream analysis.

Figure 45:
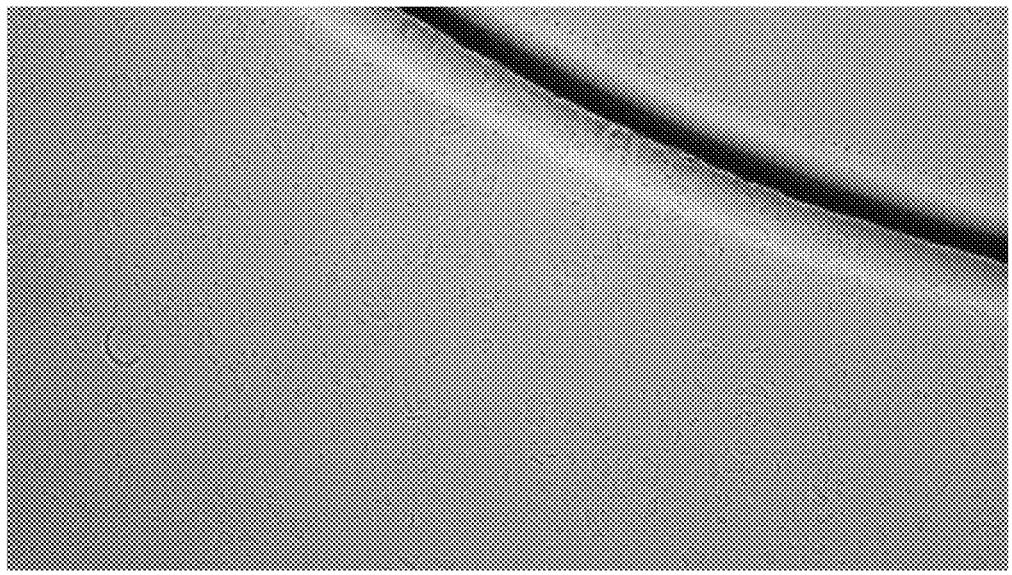
FIG. 45 shows the result of sonication on microcapsules under a second treatment regimen.

FIG. 45 shows the result of sonication on microcapsules. No intact microcapsules and large debris is observed after 40% amplitude sonication. Reaction products are available for downstream analysis.

Figure 46:
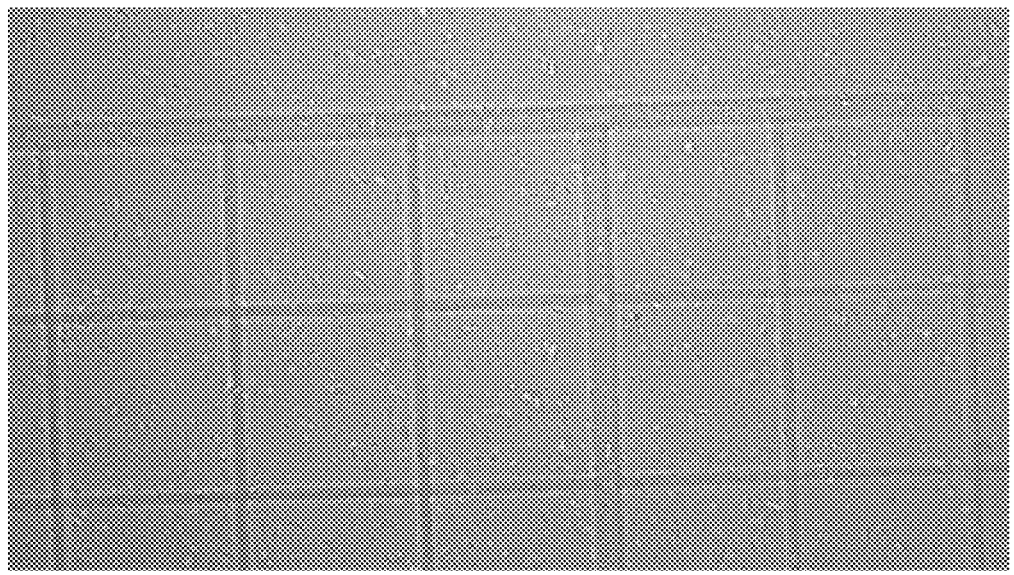
FIG. 46 shows the result of sonication on microcapsules under a third treatment regimen.

FIG. 46 shows the result of sonication on microcapsules. No intact microcapsules and small debris is observed after 80% amplitude sonication. Reaction products are available for downstream analysis.

Figure 47:
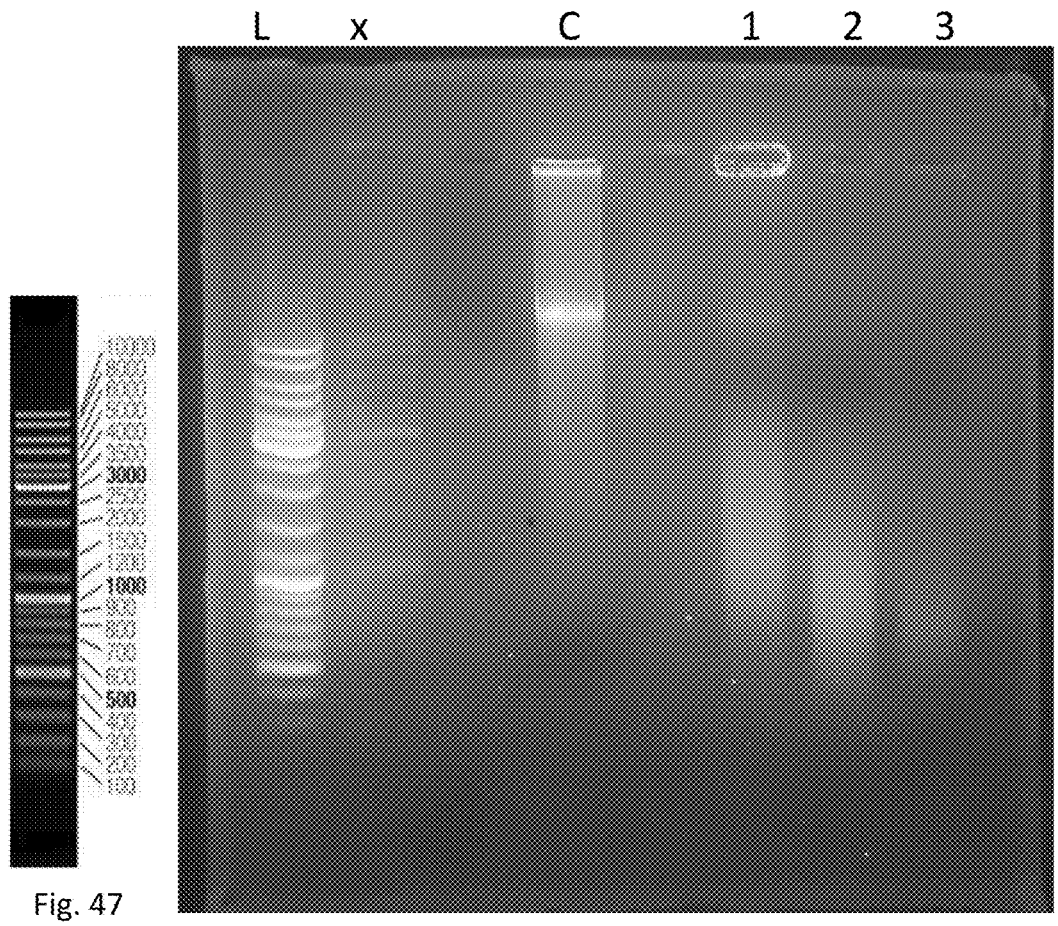
FIG. 47 presents an analysis of the effect of sonication on reaction products.
Figure 57:
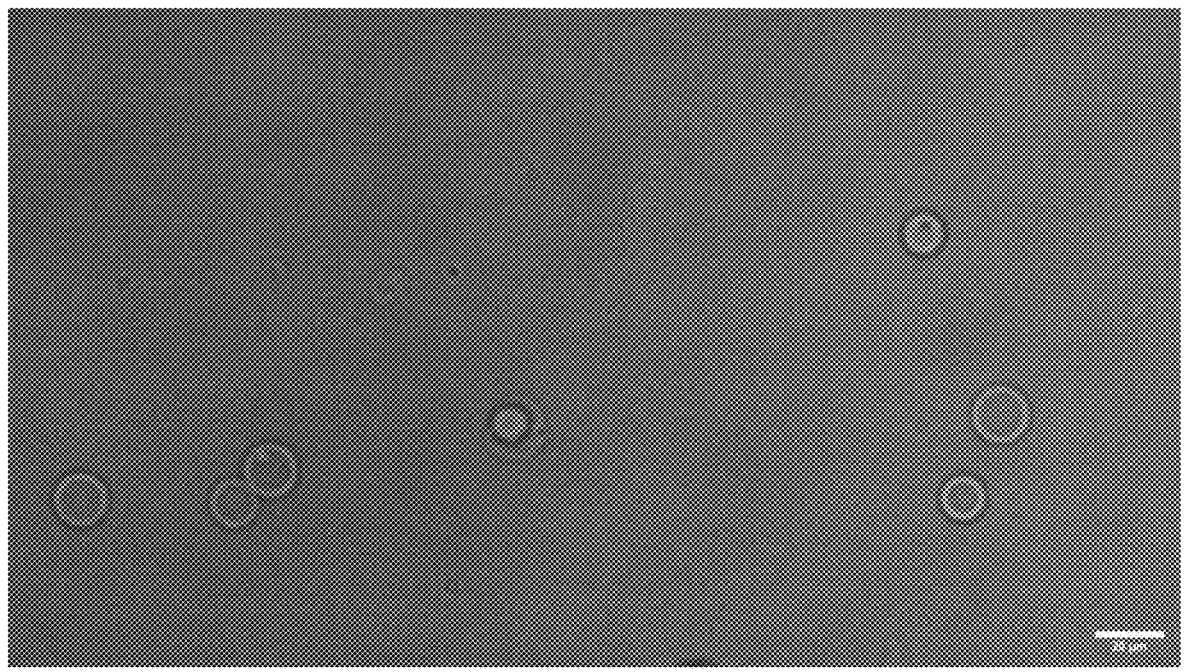
FIG. 57 shows formation of capsules of a diameter less than 20 um.

FIG. 47 presents an analysis of the effect of sonication on reaction products. Agarose gel electrophoresis shows that the MDA product inside SPCs is fragmented by sonication and the level of fragmentation depends on the amplitude of sonication, where some full-length MDA product and fragment length distribution between 3000 and 800 base pairs is observed after 20% amplitude sonication (FIG. 57 lane 1). Fragment length distribution between 1200 and 700 base pairs was observed after 40% amplitude sonication (FIG. 47, lane 2). Fragment length distribution between 800 and 600 base pairs was observed after 80% amplitude sonication (FIG. 47, lane 3). These results indicate that sonication may serve as an approach for microcapsule-contained nucleic acid fragmentation with or without concomitant release of the capsule content, alternatively to enzymatic shell degradation.

Figure 48:
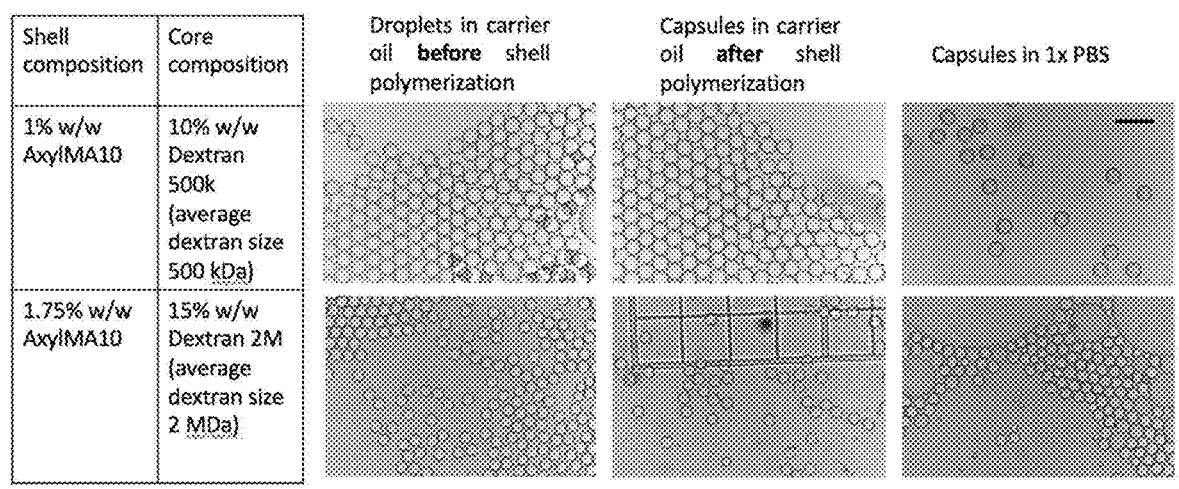
FIG. 48 shows successful microcapsule formation using methacryloyl-arabinoxylan (AxylMA10) as the shell polymer, and under varying starting material compositions.

FIG. 48 shows successful microcapsule formation using methacryloyl-arabinoxylan (AxylMA10) as the shell polymer, and under varying starting material compositions. SPCs were formed with both Dextran 500k (average molecular weight 500 kDa) and Dextran 2M (average molecular weight 2 MDa) as core polymer. The figure depicts Bright-field microscopy images of AxylMA10 shell-based SPCs at several stages of their generation, using two different average molecular weight dextrans as core polymers. Scale bar 200 um.

Figure 49:
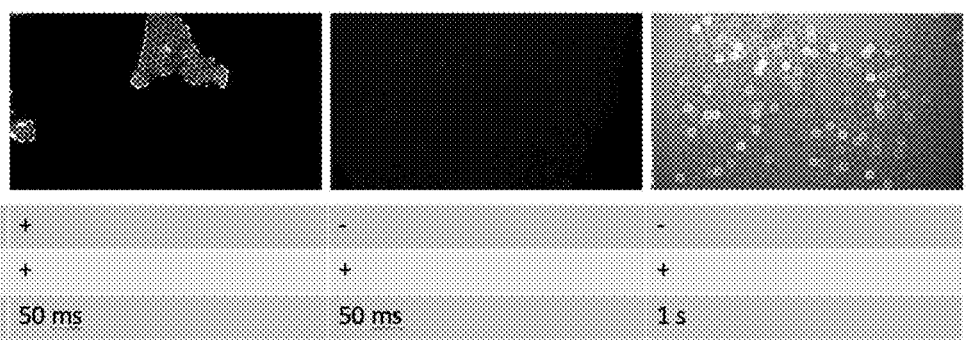
FIG. 49 presents fluorescent microscopy images of FITC-avidin-stained SPCs with (left) or without (center and right) biotin modification of the shell.

FIG. 49 presents fluorescent microscopy images of SPCs with (left) or without (center and right) biotin modification of the shell. The center and right images are the same field of view at two different exposure times. FITC-avidin stains capsules with biotin-modified shell but not those without the biotin modification.

Figure 50:
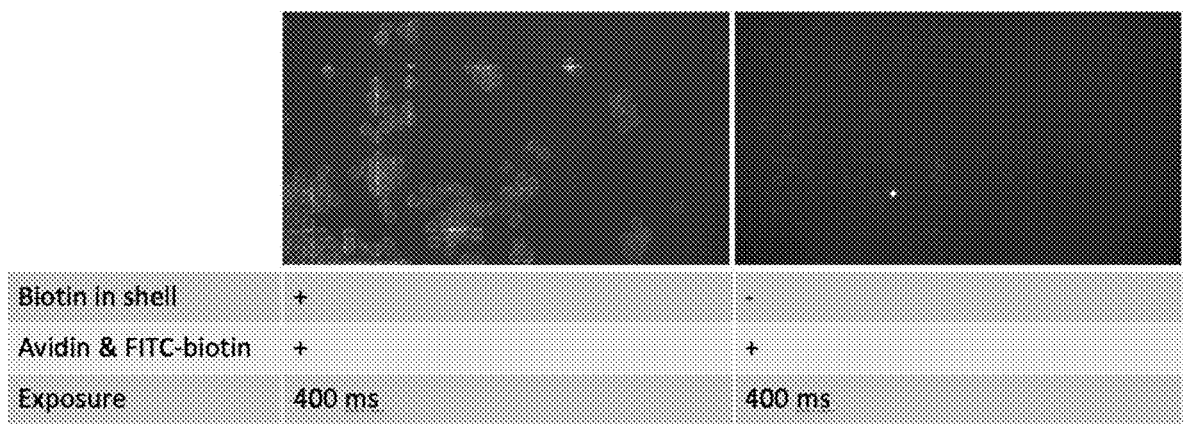
FIG. 50 presents fluorescent microscopy images of SPCs with (left) and without (right) biotin modification of the shell stained with FITC-biotin via avidin bridging.

FIG. 50 presents fluorescent microscopy images of SPCs with (left) and without (right) biotin modification of the shell stained with FITC-biotin via avidin bridging. Capsules with the biotinylated shell bind FITC-biotin via avidin bridging.

Figure 51:
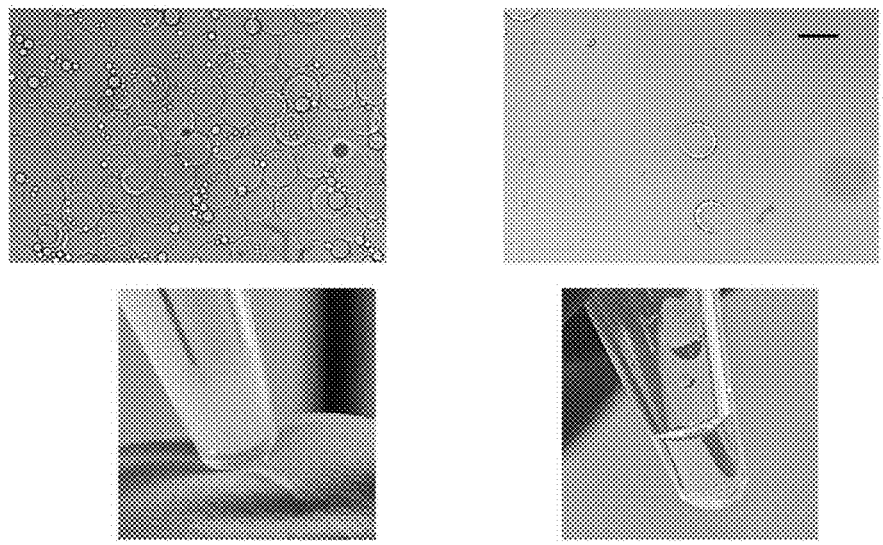
FIG. 51 presents appearance and enzymatic dissolution of SPCs with a 2-hydroxyethyl cellulose (HEC)-based shell.

FIG. 51 presents appearance and enzymatic dissolution of SPCs with a 2-hydroxyethyl cellulose (HEC)-based shell. Scale bar in microscopy images—100 um. The figure indicates that SPCs can be formed using a methacryloyl-modified 2-hydroxyethyl cellulose-based shell. Such SPCs can be dissolved by enzymatic shell digestion with a cellulase, as seen at right in the figure.

Figure 52:
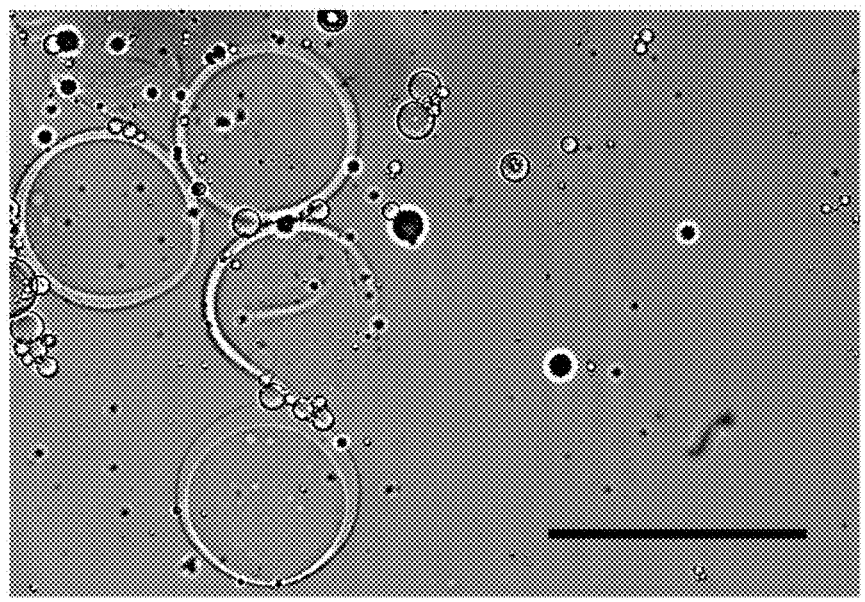
FIG. 52 depicts Bright-field microscopy image of SPCs formed using a shell polymer modified with acryloyl crosslinking moieties.

FIG. 52 depicts Bright-field microscopy image of SPCs formed using a shell polymer modified with acryloyl cross-linking moieties. Scale bar—100 um. The characteristic shell-core topology is observed.

Figure 53:
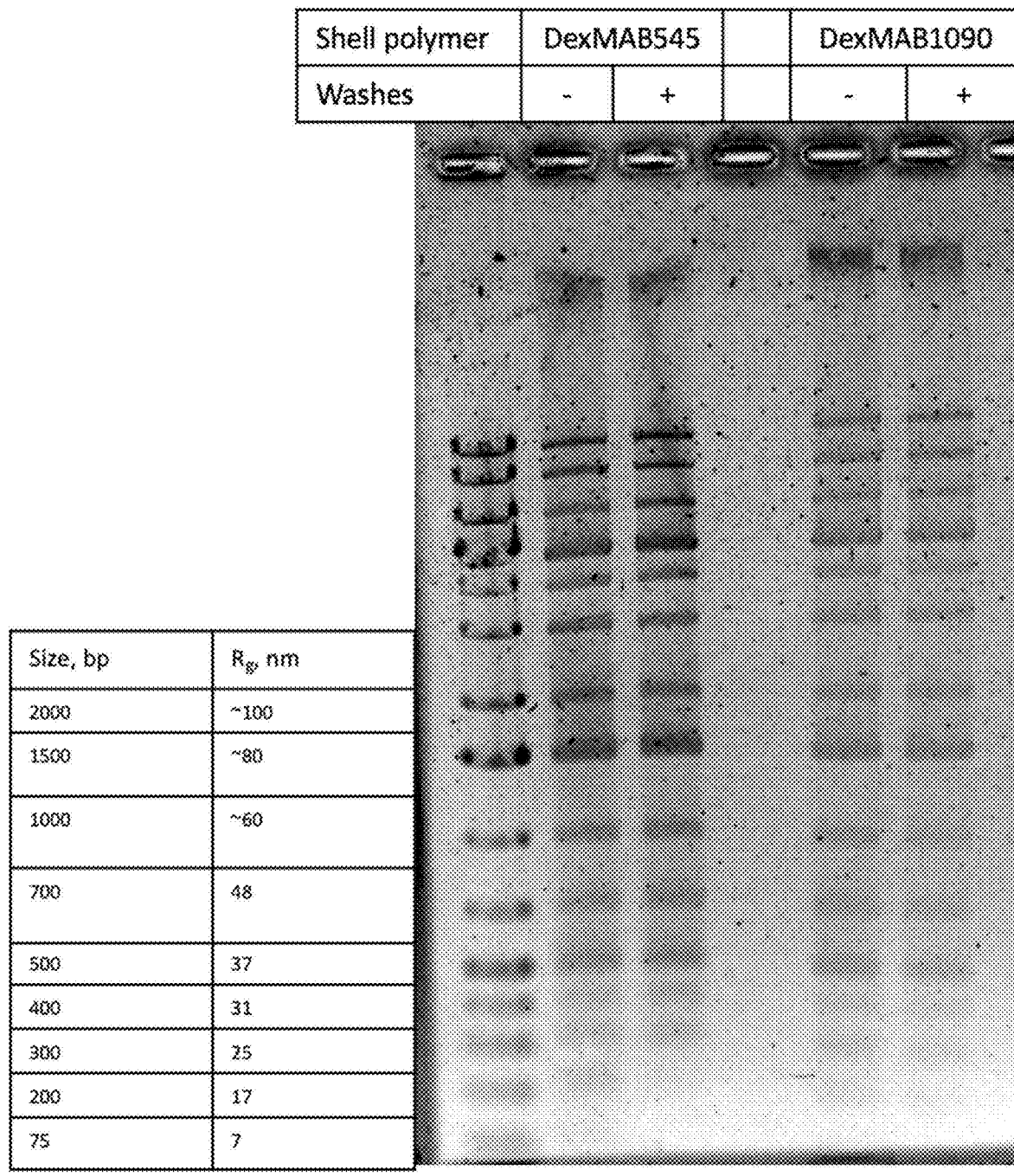
FIG. 53 shows an electrophoresis analysis of microcapsule contents retention for two shell polymers.

FIG. 53 shows an electrophoresis analysis of microcapsule contents retention for two shell polymers. The ladder is a Generuler 1 kb Plus DNA Ladder. Rg-dsDNA gyration radius calculated as described by Leonaviciene et al. As shown in FIG. 53, dsDNA fragments of 300 bp (gyration radius~25 nm) and above are retained within SPCs for the two shell polymers tested and cannot be removed from SPCs by washes. Visual evaluation of the agarose gels clearly suggests that the SPC shell based on the DexMAB545 polymer is permeable to 200 bp fragments (gyration radius~17 nm). By comparison, DexMAB1090 is less permeable as 200 bp fragments are retained better compared to DexMAB545.

Figure 54:
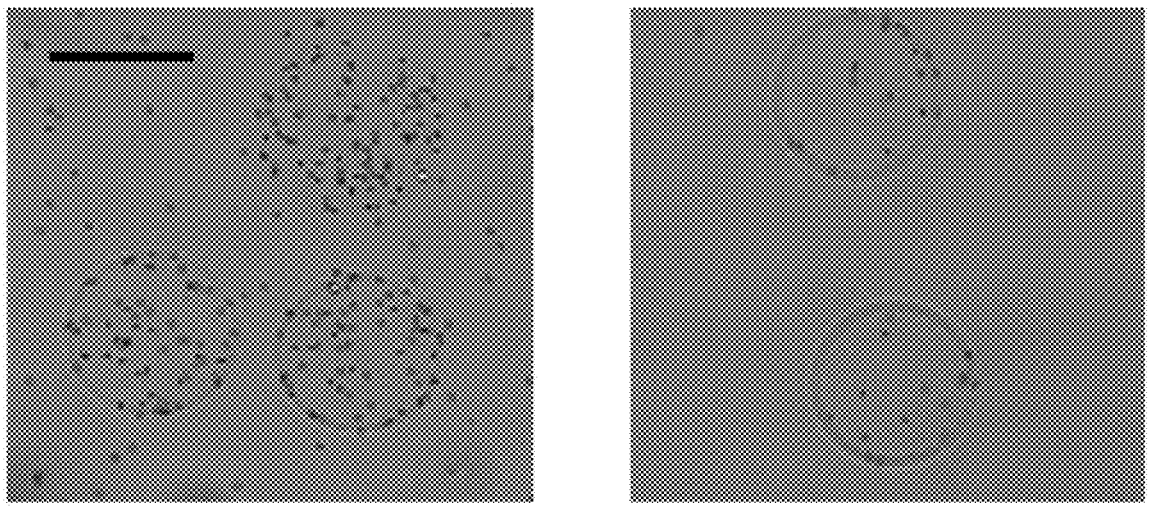
FIG. 54 presents bright-field microscopy images of SPCs with the shell pattern with 2-3 um magnetic beads.

FIG. 54 presents bright-field microscopy images of SPCs with the shell pattern with 2-3 um magnetic beads. Left—capsules in 1×PBS right after generation and breaking the water in oil emulsion. Right—capsules after 10 washes that involved vigorous vortexing to remove beads from the shell. A depletion in the number of magnetic beads in the shell can be appreciated after the procedure. Removal of the particles from the shell results in pores or holes of sizes at least as large as the particles removed.

Figure 55:
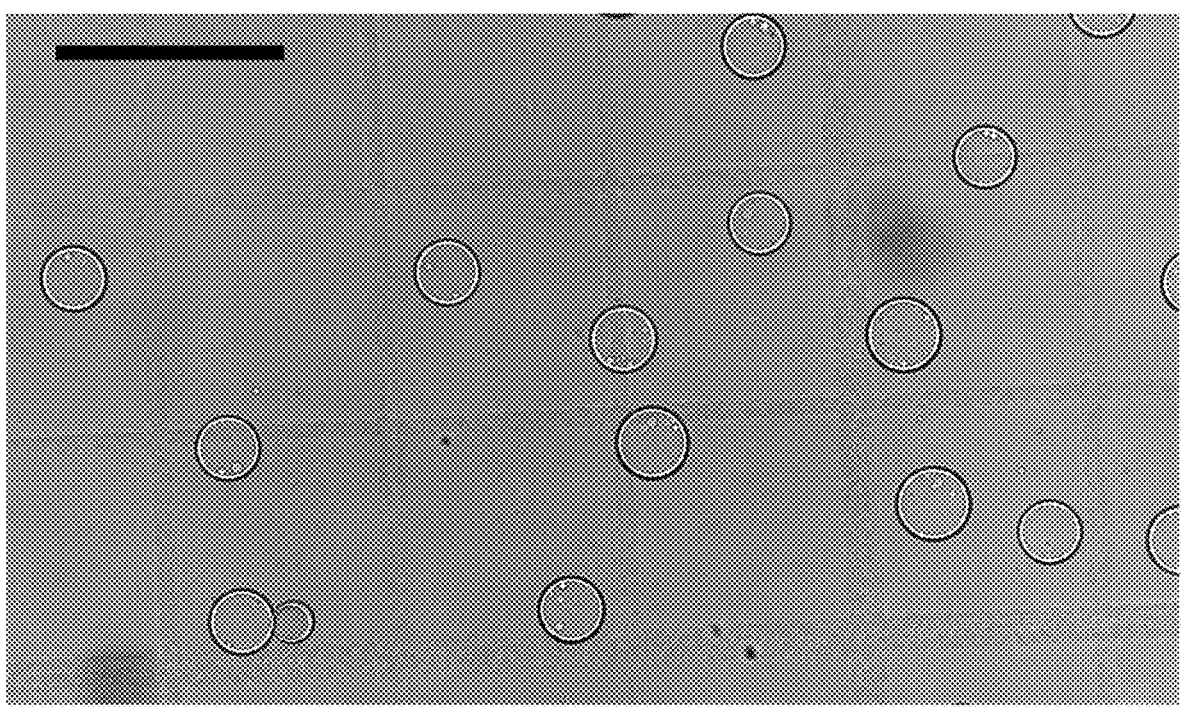
FIG. 55 shows that SPCs can be generated using the DexMAC21090 polymer, which uses the acetyl group as the hydrophilicity/hydrophobicity modifying moiety.

FIG. 55 shows that SPCs can be generated using the DexMAC21090 polymer, which uses the acetyl group as the hydrophilicity/hydrophobicity modifying moiety.

Figure 56:
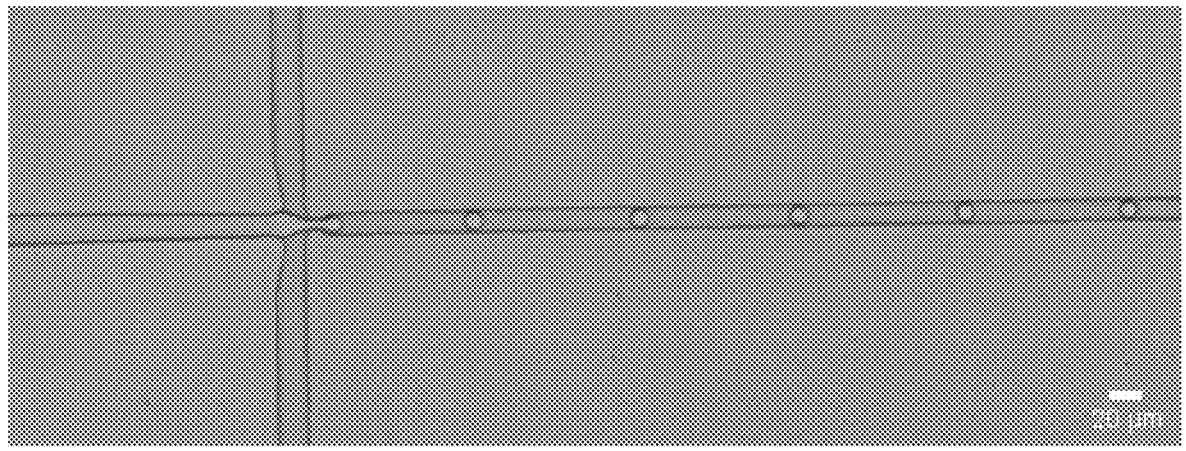
FIG. 56 shows formation of an emulsion pursuant to formation of capsules of a diameter less than 20 um.

FIG. 56 shows formation of an emulsion pursuant to formation of capsules of a diameter less than 20 um.

FIG. 57 shows formation of capsules of a diameter less than 20 um.

Figure 58:
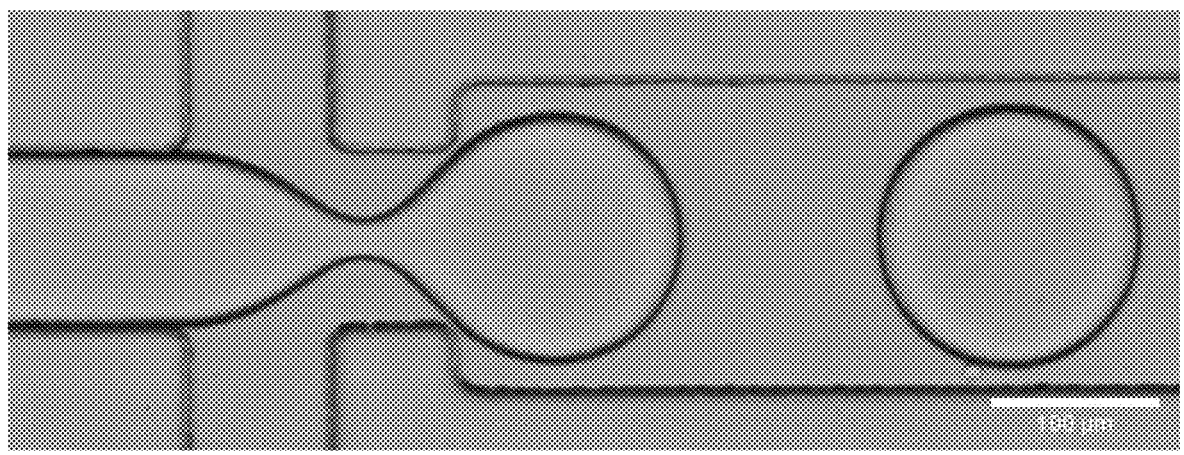
FIG. 58 shows formation of an emulsion pursuant to formation of capsules of a diameter greater than 100 um.

FIG. 58 shows formation of an emulsion pursuant to formation of capsules of a diameter greater than 100 um.

Figure 59:
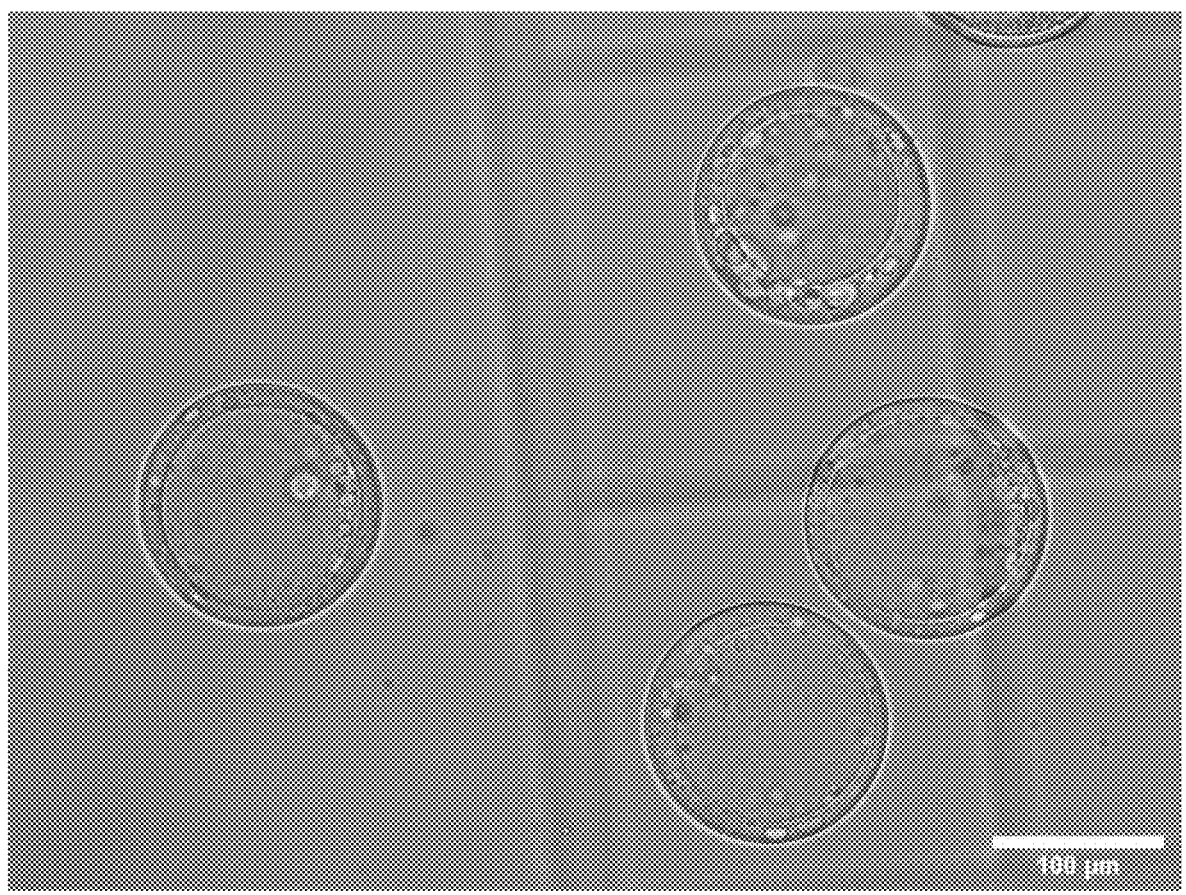
FIG. 59 shows formation of capsules of a diameter greater than 100 um.

FIG. 59 shows formation of capsules of a diameter greater than 100 um.

Figure 60:
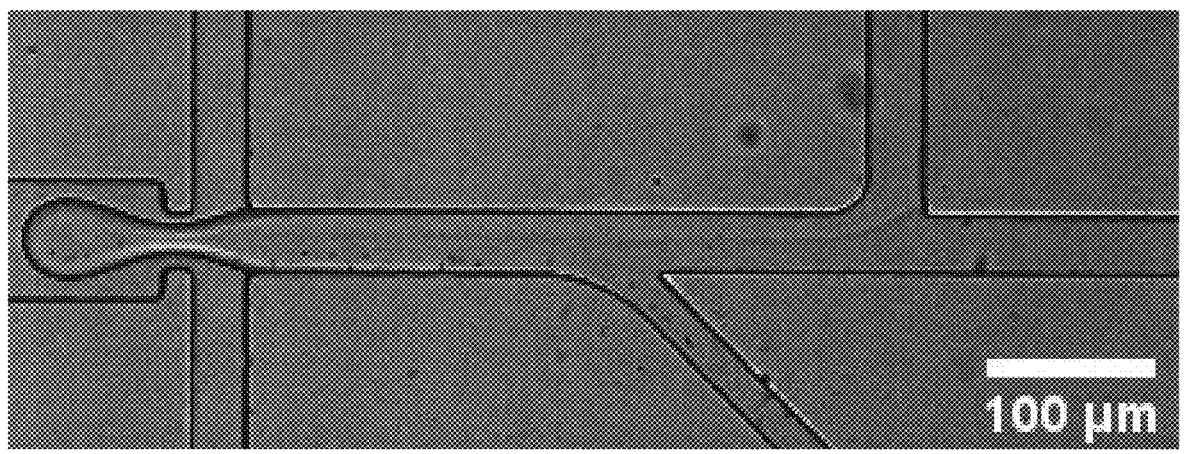
FIG. 60 shows formation of an emulsion pursuant to triple co-flow aqueous phase capsule generation.

FIG. 60 shows formation of an emulsion pursuant to triple co-flow aqueous phase capsule generation. One sees Bright-field microscopy image of Core solutions 1 and 2 (Top Right and Bottom Right respectively) making a stable flow of required proportions with Shell solution (Far Right). Particle encapsulation can be observed within the drops (Left).

Figure 61:
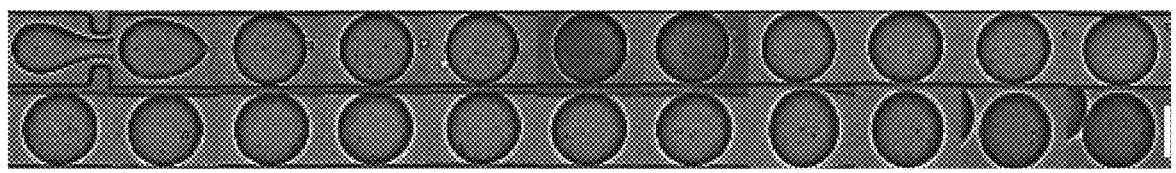
FIG. 61 presents a Bright-field microscopy image montage of one pre-SPC drop traveling along the microfluidic channel just after it has been formed in a triple co-flow chip.

FIG. 61 presents a Bright-field microscopy image montage of one pre-SPC drop traveling along the microfluidic channel just after it has been formed in a triple co-flow chip, note the 4 dark particles changing position. Vertical scale bar at 50 μm. Elapsed time is 25 ms start to finish.

Figure 62:
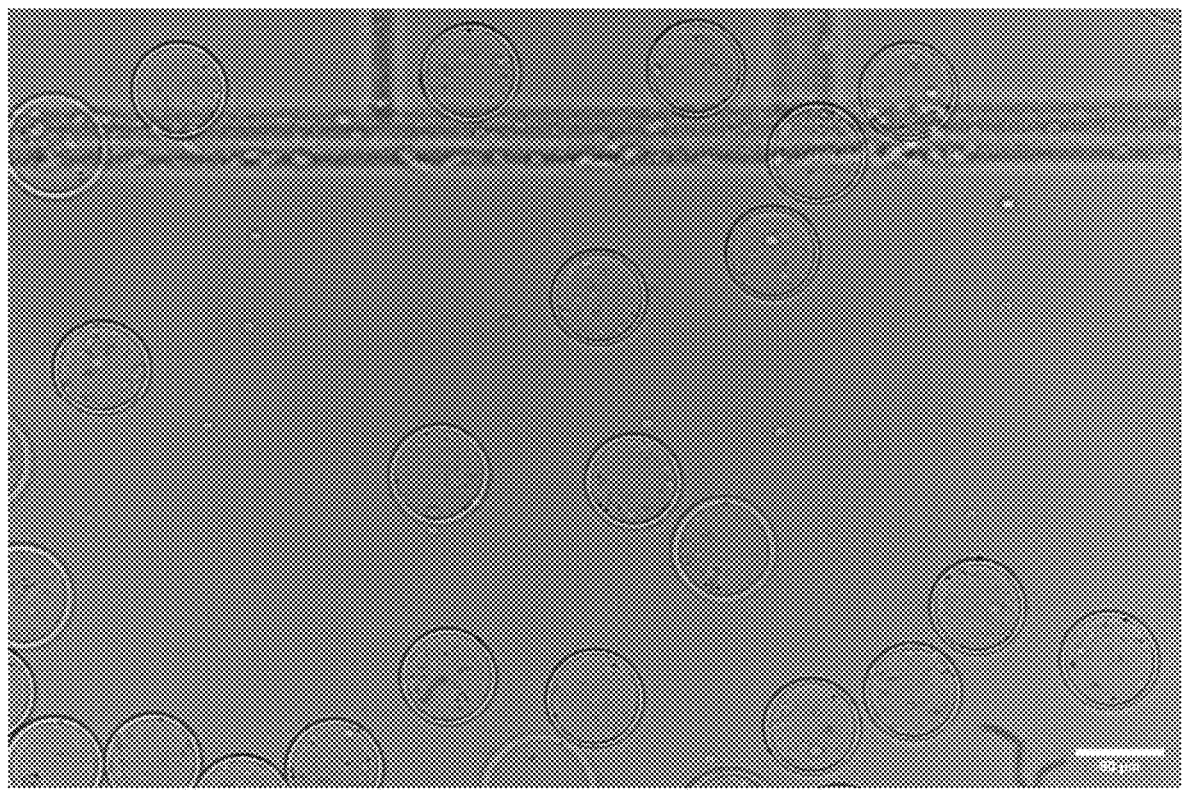
FIG. 62 shows a bright-field microscopy image of an aqueous suspension of SPCs generated using a triple co-flow chip.

FIG. 62 shows a bright-field microscopy image of an aqueous suspension of SPCs generated using a triple co-flow chip. SPCs of approx. 54 μm in diameter are formed. Note dark particles embedded within the capsules. This demonstrates that having the solutions destined for the core of the capsules separated into two (FIG. 60) did not hinder capsule formation. This way sample constituents can be effectively separated prior to the capsule generation step.

Figure 63:
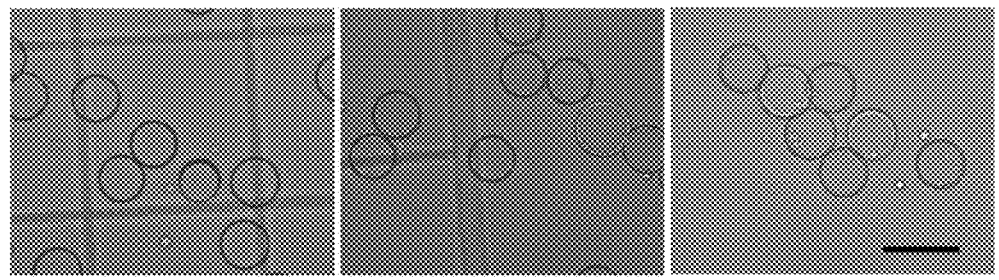
FIG. 63 shows that SPCs are successfully formed when different dextrans with average molecular weights in the range from 10 kDa to 2 MDa are used as the core polymer.

FIG. 63 shows that SPCs are successfully formed when different dextrans with average molecular weights in the range from 10 kDa to 2 MDa are used as the core polymer. The characteristic shell-core topology is observed.

Figure 64:
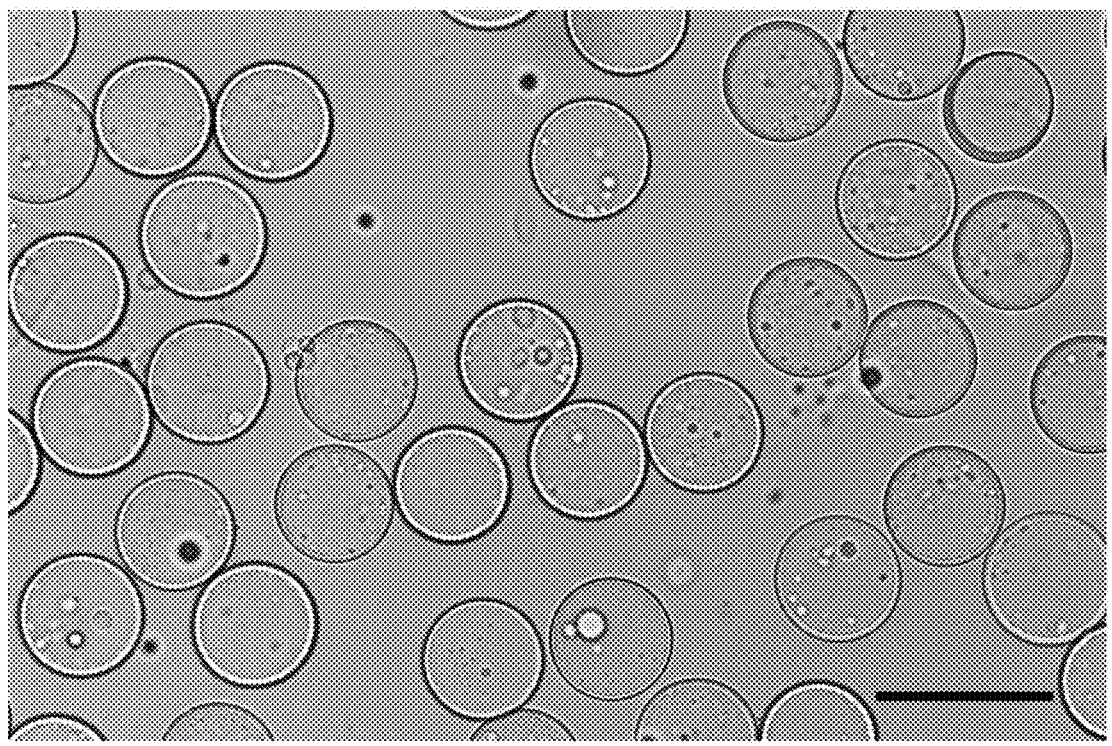
FIG. 64 shows that SPCs are successfully formed when using a blend of two shell-forming polymers with different crosslinking moieties, DexMAB1090 and DexAB50100.

FIG. 64 shows that SPCs are successfully formed when using a blend of two shell-forming polymers, DexMAB1090 and DexAB50100. The characteristic shell-core topology is observed.

NUMBERED EMBODIMENTS

The disclosure is further elucidated through listing of the following numbered embodiments. Some numbered embodiments refer to previous embodiments. This does not preclude numbered embodiments from depending from other or multiple other embodiments, such that any numbered embodiment herein is contemplated to depend from any other numbered embodiment herein.

A partial listing of numbered embodiments includes the following.

1. A process for manufacturing a composition including a plurality of microcapsules, comprising: (a) emulsifying in a droplet generation device (i) a first aqueous solution comprising a first polymer, and (ii) a second aqueous solution comprising a second polymer, in an oil, wherein: the first polymer comprises dextran modified with (i) conjugated methacryloyl cross-linking moieties and (ii) conjugated butyryl moieties; the second polymer comprises dextran not modified with conjugated methacryloyl cross-linking moieties and not modified with conjugated butyryl moieties; the first aqueous solution and/or the second aqueous solution comprises a biological entity; monodisperse water-in-oil droplets containing the first polymer, the second polymer and the biological entity are generated; and an aqueous two-phase system is formed inside the water-in-oil droplets in which a liquid core is completely surrounded by a liquid shell and the biological species is preferentially distributed in the liquid core; and (b) exposing the microcapsules to cross-linking conditions that conjugate at least a portion of the methacryloyl moieties in the first polymer, thereby forming a hydrogel shell surrounding a core in a plurality of microcapsules. A1. A composition, comprising a plurality of microcapsules each comprising a core surrounded by a shell, wherein: the shell is a hydrogel comprising a first polymer, wherein: the first polymer comprises a polysaccharide modified with a conjugated cross-linking moiety and optionally modified with a conjugated hydrophilicity/hydrophobicity-modifying moiety, and molecules of the cross-liking moiety of the first polymer are cross-linked in the hydrogel; and the core comprises a second polymer comprising a polysaccharide that does not include the cross-linking moiety and does not include the hydrophilicity/hydrophobicity-modifying moiety of the first polymer. A1.1. The composition of embodiment A1, wherein the microcapsule or portion thereof is glycosidase degradable. A2. The composition of embodiment A1 or A1.1, wherein the first polymer is a major component of the shell and the second polymer is a major component of the core. A3. The composition of embodiment A1, A1.1 or A2, wherein the first polymer and the second polymer comprise a different polysaccharide. A4. The composition of embodiment A1, A1.1 or A2, wherein the first polymer and the second polymer comprise the same polysaccharide. A5. The composition of any one of embodiments A1-A4, wherein the polysaccharide of the first polymer, or the first polymer and the second polymer, is a charge-neutral non-ionic polysaccharide. A6. The composition of embodiment A5, wherein the polysaccharide comprises monomers linked by a glycosidic bond. A7. The composition of embodiment A6, wherein the polysaccharide is a glucan. A8. The composition of embodiment A6 or A7, wherein the polysaccharide comprises pentose and/or hexose monomers. A9. The composition of embodiment A6 or A7, wherein the polysaccharide comprises glucose and/or fructose monomers. A10. The composition of any one of embodiments A5-A9, wherein the polysaccharide is naturally occurring. A10.1. The composition of embodiment A10, wherein the polysaccharide is chosen from dextran and cellulose. A10.2. The composition of embodiment A10, wherein the polysaccharide is dextran. A11. The composition of any one of embodiments A5-A9, wherein the polysaccharide is not naturally occurring. A11.1. The composition of embodiment A11, wherein the polysaccharide is ficoll. A12. The composition of any one of embodiments A5-A11.1, wherein the polysaccharide has a molecular mass of about 5,000 g/mole to about 50,000,000 g/mole. A13. The composition of embodiment A12, wherein the polysaccharide has a molecular mass of about 50,000 g/mole to about 2,000,000 g/mole. A14. The composition of embodiment A13, wherein the polysaccharide has a molecular mass of about 500,000 g/mole. A15. The composition of any one of embodiments A1-A14, wherein the first polymer comprises one type of cross-linking moiety. A16. The composition of embodiment A15, wherein the first polymer comprises two or more types of cross-linking moieties. A17. The composition of any one of embodiments A1-A16, wherein the cross-linking moiety or moieties are chosen from light-activated, chemically-activated or thermally-activated cross-linking moieties. A18. The composition of any one of embodiments A1-A17, wherein the cross-linking moiety or moieties independently are chosen from an acryloyl group or a substituted acryloyl group. A19. The composition of embodiment A18, wherein the cross-linking moiety or moieties independently are selected from acryloyl, or methacryloyl, or acryloyl and methacryloyl. A20. The composition of any one of embodiments A1-A19, wherein the second polymer comprises no cross-linking moiety. A21. The composition of any one of embodiments A1-A20, wherein the second polymer is not cross linked. A22. The composition of any one of embodiments A1-A21, wherein the first polymer comprises the hydrophilicity/hydrophobicity modifying moiety. A23. The composition of embodiment A22, wherein the hydrophilicity/hydrophobicity modifying moiety modifies water solubility of the first polymer. A24. The composition of embodiment A22 or A23, wherein the first polymer comprises one type of the hydrophilicity/hydrophobicity-modifying moiety. A25. The composition of embodiment A24, wherein the first polymer comprises two or more types of a hydrophilicity/hydrophobicity-modifying moiety. A26. The composition of any one of embodiments A22-A25, wherein the hydrophilicity/hydrophobicity-modifying moiety comprises a fatty acid acyl group. A27. The composition of embodiment A26, wherein the fatty acid is a C2-C8 fatty acid. A28. The composition of embodiment A27, wherein the hydrophilicity/hydrophobicity-modifying moiety comprises a butyryl group. A29. The composition of any one of embodiments A1-A28, wherein the second polymer comprises no hydrophilicity/hydrophobicity-modifying moiety that modifies the first polymer. A30. The composition of any one of embodiments A1-A20, wherein the cross-linking moiety, or the hydrophilicity/hydrophobicity-modifying moiety, or the cross-linking moiety and the hydrophilicity/hydrophobicity-modifying moiety, are covalently linked to the polymer backbone of the first polymer. A31. The composition of any one of embodiments A1-A30, wherein: the first polymer backbone comprises monomers, and a molar ratio of (i) the cross-linking moiety to (ii) first polymer monomer is about 0.01 to about 2.0. A31.1. The composition of any one of embodiments A1-A31, wherein: the first polymer backbone comprises monomers, and a molar ratio of (i) the cross-linking moiety to (ii) first polymer monomer is about 0.01 or greater. A31.2. The composition of any one of embodiments A1-A31, wherein: the first polymer backbone comprises monomers, and a molar ratio of (i) the cross-linking moiety to (ii) first polymer monomer is about 0.20 or less. A31.3. The composition of any one of embodiments A1-A31, wherein: the first polymer backbone comprises monomers, and a molar ratio of (i) the cross-linking moiety to (ii) first polymer monomer is about 0.01 to about 0.20. A32. The composition of any one of embodiments A22-A31.3, wherein: the first polymer backbone comprises monomers, and a molar ratio of (i) the hydrophilicity/hydrophobicity-modifying moiety to (ii) first polymer monomer is about 0.05 to about 1.0. A32.1. The composition of any one of embodiments A22-A31.3, wherein: the first polymer backbone comprises monomers, and a molar ratio of (i) the hydrophilicity/hydrophobicity-modifying moiety to (ii) first polymer monomer is about 0.10 or greater. A32.2. The composition of any one of embodiments A22-A31.3, wherein: the first polymer backbone comprises monomers, and a molar ratio of (i) the hydrophilicity/hydrophobicity-modifying moiety to (ii) first polymer monomer is about 0.80 or less. A32.3. The composition of any one of embodiments A22-A31.3, wherein: the first polymer backbone comprises monomers, and a molar ratio of (i) the hydrophilicity/hydrophobicity-modifying moiety to (ii) first polymer monomer is about 0.20 to about 0.80. A32.4. The composition of any one of embodiments A22-A31.3, wherein: the first polymer backbone comprises monomers, and a molar ratio of (i) the hydrophilicity/hydrophobicity-modifying moiety to (ii) first polymer monomer is about 0.25 to about 0.65. A33. The composition of any one of embodiments A1-A32.4, wherein: the polysaccharide of the first polymer is modified by the cross-linking moiety and is modified by the hydrophilicity/hydrophobicity-modifying moiety; the cross-linking moiety is methacryloyl; and the hydrophilicity/hydrophobicity-modifying moiety is butyryl. A34. The composition of any one of embodiments A1-A33, wherein the first polymer comprises a detectable label. A34.1. The composition of embodiment A34, wherein the detectable label comprises a fluorophore or a dye. A35. The composition of any one of embodiments A1-A34.1, wherein the first polymer comprises a binding partner moiety to which a binding partner counterpart moiety can bind. A36. The composition of embodiment A35, wherein the binding partner moiety is biotin and the binding partner counterpart moiety is avidin, or the binding partner counterpart moiety is biotin and the binding partner moiety is avidin. A37. The composition of any one of embodiments A33-A36, wherein the detectable label and/or the binding partner moiety are covalently attached to the first polymer backbone. A38. The composition of any one of embodiments A1-A37, wherein the microcapsules remain intact under pH range of about pH 2 to about pH 12 at 37 degrees Celsius for 2 hours or more. A39. The composition of any one of embodiments A1-A38, wherein the microcapsules remain intact under polymerase chain reaction thermocycling conditions. A40. The composition of any one of embodiments A1-A39, wherein the microcapsules are microspheroids. A41. The composition of embodiment A40, wherein the microcapsules are defined by a diameter of about 1 micrometer to about 10,000 micrometers. A42. The composition of embodiment A41, wherein the diameter is about 10 micrometers to about 100 micrometers. A43. The composition of any one of embodiments A40-A42, wherein the diameter of the microcapsules varies by a coefficient of variation of about 30% or less. A44. The composition of any one of embodiments A1-A43, wherein circularity of the microcapsules in the composition is about 0.8 to about 1.0. A45. The composition of any one of embodiments A1-A44, wherein concentricity of the microcapsules in the composition is about 75% or greater. A46. The composition of any one of embodiments A1-A45, wherein the shell of the microcapsules comprises pores of about 0.1 nanometers to about 500 nanometers. A47. The composition of any one of embodiments A1-A46, wherein the shell of the microcapsules comprises pores of about 10 nanometers to about 50 nanometers. A48. The composition of any one of embodiments A1-A47, wherein the shell of the microcapsules comprises pores and the microcapsules retain nucleic acid of a size of about 100 base pairs or greater. A49. The composition of any one of embodiments A1-A48, wherein the shell of the microcapsules comprises pores and the microcapsules retain nucleic acid of a size of about 500 base pairs or greater. A50. The composition of any one of embodiments A1-A49, wherein the shell of the microcapsules comprises pores and the microcapsules retain nucleic acid of a size of about 1,000 base pairs or greater. A51. The composition of any one of embodiments A1-A50, wherein the microcapsule or portion thereof is glycosidase degradable at a pH between about 3 and about 11 and at a temperature of about 80 degrees Celsius or less. A52. The composition of any one of embodiments A1-A51, wherein the microcapsule or portion thereof is glycosidase degradable at a pH between about 6 and about 8 and at a temperature of about 40 degrees Celsius or less. A53. The composition of any one of embodiments A1-A52, wherein the glycosidase is chosen from dextranase and cellulase. A54. The composition of any one of embodiments A1-A53, with the proviso that the microcapsules contain no intermediate layer between the shell and the core. A55. The composition of any one of embodiments A1-A53, with the proviso that there is no intermediate layer between the shell and the core that contains a polymer different than the first polymer and the second polymer. A56. The composition of any one of embodiments A1-A53, wherein the polymers of the microcapsules consist of the first polymer and the second polymer. A57. The composition of any one of embodiments A1-A53, wherein there is no layer on the exterior of the shell of the microcapsules. A58. The composition of any one of embodiments A1-A53, wherein the microcapsules are lipid-free and organic solvent free. A59. The composition of any one of embodiments A1-A58, wherein the composition is a liquid composition. A60. The composition of embodiment A59, wherein the composition is an aqueous liquid composition. A61. The composition of any one of embodiments A1-A58, wherein the composition is a solid composition. A62. The composition of embodiment A61, wherein the solid comprises a hydrogel. A63. The composition of any one of embodiments A1-A62, comprising a biological entity encapsulated within the core of the microcapsules. A64. The composition of embodiment A63, wherein the biological entity is chosen from a eukaryotic cell, prokaryotic cell, unicellular organism, multi-cellular organism, microorganism, bacterium, archaeon, fungus, plant, virus, organelle, liposomal vector, extracellular vesicle, nucleic acid, protein, organic molecule and biological molecule. A65. A method, comprising: contacting a composition of any one of embodiments A1-A64 with a glycosidase under enzymatic microcapsule degradation conditions. A66. The method of embodiment A65, wherein the glycosidase is capable of enzymatically degradation the polysaccharide in the first polymer and the polysaccharide in the second polymer. A67. The method of embodiment A66, wherein the polysaccharide in the first polymer is the same as the polysaccharide in the second polymer. A68. The method of any one of embodiments A65-A67, wherein at least the shell of the majority of the microcapsules is degraded enzymatically by the glycosidase. A69. The method of any one of embodiments A65-A68, wherein the enzymatic microcapsule degradation conditions are at a pH of about pH 3 to about pH 11 and are at a temperature of about 80 degrees Celsius or less. A70. The method of any one of embodiments A65-A68, wherein the enzymatic microcapsule degradation conditions are at a pH of about pH 6 to about pH 8 and at a temperature of about 40 degrees Celsius or less. A71. The method of any one of embodiments A65-A70, wherein the glycosidase is a dextranase. A72. The method of any one of embodiments A65-A70, wherein the glycosidase is a cellulase. A73. A method, comprising: exposing a composition of any one of embodiments A1-A64, to wash conditions that reduce the concentration of a component and/or remove a component encapsulated in the microcapsules. A74. The method of embodiment A73, wherein: the microcapsules contain nucleic; and the microcapsules are exposed to the wash conditions after the microcapsules have been exposed to nucleic acid processing conditions. A75. The method of embodiment A74, wherein the nucleic acid processing conditions are chosen from one or more of cell lysis conditions, nucleic acid fragmentation conditions, reverse transcription conditions, ligation conditions, MIP incorporation conditions, amplification conditions, barcode incorporation conditions, and sequencing adapter incorporation conditions. B1. A process for manufacturing a composition including a plurality of microcapsules, comprising: (a) emulsifying in a droplet generation device (i) a first aqueous solution comprising a first polymer, and (ii) a second aqueous solution comprising a second polymer, in an oil, wherein: the first polymer comprises a polysaccharide modified with a conjugated cross-linking moiety and optionally modified with a conjugated hydrophilicity/hydrophobicity-modifying moiety; the second polymer comprises a polysaccharide that does not include the cross-linking moiety and does not include the hydrophilicity/hydrophobicity-modifying moiety of the first polymer; the first aqueous solution and/or the second aqueous solution comprises a biological entity; monodisperse water-in-oil droplets containing the first polymer, the second polymer and the biological entity are generated; and an aqueous two-phase system is formed inside the water-in-oil droplets in which a liquid core is completely surrounded by a liquid shell and the biological species is preferentially distributed in the liquid core; and (b) exposing the microcapsules to cross-linking conditions that conjugate cross-linking moieties in the first polymer, thereby forming a hydrogel shell surrounding a core in a plurality of microcapsules. B2. The process of embodiment B1, wherein: the contacting in (a) comprises contacting the first aqueous solution and the second aqueous solution with a third aqueous solution; and the third aqueous solution is contained in the water-in-oil droplet. B3. The process of embodiment B2, wherein the first aqueous solution, the second aqueous solution, the third aqueous solution, or combination thereof, independently comprises a reagent and/or a biological entity. B4. The process of embodiment B3, wherein the reagent is chosen from a buffer, nucleotide, detectable agent, amino acid, enzyme, ligase, polymerase, transposase and antibody. B5. The process of embodiment B3 or B4, wherein the biological entity is chosen from one or more of a eukaryotic cell, prokaryotic cell, unicellular organism, multi-cellular organism, microorganism, bacterium, archaeon, fungus, plant, virus, organelle, liposomal vector, extracellular vesicle, nucleic acid, protein, organic molecule and biological molecule. B6. The process of any one of embodiments B1-B5, wherein the water-in-oil droplets are generated by a microfluidic device. B7. The process of embodiment B6, wherein the microfluidic device comprises a capillary assembly. B8. The process of embodiment B6 or B7, wherein the microfluidic device is a microfluidic chip. B9. The process of any one of embodiments B6-B8, wherein the microfluidic device comprises channels having a cross-section width of about 20 micrometers to about 100 micrometers. B10. The process of any one of embodiments B1-B9, wherein the water-in-oil droplets are generated by infusing the first aqueous solution, the second aqueous solution, optionally the third aqueous solution, and the oil through a flow focusing junction. B11. The process of any one of embodiments B1-B10, wherein the oil comprises a surfactant. B12. The process of embodiment B11, wherein the carrier oil comprises a fluorinated fluid and a fluorosurfactant. B13. The process of any one of embodiments B1-B12, wherein water-in-oil droplets are collected in the form of an emulsion. B14. The process of embodiment B13, wherein the emulsion is collected outside of a microfluidic device. B15. The process of any one of embodiments B1-B14, comprising, after part (a) or after part (b), separating the microcapsules from the oil into an aqueous solution. B16. The process of embodiment B15, wherein the separating comprises de-emulsification. B17. The process of embodiment B16, comprising contacting the water-in-oil droplets with perfluorooctanol. B18. The process of any one of embodiments B1-B17, wherein the first polymer is a major component of the shell and the second polymer is a major component of the core. B19. A process for manufacturing a composition including a plurality of microcapsules, comprising: (a) contacting (i) a first aqueous solution comprising a first polymer, (ii) a second aqueous solution comprising a second polymer, and (iii) an oil, under droplet-forming conditions, wherein: the first polymer comprises a polysaccharide modified with a conjugated cross-linking moiety and optionally modified with a hydrophilicity/hydrophobicity-modifying moiety; and the core comprises a second polymer comprising a polysaccharide that does not include the cross-linking moiety and does not include the hydrophilicity/hydrophobicity-modifying moiety of the first polymer; monodisperse water-in-oil droplets containing the first polymer and the second polymer are generated; and an aqueous two-phase system is formed inside the water-in-oil droplets in which a liquid core is completely surrounded by a liquid shell; and (b) cross-linking the cross-linking moieties in the first polymer, thereby forming a hydrogel shell surrounding the core in a plurality of microcapsules encapsulating the biological entity; and (c) breaking the water-in-oil droplets and releasing the microcapsules encapsulating the biological entity into an aqueous solution. B20. The process of any one of embodiments B1-B19, with the proviso that the water-in-oil droplets and the microcapsules are not sprayed. B21. A composition, comprising a plurality of microcapsules, obtainable by a process of any one of embodiments B1-B20. B22. A composition of any one of embodiments A1-A64, obtainable by a process of any one of embodiments B1-B20. C1. A method for preparing a plurality of nucleic acids for sequencing, comprising: (a) generating a plurality of microcapsules comprising biological entities, wherein: the microcapsules are suspended in an aqueous environment; and each of the biological entities comprises at least one nucleic acid molecule; (b) after part (a), contacting intact microcapsules with releasing conditions that release nucleic acid from the biological entities within intact microcapsules; (c) after part (b), exposing the intact microcapsules to nucleic acid amplification conditions that generate amplicons corresponding to target portions of the nucleic acid released in the intact microcapsules; and (d) after part (c), exposing the intact microcapsules to concatenation conditions that join a plurality of the amplicons end to end within the intact microcapsules, thereby generating one or more concatemers within particular intact microcapsules. C1.1. The method of embodiment C1, wherein the microcapsules comprise a shell surrounding a core. C1.2. The method of embodiment C1 or C1.1, wherein the microcapsules each comprise a cross-linked, porous and semipermeable shell surrounding a liquid or semi-liquid core. C1.3. The method of embodiment C1.2, wherein the microcapsule shell comprises a polysaccharide and is glycosidase degradable. C1.4. The method of embodiment C1.1, C1.2 or C1.3, wherein the shell permits primers, enzymes and assay reagents to pass through, and prevents the nucleic acids released from the biological entity escaping the microcapsule. C1.5. The method of any one of embodiments C1, C1.1, C1.2, C1.3 and C1.4, wherein: the plurality of microcapsules comprises microcapsules containing no biological entity and microcapsules containing a biological entity; and of the microcapsules containing a biological entity, a majority of the microcapsules contain a single biological entity. C2. The method of any one of embodiments C1, C1.1, C1.2, C1.3, C1.4 and C1.5, comprising, after part (d), exposing the intact microcapsules to microcapsule degradation conditions that release the concatemers from the microcapsules. C3. The method of any one of embodiments C1, C1.1, C1.2, C1.3, C1.4, C1.5 and C2, wherein parts (b), (c) and (d) are performed in a single container, or parts (b), (c), (d) and the releasing in embodiment C2 are performed in a single container. C4. The method of any one of embodiments C1-C3, comprising: placing the microcapsules or a portion thereof in a sequencing device and then releasing the concatemers from microcapsules in the sequencing device. C5. The method of any one of embodiments C1-C3, comprising: releasing the concatemers from microcapsules and then placing the concatemers or a portion thereof, or processed product thereof, in a sequencing device. C5.1. The method of embodiment C4 or C5, comprising contacting nucleic acid with library preparation conditions. C5.2. The method of embodiment C5, wherein the library preparation conditions comprise contacting nucleic acid with an adapter under adapter incorporation conditions. C5.3. The method of embodiment C5.2, wherein the adapter comprises a tether, motor or a hairpin. C6. The method of any one of embodiments C4-C5.3, comprising sequencing the concatemers. C7. The method of embodiment C6, wherein: the sequencing generates reads greater than 1,000 base pairs in length; and each read corresponds to nucleic acid from a single biological entity. C8. The method of any one of embodiments C1-C7, comprising amplifying and/or reverse transcribing, after part (b) and prior to part (c), the nucleic acid released from the biological entity within the intact microcapsules. C9. The method of any one of embodiments C1-C8, comprising, prior to part (c), tagging the nucleic acid released in part (b), or tagging nucleic acid amplified and/or reversed transcribed from the nucleic acid released in part (b), with molecular index polynucleotides (MIPs) from a plurality of different MIPs; whereby the concatemers in one microcapsule include a set of MIPs different than the set of MIPs in other microcapsules. C9.1. The method of any one of embodiments C1-C8, wherein the amplification conditions of part (c) incorporate a molecular index polynucleotide (MIP) from a plurality of different MIPs into each amplicon, whereby the amplicons in one microcapsule include a set of MIPs that is different from the set of MIPs in other microcapsules. C9.2. The method of embodiment C9 or C9.1, wherein: the sequencing generates reads each containing one or more MIPs and part of the genome sequence; and wherein individual reads sharing one or more MIPs are considered to originate from a single biological entity. C10. The method of any one of embodiments C1-C9.2, wherein the biological entities in the plurality of microcapsules is from a group of about 10 million or fewer biological entities. C11. The method of any one of embodiments C1-C10, wherein the biological entities in microcapsules independently are chosen from a eukaryotic cell, prokaryotic cell, unicellular organism, multi-cellular organism, microorganism, alga, protozoon, bacterium, archaeon, fungus, plant, virus, organelle, liposomal vector and extracellular vesicle. C12. The method of embodiment C11, wherein the organelle is a mitochondria or chloroplast. C13. The method of embodiment C11, wherein the biological entity is an antibody-producing cell, the target portions of the nucleic acid released in the intact microcapsules in part (c) are heavy chain variable (VH) domain and light chain variable (VL) domain target portions. C13.1. The method of embodiment C13, wherein the antibody-producing cell is a B-cell or hybridoma. C14. The method of embodiment C11, wherein the biological entity is a prokaryotic cell. C15. The method of embodiment C14, wherein the prokaryotic cell is a Gram-positive bacterium, a Gram-negative bacterium or an archaeon. C16. The method of embodiment C11, wherein the biological entity is a yeast cell. C17. The method of any one of embodiments C1-C16, comprising after part (b), exposing the intact microcapsules to wash conditions. C17.1. The method of embodiment C17, wherein the wash conditions comprise contacting the intact microcapsules with an aqueous solution that alters the internal composition of the microcapsules. C18. The method of embodiment C17.1, wherein the wash conditions comprise contacting the intact microcapsules with an aqueous solution that removes, or reduces, an amount of an inhibitor of the amplification conditions present in the microcapsules. C19. The method of embodiment C17.1 or C18, wherein the aqueous solution comprises a buffer. C20. The method of any one of embodiments C1-C19, comprising after (b) and prior to (c), purifying one or more of: (i) nucleic acid released into the intact microcapsules, (ii) nucleic acid amplified prior to part (c), and (iii) amplicons generated in part (c). C21. The method of any one of embodiments C1-C20, wherein the amplification conditions of part (c) or other amplification comprise contacting nucleic acid in the microcapsules with a DNA polymerase, RNA polymerase, reverse transcriptase, or combination thereof. C22. The method of any one of embodiments C1-C21, wherein the microcapsules are microcapsules of any one of embodiments A1-A64, B21 and B22. C23. The method of any one of embodiments C1-C22, with the proviso that a particle comprising a barcode nucleic acid is not contacted with a microcapsule. C24. The method of any one of embodiments C1-C23, with the proviso that the biological entity and nucleic acid of the biological entity is not fixed to a solid support or in a matrix, and is not contacted with a barcode polynucleotide. C25. The method of any one of embodiments C1-C24, with the proviso that nucleic acid is not exposed to precipitation conditions that generate precipitated nucleic acid. C26. The method of embodiment C25, with the proviso that nucleic acid is not exposed to rehydration conditions that rehydrate precipitated nucleic acid. D1. A method for preparing a plurality of nucleic acids for sequencing, comprising: (a) generating a plurality of microcapsules comprising biological entities, wherein: the microcapsules are in an aqueous environment; the plurality of microcapsules comprises on average no more than one of the biological entities per microcapsule; and each of the biological entities carries at least one nucleic acid molecule; (b) after part (a), contacting intact microcapsules with releasing conditions that release nucleic acid from the biological entity within intact microcapsules; (c) after part (b), exposing the intact microcapsules to amplification conditions that generate amplicons of the nucleic acid in the intact microcapsules; (d) after part (c), (i) splitting the intact microcapsules into separate compartments, wherein each of the compartment contains more than one of the intact microcapsules, (ii) exposing the intact microcapsules in each compartment to barcode polynucleotide linkage conditions that attach a barcode polynucleotide species to nucleic acids in the microcapsule, wherein the barcode polynucleotide species attached to nucleic acids in each of the microcapsules in a particular compartment is different than the barcode polynucleotide species attached to nucleic acids in the microcapsules within other compartments; and (iii) pooling the intact microcapsules from the compartments; and (e) repeating (d) at least one time, thereby generating barcoded nucleic acid in the intact microcapsules. D2. The method of embodiment D1, wherein the microcapsules comprise a shell surrounding a core. D3. The method of embodiment D1 or D2, wherein the microcapsules each comprise a cross-linked porous and semi-permeable shell surrounding a liquid or semi-liquid core. D3.1. The method of embodiment D3, wherein the microcapsule shell comprises a polysaccharide and is glycosidase degradable. D4. The method of embodiment D2, D3 or D3.1, wherein the shell permits primers, enzymes and assay reagents to pass through, and prevents the nucleic acids released from the biological entity escaping the microcapsule. D5. The method of any one of embodiments D1-D4, wherein: the plurality of microcapsules comprises microcapsules containing no biological entity and microcapsules containing a biological entity; and of the microcapsules containing a biological entity, the majority of the microcapsules contain a single biological entity. D6. The method of any one of embodiments D1-D5, wherein part (d) is repeated in part (e) a number of times until a predetermined number of the barcode polynucleotide species is attached to nucleic acid in the microcapsules. D7. The method of any one of embodiments D1-D6, comprising after part (b), exposing the intact microcapsules to wash conditions. D8. The method of embodiment D7, wherein the wash conditions comprise contacting the intact microcapsules with an aqueous solution that alters the internal composition of the microcapsules. D9. The method of embodiment D7, wherein the wash conditions comprise contacting the intact microcapsules with an aqueous solution that removes, or reduces, an amount of an inhibitor of the amplification and/or reverse transcription conditions present in the microcapsules. D10. The method of embodiment D7 or D8, wherein the aqueous solution comprises a buffer. D11. The method of any one of embodiments D1-D10, wherein after part (b) but prior to part (c), nucleic acid in the intact microcapsules is tagged with a molecular index polynucleotide (MIP). D11.1. The method of embodiment D11, wherein the MIP is about 4 consecutive nucleotides to about 50 consecutive nucleotides in length. D12. The method of any one of embodiments D1-D11.1, wherein prior to part (c) or after part (c), nucleic acid in the intact microcapsules is exposed to fragmentation conditions. D13. The method of embodiment D13, wherein the fragmentation conditions result in nucleic acid fragments of about 100 base pairs (bp) to about 100 kilobase pairs (kbp) in length. D14. The method of embodiment D13, wherein the fragments are about 100 bp to about 10 kbp in length. D15. The method of any one of embodiments D12-D14, wherein the fragmentation conditions comprise exposing nucleic acid in intact microcapsules to a nuclease, a chemical agent that generates hydroxy radicals, and/or ultrasound. D16. The method of any one of embodiments D1-D15, wherein the amplification conditions comprise contacting the intact microcapsules with DNA polymerase, RNA polymerase, or combination thereof. D16.1. The method of any one of embodiments D1-D16, comprising, prior to (c), exposing nucleic acid released in part (b) to reverse transcription conditions. D16.2. The method of embodiment D16.1, wherein the reverse transcription conditions comprise contact nucleic acid with reverse transcriptase. D17. The method of any one of embodiments D1-D16.2, wherein the microcapsules in part (d) are distributed in wells of a plate. D18. The method embodiment D17, wherein the plate is a 96-well plate or a 384-well plate. D19. The method of embodiment D17 or D18, wherein each well contains a different barcode polynucleotide. D20. The method of any one of embodiments D17-D19, wherein the barcode polynucleotide in each well is about 4 consecutive nucleotides to about 100 consecutive nucleotides in length. D21. The method of any one of embodiments D17-D19, wherein the barcode polynucleotide in each well is about 6 consecutive nucleotides to about 18 consecutive nucleotides in length. D22. The method of any one of embodiments D1-D21, wherein each barcode polynucleotide comprises a molecular identifier polynucleotide (MIP). D23. The method of any one of embodiments D1-D22, wherein each barcode polynucleotide comprises a polymerase chain reaction (PCR) adapter polynucleotide. D24. The method of any one of embodiments D1-D23, comprising, after part (e), exposing the intact microcapsules to microcapsule degradation conditions that release the barcoded nucleic acid, thereby generating released barcoded nucleic acid. D25. The method of embodiment D24, wherein the microcapsule degradation conditions comprise a glycosidase. D26. The method of embodiment D24 or D25, wherein the released barcoded nucleic acid is exposed to purification conditions, thereby generating purified barcoded nucleic acid. D27. The method of any one of embodiments D1-D26, comprising contacting nucleic acid with library preparation conditions. D28. The method of embodiment D27, wherein the library preparation conditions comprise contacting nucleic acid with an adapter under adapter incorporation conditions. D29. The method of any one of embodiments D24-D28, comprising sequencing the released barcoded nucleic acid and/or the purified barcoded nucleic acid. D30. The method of any one of embodiments D1-D29, with the proviso that in part (d) the nucleic acid encapsulated by the microcapsules is not fixed. D31. The method of any one of embodiments D1-D30, wherein the microcapsules are microcapsules of any one of embodiments A1-A64, B21 and B22. E1. A method for preparing a plurality of nucleic acids for sequencing, comprising: (a) generating a plurality of microcapsules comprising biological entities, wherein: the microcapsules are in an aqueous environment; the plurality of microcapsules comprises on average no more than one of the biological entities per microcapsule; and each of the biological entities carries at least one nucleic acid molecule; (b) after part (a), contacting intact microcapsules with releasing conditions that release nucleic acid from the biological entity within intact microcapsules; (c) after part (b), exposing the intact microcapsules to nucleic acid processing conditions that generate processed nucleic acid in the intact microcapsules; (d) after part (c), combining the intact microcapsules with microparticles comprising barcode polynucleotide species under droplet forming conditions that combine an individual intact microcapsule with a microparticle comprising a barcode polynucleotide species in a droplet, wherein the barcode polynucleotide species in each droplet is different than the barcode polynucleotide species in the other droplets; (e) optionally exposing, after or during part (d), the droplets to microcapsule degradation conditions that release the nucleic acid contained within the microcapsules into the interior of the droplets; and (f) exposing, after part (d) or after part (e), the droplets to barcode polynucleotide incorporation conditions that link barcode polynucleotides to nucleic acid in the droplets, thereby generating barcoded nucleic acid in the droplets. E1.1. The method of embodiment E1, comprising exposing nucleic acid released from the biological entity after part (b) to nucleic acid processing conditions. E2. The method of embodiment E1 or E1.1, wherein the nucleic acid processing conditions comprise exposing the nucleic acid to reverse-transcription conditions and/or to amplification conditions that generate amplicons of the nucleic acid. E3. The method of embodiment E1, E1.1 or E2, wherein the nucleic acid processing conditions comprise exposing the nucleic acid to oligonucleotide probe annealing conditions that anneal one or more oligonucleotide probes to nucleic acid. E4. The method of any one of embodiments E1-E3, comprising, prior to part (d), exposing microcapsules to selection conditions that select microcapsules containing released nucleic acid and/or processed nucleic acid. E5. The method of any one of embodiments E1-E4, wherein the microcapsules comprise a shell surrounding a core. E6. The method of any one of embodiments E1-E5, wherein the microcapsules each comprise a cross-linked porous and semi-permeable shell surrounding a liquid or semi-liquid core. E6.1. The method of embodiment E6, wherein the microcapsule shell comprises a polysaccharide and is glycosidase degradable. E7. The method of embodiment E5, E6 or E6.1, wherein the shell permits primers, enzymes and assay reagents to pass through, and prevents the nucleic acids released from the biological entity escaping the microcapsule. E8. The method of any one of embodiments E1-E7, wherein: the plurality of microcapsules comprises microcapsules containing no biological entity and microcapsules containing a biological entity; and of the microcapsules containing a biological entity, the majority of the microcapsules contain a single biological entity. E9. The method of any one of embodiments E1-E8, wherein in part (f) the barcode polynucleotide species attached to the nucleic acid is about 10 consecutive nucleotides to about 100 consecutive nucleotides in length. E9.1. The method of embodiment E9, wherein in part (f) the barcode polynucleotide species attached to the nucleic acid is about 16 consecutive nucleotides to about 90 consecutive nucleotides in length. E9.2. The method of any one of embodiments E1-E8, wherein part (f) is repeated a number of times until a predetermined number of the barcode polynucleotide species is attached to nucleic acid in the droplets. E9.3. The method of embodiments E9.2, wherein part (f) is repeated about 1 to about 5 times. E9.4. The method of embodiment E9.3, wherein part (f) is repeated about 1 to about 3 times. E9.5. The method of any one of embodiments E9.2 to E9.4, wherein the total length of the barcode polynucleotide species attached to the nucleic acid is about 10 consecutive nucleotides to about 100 consecutive nucleotides in length. E9.6. The method of embodiment E9.5, wherein the total length of the barcode polynucleotide species attached to the nucleic acid is about 16 consecutive nucleotides to about 90 consecutive nucleotides in length. E10. The method of any one of embodiments E1-E9.6, comprising after part (b), exposing the intact microcapsules to wash conditions. E11. The method of embodiment E10, wherein the wash conditions comprise contacting the intact microcapsules with an aqueous solution that alters the internal composition of the microcapsules. E12. The method of embodiment E10, wherein the wash conditions comprise contacting the intact microcapsules with an aqueous solution that removes, or reduces, an amount of an inhibitor of the amplification and/or reverse transcription conditions present in the microcapsules. E13. The method of embodiment E11 or E12, wherein the aqueous solution comprises a buffer. E14. The method of any one of embodiments E1-E13, wherein after part (b), prior to part (c) and/or as part of part (c), nucleic acid in the intact microcapsules is tagged with a molecular index polynucleotide (MIP). E14.1. The method of embodiment E14, wherein the MIP is about 4 consecutive nucleotides to about 50 consecutive nucleotides in length. E15. The method of any one of embodiments E1-E14.1, wherein prior to part (c), as part of part (c) and/or after part (c), nucleic acid in the intact microcapsules is exposed to fragmentation conditions. E16. The method of embodiment E15, wherein the fragmentation conditions result in nucleic acid fragments of about 100 base pairs (bp) to about 100 kilobase pairs (kbp) in length. E17. The method of embodiment E16, wherein the fragments are about 100 bp to about 10 kbp in length. E18. The method of any one of embodiments E15-E17, wherein the fragmentation conditions comprise exposing nucleic acid in intact microcapsules to a nuclease, a chemical agent that generates hydroxy radicals, and/or ultrasound. E19. The method of any one of embodiments E2-E18, wherein the amplification conditions comprise contacting the intact microcapsules with DNA polymerase, RNA polymerase, or combination thereof. E19.1. The method of any one of embodiments E1-E19, wherein the nucleic acid processing conditions comprise exposing nucleic acid released in part (b) to reverse transcription conditions. E19.2. The method of embodiment E19.1, wherein the reverse transcription conditions comprise contacting nucleic acid with reverse transcriptase. E20. The method of any one of embodiments E1-E19.2, wherein each barcode polynucleotide is about 10 consecutive nucleotides to about 100 consecutive nucleotides in length. E21. The method of embodiment E20, wherein each barcode polynucleotide is about 16 consecutive nucleotides to about 90 consecutive nucleotides in length. E22. The method of any one of embodiments E1-E21, wherein each barcode polynucleotide comprises a molecular identifier polynucleotide (MIP). E23. The method of any one of embodiments E1-E22, wherein each barcode polynucleotide comprises a polymerase chain reaction (PCR) adapter polynucleotide. E24. The method of any one of embodiments E1-E23, wherein part (e) is not performed, and comprising, after part (f), exposing the intact microcapsules to microcapsule degradation conditions that release the barcoded nucleic acid, thereby generating released barcoded nucleic acid. E25. The method of any one of embodiments E1-E24, wherein the microcapsule degradation conditions comprise contacting the microcapsules with a glycosidase. E26. The method of any one of embodiments E1-E25, comprising separating the barcoded nucleic acid from the droplets. E27. The method of embodiment E26, comprising exposing the barcoded nucleic acid to purification conditions, thereby generating purified barcoded nucleic acid. E28. The method of any one of embodiments D1-D27, comprising contacting nucleic acid with library preparation conditions. E29. The method of embodiment E28, wherein the library preparation conditions comprise contacting nucleic acid with an adapter under adapter incorporation conditions. E30. The method of any one of embodiments E26-E29, comprising sequencing the barcoded nucleic acid and/or the purified barcoded nucleic acid. E31. The method of any one of embodiments E1-E30, wherein the microcapsules are microcapsules of any one of embodiments A1-A64, B21 and B22. E32. The method of any one of embodiments E1-E31, wherein the droplet generation conditions comprise: an inlet for a continuous phase; an inlet for a first aqueous fluid comprising the first polymer; an inlet for a second aqueous fluid comprising the second polymer; a microchannel where the first aqueous fluid and the second aqueous fluid are combined; a flow focusing junction where continuous phase meets the first aqueous fluid, or the second aqueous fluid, or the first aqueous fluid and the second aqueous fluid; a channel where droplet generation occurs; and a water-in-oil droplet collection outlet. E33. The method of embodiment E32, wherein the continuous phase is a carrier oil. F1. A kit, comprising a first polymer and a second polymer, wherein: the first polymer comprises a polysaccharide modified with a conjugated cross-linking moiety and optionally modified with a conjugated hydrophilicity/hydrophobicity-modifying moiety, and the second polymer comprises a polysaccharide that does not include the cross-linking moiety and does not include the hydrophilicity/hydrophobicity-modifying moiety of the first polymer. F2. The kit of embodiment F1, comprising instructions for using the first polymer and the second polymer. F3. The kit of embodiment F2, wherein the instructions are for manufacturing microcapsules according to the process of any one of embodiments B1-B22. F4. The kit of embodiment F2 or F3, wherein the instructions are for manufacturing microcapsules in a composition of any one of embodiments A1-A64. F5. The kit of any one of embodiments F2-F4, wherein the instructions are for using microcapsules according to a method of any one of embodiments A65-A75, C1-C26, D1-D31 or E1-E33. F6. A kit, comprising reagents, and optionally microcapsules, for conducting a method of any one of embodiments A65-A75, C1-C26, D1-D31 or E1-E33. F7. The kit of embodiment F6, comprising instructions for conducting a method of any one of embodiments A65-A75, C1-C26, D1-D31 or E1-E33. Supplemental any previous embodiment, such as embodiment proposal 1. A method of performing a multistep reaction, comprising: containing a substrate in a microcapsule; contacting the substrate to a first reagent in the microcapsule to perform a first reaction step; replacing the first reagent with a second reagent in the microcapsule to perform a second reaction step; and releasing the reacted substrate from the microcapsule. 2. The method of any previous embodiment, such as embodiment 1, wherein the substrate comprises a biological material. 3. The method of any previous embodiment, such as embodiment 1, wherein the substrate comprises a cell. 4. The method of any previous embodiment, such as embodiment 1, wherein the substrate comprises cellular contents. 5. The method of any previous embodiment, such as embodiment 1, wherein the substrate comprises a protein. 6. The method of any previous embodiment, such as embodiment 1, wherein the substrate comprises a nucleic acid. 7. The method of any previous embodiment, such as embodiment 1, wherein the microcapsule comprises a hydrophilic shell. 8. The method of any previous embodiment, such as embodiment 1, wherein the microcapsule comprises a porous shell. 9. The method of any previous embodiment, such as embodiment 1, wherein the microcapsule comprises an aqueous core. 10. The method of any previous embodiment, such as embodiment 1, wherein the microcapsule comprises a degradable shell. 11. The method of any previous embodiment, such as embodiment 1, wherein the microcapsule comprises a polymer. 12. The method of any previous embodiment, such as embodiment 1, wherein the microcapsule comprises a carbohydrate. 13. The method of any previous embodiment, such as embodiment 1, wherein the microcapsule comprises a polysaccharide. 14. The method of any previous embodiment, such as embodiment 13, wherein the polysaccharide is crosslinked. 15. The method of any previous embodiment, such as embodiment 10, wherein the degradable shell is enzymatically degradable. 16. The method of any previous embodiment, such as embodiment 10, wherein the degradable shell is degradable under biological conditions. 17. There method of any previous embodiment, such as embodiment 16, wherein the biological conditions comprise at least one of a temperature ranging from 4 C to 65 C, a pH ranging from 5 to 9, or from 6-8 or 3-11. 18. The method of any previous embodiment, such as embodiment 1, wherein the first reagent comprises a cell lysis reagent. 19. The method of any previous embodiment, such as embodiment 1, wherein the first reagent comprises a protein denaturant. 20. The method of any previous embodiment, such as embodiment 1, wherein the first reagent disrupts protein secondary structure. 21. The method of any previous embodiment, such as embodiment 1, wherein the first reagent comprises a reverse transcriptase. 22. The method of any previous embodiment, such as embodiment 1, wherein the second reagent comprises a reverse transcriptase 23. The method of any previous embodiment, such as embodiment 1, wherein the second reagent comprises a DNA polymerase. 24. The method of any previous embodiment, such as embodiment 1, wherein the second reagent comprises a nucleic acid oligomer. 25. The method of any previous embodiment, such as embodiment 1, wherein the second reagent comprises a ligase. 26. The method of any previous embodiment, such as embodiment 1, wherein the second reagent comprises an antibody. 27. The method of any previous embodiment, such as embodiment 1, wherein the first reaction step and the second reaction step are not compatible. 28. The method of any previous embodiment, such as embodiment 27, wherein conditions necessary for the first reaction step preclude performance of the second reaction step. 29. The method of any previous embodiment, such as embodiment 1, wherein replacing does not change microcapsule volume. 30. The method of any previous embodiment, such as embodiment 9, wherein replacing does not change microcapsule volume 31. The method of any previous embodiment, such as embodiment 1, wherein replacing comprises washing the microcapsule under conditions such that the first reagent diffuses out of the microcapsule. 32. The method of any previous embodiment, such as embodiment 1, wherein replacing comprises washing the microcapsule under conditions such that the second reagent diffuses into the microcapsule. 33. The method of any previous embodiment, such as embodiment 1, wherein releasing the reacted substrate comprises melting the microcapsule. 34. The method of any previous embodiment, such as embodiment 1, wherein releasing the reacted substrate comprises dissolving the microcapsule. 35. The method of any previous embodiment, such as embodiment 1, wherein releasing the reacted substrate comprises enzymatically digesting the microcapsule. 36. The method of any previous embodiment, such as embodiment 1, comprising performing a sequencing reaction using the reacted substrate as a template subsequent to the releasing. 37. The method of any previous embodiment, such as embodiment 1, comprising culturing the reacted substrate. 38. The method of any previous embodiment, such as embodiment 1, comprising performing any one or more of lysis, protease treatment, DNase treatment, RNase treatment, reverse transcription, ligation, USER uracil degradation, barcoding, concatenation, antibody binding, or any other suitable reaction mentioned herein or contemplated in the art for nucleic acid, protein or other analyte reaction. 39. A method of generating a population of microcapsules having a uniform minimum wall thickness, comprising: providing a mixture of monomers, said mixture comprising hydrophilic monomers and hydrophobic monomers; suspending an emulsion of droplets of said mixture in a hydrophobic carrier, and polymerizing the hydrophobic monomers. 40. The method of any previous embodiment, such as embodiment 39, wherein the mixture of monomers comprises hydrophilic monomers and hydrophobic monomers sharing a common monomer core structure. 41. The method of any previous embodiment, such as embodiment 40, wherein the common monomer core structure comprises a saccharide. 42. The method of any previous embodiment, such as embodiment 40, wherein the hydrophobic monomers comprise a conjugated cross-linking moiety. 43. The method of any previous embodiment, such as embodiment 40, wherein the hydrophobic monomers comprise a conjugated hydrophilicity/hydrophobicity-modifying moiety 44. The method of any previous embodiment, such as embodiment 39, wherein the hydrophobic monomers comprise hydrophobic modification to hydrophilic monomer core structures s. 45. The method of any previous embodiment, such as embodiment 39, wherein polymerizing the hydrophobic monomers comprises cross-linking. 46. The method of any previous embodiment, such as embodiment 39, wherein the method generates a population having a concentricity of at least 50% 47. The method of any previous embodiment, such as embodiment 39, wherein the method generates a population having a concentricity of at least 60%. 48. The method of any previous embodiment, such as embodiment 39, wherein the method generates a population having a concentricity of at least 75%. 49. The method of any previous embodiment, such as embodiment 39, wherein the method generates a population having a concentricity of at least 90%. 50. The method of any previous embodiment, such as embodiment 39, wherein the method generates a population having a circularity of at least 0.8 51. The method of any previous embodiment, such as embodiment 39, wherein the method generates a population having a circularity of at least 0.9. 52. The method of any previous embodiment, such as embodiment 39, wherein the method generates a population having diameters of 10 micrometers to 100 micrometers. 53. The method of any previous embodiment, such as embodiment 39, wherein the method generates a population having diameters of 1 micrometer to 1000 micrometers. 54. The method of any previous embodiment, such as embodiment 39, wherein the method generates a population having diameters that vary by a coefficient of variation of no more than 30%. 55. A method of modulating microcapsule porosity, comprising modulating microcapsule precursor constituent concentration. 56. The method of any previous embodiment, such as embodiment 55, comprising selecting a polymer having desired porosity characteristics, or introducing and removing microparticles of desired pore size, or changing surface chemistry so as to produce a charge that impacts porosity of the microcapsule as to a particularly charged set of particles, such as negative charge so as to reduce porosity as to negatively charged molecules such as nucleic acids. 57. The method of any previous embodiment, such as embodiment 55, wherein the shell of the microcapsules comprises pores of about 0.1 nanometers to about 500 nanometers. 58. The method of any previous embodiment, such as embodiment 55, wherein the shell of the microcapsules comprises pores of about 10 nanometers to about 50 nanometers. 59. The method of any previous embodiment, such as embodiment 55, wherein the shell of the microcapsules comprises pores and the microcapsules retain nucleic acid of a size of about 100 base pairs or greater. 60. The method of any previous embodiment, such as embodiment 55, wherein the shell of the microcapsules comprises pores and the microcapsules retain nucleic acid of a size of about 500 base pairs or greater. 61. The method of any previous embodiment, such as embodiment 55, wherein the shell of the microcapsules comprises pores and the microcapsules retain nucleic acid of a size of about 1,000 base pairs or greater. 62. A method of labeling a nucleic acid population, comprising: encasing the nucleic acid population in a microcapsule; amplifying the nucleic acid population; contacting the nucleic acid population to a first barcode under conditions that allow attachment of copies of the first barcode to the nucleic acid population; removing unattached copies of the first barcode from the microcapsule; contacting the nucleic acid population to a second barcode under conditions that allow attachment of copies of the second barcode to the nucleic acid population; and releasing the nucleic acid population from the microcapsule. 63. The method of any previous embodiment, such as embodiment 62, wherein the nucleic acid population comprises nucleic acid transcripts. 64. The method of any previous embodiment, such as embodiment 62, wherein the nucleic acid population comprises cDNA molecules. 65. The method of any previous embodiment, such as embodiment 62, wherein the nucleic acid population comprises genomic nucleic acid molecules. 66. The method of any previous embodiment, such as embodiment 64, wherein the cDNA molecules are reverse transcribed from mRNA templates within the microcapsule. 67. The method of any previous embodiment, such as embodiment 62, wherein, prior to amplifying, the microcapsule is subjected to cell lysis conditions. 68. The method of any previous embodiment, such as embodiment 62, wherein, prior to amplifying, the microcapsule is subjected to reverse transcription conditions. 69. The method of any previous embodiment, such as embodiment 62, wherein, prior to amplifying, the microcapsule is subjected to DNase conditions. 70. The method of any previous embodiment, such as embodiment 62, wherein, prior to amplifying, the microcapsule is subjected to RNase conditions. 71. The method of any previous embodiment, such as embodiment 62, wherein amplifying comprises at least one PCR cycle. 72. The method of any previous embodiment, such as embodiment 62, wherein amplifying comprises at least two PCR cycles. 73. The method of any previous embodiment, such as embodiment 62, wherein amplifying comprises at least three PCR cycles. 74. The method of any previous embodiment, such as embodiment 62, wherein amplifying comprises at least five PCR cycles. 75. The method of any previous embodiment, such as embodiment 62, wherein amplifying comprises at least ten PCR cycles. 76. The method of any previous embodiment, such as embodiment 62, wherein conditions that allow attachment comprise ligation conditions. 77. The method of any previous embodiment, such as embodiment 76, wherein the conditions exhibit an efficiency of single barcode addition of at least 10%. 78. The method of any previous embodiment, such as embodiment 76, wherein the conditions exhibit an efficiency of single barcode addition of at least 50%. 79. The method of any previous embodiment, such as embodiment 76, wherein the conditions exhibit an efficiency of single barcode addition of at least 60%. 80. The method of any previous embodiment, such as embodiment 76, wherein the conditions exhibit an efficiency of single barcode addition of at least 70%. 81. The method of any previous embodiment, such as embodiment 76, wherein the conditions exhibit an efficiency of single barcode addition of at least 80%. 82. The method of any previous embodiment, such as embodiment 76, wherein the conditions exhibit an efficiency of single barcode addition of at least 90%. 83. The method of any previous embodiment, such as embodiment 76, wherein the conditions exhibit an efficiency of single barcode addition of at least 95%. 84. The method of any previous embodiment, such as embodiment 62, wherein the nucleic acid population is tagged by both the first barcode and the second barcode at a success rate of at least 50%. 85. The method of any previous embodiment, such as embodiment 62, wherein the nucleic acid population is tagged by both the first barcode and the second barcode at a success rate of at least 90%. 86. The method of any previous embodiment, such as embodiment 62, wherein the nucleic acid population is tagged by both the first barcode and the second barcode at a success rate of at least 99%.

The disclosure is further elucidated through the following additional numbered embodiments, including 1. A method of performing a series of reactions in a constant microfluidic volume, comprising: enclosing the microfluidic volume in a droplet; performing a first reaction using a first reagent in the constant microfluidic volume; exchanging the first reagent for a second reagent; and performing a second reaction using the second reagent in the constant microfluidic volume. 2. The method of embodiment 1, wherein the droplet comprises a semipermeable shell. 3. The method of embodiment 2, wherein exchanging the first reagent for a second reagent comprises trafficking the first reagent and the second reagent through the semipermeable shell. 4. A method of performing a series of reactions in a droplet without diluting the droplet, comprising: Performing a first reaction in the droplet; exchanging the first reagent for a second reagent; and performing a second reaction using the second reagent in the droplet. 5. The method of embodiment 4, wherein exchanging the first reagent for a second reagent comprises removing a substantial portion of the first reagent. 6. The method of embodiment 4 or 5, wherein adding the second reagent does not comprise diluting the droplet. 7. The method of embodiment 4 or 5, wherein adding the second reagent does not comprise substantially changing the volume of the droplet.

EXAMPLES

The disclosure is further elucidated through the examples presented below. Examples are demonstrative of the breadth of the scope of the disclosure as well as possession of the disclosure herein. Elements of the examples are broadening as to the scope of the disclosure in demonstrating increased breadth of implementation. They are further limiting on some but not all embodiments of the disclosure above and throughout.

Example 1: Dextran Modification with Butyryl and Methacryloyl Moieties

This example describes the chemical synthesis of dextran modified with methacryloyl and butyryl moieties (Dex-MAB) for use as the shell-forming polymer of microcapsules (FIG. 1A). DexMAB and dextran form an aqueous two-phase system (ATPS) necessary for microcapsule formation. Methacryloyl moieties allow for controlled shell polymerization after encapsulation and before releasing the microcapsules from the continuous oil phase. Without being limited by theory, it is expected that both methacryloyl and butyryl moieties contribute to the formation of the ATPS by changing the solubility of modified dextran compared to non-modified dextran used as the core phase. The level of substitution is defined as the molar ratio of modifying moieties and glucose units (FIG. 3). For example, Dex-MAB-10-90 means that during reaction setup, the concentrations of glycidyl methacrylate (GMA) and R-(−)-glycidyl butyrate (GB) were such as to achieve a methacryloyl-to-glucose-unit ratio of 0.1 (or 10%) and a butyryl-to-glucose unit ratio of 0.9 (or 90%). As there are three hydroxyl groups that can be modified per glucose unit, the maximum total degree of substitution is 300% given this definition.

Described is the synthesis of DexMAB-10-90 as a specific example. HNMR analysis of the product revealed an actual degree of substitution of 6 and 57% by methacryloyl and butyryl moieties, respectively (FIG. 4). Other degrees of substitution can be achieved by varying the molar equivalents of GB and GMA. FIG. 3 and FIG. 4 illustrate dextran substitution with butyryl and methacryloyl moieties.

FIG. 3 shows an anticipated dextran substitution product under alkaline conditions. See, e.g., van Dijk-Wolthuis et al., Macromolecules 30(11):3411-3 (1997); and Reis et al., J. organic chemistry 74(10):3750-7 (2009). FIG. 4 shows an HNMR spectrum of DexMAB.

Table 1 below lists materials used for methacryloyl- and butyryl-substituted dextran synthesis.

TABLE 1

| Material | CAS number | Catalogue number | Amount | Equivalent, mol % |
|---|---|---|---|---|
| Dextran, MW 500 K (Dex) | 9005-54-0 | Sigma-Aldrich, cat. no. 31392 | 1004 mg | 100 |
| R-(—)-Glycidyl butyrate (GB) | 106-91-2 | Sigma-Aldrich, cat. no. 338125 | 763 uL | 90 |
| Glycidyl methacrylate (GMA) | 60456-26-0 | Sigma-Aldrich, cat. no. 151238 | 80 uL | 10 |
| Dimethylsulfoxide 99.7% (DMSO), extra dry | 67-68-5 | Acros, cat. no. 348440010 | 8 + 1 + 1 mL | n/a |
| 4-Dimethylaminopyridine (DMAP) | 1122-58-3 | Sigma-Aldrich, cat. no. 107700 | 139 mg | 20 |
| 1M HCl solution | n/a | n/a | 1.20 mL | 20 |
| Deionized water | n/a | n/a | | n/a |
| Dialysis hose, MWCO 14 kDa | n/a | Roth, cat. no. 1780.1 | | n/a |

DMSO was placed in a round bottom flask fitted with a magnetic stirrer and flushed with argon for 10 minutes. Dextran 500K was dissolved in DMSO in one-gram portions. Once dissolved, DMAP was added to the reaction mixture, flushed with argon for 10 min, and mixed until dissolved. In a separate vial, GMA and GB were mixed in ratios specified in Table 1 with twice the volume of DMSO and the mixture was transferred to the main reaction mixture. The mixture was then capped with a glass stopper and left stirring for 48 hours. The reaction was quenched with 1M HCl, equimolar to the base, to neutralize DMAP. Then, the reaction mixture was dialyzed against deionized water for three days, changing the water every 3-4 hours during work hours. After dialysis, the product was freeze-dried to yield a highly electrostatic white or slightly yellowish powder. The product was analyzed by NMR to determine the observed degree of substitution. H-NMR analysis involved the following steps:

a) The spectrum was zoomed to 0-10 ppm and ±5000 arbitrary intensity units.
b) Spectrum was aligned to residual water signal, assigned 4.79 ppm if recorded in $D_2O$.
c) The anomeric proton integral $S_{4.9-5.05}$, range 4.9-5.05 ppm, was normalized to 1, to represent 100% of the sample (1H).
d) Methacryloyl moiety protons integrals $S_{6.26}$ and $S_{5.77}$ were calculated at 6.26 ppm and 5.77 ppm, respectively.
e) The methacryloyl moiety methyl group integral $S_{1.94}$ was calculated at 1.94 ppm (3H).
f) As a sanity check, $S_{6.26}:S_{5.77}:S_{1.94}$ was confirmed to be equal to 1:1:3.
g) The butyryl moiety terminal group integral $S_{0.92}$ was calculated at 0.92 ppm (3H).
h) The degree of substitution with the methacryloyl moiety ($DS_{MA}$) was calculated as $DS_{MA}=S_{1.94}*(1/S_{4.9-5.05})*(1/3)$.
i) The degree of substitution with the butyryl moiety ($DS_{Bu}$) was calculated as $DS_{Bu}=S_{0.92}*(1/S_{4.9-5.05})*(1/3)$.

Example 2: Microcapsule Generation

This example describes the microfluidic generation of microcapsules of different diameter in 1×PBS in the 42-88 um. The generation of smaller and larger microcapsules is described in separate examples. The choice of flow rates and channel geometries determines the microcapsule size achieved. For example, the generation of microcapsules having a radius of about 42 micrometers is detailed. Table 2 summarizes the results of testing fifteen different microfluidic chip geometry and reagent injection flow rate combinations. The specific shell and core polymers used in this example are DexMAB-10-90 and Dextran (MW 500k) but the experimental steps are the same for different polymer combinations.

FIG. 2A-FIG. 2E illustrate generation of microcapsules. FIG. 2A is a schematic of the microfluidic device used for microcapsule generation with inlets for the Core solution, Shell solution, and Droplet Stabilization Oil specified. FIG. 2B is a photograph of the droplet generation process, highlighting the region of the microfluidic chip designated by a dashed rectangle in FIG. 2A. Arrows designate the direction of flow. FIG. 2C is a photograph of the resulting water-in-oil emulsion. FIG. 2D is a photograph of the same microcapsule as in FIG. 2C after transfer into 1×PBS. FIG. 2E is an expanded view of an 85-micrometer diameter microcapsule with clearly visible shell and core.

Table 2 below is a DexMAB-10-90 shell polymer-based microcapsule size chart. The column "Chip" provides the catalogue number of the microfluidic chip at Droplet Genomics. Microcapsule diameters are given in water-in-oil emulsion and in aqueous buffer (1×PBS). Depending on the aqueous buffer used, microcapsules swell to different degrees relative to the diameter of droplets prior to breaking the emulsion.

TABLE 2

| Chip | Nozzle width, um | Channel height, um | Core flow rate, uL/h | Shell flow rate, uL/h | Oil flow rate, uL/h | Average diameter in emulsion, um | Average diameter in 1x PBS, um | Drops per second |
| --- | --- | --- | --- | --- | --- | --- | --- | --- |
| CED 20 × 20 | 20 | 20 | 35 | 35 | 350 | 33.8 | 41.7 | 966 |
| CED 20 × 20 | 20 | 20 | 35 | 35 | 210 | 39.0 | 45.4 | 604 |
| CED 20 × 20 | 20 | 20 | 35 | 35 | 140 | 42.3 | 52.3 | 423 |
| CCF 20 × 30 | 20 | 30 | 65 | 65 | 390 | 53.5 | 61.8 | 485 |
| CED 30 × 30 | 30 | 30 | 65 | 65 | 650 | 47.8 | 62.0 | 510 |
| CED 30 × 30 | 30 | 30 | 65 | 65 | 520 | 52.2 | 62.3 | 507 |
| CED 40 × 40 | 40 | 40 | 100 | 100 | 900 | 57.7 | 65.4 | 603 |
| CED 30 × 30 | 30 | 30 | 65 | 65 | 390 | 58.0 | 68.0 | 390 |
| CCF 20 × 30 | 20 | 30 | 65 | 65 | 260 | 60.4 | 69.3 | 341 |
| CED 40 × 40 | 40 | 40 | 100 | 100 | 600 | 63.7 | 73.7 | 433 |
| CED 30 × 30 | 30 | 30 | 65 | 65 | 260 | 62.8 | 74.2 | 303 |
| CED 40 × 40 | 40 | 40 | 75 | 75 | 450 | 64.3 | 75 | 312 |
| CED 40 × 40 | 40 | 40 | 75 | 75 | 300 | 71.2 | 78.1 | 242 |
| CED 40 × 40 | 40 | 40 | 100 | 100 | 300 | 76.1 | 85.6 | 262 |
| CED 40 × 40 | 40 | 40 | 75 | 75 | 225 | 76.9 | 88.8 | 181 |

The following Table 3 provides information for materials utilized.

TABLE 3

| Material | Catalogue number |
| --- | --- |
| DexMAB-10-90 (methacryloyl- and butyryl- modified dextran) | Not applicable |
| Dextran MW 500K (solid) | Sigma-Aldrich, cat. no. 31392 |
| LAP (lithium phenyl-2,4,6-trimethylbenzoylphosphinate) | Sigma-Aldrich, cat. no. 900889-1G |

TABLE 3-continued

| Material | Catalogue number |
| --- | --- |
| 405 nm LED device | Droplet Genomics, cat. no. DG-BRD-405 |
| Microfluidic device (20 um channel height, 20 um nozzle) | Droplet Genomics CED-20-20 |
| DSO (Droplet Stabilization Oil) | Droplet Genomics, cat. no. DG-DSO-15 |
| HFE7500 | 3M, cat. no. Novec 7500 |
| PFO (1H,1H,2H,2H-Perfluorooctanol) | Fluorochem, cat. no. 007128 |
| 10% Pluronic F68 | Thermo Fisher, cat. no. 24040-032 |

The Shell solution (1000 w/w DexMAB-10-90, 0.2% w/w LAP, 1×PBS) and the Core solution (10% w/w Dextran 500K, 1×PBS) were co-encapsulated using a co-flow microfluidic device (20 micrometer height, 20 micrometer nozzle) (FIGS. 2A and 2B) on a syringe pump-based instrument (Droplet Genomics, Onyx). The flow rates for the Shell solution, Core solution and Droplet Stabilization Oil (DSO) were 35, 35, and 350 ul/h, respectively. The resulting emulsion was collected into a 1.5-ml tube for 30 min, after which it was exposed to a 405 nm light for 30s (Droplet Genomics, cat. no. DG-BRD-405). A microscopy image of the water-in-oil emulsion was taken for diameter measurement (FIG. 2C, Table 2). Next, the excess DSO from the bottom of the tube was removed, and 300 ul of 1×PBS with 0.10% Pluronic-F68 and 300 ul of 20% v/v PFO in HIFE7500 were added to break the emulsion. The resulting aqueous top layer, containing the microcapsules, was transferred into a fresh tube followed by 3 washes in 1×PBS with 0.1% Pluronic-F68. A wash consisted of concentrating microcapsules at the bottom of the tube by centrifugation for 1 min at 1000 g followed by removal of supernatant and addition of fresh buffer. A microscopy image of microcapsules in 1×PBS loaded on a hemocytometer was taken for diameter measurement (FIGS. 2D and 2E, Table 2).

Example 3: Shell Permeability Assessment by Polymerase Chain Reaction (PCR)

This example describes a procedure for determining the minimal PCR amplicon size retained by a given microcapsule shell polymer. Two polymer compositions, DEXMAB-5-45 and DEXMAB-10-90, were assessed. For these shell polymers, 1000 bp and 500 bp, respectively, was determined from microscopy images as the minimum amplicon size robustly retained within microcapsules. FIG. 15A and FIG. 15B show an experimental approach to determine retained amplicon size within microcapsules. FIG. 15A illustrates a schematic of the assessment. Bacterial cells were encapsulated into microcapsules such that on average there are one or fewer cells per microcapsule (1). Following lysis and washes (2), the same microcapsule suspension was distributed into 6 PCR reactions (3). Each PCR produced amplicons of a different defined size. FIG. 15B provides imaging results showing microcapsules post-PCR. Rows represent two different shell polymers. Each column represents a different amplicon size. Microcapsules were approximately 50 μm in diameter. The same imaging conditions (microscope, magnification, illumination, exposure time) were used for all images in a given row. The dashed rectangles highlight images showing retention of the amplicons. The retention threshold values are 1000 bp and 500 bp for DexMAB-5-45 and DexMAB-10-90, respectively. Amplicon sizes smaller than the retention threshold led to a marked increase in the fraction of fluorescent microcapsules. Notably, by selecting polymer reagents, for microcapsule synthesis, one may modulate microcapsule porosity. It is noted that DexMAB-10-90 showed auto-fluorescence in the green channel.

In addition to the materials list for microcapsule generation provided in Example 2, reagents listed in Table 4 were used.

TABLE 4

| Materials for assessing amplicons | |
| --- | --- |
| Material | Catalogue number |
| DexMAB-5-45 | Not available |
| DexMAB-10-90 | Not available |
| Triton X-100 | Sigma-Aldrich, T8787-50ML |
| Ready-Lyse lysozyme solution | Lucigen, R1804M |
| Proteinase K | Thermo Scientific, EO0491 |
| E. coli MG1655 | Not available |
| Dream Taq Hot Start Green PCR Master Mix | Thermo Scientific, K9021 |
| Primers designed for various length amplicons from E. Coli genome | IDT, Standard desalting, custom order |
| SYTO ™ 9 Green Fluorescent Nucleic Acid Stain | Thermo Scientific, S34854 |

E. coli cells were encapsulated into microcapsules such that there were one or fewer cells per microcapsule on average. The Shell solution was composed of 10% w/w DexMAB-5-45 or DexMAB-10-90; 0.2% w/v lithium phenyl-2,4,6-trimethylbenzoylphosphinate (LAP) (Sigma-Aldrich, 900889-1G) and 1×PBS. The Core solution was composed of 10% w/w Dextran 500k, 1×PBS, and E. coli cells. Microcapsules were produced on a microfluidics chip 40 μm height and having a nozzle 40 μm wide using the following flow rates of 50, 50, and 300 ul/h for the Core solution, Shell solution and Droplet Stabilization oil, respectively.

The collected emulsion was exposed to 405 nm light for 30 seconds to induce shell polymerization. 300 μl of Washing buffer (10 mM Tris-HCl (pH 7.5), 0.1% Triton X-100), and 300 μl of 20% PFO in HFE7500 were added per 100 μl of emulsion to release microcapsules into the aqueous phase. The oil (bottom) phase was removed and microcapsules were washed 2 times in Washing buffer. Washes were performed by centrifuging microcapsules at 1000 g for 1 min and removing the supernatant. Cell lysis was performed by incubating in microcapsules in 50 U/μl lysozyme (Lucigen, R1804M), 0.2 mg/ml proteinase K, 0.1% Triton X-100, 1 mM EDTA, 10 mM Tris-HCl (pH 7.5) for 30 min at 37 degrees Celsius, followed by 30 min at 50 degrees Celsius. Following lysis, microcapsules were washed 5 times in Washing buffer.

6 PCR reactions with different sets of primers were prepared. Each reaction consisted of 20 μl of packed microcapsules (i.e., with most supernatant removed), 2.5 μl of nuclease-free water, 2.5 μl primers (10 μM each) and 25 μl 2×PCR master mix (Thermo Scientific, K9021). To obtain amplicons of different size in the range 100-1000 bp, 1 universal reverse primer and 6 different forward primers targeting the OmpA gene were used. Sequences are provided in Table 5.

TABLE 5 primers utilized for amplicon retention test (Table discloses SEQ ID NOS 1-7, respectively, in order of appearance).

| Primer name | Primer sequence | Approximate amplicon size, bp | Exact amplicon size, bp |
|---|---|---|---|
| OmpA_fw_100 | TGA AAC AGC GTG CTG CAC TGA (SEQ ID NO: 1) | 100 | 96 |
| OmpA_fw_200 | CAG TCT GTT GAT TAC CTG ATC TCC (SEQ ID NO: 2) | 200 | 202 |
| OmpA_fw_300 | CCT GGA TCC GAA AGA CGG TTC (SEQ ID NO: 3) | 300 | 296 |
| OmpA_fw_400 | TTC ACT CTG AAG TCT GAC GTT CTG TTC (SEQ ID NO: 4) | 400 | 394 |
| OmpA_fw_500 | TGC TGA GCC TGG GTG TTT CC (SEQ ID NO: 5) | 500 | 492 |
| OmpA_fw_1000 | AGT GGC ACT GGC TGG TTT CG (SEQ ID NO: 6) | 1000 | 1010 |
| OmpA_rev | CCT GCG GCT GAG TTA CAA CG (SEQ ID NO: 7) | — | — |

The PCR thermal program was: 95 degrees Celsius for 3 min; (95 degrees Celsius for 30s, 52 degrees Celsius for 30s, 72 degrees Celsius for 1 min)×30; 72 degrees Celsius for 5 min; +4° C. hold. Following PCR, 5 µl of 50 µM SYTO9 dye were added to 50 µl of PCR mix. Then, the microcapsules were washed 5 times with Washing buffer and imaged using a fluorescent microscope.

Example 4: Shell Polymer Characterization

This example describes characterization of newly synthesized shell polymers (described in Example 1), which includes: a microcapsule formation assay (see, e.g., Example 2), dextranase release test, and a PCR amplicon retention test (see, e.g., Example 3). Microcapsule formation is the first prerequisite for a given core and shell polymer pair. Controllable shell polymer disintegration enables the release of microcapsule content when desired, and in the case of dextran-based polymers can be achieved by dextranase or other backbone polysaccharide-specific enzyme treatment. In the case of dextran-based shells, it was observed that greater than 2000 substitution with methacryloyl moieties prevents dextranase digestion (Table 6). However, as exemplified by the polymer DexMAB-25-75 (see abbreviations explained below), pre-treatment of capsules with alkaline conditions makes then susceptible to dextranase digestion (Table 6). A likely explanation is the alkaline hydrolysis of ester bonds by which the modifying moieties are attached to the backbone polysaccharide (FIG. 3) making the backbone more accessible to enzyme hydrolysis. Importantly, alkaline treatment alone did not change the appearance of SPCs under bright-field microscopy, nor a reduction in the volume of SPCs in the tube. While on-demand microcapsule content release under mild enzymatic conditions is desirable, shell polymers that do not satisfy this criterion are still useful, for example, for digital microcapsule analysis. In the case of a shell based on different polymers, dextranase can be used to digest the unmodified dextran used as the core polymer. The resulting glucose mono- and oligomers can be washed out of microcapsules, which may be desirable in certain applications. Ficoll shell-based microcapsules undergo a 15% reduction in diameter after dextranase treatment to digest the core (FIG. 16 and FIG. 17).

Table 6 provides a summary of results from characterizing several degrees of dextran (Dex), hydroxyethylcellulose (HEC), Ficoll (Fic), and arabinoxylan (Axyl), substitution with methacryloyl (MA), acryloyl (A), butyryl (B), acetyl (C2), and biotin (Bio), or their combinations. The polymer name (column 1) encodes the target degree of substitution during the reaction setup. The level of substitution is defined as the molar ratio of modifying moieties and glucose units. For example, DexMAB-10-90 means that during reaction setup, the concentrations of GMA and GB were such as to achieve a methacryloyl-to-glucose-unit ratio of 0.1 (or 10%) and a butyryl-to-glucose unit ratio of 0.9 (or 90%). Column 2 provides the NMR-determined actual degree of substitution (second columns). Columns 3 and 4 provide a non-limiting example of shell and core polymer concentrations that allow robust microcapsule formation. In the case of DexMA-20 polymer, aqueous phase separation could not be achieved using 10% w/w of core polymer and 10% w/w of shell polymer, resulting in bead rather than microcapsule formation. Column 5 summarizes whether the cross-linked shell polymer can be hydrolyzed by relatively mild enzymatic conditions involving an enzymatic treatment of 5 min at room temperature. Dextranase was used for Dex-based shells, invertase for Ficoll-based shells. FicMAB-10-90 was resistant to invertase treatment. For shell compositions resistant to mild hydrolysis, column 6 provides, if determined, alternative harsher dextranase digestions conditions confirmed to dissolve a gel of cross-linked shell polymer. Column 7 provides the minimum size of robustly retained PCR amplicons for each shell polymer.

TABLE 6

| 1 Shell polymer name | 2 NMR-determined substitution | 3 % core and shell polymer for robust microcapsule production | | 4 | 5 Crosslinked shell polymer hydrolyzed by enzymatic treatment 5 min at room temperature | 6 If available, alternative conditions for crosslinked shell polymer digestion by backbone-specific enzyme | 7 Minimum amplicon size retained |
|---|---|---|---|---|---|---|---|
| | | Shell polymer concentration, % w/w | Core polymer (Dex500) concentration, % w/w | | | | |
| DexMAB-05-50 | (<1)-31 | No phase separation with dextran in a bulk test | | | | | |
| DexMAB-2-50 | 1.5-30 | 10 | 10 | | YES | | Does not survive PCR cycling |
| DexMA-20 | 16 | Not applicable, bead rather than microcapsule formation | | | No | 1) 10 min at 37 degrees Celsius; 2) 5 min at 60 degrees Celsius with dextranase | Not applicable |
| DexMA-30 | 30 | 10 | 10 | | No | Not available | No data |
| DexMA-50 | No data | 10 | 10 | | No | Not available | 100 |
| DexMA-95 | 123 | 5 | 5 | | No | Not available | No data |
| DexMAB-5-45 | 2-27 | 10 | 10 | | YES | | 1000 |
| DexMAB-5-95 | 3-60 | 10 | 10 | | YES | | 500 |
| DexMAB-10-40 | 10-38 | 10 | 10 | | YES | | No data |
| DexMAB-10-90 | 6-57 | 10 | 10 | | YES | | 500 |
| DexMAB-20-60 | 16-43 | 7.5 | 7.5 | | No | 1) 10 min at 37 degrees Celsius; 2) 5 min at 60 degrees Celsius; 3) 4 h at room temp with dextranase | Does not survive PCR cycling |
| DexMAB-25-75 | 15-40 | 5 | 5 | | No | 15 min pre-treatment of SPCs with 0.4M KOH followed by washes with 1xPBS + 0.1% pluronic F68 and 15 min treatment with dextranase at room temp. | 300 |
| DexMAB-10-Max | qualitative presence of substitution | Difficult to dissolve | | | | | |
| DexAB-50-100 | 9-42 | 10 | 10 | | No data | No data | No data |
| DexMAC2-10-90 | 5-50 | 10 | 10 | | No data | No data | No data |
| DexMA-200 | 110 | 5 | 5 | | No data | No data | No data |
| DexMA-250 | | Difficult to dissolve | | | | | |
| DexBio1MAB-10-90 | 6-45 (and biotin ~1) | 10 | 10 | | No data | No data | No data |
| AxylMA-10 | qualitative presence of substitution | 1 | 10 | | No data | No data | No data |
| HEC-20-80 | qualitative presence of substitution | 2.5 | 2.5 | | No | 50 ul SPCs + 5 ul of cellulase + 5 ul of 1M HCl (acidic conditions) overnight at room temp. | No data |
| HECMA-100 | qualitative presence of substitution | Difficult to dissolve | | | | | |

TABLE 6-continued

| 1<br>Shell polymer name | 2<br>NMR-determined substitution | 3<br>% core and shell polymer for robust microcapsule production | | 5<br>Crosslinked shell polymer hydrolyzed by enzymatic treatment 5 min at room temperature | 6<br>If available, alternative conditions for crosslinked shell polymer digestion by backbone-specific enzyme | 7<br>Minimum amplicon size retained |
|---|---|---|---|---|---|---|
| | | Shell polymer concentration, % w/w | Core polymer (Dex500) concentration, % w/w | | | |
| FicMAB-10-90 | qualitative presence of substitution | 10 | 10 | No | Not available | 300 |

FIG. 16 and FIG. 17 illustrate ficoll shell-based microcapsules in 1×PBS before and after dextranase treatment, respectively.

Microcapsule formation was tested by encapsulating the shell (modified dextran) and core (dextran) polymers using a microfluidics chip 40 μm height and having a nozzle 40 μm wide. Polymer concentration may be varied anywhere from 1-15% w/w, where a standard working range was 5-10% w/w. It is desirable to achieve the lowest working concentration in order to decrease viscosity, maximize flow rates and emulsion generation rate. Upon shell polymerization by exposure to 405 nm light (Droplet Genomics, cat. No. DG-BRD-405), microcapsules were washed and microscopy images were taken. Successfully formed microcapsules were characterized by a discernable shell (FIG. 2E).

Dextranase release was tested at room temperature by mixing 8 μl of packed microcapsules in 1×PBS with 2 μl of dextranase (Sigma Aldrich, cat. No. D0443-50ML) diluted 100× with 1×PBS. For soluble dextran-based shell polymers with less than 20% methacryloyl substitution, microcapsule disintegration occurred in less than 5 min. For the Ficoll-based composition, 20 uL of packed microcapsules were subjected to 40 uL of invertase (Sigma-Aldrich, cat. No. i4504, 100 mg/mL, approx. 450 U/mg enzyme activity) in 3M acetate buffer (pH 5.2) for 3 hours at 37 degrees Celsius or overnight at 45 degrees Celsius. Neither of these conditions led to microcapsule degradation.

PCR amplicon retention was tested as detailed in Example 3.

It also has been demonstrated that four bacterial strains and two mammalian cell lines can grow within the core-shell microcapsules (e.g., in DexMAB250 or DexMAB1090). It also has been confirmed that dextranase treatment does not affect cell viability. As a specific example, single mammalian-cell derived colonies have been expanded within microcapsules, individual cell-encapsulated microcapsules have been placed into separate wells by serial dilution, microcapsules in the wells have been degraded with dextranase, and the micro-colonies from the wells have been expanded further in full-scale cell culture.

Example 5: Degradable Microcapsules for High Molecular Weight (HMW) DNA Isolation This example describes methodology for utilizing microcapsules to process high molecular weight (HMW) DNA. The approaches take advantage of:
a) selective permeability of the microcapsule shell, which retains HMW DNA but allows buffer exchange, and the diffusion of enzymes and lysate components;
b) enzymatic degradability of the shell under mild conditions which prevent DNA hydrolysis or denaturation;
c) processing core-shell microcapsule suspensions as typical aqueous solutions, using standard liquid handling equipment, including pipettes, reaction tubes, and multi-well plates; and
d) HMW DNA entrapped within microcapsules is protected by the microcapsule shell from mechanical shearing during pipetting.

Eukaryotic or prokaryotic cells are encapsulated into microcapsules. Lysis is performed to release HMW DNA from the cell, and lysate components are washed out by buffer exchange. The microcapsule-contained HMW DNA is then subjected to further processing, which can include digestion by restriction endonucleases, fragmentation, DNA end-repair, A-tailing, adapter ligation, and/or probe annealing, depending on the read-out technology used. Examples of such technologies include long-read sequencing (LRS; e.g., Oxford Nanopore), optical mapping, and restriction pattern analysis by pulse-field gel electrophoresis. The processed DNA is loaded onto the instrument (e.g., sequencing flow cell, optical mapping chip, pulse-field gel electrophoresis (PFGE) gel) and only then is released from the microcapsules by enzymatic hydrolysis of the shell. Such a workflow facilitates the handling of fragile and viscous HMW DNA solutions, avoids time-consuming DNA precipitation and rehydration steps, and is automation-ready.

FIG. 18 illustrates a particular workflow for HMW DNA isolation and processing within microcapsules for long DNA molecule read-out technologies. Cells are compartmentalized into microcapsules (1) such that the majority of microcapsules have at least one cell. Cells are lysed to release DNA (2), and washes are performed to remove lysate components. Next, HMW DNA is processed using read-out method-specific protocols (3). Examples include library preparation for long-read sequencing, DNA labeling for optical mapping, and restriction digest for fragment analysis. The processed DNA, which is ready for analysis, is loaded onto the read-out instrument while still within microcapsules (4), and only then released by enzymatic hydrolysis of the shell.

In a specific implementation, E. coli cells are encapsulated into microcapsules to achieve 5 or more cells per microcapsule on average. The water-in-oil droplet formation, shell polymerization, and microcapsule release into aqueous phase procedure is performed as described in previous examples. E. coli cells are lysed using ready-made lysis reagents from commercial suppliers (e.g., ThermoFisher Scientific, cat. No. K0721), or an in-house approach that may include SDS, proteinase K, lysozyme, and/or RNAse A treatment, as well as elevated temperatures. In one approach, lysis is performed by incubating bacteria-containing microcapsules for 30 minutes in 10 mM Tris-HCl 7.5, 0.1% v/v Triton X-100, 1 mM EDTA, 50 U/ul lysozyme, 100 ug/ml Rnase A at 37 degrees Celsius, followed by the addition of 200 ug/ml Proteinase K and 1% (w/v) SDS, and incubating for 30 minutes at 50 degrees Celsius. Following lysis, 5-10 washes in Washing buffer (10 mM Tris-HCl (pH 7.5), 0.1% Triton X-100) is performed. During washes, microcapsules are collected at the bottom of the tube by centrifugation (e.g., 1 min at 1000 g). Further processing depends on the choice of the read-out technology.

For use with Oxford Nanopore sequencing as an example of LRS, HMW DNA within microcapsules are further processed using sequencing library preparation reagents recommended by the manufacturer (e.g., Ligation Sequencing Kit, Oxford Nanopore, cat. No. SQK-LSK109), and purification steps can be replaced using magnetic beads with buffer exchange of the microcapsule suspension, as addressed hereafter (e.g., Example 6). Prior to library preparation, fragmentation of genomic DNA into smaller fragments of 100s of kilobases may be performed. After library preparation, microcapsules are loaded directly into a Flongle or MinION flow cell, followed by the addition of a glycosidase specific to the shell polymer used to release DNA from microcapsules (e.g., dextranase for modified dextran shell polymer).

For optical DNA mapping, which can be implemented using a Bionano Genomics Saphyr instrument as an example, microcapsule-contained HMW DNA is labeled using a reagent kit suggested by the manufacturer (e.g., Bionano Prep Direct Label and Stain (DLS) Protocol, Bionano Genomics, cat. No. 80005), replacing membrane-based clean-up steps with microcapsule washes. The labeled DNA is released from microcapsules by glycosidase treatment after microcapsule loading onto the Saphyr chip flow cell.

For restriction fragment analysis using pulsed-field gel electrophoresis (PFGE), microcapsule-contained HMW DNA is digested using a restriction enzyme producing a characteristic restriction profile, such as NotI. Microcapsules are loaded into the well of an agarose gel, followed by the addition of a glycosidase enzyme into the same well. Both the microcapsule suspension and the enzyme solution are premixed with glycerol to facilitate loading into the well. PFGE is performed using standard parameters used for bacteria typing.

Example 6: Single-Cell B Cell Receptor (BCR) Nucleic Acid Sequencing Using Microcapsules This example describes an application of nucleic acid concatenation within microcapsules for recovering nucleic acid encoding native pairs of B cell receptor (BCR) heavy-chain and light-chain.

FIG. 20 details the methodology, which starts with anti-body-producing cell compartmentalization into microcapsules such that the majority of microcapsules contain one or zero cells. Cells then are lysed and BCR gene transcripts are enriched using reverse transcription and targeted PCR. The use of microcapsule enables buffer exchange between individual steps to allow optimal reaction conditions. The resulting amplicons of heavy- and light-chain cDNA are then concatenated into long DNA molecules, e.g., using ligation or Gibson assembly. From that step, concatemers from multiple microcapsules can be merged by enzymatic hydrolysis of the shell and taken further through sequencing library preparation and sequencing. As the method requires read lengths of greater than 1000 bp, and can benefit from ready lengths of greater than 10,000 bp, long-read sequencing technologies generally are used (e.g., Oxford Nanopore, PacBio).

A central step of the methodology is the physical linking of target molecules within a given microcapsule into concatemers, and obtaining sequencing reads spanning at least part of the concatemer units. There are several different approaches for performing steps between cell encapsulation into microcapsules and concatenation. There also are several different approaches for performing steps after forming concatemers. For example, concatemer release from microcapsules can be performed directly after concatenation (as illustrate in FIG. 20), after sequencing library preparation, or after loading microcapsules into a sequencing component (e.g., a Nanopore flow cell cartridge).

FIG. 20 illustrates a general methodology for BCR heavy- and light-chain pair sequencing enabled by microcapsules and long-read sequencing. Antibody-producing cells are compartmentalized into microcapsules (#1), then lysed (#2) retaining the nucleic acids within the microcapsule. Next, reverse transcription (RT) of the whole polyadenylated transcriptome is performed (#3).

Alternatively, gene-specific primers can be used at the RT step. Heavy- and light-chain cDNA is enriched in two rounds of semi-nested PCR (#4). The resulting amplicons within microcapsules are then concatenated by ligation or Gibson assembly. Buffer exchange is performed between the individual steps performed within microcapsules (#2-#6). Concatemers from individual microcapsules are pooled by enzymatic hydrolysis of the microcapsule shell, and library preparation is further performed using protocols specific for the long-read sequencing technology used (#7). Notably, all or part of the sequencing library preparation, including sequencing-technology adapter ligation, can be performed with DNA still within SPCs. In this scenario, purification steps typically using magnetic beads or columns are replaced by SPC washes. Information within a given sequencing read originates from the same microcapsule, and therefore the same cell. Heavy- and light-chain sequences present in the same read represent native pairs.

FIG. 21 outlines a specific experiment including the mixing of two mouse hybridoma cell lines. To avoid different cell line doublets caused by random encapsulation of cells in SPCs during their formation, 9e10 (ATCC® CRL-1729) and TNFalpha (Sigma Aldrich 92030603) cells were encapsulated into SPCs separately. The resulting SPCs were then mixed at an equal ratio before proceeding with the workflow further. When using such a strategy, trans-cell line heavy- and light-chain pairs can only be explained by nucleic acid diffusion between SPCs. All further steps were performed as a single-tube reaction. Cells were lysed, and heavy- and light-chain amplicons were enriched by gene specific RT with template-switching and two PCR reactions. Proteinase K treatment was performed to remove DNA polymerase molecules which remained bound to amplicons ends preventing efficient USER (Uracil-specific Excision Reagent) for the creation of sticky ends for efficient subsequent amplicon concatenation by ligation. As detailed in FIG. 22, the sticky DNA ends by design only allow the formation of circular concatenation products if both heavy- and light-chain fragments are present in the concatemer. Linear concatenation products were removed by exonuclease treatment, and circular concatenation products were amplified by multiple-displacement amplification (MDA). The amplification step is critical to generate a sufficient amount of material for Nanopore sequencing. Next, debranching was performed using the T7 endonuclease, and the resulting linear fragments were taken through Nanopore library while still in SPCs. The material from SPCs was released by dextranase treatment before loading onto a Nanopore flow cell.

In FIG. 22, concatenation of heavy- and light-chain amplicons for single-cell BCR sequencing using SPCs and long-read sequencing is depicted. After gene-specific RT and two rounds of enrichment PCR, amplicons with uracil bases in the 5' end are generated. The Uracil-Specific Excision Reagent (USER) is used to generate a single nucleotide gap at the location of the uracil residue, followed by the dissociation of the resulting 5-mer creating a 6-base 3' overhang for sticky-end ligation. By sticky end design, the formation of a concatemer containing both a heavy and a light chain amplicon is a prerequisite for circular product formation. Linear concatenation products are removed by exonuclease treatment, while circular products serve as the template for subsequent MDA.

Further detailed is the experimental procedure used in the workflow is presented in FIGS. 20, 21, and 22.

Encapsulation. Anti-cMyc-secreting 9E10 mouse (ATCC® CRL-1729) and anti-TNF-α-secreting M357-101-4 mouse (Sigma Aldrich 92030603) cells were inoculated separately in 25 cm2 culture flask with 5 mL of complete media (45 mL RPMI-1640 (Gibco, 21875034), 5 mL 100% FBS (Gibco, 15250061), 0.5 mL 100× GlutaMax (Thermo Scientific, 35050038), 0.5 mL 10000 U/mL Penicillin-Streptomycin (Gibco, 15140148)) and incubated at 37° C. for three days. The culture media was discarded, cells were washed with 5 mL of 1×PBS (Invitrogen, AM9625). Then cells were incubated at 37° C. for 3 min with 1 mL of 1× TrypLE (Thermo Scientific, 12563011) for detachment. When ≥90% of cells have detached 5 mL of fresh complete media was added followed by cell transfer to a 15 mL conical tube and centrifuged at 300×g for 5 min. The supernatant was discarded and cells were washed with 10 mL of 1×PBS supplemented with 0.1% Pluronic F-68 (Gibco, 24040032) and centrifuged at 300×g for 5 min. The cell pellet was then resuspend in 200 μL 1×PBS. Total number of cells and percent viability determined using Invitrogen Countess Automated Cell Counter. The Shell solution was prepared by mixing 100 μL 20% w/w Dex-MAB1090 with 100 μL nuclease-free water. The core solution was prepared by mixing 100 μL 20% w/w dextran 500k, 25 μL of 4% LAP (Merck, 900889), 20 μL 100 mM DTT (Sigma-Aldrich, 43816), 2 μL 10% Pluronic F-68, and 53 μL of cells diluted with 1×PBS. The cell concentration was aimed at 0.1 occupancy of SPCs. 9E10 and TNFα were encapsulated separately. ~200 μL of the working solutions were added into two different 1-mL syringe back-filled with ~300 μL HFE-7500 (3M, Novec 7500) and 1 mL of 0.25% DSO (Droplet Genomics, DG-DSO-20) was added into another 1-mL syringe. SPCs were generated with flow rates of 100 μL/hr; 100 μL/hr; 700 μL/hr for shell, core and DSO, respectively in a CF-60 microfluidic device (Droplet Genomics). The shell was polymerized by placing the tube of collected emulsion in the 405 nm LED device (Droplet Genomics) and exposing the emulsion to light for 30 s. Excess oil was removed, followed by breaking the emulsion with 20% PFO (Fluorochem, 007128) in HFE7500.

Cell Lysis. SPCs were 3× washed with Wash Buffer (10 mM Tris-HCl pH 7.5 (Invitrogen, 15575027), 0.1% Pluronic F-68 (Gibco, 24040032)). Washed SPCs with 9E10 and TNFα were pooled together to get ~200 μL of SPCs. SPCs were then suspended in 1 mL of Lysis Buffer (Fisher Scientific, K0731) supplemented with 80 μL 1 M DTT (Sigma-Aldrich, 43816-10ML) and incubated for 1 min at room temperature and centrifuged at 1000×g for 1 min. This step was repeated twice. Then SPCs were washed 5× with 1 mL of Wash Buffer supplemented with Proteinase K (10 mM Tris-HCl pH 7.5 (Invitrogen, 15575027), 1 mM EDTA (Invitrogen, 15575-038), 0.1% Triton x-100 (Sigma-Aldrich, T8787-100ML), Proteinase K (Thermo Scientific, K0731)) with 1 min incubations at room temperature while the first incubation was held for 10 min. Next, SPCs were washed 10× with 1 mL of Wash Buffer with EDTA (10 mM Tris-HCl pH 7.5, 0.1% Triton x-100, 1 mM EDTA) for Proteinase K removal. Then, SPCs were washed 3× with 0.5 mL of Wash Buffer with RiboLock (10 mM Tris-HCl pH 7.5, 0.1% Triton x-100, 0.5 U/μL RiboLock (Fisher Scientific, E00382)). 200 μL of wased SPCs were then mixed with 429 μL of Wash Buffer with RiboLock, 70 μL 10× Dnase I Reaction Buffer (Fisher Scientific, EN0521) and 1 μL Dnase I (Fisher Scientific, EN0521) and incubated for 30 min at 37° C. After the incubation 1 μL of 0.5 M EDTA was added per 100 μL sample and incubated for 10 min at 65° C. to inactivate Dnase I. Then SPCs were washed 3× with 0.5 mL of wash buffer with RiboLock Reverse transcription. Reverse transcription was performed by mixing 200 μL SPCs with 30 μL nuclease-free water, 80 μL 5×RT Buffer (Fisher Scientific, EP0753), 20 μL 10 mM dNTP (Fisher Scientific, R0192), 20 μL 20×RT_GS primer mix (Table 7, standard desalting, IDT, primer sequences from Chromium Next GEM Single Cell V(D)J Reagent Kits v.1.1 (10× Genomics)), 20 μL 20 μM RT_TSO (5' AAGCAGTGGTAT-CAACGCAGAGTACATrGrGrG (SEQ ID NO: 8), HIPLC, IDT), 10 μL 40 U/μL RiboLock (Fisher Scientific, E00382), 20 μL 200 U/μL RT Maxima H Minus (Fisher Scientific, EP0753). Sample was mixed by vortexing and then placed in a thermal cycler and incubated at 50° C. for 45 min followed by inactivation at 85° C. for 5 min. The SPCs were then washed 3 times with wash buffer (10 mM Tris-HCl pH 7.5 (Invitrogen, 15575027), 0.1% Triton X-100 (Sigma-Aldrich, T8787)).

Table 7: 20×RT_GS primer mix. Primer sequences and molar ratios are those used for mouse BCR enrichment PCR1 as described in Chromium Next GEM Single Cell V(D)J Reagent Kits v.1.1 (10× Genomics)).

TABLE 7

20X BCR_M1 primer mix. Table discloses SEQ ID NOS 9-20, respectively in order of appearance.

| Reagent Name | Initial conc. | Primer Name | Sequence (5'-3') | Mfgr | Purification | Final Conc |
|---|---|---|---|---|---|---|
| 20X RT_GS | 7.5 uM | Mouse_BCR_mix_1_R1 | TCAGCACGGGACAAAC TCTT (SEQ ID NO: 9) | IDT | STD | 0.375 uM |

TABLE 7-continued

20X BCR_M1 primer mix. Table discloses SEQ ID NOS 9-20, respectively in order of appearance.

| Reagent Name | Initial conc. | Primer Name | Sequence (5'-3') | Mfgr | Purification | Final Conc |
|---|---|---|---|---|---|---|
| | 3.5 uM | Mouse_BCR_mix_1_R2 | GCAGGAGACAGACTCT TCTCCA (SEQ ID NO: 10) | IDT | STD | 0.175 uM |
| | 2 uM | Mouse_BCR_mix_1_R3 | AACTGGCTGCTCATGG TGT (SEQ ID NO: 11) | IDT | STD | 0.1 uM |
| | 6 uM | Mouse_BCR_mix_1_R4 | TGGTGCAAGTGTGGTT GAGGT (SEQ ID NO: 12) | IDT | STD | 0.3 uM |
| | 5 uM | Mouse_BCR_mix_1_R5 | TGGTCACTTGGCTGGTG GTG (SEQ ID NO: 13) | IDT | STD | 0.25 uM |
| | 5 uM | Mouse_BCR_mix_1_R6 | CACTTGGCAGGTGAAC TGTTTTCT (SEQ ID NO: 14) | IDT | STD | 0.25 uM |
| | 6 uM | Mouse_BCR_mix_1_R7 | AACCTTCAAGGATGCT CTTGGGA (SEQ ID NO: 15) | IDT | STD | 0.3 uM |
| | 10 uM | Mouse_BCR_mix_1_R8 | GGACAGGGATCCAGAG TTCCA (SEQ ID NO: 16) | IDT | STD | 0.5 uM |
| | 2.5 uM | Mouse_BCR_mix_1_R9 | AGGTGACGGTCTGACT TGGC (SEQ ID NO: 17) | IDT | STD | 0.125 uM |
| | 2.5 uM | Mouse_BCR_mix_1_R10 | GCTGGACAGGGCTCCA TAGTT (SEQ ID NO: 18) | IDT | STD | 0.125 uM |
| | 5 uM | Mouse_BCR_mix_1_R11 | GGCACCTTGTCCAATC ATGTTCC (SEQ ID NO: 19) | IDT | STD | 0.25 uM |
| | 2 uM | Mouse_BCR_mix_1_R12 | ATGTCGTTCATACTCGT CCTTGGT (SEQ ID NO: 20) | IDT | STD | 0.1 uM |

Primer sequences and molar ratios are those used for mouse BCR enrichment PCR1 as described in Chromium Next GEM Single Cell V(D)J Reagent Kits v.1.1 (10× Genomics)).

BCR enrichment PCR I and IL. BCR enrichment PCR I was performed by mixing 190 µL SPCs with 26 µL nuclease-free water, 24 µL 20×BCR_M1 primer mix (Table 8A, standard desalting, IDT, primer sequences are taken from Chromium Next GEM Single Cell V(D)J Reagent Kits v.1.1 (1 OX Genomics)) and 240 µL 2×Q5 High-Fidelity Master Mix (NEB, M0492S). The sample was mixed by vortexing and then placed in a thermal cycler with parameters: 98° C. for 45 s, 13 cycles of 98° C. for 20 s, 67° C. for 15 s, 72° C. for 15 s, final extension at 72° C. for 1 min. The SPCs were then washed 3 times with wash buffer (10 mM Tris-HCl pH 7.5 (Invitrogen, 15575027), 0.100 Triton X-100 (Sigma-Aldrich, T8787)). BCR enrichment PCR II was performed by mixing 110 µL SPCs with 2.5 µL nuclease-free water, 12.5 µL 20×BCR_M2_U primer mix (Table 8A, standard desalting, IDT) and 125 µL 2×KAPA HiFi HotStart Uracil+ ReadyMix (Roche, 07959052001). The sample was mixed by vortexing and then placed in a thermal cycler with the same parameters as BCR enrichment PCR L. The SPCs were then washed 3 times with wash buffer (10 mM Tri s-HCl pH 7.5 (Invitrogen, 15575027), 0.100 Triton X-100 (Sigma-Aldrich, T8787)).

TABLE 8A

20X BCR 2M_U primer mix. Table discloses SEQ ID NOS 21, and 9-20, respectively, in order of appearance.

| Reagent Name | Initial conc. | Primer Name | Sequence (5'-3') | Mfgr | Purification | Final Conc |
|---|---|---|---|---|---|---|
| 20X BCR_M1 | 20 uM | PCR1_tso_2020rz | AAGCAGTGGTATCAAC GCAGAG (SEQ ID NO: 21) | IDT | PAGE | 1 uM |
| | 7.5 uM | Mouse_BCR_mix_1_R1 | TCAGCACGGGACAAAC TCTT (SEQ ID NO: 9) | IDT | STD | 0.175 uM |
| | 3.5 uM | Mouse_BCR_mix_1_R2 | GCAGGAGACAGACTCT TCTCCA (SEQ ID NO: 10) | IDT | STD | 0.1 uM |
| | 2 uM | Mouse_BCR_mix_1_R3 | AACTGGCTGCTCATGG TGT (SEQ ID NO: 11) | IDT | STD | 0.3 uM |

TABLE 8A-continued

20X BCR 2M_U primer mix. Table discloses SEQ ID NOS 21, and 9-20, respectively, in order of appearance.

| Reagent Name | Initial conc. | Primer Name | Sequence (5'-3') | Mfgr | Purification | Final Conc |
|---|---|---|---|---|---|---|
| | 6 uM | Mouse_BCR_mix_1_R4 | TGGTGCAAGTGTGGTT GAGGT (SEQ ID NO: 12) | IDT | STD | 0.25 uM |
| | 5 uM | Mouse_BCR_mix_1_R5 | TGGTCACTTGGCTGGTG GTG (SEQ ID NO: 13) | IDT | STD | 0.25 uM |
| | 5 uM | Mouse_BCR_mix_1_R6 | CACTTGGCAGGTGAAC TGTTTTCT (SEQ ID NO: 14) | IDT | STD | 0.3 uM |
| | 6 uM | Mouse_BCR_mix_1_R7 | AACCTTCAAGGATGCT CTTGGGA (SEQ ID NO: 15) | IDT | STD | 0.5 uM |
| | 10 uM | Mouse_BCR_mix_1_R8 | GGACAGGGATCCAGAG TTCCA (SEQ ID NO: 16) | IDT | STD | 0.125 uM |
| | 2.5 uM | Mouse_BCR_mix_1_R9 | AGGTGACGGTCTGACT TGGC (SEQ ID NO: 17) | IDT | STD | 0.125 uM |
| | 2.5 uM | Mouse_BCR_mix_1_R10 | GCTGGACAGGGCTCCA TAGTT (SEQ ID NO: 18) | IDT | STD | 0.25 uM |
| | 5 uM | Mouse_BCR_mix_1_R11 | GGCACCTTGTCCAATC ATGTTCC (SEQ ID NO: 19) | IDT | STD | 0.1 uM |
| | 2 uM | Mouse_BCR_mix_1_R12 | ATGTCGTTCATACTCGT CCTTGGT (SEQ ID NO: 20) | IDT | STD | |

Primer sequences are modified from those used for mouse BCR enrichment PCR2 as described in Chromium Next GEM Single Cell V(D)J Reagent Kits v.1.1 (10× Genomics). The modification entails the addition of sequences for sticky-end ligation at the 5'end.

TABLE 8B

Table discloses SEQ ID NOS 22-24, respectively, in order of appearance

| Reagent Name | Initial conc. | Primer Name | Sequence (5'-3') | Mfgr | Purification | Final Conc |
|---|---|---|---|---|---|---|
| 20X BCR_2M_U | 20 uM | PCR2_tso_U | AACGTUAAGCAGTGGT ATCAACGCAGAG (SEQ ID NO: 22) | IDT | STD | 1 uM |
| | 10 uM | R8_U | AATGAGUCCCTTGACC AGGCATCC (SEQ ID NO: 23) | IDT | STD | 0.5 uM |
| | 10 uM | R12_U | ACTCATUGAAGCACAC GACTGAGGCAG (SEQ ID NO: 24) | IDT | STD | 0.5 uM |

Electropherograms were used to confirm identity and purity of enriched BCR product amplified from 9E10 and TNFα. BCR light-chain: ~550 bp. Heavy chain: ~600-670 bp. A sample of SPCs was taken after BCR enrichment PCR II, treated with dextranase to release the amplicons, and AMPure XP purified (0.8×) before loading on an Agilent Bioanalyzer HS DNA chip.

Proteinase K treatment. After PCR reaction an aliquot of 140 µL SPCs was taken and mixed with 3 µL Proteinase K (Thermo Scientific, E00491) and 57 µL nuclease-free water. The sample was mixed by vortexing and then placed in a thermal cycler and incubated at 37° C. for 30 min followed by enzyme inactivation at 68° C. for 10 min. The SPCs were then washed 5 times with wash buffer (10 mM Tris-HCl pH 7.5 (Invitrogen, 15575027), 0.1% Triton X-100 (Sigma-Aldrich, T8787)). USER enzyme treatment. USER reagent treatment was performed by mixing 100 µL SPCs with 79 µL nuclease-free water, 20 µL 10× rCutSmart Buffer (NEB, M5505L), 1 µL USER reagent (NEB, M5505L). The sample was mixed by vortexing and then placed in a thermal cycler and incubated at 37° C. for 15 min. The SPCs were then washed 5 times with wash buffer (10 mM Tris-HCl pH 7.5 (Invitrogen, 15575027), 0.1% Triton X-100 (Sigma-Aldrich, T8787)).

Ligation. Ligation was performed by mixing 100 µL SPCs with 76 µL nuclease-free water, 20 µL 10×T4 DNA Ligase Buffer (Thermo Scientific, EL0012), 4 µL T4 DNA Ligase 5 U/µL (Thermo Scientific, EL0012). The sample was mixed by vortexing and then placed in a thermal cycler and incubated at 22° C. for 1 hr followed by enzyme inactivation at 70° C. for 5 min. The SPCs were then washed 3 times with wash buffer (10 mM Tris-HCl pH 7.5 (Invitrogen, 15575027), 0.1% Triton X-100 (Sigma-Aldrich, T8787)).

An electropherogram was used to confirm formation of ligated BCR heavy- and light-chains products.

Exonuclease treatment. Exonuclease treatment was performed by mixing 80 µL SPCs with 88 µL nuclease-free water, 20 µL 10×NEB T7 Buffer 2 (NEB), 4 µL Exonuclease I (Fisher Scientific, EN0582), 4 µL Exonuclease III (Fisher Scientific, EN0191) and 4 µL Lambda Exonuclease (Fisher Scientific, EN0562). The sample was mixed by vortexing and then placed in a thermal cycler and incubated at 22° C. for 1 hr followed by enzyme inactivation at 70° C. for 5 min. The SPCs were then washed 3 times with wash buffer (10 mM Tris-HCl pH 7.5 (Invitrogen, 15575027), 0.1% Triton X-100 (Sigma-Aldrich, T8787)).

MDA. MDA was performed by mixing 40 µL SPCs with 26 µL nuclease-free water, 10 µL 10× EquiPhi29 Buffer (Thermo Scientific, B39), 10 µL dNTP Mix (Thermo Scientific, R0192), 1 µL 0.1 M DTT solution, 1 µL 10% Triton X-100, 5 µL Exo-Resistant Random Primer Mix (Thermo Scientific, SO181), 5 µL 10 U/µL EquiPhi29 DNA Polymerase (Thermo Scientific, A39391), 2 µL 0.1 U/µL Pyrophosphatase (Thermo Scientific, EF0221). The sample was mixed by pipetting and then placed in a thermal cycler and incubated at 45° C. for 1 hr followed by enzyme inactivation at 65° C. for 10 min. A fluorescent microscopy image (FIG. 23) of SPCs post-MDA revealed, as expected, DNA presence in some but not all SPCs. In FIG. 23, BCR heavy- and light-chain concatemers amplified by MDA inside SPCs. DNA is stained with SYTO9 green fluorescent nucleic acid stain and imaged using a fluorescent microscope equipped with FITC filter (excitation 480/30, emission 535/40).

T7E1 Debranching. T7E1 Debranching reaction was performed by mixing 20 µL of SPCs with 14 L nuclease-free water, 4 µL 10× NEBuffer 2 (NEB, B7002S), 2 µL 10 U/µL T7 Endonuclease I (NEB, M0302L) and mixed by vortexing. Then sample was placed in a thermal cycler and incubated at 37° C. for 2 hr. The sample was washed 3× with wash buffer (10 mM Tris-HCl pH 7.5 (Invitrogen, 15575027), 0.1% Triton X-100 (Sigma-Aldrich, T8787)).

Library Preparation for Nanopore Sequencing and Sequencing. A sequencing ready library was constructed based on Ligation sequencing amplicons V14 protocol and using Ligation Sequencing Kit V14 (Oxford Nanopore Technologies (ONT), SQK-LSK114) on 20 µL of SPCs as input. After Nanopore adapter ligation, SPCs were dissolved by adding 1 µL of dextranase (Sigma-Aldrich, D0443) and nuclease-free water to achieve a total volume of 100 ul. AMPure purification (beads included in the SQK-LSK114 kit) was performed with 0.5× ratio. 17 fmol of the prepared library were sequenced on a R10.4.1 flow cell, MinION (ONT). 260 bps condition for chosen for accuracy. Reads were base called using Guppy 6.3.8 with 260 bps SUP mode. Concatenated reads were first cut at PCR primer sites, and the resulting inserts were then filtered by size >400 bp and mapped using Minimap2 with default parameters for ONT sequencing, and options—secondary=no—sam-hit-only to discard unmapped reads and secondary alignments.

Table 9 below summarizes the results of the experiment. Out of all base called reads, 3.6% of the reads mapped to the reference that includes expected TNFalpha and 9e10 hybridoma cell line heavy- and light-chain sequences. Most of the reads (68%) were unmapped, others did not pass filtering on length and quality. While it is desirable to obtain a higher fraction of mapped reads for practical application of the workflow, the 10,962 mapped reads revealed a low level of mixed-cell line concatemers (6.3%), with 52.7% and 41% of H-L concatemer corresponding to native pairs for TNFalpha and 9e10 cells, respectively

TABLE 9

Read analysis summary. H-L concatemer - heavy-light chain concatemer.

|  | Reads | % all | % H-L concatemers |
|---|---|---|---|
| # of base called reads | 307 372 | 100 | — |
| ≥400 bp reads | 249 664 | 81 | — |
| Unmapped | 209 346 | 68 | — |
| Mapped, mapQ < 60 | 4 194 | 1.4 | — |
| Heavy- and light-chain concatemers | 10 962 | 3.6 | 100 |
| TNFalpha H-L pairs only | 5778 | 1.9 | 52.7 |
| 9e10 H-L pairs only | 4492 | 1.5 | 41.0 |
| Mixed H-L pairs | 692 | 0.2 | 6.3 |
| Other (e.g., only 1 chain reads) | 25 162 | 8.2 | — |

Example 7: UMI-Assisted Concatemer Demultiplexing

This example describes a variation of concatenation methodology that does not require all targets of interest from a single cell to be part of the same concatemer to be successfully demultiplexed by cell of origin. Here, targets from a single cell are tagged with a unique set of UMIs (1 UMI per target). UMIs are random sequences sampled from a pool of poly-N oligos and methodology is illustrated FIG. 24 and FIG. 25. Given a large enough pool of poly-N oligos (e.g., $100*m*n$, where m is the number of cells studied and n is the number of targets), each sample of UMIs is essentially unique and constitutes the cellular "barcode". Next, the UMI-tagged targets are amplified (e.g., by PCR) and then concatenated. Concatemer reads originating from the same cell share one or more UMIs, while all the information from one given read is from the same cell. This demultiplexing approach is based on a "1 UMI set=1 read" principle.

FIG. 24 illustrates the "1 UMI set=1 cell" principle. Steps shown here correspond to steps 4-5 in FIG. 25. Nucleic acids (Nas) within individual microcapsules are tagged with unique molecular identifiers (UMIs), e.g., by ligation or Gibson assembly. The UMI-tagged Nas are amplified and concatenated within microcapsules. Next, concatemers containing UMIs are pooled in bulk solution, prepared for sequencing, and sequenced using standard protocols for long-read sequencing platforms. The resulting reads are demultiplexed by shared UMI information within the long reads.

FIG. 25 illustrates an example of a possible methodology for studying a given genomic target panel in single-cell using UMI-tagging and concatenation in microcapsules. For example, a cancer panel of 10-100 amplicons could be used. Cells of interest are first encapsulated into microcapsules so that the majority of microcapsules containing a cell contain one cell. Cells are lysed and PCR amplification is performed to enrich the target sequences in a multiplex PCR. The resulting amplicons are UMI-tagged using Gibson assembly, and then subject to further amplification and concatenation. From there, the material from all the microcapsules is pooled by enzymatic shell hydrolysis and further library preparation and long-range sequencing (e.g., Oxford Nanopore) is performed using standard protocols. FIG. 26 further details one possible concatemer assembly strategy at the level of DNA sequence elements.

FIG. 25 illustrates a workflow for multiplex PCR amplicon sequencing in single cells using target concatenation within microcapsules. Cells or other nucleic acid (NA)- containing particles are encapsulated into microcapsules (#1), then lysed (#2) retaining nucleic acid within the microcapsules. Next, a limited number of PCR cycles (less than 10 cycles) is performed to amplify target DNA sequences of interest (#3). Amplicons are UMI-tagged (#4) and amplified further (#5). The resulting UMI-tagged amplicons within microcapsules are then concatenated by ligation or Gibson assembly (#6). Buffer exchange is performed between the individual steps performed within microcapsules (#2-#6). Concatemers from individual microcapsules are pooled by enzymatic hydrolysis of the microcapsule shell (#7), and library preparation is further performed using recommended protocols for the long-read sequencing technology used (#8). Concatemer reads that share one or more UMIs are from the same cell.

FIG. 26 provides a schematic of a specific workflow for target amplification, UMI-tagging, and concatenation. DNA contained multiple targets of interest are amplified using a panel of primers for multiplex PCR (#1). The number of cycles is 2-10. The resulting amplicons are tagged with UMIs (#2) using Gibson assembly and duplex DNA oligonucleotides having the structure Bridge-UMI-GSfw or Bridge-UMI-Gsrev, where "GSfw" and "Gsrev" are the PCR1 primer sequences and "Bridge" serves as an adapter for the single-primer PCR2 (#3), and as the overlapping sequence between amplicons to be concatenated in the subsequent step (#4). "GSfw" refers to gene-specific forward primer, and "Gsrev" refers to gene-specific reverse primer.

FIGS. 27A and 27B provide anticipated results based on two in silico simulations of the workflow and the "1 UMI set=1 cell" principle described in FIGS. 24-26. To enable a successful graph-based read demultiplexing by shared UMIs as shown in FIG. 27A, the number of reads and/or the concatemer length must be sufficient for the chosen number of cells, genomic targets, and PCR1 amplification cycles. For example, increasing the number of PCR1 cycles from 5 (FIG. 27A) to 10 (FIG. 27B), while keeping the other parameters constant, leads to incomplete demultiplexing of the data and the presence of "orphan" reads that do not share UMIs with any other read. Simulations like these can be used to decide in advance on the sequencing depth needed for the "1 UMI set=1 cell" principle to work successfully and prevent "orphan" reads.

FIGS. 27A-27B illustrate in silico simulations of the workflow in FIG. 24 and the "1 UMI set=1 cell principle" (FIG. 25). FIG. 27A illustrates an example of parameter choice leading to unambiguous demultiplexing of all reads. The scatter plots on the right show the result of a force-directed layout of a k-nearest neighbor (kNN) graph of reads. Each dot is a read. Two given dots are connected by an edge if they share one or more UMIs. Shades of gray correspond to Leiden clustering result. The force-directed layout is performed for purposes of visualization in 2D. In simulation 1, reads form clear clusters. Reads within a given cluster are all from the same original microcapsule. There are no "orphan" reads, i.e., reads that do not belong to any cluster. FIG. 27B illustrates an example of parameter choice leading to orphan reads and therefore incomplete demultiplexing of the reads by microcapsule of origin. Orphan reads form the outer circle in the scatter plots and lack edges to other reads. Relatively to simulation 1, only the number of DNA target pre-amplification cycles (#3 in FIG. 25) prior to introducing UMIs was changed. This increased the number of unique molecules for UMI-tagging from 640 to 20,480 (32-fold), and the sequencing depth e.g., number of reads) was not sufficient to avoid orphan reads. The problem can be solved not only by increasing the sequencing depth but also by increasing the concatemer length.

Example 8: Concatenation and Sequencing of 3 Amplicons from Bacterial Genomes

In a previous example we described the use of the "1-read-1-cell" principle enabled by DNA target concatenation within SPCs to sequence native BCR heavy- and light-chain pairs, e.g., two targets in mammalian cells. This example extends the approach to 3 targets and bacterial cells, which are harder to lysis compared to mammalian cells. FIG. 28 provides an outline of the experiment performed. E. coli cells harboring a plasmid encoding GFP and the Ampicillin resistance gene (AmpR) were encapsulated into SPCs separately from B. subtilis cells lacking GPF and AMP genes. Right after SPC generation, SPCs containing the two species were mixed and processed further as a single-tube reaction. Target 16S, GFP, and AmpR gene sequences were amplified by PCR. Proteinase K treatment was performed to remove DNA polymerase molecules which remained bound to amplicons ends preventing efficient USER (Uracil-specific Excision Reagent) for the creation of sticky ends for efficient subsequent amplicon concatenation by ligation (FIG. 29). The ligation products were then release from SPCs by dextranase treatment, and full-size concatemers containing all 3 targets were enriched by PCR (see "PCR2-fw" and "PCR2-rv" annealing sites in FIG. 29), followed by Nanopore library preparation and sequencing. Since only E. coli cells harbor the plasmid with GFP and AMP genes, only 16S[E. coli]-AmpR-GFP concatemers should be observed in the data, with no 16S[B. subtilis]-AmpR-GFP. The presence of the latter cannot be explained by random arrival of cells into SPCs during their generation since E. coli and B. subtilis cells were encapsulated separately. 16S[B. subtilis]-AmpR-GFP can only occur as a result of undesired amplicon diffusion between SPCs.

FIG. 29 depicts in-SPC concatenation of amplicons of 3 targets from a single-bacterial cell. USER—Uracil-specific excision reagent.

Further is described the detailed experimental procedure and the results obtained.

Encapsulation. *Escherichia coli* (DH5α, with pUC-GFP vector which includes the ampicillin-resistance gene) and *Bacillus subtilis* (ATCC 6633) cells were inoculated in 5 mL of liquid LB media separately, and incubated at 37° C. overnight. LB media for *E. coli* (DH5α, with pUC-GFP vector) was supplemented with 5 µL of 50 mg/mL ampicillin. The absorbance was measured at OD600. The samples were centrifuged at 1000×g for 5 min, resuspended in 1×PBS buffer (Invitrogen, AM9625) by aiming final density at 2 OD. The Shell Solution was prepared by mixing 100 µL 20% w/w DexMAB1090 shell polymer with 100 µL nuclease-free water (Invitrogen, AM9932). The Core Solution was prepared by mixing 100 µL of 20% w/w Dextran 500k in 1×PBS, 25 µL of 4% LAP (Merck, 900889), 20 µL of 100 mM DTT (Sigma-Aldrich, 43816) and 55 µL of cells diluted with 1×PBS. Cell concentration was aimed at 0.1 occupancy of SPCs. *E. coli* and *B. subtilis* cells were encapsulated separately. ~200 µL of the working solutions were transferred into two different 1 mL syringe back-filled with ~300 µL HFE-7500 (Sigma-Aldrich, 98-0212-2929-3), and 1 mL of 0.25% DSO (Droplet Genomics, DG-DSO-20) was transferred into another 1 mL syringe. SPCs were generated with flow rates of 100 µL/hr; 100 µL/hr; 700 µL/hr for shell, core and DSO, respectively in a CF-60 microfluidic device (Droplet Genomics). The shell was polymerized by placing the tube of collected emulsion in the 405 nm LED device (Droplet Genomics) and exposing the emulsion to light for 30 s. Excess oil was removed, followed by breaking the emulsion with 20% PFO (Fluorochem, 007128) in HFE7500.

Semi-Permeable Capsules (SPCs) Fixation in Methanol. SPCs containing E. coli and B. subtilis cells were fixed separately. SPCs were washed 3 times with 1 mL wash buffer (10 mM Tris-HCl pH 7.5 (Invitrogen, 15575027), 0.1% Triton X-100 (Sigma-Aldrich, T8787)). For each 200 µL of SPCs sample 800 µL of methanol (Sigma-Aldrich, 34860-2.5L-R) were added while gently shaking. Samples fixed with methanol were stored at −20° C. for later use.

Bacteria Lysis. 0.4 mL of each SPCs sample with E. coli and B. subtilis cells fixed in methanol were pooled together. The obtained 0.8 mL mixed SPCs sample was centrifuged for 1 min at 1000×g. The resulting pellet was washed 5 times with 1 mL of Wash Buffer (10 mM Tris-HCl pH 7.5 (Invitrogen, 15575027), 0.1% Triton X-100 (Sigma-Aldrich, T8787)). The supernatant was removed and 500 µL of Alkaline Lysis Solution (800 mM KOH (Roth, 7949), 20 mM EDTA (Invitrogen, 15575020), 200 mM DTT (Sigma-Aldrich, 43816) was added. The volume was adjusted to 1 mL with Wash Buffer. The tube was placed into a rotator for 15 min at room temperature. The SPCs were then washed 5 times with Neutralization Buffer (1 M Tris-HCl pH 7.5 (Invitrogen, 15575027), 0.1% Triton X-100 (Sigma-Aldrich, T8787)), followed by 5 washes with Wash Buffer.

PCR. PCR was performed by mixing 50 µL of SPCs with 1 µL nuclease-free water, 3 µL 10 µM 16SU primer mix (16S_27F 5'AGAGTTTGATCMTGGCTCAG (SEQ ID NO: 25) and 16S_1492R_U 5'ACTCATUTACG-GYTACCTTGTTAYGACTT (SEQ ID NO: 26), standard desalting, IDT), 3 µL 10 µM GFP primer mix (E. coli_GFP_F_U 5'ACAAG-GUATGCGTAAAGGCGAAGAGCT (SEQ ID NO: 27) and E. coli_GFP_R 5'CCTGGTCATCATTTGTACAGTTC (SEQ ID NO: 28), standard desalting, IDT), 3 µL 10 µM AMP primer mix (E. coli_AmpR_F_U 5'AAT-GAGUGAGTAAACTTGGTCTGACAG (SEQ ID NO: 29) and E. coli_AmpR_R_U 5'ACCTTGUAATGGTTTCTTA-GACGTCAG (SEQ ID NO: 30), standard desalting, IDT), 60 µL 2×KAPA HiFi HotStart Uracil+ ReadyMix (Roche, 07959052001). The sample was mixed by pipetting and then placed in thermal cycler with parameters: 95° C. for 3 min, 30 cycles of 98° C. for 30 s, 55° C. for 30 s, 72° C. for 1 min, final extension at 72° C. for 5 min. The SPCs were then washed 3 times with Wash Buffer (10 mM Tris-HCl pH 7.5 (Invitrogen, 15575027), 0.1% Triton X-100 (Sigma-Aldrich, T8787)). An electropherogram of the PCR product was used to confirm the expected peaks present. The electropherogram of PCR products amplified from B. subtilis (ATCC 6633) and E. coli (DH5α, with pUC-GFP vector) cells exhibited observed peaks correspond to the following amplicons: 770 bp—GFP from E. coli; 1217 bp—AmpR from E. coli, 1735 bp—16S from E. coli and 1895 bp—16S from B. subtilis.

Proteinase K treatment. After PCR an aliquot of 40 µL SPCs was taken and mixed with 1.5 µL Proteinase K (Thermo Scientific, E00491) and 58.5 µL nuclease-free water. The sample was mixed by vortexing and then placed in a thermal cycler and incubated at 37° C. for 30 min followed by enzyme inactivation at 68° C. for 10 min. The SPCs were then washed 5 times with Wash Buffer. USER enzyme treatment. USER enzyme treatment was performed by mixing 40 µL SPCs with 49 µL nuclease-free water, 10 µL 10× rCutSmart Buffer (NEB, M5505L), 1 µL USER enzyme (NEB, M5505L). The sample was mixed by vortexing and then placed in a thermal cycler and incubated at 37° C. for 15 min. The SPCs were then washed 5 times with Wash Buffer.

Ligation. Ligation reaction was performed by mixing 40 µL of SPCs with 46 µL nuclease-free water, 10 µL 10× T4 DNA Ligase Buffer (Thermo Scientific, EL0012), 4 µL T4 DNA Ligase 5 U/µL (Thermo Scientific, EL0012). The sample was mixed by vortexing and then placed in a thermal cycler and incubated at 22° C. for 1 hr followed by enzyme inactivation at 70° C. for 5 min. The SPCs were then washed 3 times with Wash Buffer. An electropherogram of the ligation product was generated. It reveals the presence of the expected ~3-4 kb concatemers, that are absent before ligation. The amplicon corresponding to AmpR (~1.2 kb) must have been the limiting substrate of the concatenation reaction since it is depleted after concatenation.

DNA extraction. SPCs were dissolved by adding 1 µL of dextranase (Sigma-Aldrich, D0443) and nuclease-free water up to 100 µL. The sample was mixed by vortexing, followed by 0.8× AMPure purification (AMPure XP, A63881). Elution was performed in 20 µL of nuclease-free water. Ligation product enrichment. Ligation product enrichment was performed by mixing 1 µL (~3 ng) of purified DNA after ligation with 12.3 µL nuclease-free water, 0.7 µL 10 µM 16S-GFP primer mix (16S_27F 5'AGAGTTT-GATCMTGGCTCAG (SEQ ID NO: 25) and E. coli_GFP_R 5'CCTGGTCATCATTTGTACAGTTC (SEQ ID NO: 28), standard desalting, IDT), 14 µL 2×KAPA HiFi HotStart ReadyMix (Roche, 07958927001). The sample was mixed by pipetting and then placed in thermal cycler with parameters: 95° C. for 3 min, 15 cycles of 98° C. for 30 s, 55° C. for 30 s, 72° C. for 4 min, final extension at 72° C. for 5 min.

Library Preparation for Nanopore Sequencing and Sequencing. The sequencing ready library was constructed based on the Ligation Sequencing Amplicons V14 protocol and using Ligation Sequencing Kit V14 (Oxford Nanopore Technologies (ONT), SQK-LSK114) from 400 ng of DNA as input. AMPure purifications (beads included in the SQK-LSK114 kit) were performed with a 0.6× bead ratio. The library was sequenced on a R10.4.1 flow cell, MinION (Oxford Nanopore Technologies). 260 bps condition was used for accuracy. Reads were base called using Guppy 6.3.8 with 260 bps in SUP mode. The concatenated reads were first cut at PCR primer sites, and the resulting inserts were then mapped using Minimap2 with default parameters for ONT sequencing, and options—secondary=no—sam-hit-only to discard unmapped reads and secondary alignments. Table 10 below summarizes the sequencing data analysis results. 63.8% of reads passed filtering on read length. Out of those, 78.1% of reads mapped to all of E. coli 16S, AmpR, and GFP sequences. Only 0.51% of reads contained B. subtilis 16S, AmpR, and GFP sequences in the same read, which could only occur from amplicon diffusion between SPCs or mechanical SPC rupture right before and during ligation. FIG. 30 reveals the mapping positions on a sample of 100 reads determined to contain all of E. coli 16S, AmpR, and GFP sequences.

TABLE 10

Summary of sequencing data analysis.

| | Reads | % all | % >3000 bp reads | Average length, bp |
|---|---|---|---|---|
| SUP base called | 107 290 | 100 | — | |
| >3000 bp reads | 68 478 | 63.8 | 100 | |

TABLE 10-continued

Summary of sequencing data analysis.

| | Reads | % all | % >3000 bp reads | Average length, bp |
|---|---|---|---|---|
| E. coli 16S + AmpR + GFP | 53 514 | 49.9 | 78.1 | 3 351 |
| B. subtilis 16S + AmpR + GFP | 350 | 0.33 | 0.51 | 3 432 |

In FIG. 30, a sample of 100 reads determined to contain all of E. coli 16S, AmpR, and GFP in the same read. Mapped regions of the read are color-coded by reference gene (see legend). AMP—Ampicillin resistance gene.

Example 9: Single-Cell RNAseq by Microcapsule Split-and-Pool Barcoding

This example describes split-and-pool barcode assembly on microcapsule-entrapped nucleic acid derived from single cells. The semi-permeable shell of the microcapsules retains cell-derived nucleic acid (e.g., mRNA, genomic and plasmid DNA) the size of which is above the shell permeability threshold. Depending on the shell polymer composition, this threshold can be greater than 200 base pairs (bp), greater than 500 bp, greater than 1000 bp, or greater. Barcoding oligonucleotides, which are typically less than 200 bp, can diffuse freely through the shell. FIG. 6 details a generalized workflow for split-and-pool barcoding of microcapsule-entrapped nucleic acids. This example describes the implementation for eukaryotic single-cell mRNAseq (FIG. 8A, FIG. 9A, FIG. 11, FIG. 12).

Encapsulation.

K562 (human) and 9e10 (mouse) cells incubated in RPMI media were collected (300×g centrifugation for 1 minute) and washed with 10 ml of 1×PBS (Invitrogen, AM962) supplemented with Pluronic F-68 (Gibco, 24040032; final concentration 0.1%), then resuspended at 3.15 million cells/ml in 1×PBS with Pluronic F-68. Shell solution was prepared by mixing 100 μL 20% w/w DexMAB shell polymer with 20 μL 100 mM DTT (Sigma-Aldrich, 43816) and 80 μL 1×PBS. Core solution was prepared by mixing 100 μL core solution (Droplet Genomics, 20% Dextran 500) with 5 μL of 4% LAP (900889, Merck) with 95 μL of cells in 1×PBS with Pluronic F-68 (two separate core solution samples). Cell concentration was aimed at 0.1 occupancy of SPCs. ~200 μL of the working solutions were added into two different 1-mL syringes back-filled with ~300 μL HFE-7500 (Sigma-Aldrich 98-0212-2929-3) and 1 mL of 0.25% DSO (Droplet Genomics, DG-DSO-20) was added into another 1-mL syringe. The run was started for generating SPCs with flow rates of 100 μL/hr; 100 μL/hr; 700 μL/hr for shell, core and DSO, respectively in CF-60 microfluidic device (Droplet Genomics). Two runs with different cells were done with identical parameters. Separate emulsions of cells were generated for 20 minutes, encapsulating approximately 50 000 cells of each strain. The shell was then polymerized by placing the tube of collected emulsion in the 405 nm LED device (Droplet Genomics) and exposed the emulsion to light for 40 s. Excess oil was removed, followed by breaking the emulsion, with 20% PFO (Fluorochem, 007128) and washed 3 times with 1×PBS with Pluronic F-68. The resulting semi-permeable capsules (SPCs) were mixed together to the total volume of 400 μl.

Cell Lysis.

SPCs were split into 4 tubes and washed (1000×g, 1 minute) 2 times with 1 mL Lysis buffer (8 mL lysis buffer from GeneJET RNA Purification kit (Thermo Fisher Scientific, K0731), +320 μL 1M DTT) with 1 min. incubation between washes (all incubations in this section carried out at room temperature). Then SPCs were washed 5 times with 1 ml WB1 (wash buffer 1; 10 mM Tris-HCl (Invitrogen, 15568025), 1 mM EDTA (Invitrogen, 15575020), 0.1% Triton X-100 (Roth, 3051.3), supplemented with Proteinase K (Thermo Fisher Scientific, E00491) to a final concentration of 0.33 mg/ml. 10 min. incubation for first wash, 1 min. incubations for following washes. SPCs were then washed 10 times with 1 mL WB1 and washed 3 times with 500 μL of WB2 (wash buffer 2; 10 mM Tris-HCl 7.5, 0.1 Triton X-100) supplemented with 40 U/μL Ribolock Rnase Inhibitor (Thermo Fisher Scientific, E00382) at final concentration of 0.5 U/μL.

DNase I Treatment.

500 μL of SPCs suspension in wash buffer were mixed with 55 μL 10× DNAse I buffer, 5 μL 1 U/μL DNAse I (Thermo Fisher Scientific, EN0525). SPCs were incubated for 30 min at 37° C., followed by addition of 56 μL of 50 mM EDTA and incubation for 10 min. at 65° C. SPCs were washed 3 times with 500 μL of WB2 (wash buffer 2; 10 mM Tris-HCl 7.5, 0.1 Triton X-100) supplemented with 40 U/μL Ribolock Rnase Inhibitor at final concentration of 0.5 U/μL.

Reverse Transcription (RT).

SPCs were suspended in 800 μl of WB2. 700 μl of RT master mix was prepared: 88 μL 10 mM dNTPs (Thermo Fisher Scientific, R0192), 34 μL 500 μM Template Switching Oligo (Metabion), 44 μL 40 U/μL Ribolock Rnase Inhibitor, 88 μL 200 U/μL Maxima H-Reverse Transcriptase, 352 μL 5×RT buffer (Thermo, EP0752), 96.8 μL water, nuclease free (Invitrogen, 10977015). In 13 different PCR-tubes 50 μl of SPCs suspension were combined with 40 μl of RT master mix and 10 μl of unique RT primer containing barcode D (Integrated DNA Technologies). Tubes were put in thermocycler and reaction was carried out: 60 minutes at 50° C., 5 minutes at 85° C., hold at 4° C. SPCs were collected to two 1.5-ml tubes and washed with 1 ml of WB2 3 times.

cDNA Enrichment PCR.

Washed SPCs were suspended in 360 μl of WB2. 55 μl of master mix (44 μL of 10 μM PCR primer mix, 440 μl of 2×KAPA HiFi Uracil+PCR ready mix (Roche, KK2801) were mixed with 45 μl of SPCs suspension in PCR-tubes. The tubes were placed in thermocycler and program was run: 40 s at 98° C., [20 s at 98° C., 30 s at 63° C., 6 min at 72° C., repeated 10 cycles total], 1 min at 72° C., hold at 4° C.

Proteinase K Treatment.

SPCs were collected to two 1.5-ml tubes and washed with 1 ml WB2 3 times. After last wash 200 μl of suspension is left in the tube. 2.5 μl of 20 mg/ml Proteinase K was added to each tube, the tubes were incubated for 30 minutes at 37° C., followed by inactivation for 10 minutes at 68° C. SPCs were washed 5 times with WB2.

USER Treatment.

100 μl of packed SPCs were mixed with 20 μL 10× CutSmart buffer, 2 μL of 1 U/μL USER enzyme (NEB, M5505S) and 78 μL nuclease free water, and incubated for 15 minutes at 37° C. SPCs were washed 3 times with 1 ml WB2.

Barcode Ligation.

Master Plate Preparation (300/600 μM). 96 sets of barcode C, B, and A were received in master plates containing 300 μM (or 600 μM for barcode B) of oligos in solution, in 96 well plates. Master plates were briefly centrifuged (300× g, 30 s) and put into the thermal cycler for oligo annealing starting from 95° C. by gradually decreasing the temperature to 20° C., in ~60 min and final hold at 20° C.

Working Plate (15 μM) Preparation from Master Plates (300/600 μM). 1 μL of oligos from A, B, C master plates were transferred into each well of working plate containing 19 μL of nuclease-free water (or 39 μL for barcode B) to reach 15 μM oligo concentration. Then, each well was mixed by pipetting and 10 μl of each oligo were aliquoted to other working plates resulting in 2 working plates containing 10 μl of 15 μM barcode oligos (4 plates for barcode B). Plates were centrifuged for 1 min at 1000×g and stored at −20° C.

Barcode ligation in working plates. The following step is repeated 3 times for each barcode starting with barcode C and finishing with barcode A: SPCs were washed 3 times with 1 ml 1× ligation buffer supplemented with Triton X-100 to a final concentration of 0.1%, leaving 1 ml of suspension after last wash. 100.8 μL 5 U/μL T4 ligase (Thermo Fisher Scientific, EL0012), 302.4 μL 10× T4 ligase buffer and 705.6 μL water, nuclease-free were added to SPCs suspension resulting in ligation master mix. 20 μl of master mix was added to each well of the barcode working plate and the plates were incubated in thermocycler for 15 min. at 20° C. After incubation 30 μl of STOP-25 buffer (10 mM Tris-HCl, 0.1% Tween 20, 100 mM KCl, 25 mM EDTA) was added to each well to stop the reaction. SPCs were pooled into a 15-ml tube and each well of the plate was rinsed with 20 μl of STOP-25 buffer and collected into the same 15-ml tube. Sample volume was adjusted to 8 mL with STOP-25 buffer and the sample was incubated at room temperature for 5 minutes. SPCs were split into 2-ml tubes and washed 5 times with 1 ml WB2.

Library Preparation and Illumina Sequencing.

SPCs aliquot of 1000 was taken from 100k barcoded cells. SPCs were dissolved with 1 μL of Dextranase (Sigma Aldrich, D0443), reaction volume was adjusted to 100 μL with nuclease free water. DNA was purified with 0.8× AMPure XP beads (Beckman Coulter, A63881). Sequencing ready libraries were constructed with the NEBNext® Ultra™ II FS DNA Library Prep Kit (NEB, #E7805S) using 50 ng of DNA as input and sequenced on a MiSeq sequencing system (Illumina) using a Miseq Nano v2 300 cycle kit. Reads lengths were specified as 254 cycles for read 1, 20 cycles for read 2, 20 cycles for i7 read (specified in sample sheet by entering a mock 20-nt i7 sequence), 6 cycles for i5 read (specified in sample sheet by entering a mock 6-nt i5 sequence).

Data Processing.

Bcl2fastq was used to generate a separate fastq file for each of the 4 sequencing reads. STAR-solo was used for alignment to a mixed human-mouse reference genome (GRCh38 and GRCh39) and read demultiplexing by barcode.

Results.

K562 and 9e10 cells were encapsulated (lambda=0.1) into SPCs, their RNA converted to cDNA, which was amplified and modified for barcode ligation. After barcoding an aliquot of SPCs was taken for sequencing library preparation representing 1000 cells, DNA was fragmented to around 400 bp size, amplified using PCR and resulting DNA was analyzed by Agilent 2100 Bioanalyzer. The result shows the electropherogram of the final library before sequencing obtained on a Agilent 2100 Bioanalyzer instrument. The average library size was 400 bp.

The output summary of running STAR-solo is provided in FIG. 32. 672786 reads were obtained, of which, 91.8% had the correct barcode assembly. 73% of reads were uniquely mapped to the reference genome. The results show that no significant species mixing occurs during barcoding (FIGS. 30 and 31) and human cells can be easily differentiated from mouse cells using unbiased visualization in 2D with UMAP (FIG. 35).

FIG. 33 shows a Human vs mouse count barn-yard plot scatter plot of cells with number of reads aligned to mouse and human genomes. Each dot is a cell barcode. Cells are assigned to either K562 (human) or 9e10 (mouse) if more than 99% of reads associated with that barcode are mapping to one genome. Otherwise, cell barcodes are identified as mixed genomes. A permissive filtering of barcodes including all barcodes with at least one count was used for generating this plot. Barcodes with mixed species reads gravitated near the origin of the x-y axis.

FIG. 34 shows a distribution of barcodes by human countfraction includes all barcodes with at least one count. As expected, the vast majority of barcodes have exclusively human or exclusively mouse counts but not both.

FIG. 35 shows an unbiased 2D visualization of ~1000 barcodes with >200 counts. Upon performing unbiased 2D visualization of barcodes using UMAP, two distinct cell clusters were observed, and corresponded to mouse and human cell cells (human—710 barcodes, mouse—249 barcodes, mixed—2 barcodes).

Example 10: High-Throughput Single-Microbe DNA Sequencing Using Barcoding Beads

The study of single-microbe nucleic acids (NAs) has been previously demonstrated using droplets. Workflows for sequencing single-microbe genomic DNA involve cell lysis and whole genome amplification as first steps. The inhibitory effect of lysis reagents is compensated by lysate dilutions with amplification reagents achieve by droplet merging (e.g., Hosokawa et al., Sci Rep. 7(1): 5199 (2017); Zheng et al., bioRxiv, 2020: p. 2020.12.14.422699). Droplets with single amplified genomes (SAGs) are then either hand-picked for further barcoding in wells or subjected to another two rounds of droplet merging to achieve NA barcoding in drops (e.g., Zheng et al., bioRxiv, 2020: p. 2020.12.14.422699), resulting in a workflow that is prohibitively complex. However, dilution by droplet merging only helps with relatively mild chemical and enzymatic lysis conditions. Harsh reagents such as SDS are known to inhibit polymerases even at concentrations 100× lower than those in the lysis buffer (e.g., Goldenberger et al., PCR Methods Appl, 4(6): 368-70 (1995)). Similarly, protease-treatment is known to improve the quality of extracted NAs, but without complete removal of proteases, any subsequent enzymatic reaction would be inhibited. Further, multiple metagenomic studies have demonstrated pronounced lysis-related biases in DNA composition of environmental and human microbiota samples (e.g., Sasada et al., J. Biomolecular Techniques: JBT, 2020. 31 (Suppl): p. S30-S31; Keisam et al., Sci Rep, 2016. 6: p. 34155). The susceptibility to lytic agents differs among microbial taxa due to differences in the cell wall structure and composition (e.g., Shehadul Islam et al., Micromachines, 2017. 8(3): p. 83). Therefore, compromising on lytic agent choice to satisfy technical constraints posed by the use of droplets inevitably leads to biases and causes hard-to-lyse microbes to be overlooked.

This example illustrates barcoding and sequencing of single-amplified microbial genomes. The approach in this sample also is directly applicable to the analysis of DNA of other organisms, e.g., higher eukaryote cells. Microcapsules enable no-compromise multi-step microbe lysis while maintaining compartmentalization of individual genomes and compatibility with downstream enzymatic reactions, including barcoding in droplets.

An overall strategy using microcapsule-entrapped cell lysis to overcome limitations of regular water-in-oil droplets is detailed in this particular example and is best understood along with FIG. 40. Individual microbial cells are isolated in microcapsules such that the majority of microcapsules contain one or no cell. The encapsulation of microbial cells is Poissonian, and a typical regime is to achieve, on average, less than 0.3 cells/microcapsule, and more preferably less than 0.1 cells/microcapsule. The compartmentalized cells are lysed to generate single-cell lysates that retain most of the nucleic acids inside the microcapsules. Whole-genome amplification is then performed by multiple displacement amplification (MDA), producing a hyper-branched DNA product, which is fragmented to obtain DNA fragments large enough to be retained within the microcapsule. The DNA size cut-off of the microcapsule depends on the nature and concentration of the shell polymer used. The cutoff can be a size greater than 100 base pairs (bp), greater than 200 bp, greater than 500 bp, greater than 1000 bp or larger. Post fragmentation, end-repair and A-tailing are performed yielding microcapsule-entrapped DNA ready for barcoding by barcode bearing-oligonucleotide ligation in drops. Microcapsules with fragmented and A-tailed DNA are co-encapsulated in droplets with barcode-bearing beads, a shell degrading enzyme, and ligation reagents such that greater than 50%, and often greater than 80%, or the droplets contain exactly one microcapsule and one barcoding bead.

A barcoding oligonucleotide design that allows efficient ligation to A-tailed DNA fragments includes a double-stranded region at one of the ends. This double-stranded region has a single overhanging T at the 3' end (FIG. 40). Following the barcoding of DNA fragments, droplets are merged and further library processing is performed on the pooled material. One strategy, shown as option A in FIG. 40, is to proceed with whole-genome sequencing. The resulting sequencing reads encode both the barcode information and the genomic sequence. Reads can then be grouped by barcode to identify reads originating from the same microcapsule and therefore the same cell. The whole-genome sequencing approach is of interest for applications such as de novo genome assembly of previously unidentified organisms.

A second strategy that can be implemented, which is shown as option B in FIG. 40, is to only amplify sequences of genes of interest and perform targeted sequencing. One notable scenario where this strategy is of interest is in taxonomy-function linkage, where a fraction of the pooled material is used to select for phylogenetic markers and another fraction of the material is used to select genes of interest, such as antibiotic resistance genes. Targeted sequencing allows the study of orders of magnitude larger numbers of single cells without an increase in sequencing cost. The targeted libraries contain the barcode information which is used to link reads originating from the same cell in silico.

A third strategy is to perform both whole-genome sequencing and targeted sequencing of phylogenetic markers. The information obtained from the targeted library allows linking barcodes with specific cell types, which in turn allows the pooling of all reads coming from the same cell type, this way improving the genome coverage of de novo assembly applications.

FIG. 40 illustrates a specific example of an experimental approach for single-cell DNA sequencing. Cells are encapsulated in semi-permeable compartments (microcapsules) such that the majority of microcapsules contain one or zero cells (#1). Cells are lysed to release genomic DNA, followed by washes to remove components of the lysate that could inhibit subsequent reactions (#2). Individual genomes are amplified within microcapsules by multiple displacement amplification (MDA) to obtain single-amplified genomes (SAGs). (#3). Upon buffer exchange, fragmentation and A-tailing is performed (#4), resulting in microcapsule-entrapped barcoding-ready nucleic acids. Barcoding is performed in droplets by co-encapsulating fragmented SAG-bearing microcapsules with barcoding-oligonucleotide-bearing beads (#5). One end of the barcode-bearing oligonucleotide is double-stranded and has a single T overhang at the 3' end for efficient ligation with microcapsule-contained DNA fragments having a 3' A overhang. Once in a droplet, barcodes are released and the microcapsule shell is disintegrated by shell-degrading enzyme treatment. Following the barcoding of DNA fragments, droplets are merged (#6) and further library processing is performed on the pooled material. The resulting barcoded material can be used for at least two sequencing strategies.

As illustrated in FIG. 40, one strategy is to perform whole genome sequencing, which is of interest for applications such as genome assembly (#7). Another strategy relies on targeted amplification and sequencing of one or several genes of interest along with the barcode sequence (#8). Taxonomy-function linkage is an example of an application where targeted sequencing is of interest. In a taxonomy-function linkage assay, a functional gene of interest, such as an antibiotic resistance gene, can be linked to a specific taxon, identified from phylogenetic marker genes (e.g., 16S rRNA, other small subunit rRNA (ssu-rRNA) genes, recA, RpoB).

A conventional experiment for assessing single-cell sequencing approaches is a species mixing experiment using two well-characterized organisms for which each reference genome is known.

FIGS. 41A-41E show results of such an experiment using the procedure described herein, revealing a clear separation of *E. coli* and *B. subtilis* sequencing reads and the absence of cross-contamination. Microcapsules containing *B. subtilis* were generated separately from microcapsules containing *E. coli* cells. Microcapsules containing genomes of the two different species were mixed in equal ratios after SAG generation by MDA. Such experiment design set a particularly high expectation for the absence of mixed genomes in the data as they cannot be explained by two bacteria of different species entering the same microcapsule. Data analysis of the resulting reads revealed that 93% of reads had a correct barcode structure and 89% of reads mapped to the reference mix-species genome. Barcodes with greater than 30,000 mapped reads were not considered.

FIGS. 41A-41E show experimental results from applying the approach detailed in FIG. 40 for whole microbial genome sequencing. FIG. 41A shows single amplified genomes (SAGs) stained with a DNA-binding fluorescent dye (Cyto 9). FIG. 41B shows an electropherogram of fragmented SAG DNA prior to barcoding. FIG. 41C shows fragmented SAG-containing microcapsule co-encapsulation with barcoding beads. Barcoding beads were delivered through (i), ligation reagents through (ii), and microcapsules through (iii). FIG. 41D shows an electropherogram of final DNA libraries loaded onto an Illumina MiSeq sequencer. FIG. 41E shows the number of reads mapping to *E. coli* and *B. subtilis* genomes for each barcode. *E. coli* and *B. subtilis* SAG-bearing microcapsules were mixed approximately equal ratios prior to barcoding.

Another measure of method performance is the breadth of genome coverage for a given sequencing depth, where depth is the percentage of genome covered by the sequencing data at least once, and depth is the total number of sequencing bases divided by the size of the reference. After observing a lack of correlation between depth and breadth in initial experiments (FIG. 42A), it was hypothesized that the reason was suboptimal lysis preventing genomic DNA accessibility to amplification reagents. Experimental results using *E. coli* (FIGS. 42A-42D) revealed that the addition of a SDS lysis step had a small positive effect, and that including alkaline lysis led to a marked improvement, as judged by dots approaching the theoretical maximum breadth for a given depth. Microcapsules allow combining multiple lysis strategies to ensure uniform representation of different species in complex samples.

Figure 42A:
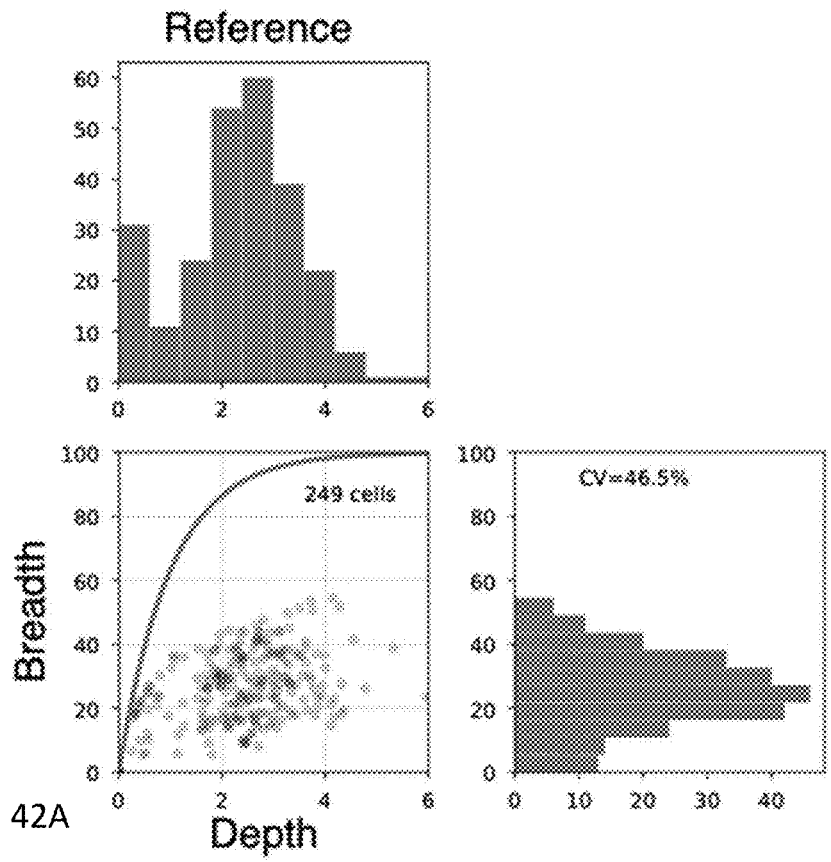
FIGS. 42A-42D show bacterial lysis optimization results.
Figure 42B:
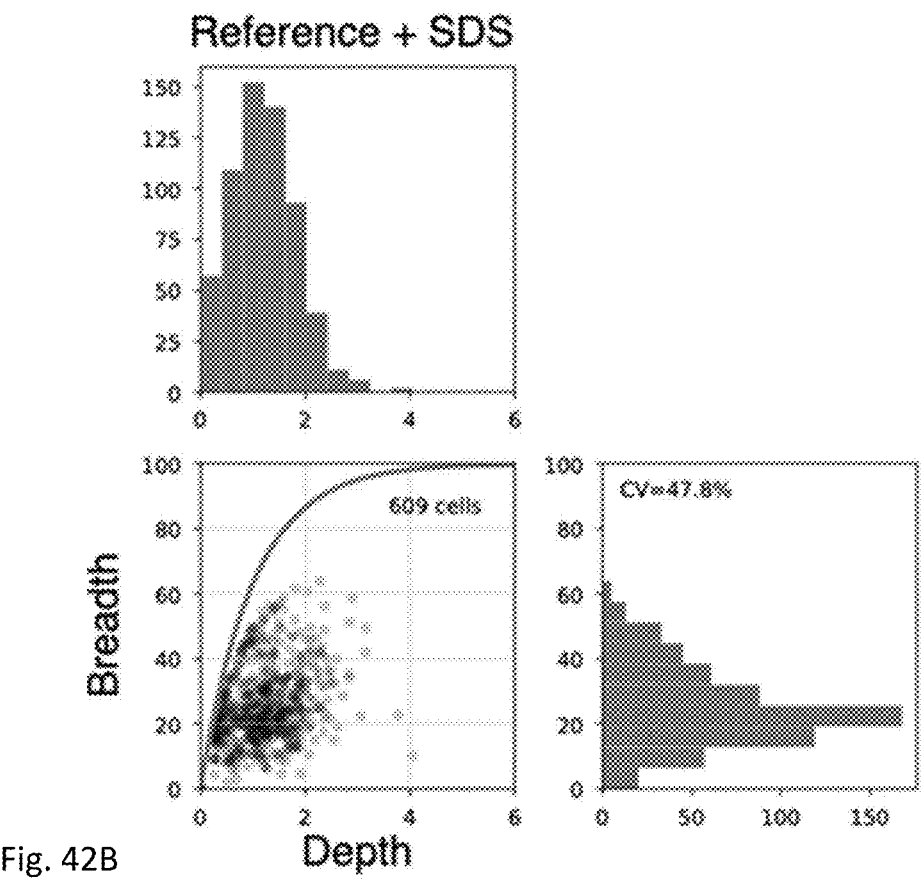
Figure 42C:
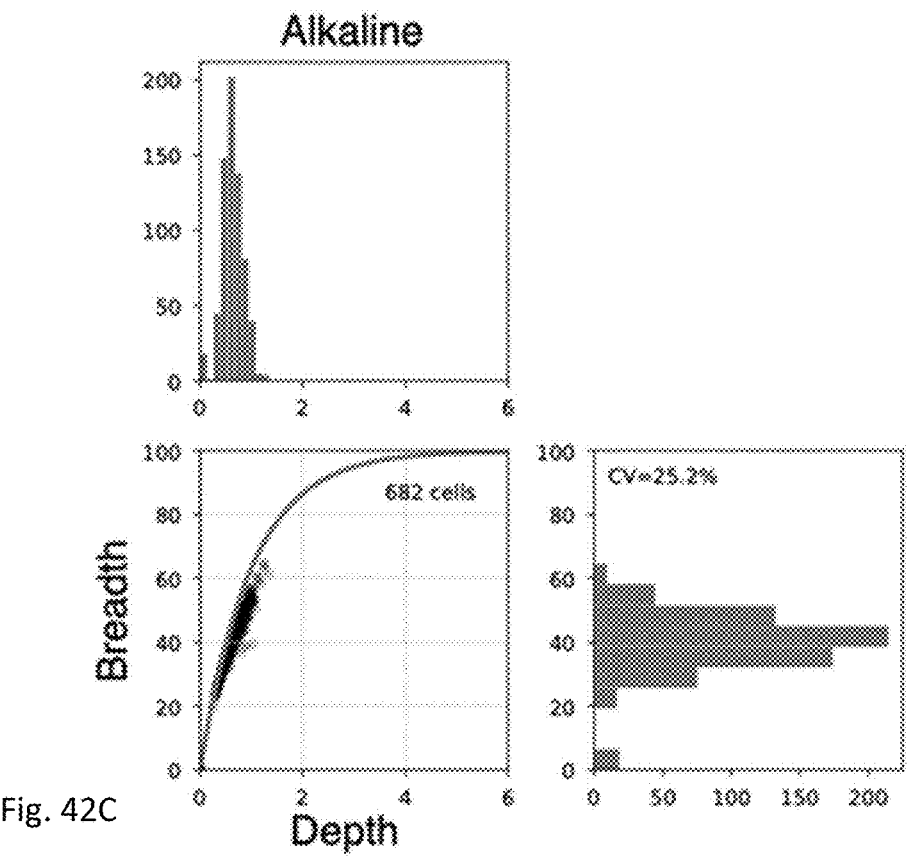
Figure 42D:
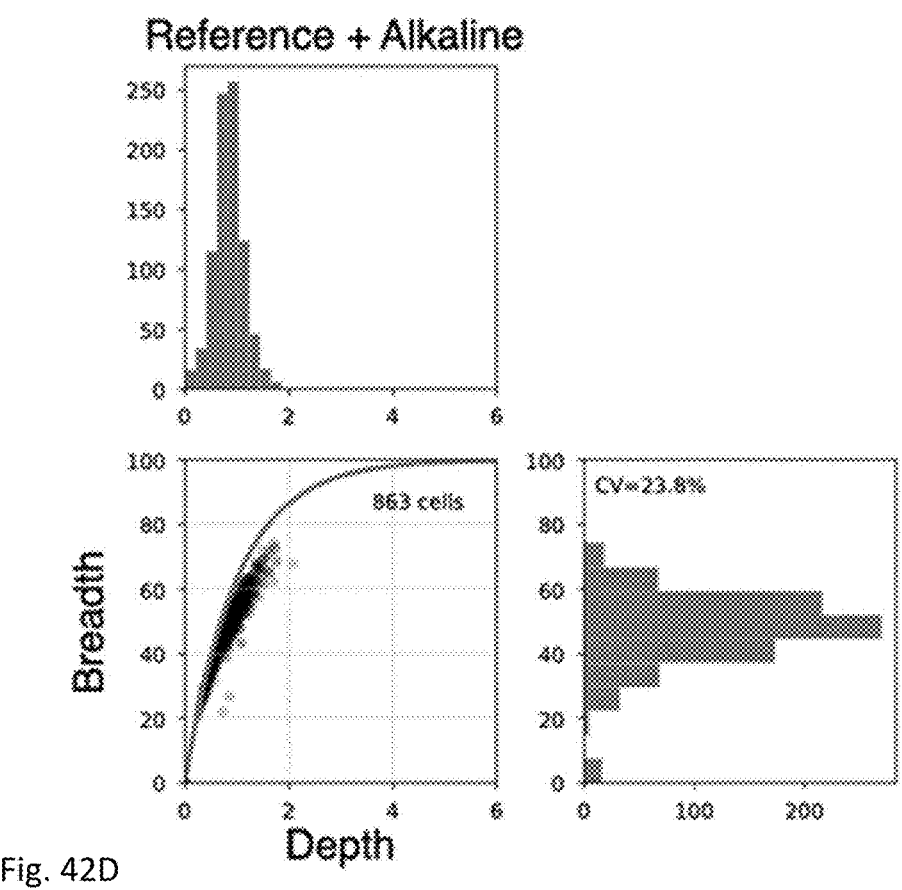

FIGS. 42A-42D show bacterial lysis optimization results. Dots in the scatter plots represent individual barcodes (e.g., cells). Breadth is defined as the percentage of the reference *E. coli* genome covered at least once. Depth is defined as the average number of bases in the sequencing data per base in the reference genome. Both measures were obtained from BAM files after aligning the sequencing data to the *E. coli* reference genome using STARsolo. The solid line represents the maximum expected breadth for a given depth. The experimental procedure was as described below with MDA performed for 1 h, and modifications to the lysis conditions. FIG. 42A shows results for reference lysis conditions: 50 U/ul lysozyme, 0.2 mg/ml Proteinase K, incubation at 37 degrees Celsius for 30 min followed by 50 degrees Celsius for 30 min. FIG. 42B shows results for reference conditions and SDS: 0.5% SDS was added to the 500 C incubation. FIG. 42C shows results for alkaline lysis conditions: 0.4M KOH, 10 mM EDTA, 100 mM DTT for 15 min at RT. FIG. 42D shows results for reference lysis conditions with alkaline lysis conditions (e.g., reference lysis conditions (FIG. 42A) followed by alkaline conditions (FIG. 42C)).

FIGS. 41A-41E summarize the results of a specific experiment demonstrating the lack of cross-contamination between microcapsules and/or droplets by applying the workflow shown in FIG. 40 to barcode and sequence amplified genomes of *E. coli* and *B. subtilis* cells. For the purpose of this experiment, a suspension of bacteria in 1×PBS (concentration 0.020D) was mixed in an equal ratio with a 20% w/w dextran solution (MW500; Sigma-Aldrich, cat. no. 31392-10G) in 1×PBS to obtain the core solution. The core solution was then co-encapsulated into water-in-oil droplets together with the shell solution composed of 10% w/w modified dextran and 0.2% w/v lithium phenyl-2,4,6-trimethylbenzoylphosphinate (LAP, Sigma Aldrich, cat. no. 900889-1G) using a microfluidics chip m height and having a nozzle 40 μm wide. The flow rates used were 100 μl/h, 100 μl/h, and 700 l/h for the core solution, shell solution, and the continuous oil phase, respectively. Droplet Stabilization Oil (Droplet Genomics, cat. no. DG-DSO-15) was used as the continuous phase. While the modified dextran used in this example is dextran modified by methacryloyl and butyryl moieties and referred to as DexMAB1090 herein, other modified dextrans can be utilized (see, e.g., Table 11). The collected emulsion was exposed to 405 nm light (LED device, Droplet Genomics, cat. no. DG-BRD-405) for 30 s to induce shell polymerization. 300 μl of Washing buffer (10 mM Tris-HCl (pH 7.5), 0.1% Triton X-100) and 300 μl of 20% PFO (Fluorochem, cat. no. 007128) in HFE7500 were added per 100 μl of emulsion to release microcapsules into the aqueous phase. The oil (bottom) phase was removed and microcapsules were washed 2 times in Washing buffer. Washes were performed by sedimenting the microcapsules containing cells by centrifugation at 1000 g for 1 min and removing the supernatant.

Cell lysis was performed by incubating in microcapsules in 50 U/μl lysozyme (Lucigen, cat. no. R1804M), 0.2 mg/ml proteinase K (ThermoFisher Scientific, cat. no. E00492), 0.1% Triton X-100, 1 mM EDTA, 10 mM Tris-HCl (pH 7.5) for 30 min at 37 degrees Celsius, followed by 30 min at 50 degrees Celsius. Following lysis, microcapsules were washed 5 times in Washing buffer. The MDA reaction mix was prepared by combining the following components shown in Table 11.

TABLE 11

| Component | Volume, μL | Final concentration |
|---|---|---|
| Microcapsule-entrapped cell lysate containing nucleic acids | 40 | 40% |
| Exo-resistant random primers (ThermoFisher, cat. no. SO181) | 5 | 25 uM |
| dNTPs (ThermoFisher, cat. no. R0192 ) | 10 | 1 mM |
| DTT (ThermoFisher, cat. no. 707265ML) | 1 | 1 mM |
| 10% v/v Triton X-100 in water (Sigma-Aldrich, T8787-100ML) | 1 | 0.1% |
| Nuclease-free water | 26 | — |
| 10X EquiPhi29 reaction buffer | 10 | 1X |
| EquiPhi29 (ThermoFisher, cat. no. A39391) | 5 | 0.5 U/ul |
| Pyrophosphatase (ThermoFisher, cat. no. EF0221) | 2 | 0.002 U/ul |
| Total volume | 100 | |

The MDA reaction mixture was incubated at 45 degrees Celsius for overnight (~16 h), followed by enzyme inactivation at 65 degrees Celsius for 10 min. 3 washes in Washing buffer were performed.

FIG. 41A shows a fluorescent microscopy image of microcapsules containing single amplified genomes entrapped in microcapsules post-MDA stained with CYTO9 dye. For imaging purposes, 3 μl of closely-packed microcapsules were mixed with 7 μl of 5 μM CYTO9 (ThermoFisher, cat. no. S34854) diluted in water and the resulting 10 6 are loaded onto a hemocytometer.

Before fragmentation of microcapsule-entrapped SAGs, 30 of microcapsules were washed 5× in Washing buffer and most of the supernatant was removed leaving 30 of total volume. The following fragmentation mix shown in Table 12 was prepared on ice in a thin-wall 0.2-ml PCR tube.

TABLE 12

| Component | Volume, μL |
|---|---|
| microcapsules containing SAGs | 20 |
| Water | 6 |
| NEBNext Ultra FS Reaction buffer (vortex before use)(NEB, cat. nr. E7805S) | 7 |
| NEBNext Ultra FS Enzyme mix (vortex before use) | 2 |
| Total | 35 |

The fragmentation mix was exposed to the following thermal program: 37 degrees Celsius for 6 min; 65 degrees Celsius for 30 min; 4 degrees Celsius hold. After fragmentation, microcapsules were washed 10 times in 1× T4 DNA ligase buffer (ThermoFisher, cat. no. B69) supplemented with 1% v/v Igepal CA-630 (Sigma Aldrich, cat. no. 56741-50ML-F). FIG. 41B shows an electropherogram of the fragmented DNA released from microcapsules by dextranase treatment.

Barcoding of microcapsule-entrapped fragmented SAGs was performed by co-encapsulating the following components listed in Table 13 in a microfluidic device (FIG. 41C).

TABLE 13

| Component | Flow rate | Inlet nr in FIG. 41C. |
|---|---|---|
| microcapsules containing fragmented SAGs in 1x T4 DNA ligase supplemented with 1% v/v Igepal CA-630 | 55 µl/h | iii |
| Barcoding hydrogel beads in SAGs in 1x T4 DNA ligase supplemented with 1% v/v Igepal CA-630 | 70 µl/h | i |
| Ligation mix: 30 µl NEBNext Ultra II Ligation Master Mix, 1 µl NEBNext Ligation Enhancer, 1 µl Dextranase | 175 µl/h | ii |

Upon collection of the emulsion on ice, barcodes were released by photocleavage and the emulsion was incubated at 20 degrees Celsius for 15 min. After barcoding by ligation in drops, the emulsion was aliquoted into libraries of desired size. For example, results shown in FIGS. 41D and 41E were obtained from 5 µl of emulsion. The emulsion was broken and the reaction was immediately stopped by the addition of EDTA. Similar to other examples, hydrogel beads were removed by spinning the pooled material through a Zymo Spin-IC column. Next, the barcoded DNA underwent 0.6× AMPure purification and was eluted in 50 µl of water.

Further library preparation steps involved a second fragmentation and adapter ligation (NEBNext® Ultra™ II FS DNA Library Prep Kit for Illumina, NEB, cat. no. E7805S), 0.8× AMPure purification, amplification by PCR to introduce Illumina adapters (KAPA HiFi HotStart ReadyMix, Roche, cat. no. KK2601), double size selection (0.6-0.8× AMPure), and capillary electrophoresis (Bioanalyzer) to obtain the final library shown in FIG. 41D. The library was sequenced on an Illumina MiSeq instrument using a MiSeq 150-cycle kit v3.

Example 11: Capsule Generation Using Chemically Induced Polymerization

SPC generation and polymerization. Four formulations of shell/core solutions were made, each differing in percentage and location (core vs. shell) of ammonium persulfate (APS) (A3678, Sigma-Aldrich) and TEMED (T22500, Sigma-Aldrich):

Formulation 1: Shell phase—50 µL DexMAb 10:90 (Droplet Genomics), 10 µL 100 mM DTT solution (Sigma-Aldrich, 646563), 1 µL TEMED (final concentration in shell phase—1%), 39 µL 1×PBS solution (Invitrogen, AM9625). Core phase—50 µL 2× Core solution (Droplet Genomics), 10 µL 10% APS solution (final concentration in core phase—1%), 40 µL 1×PBS solution;

Formulation 2: Shell phase—50 µL DexMAb 10:90, 10 µL 100 mM DTT solution, 10 µL 10% APS solution (final concentration in shell phase—1%), 30 µL 1×PBS solution. Core phase—50 µL 2×Core solution, 1 µL TEMED (final concentration in core phase—1%), 49 µL 1×PBS solution;

Formulation 3: Shell phase—50 µL DexMAb 10:90, 10 µL 100 mM DTT solution, 40 µL 1×PBS solution. Core phase—50 µL 2× Core solution, 10 µL 10% APS solution, 1 µL TEMED, 39 µL 1×PBS solution;

Formulation 4: Shell phase—50 µL DexMAb 10:90, 50 µL 10% APS (final concentration in shell phase—5%). Core phase—50 µL 2× Core solution, 5 µL TEMED (final concentration in core phase—5%), 10 µL 100 mM DTT solution, 35 µL 1×PBS solution.

Core and shell bases were loaded into 1-mL syringes (BD, 309628) pre-filled with 500 µL HFE7500 (Acota, 297730-93-9). 1% Droplet Stabilization Oil (Droplet Genomic) was diluted to 0.25% in HFE7500 and loaded into an empty syringe. Needles (Agani, AN*2716R1) with pre-attached tubing (Adtech, 81925) were mounted on the syringes. For SPC generation, ONYX device (Droplet Genomics) and a CF-60-10 chip (Droplet Genomics) was used. The chip was primed using the following flowrates: DSO—700 µL/hr; Core base—300 µL/hr; Shell base—300 µL/hr. Once the chip was primed, the Core base and Shell base flowrates were adjusted to 100 L/hr. Once the flowrates stabilized, the emulsion collection was started—the emulsion was collected into 2 mL tubes under 300 µL of light mineral oil. After 1 hour, the run was stopped, and the emulsion was polymerized by incubating at 60° C. overnight. The oil under the emulsion was removed by pipetting and the SPCs were released by adding 300 µL of 20% PFO (Fluorochem, 647-42-7) and 300 µL 1×PBS solution. The SPCs were then washed 3 times with 1 mL 1×PBS solution supplemented with 0.1% Pluronic F-68 (Gibco, 24040032). The samples were imaged under a light microscope.

Results—High concentrations of APS and TEMED (above 1%) are needed for SPC polymerization. Of the four formulations tested, only when using 5% of TEMED in the core phase and 5% APS in the shell phase (formulation number 4), SPC polymerization was observed. FIG. 43 depicts the results as a bright-light microscopy image of SPC suspension in aqueous buffer after polymerization. Formulation 4 was used (5% TEMED in core phase, 5% APS in shell phase). SPCs approx. 60 µm in diameters are formed. After polymerization, SPCs of approximately 60 µm diameter were observed. The SPCs had clear boundaries between core and shell bases. When using 1% of TEMED in the core phase and 1% APS in the shell phase (formulation number 2) or 1% of APS and 1% of TEMED both in the core phase (formulation number 3), no polymerization was observed—after breaking the emulsion, no SPCs were visible in the tube, thus the samples were not imaged. When using 1% TEMED in the shell phase and 1% APS in the core phase, the shell phase polymerized in the tube, shortly after addition of TEMED, thus SPC generation was not performed.

Example 12: Single-Cell DNAseq by Microcapsule Split-and-Pool Barcoding

Provided hereafter is specific methodology for implementing scDNAseq by microcapsule split-and-pool barcoding (FIG. 8B and FIG. 9B). In this example, "barcode D", "barcode C", "barcode B", and "barcode A" refer to barcodes "WWWWWWWW", "XXXXXXXX", "YYYYYYYY", and "ZZZZZZZZ", respectively (FIG. 10).

FIG. 6 outlines the species-mixing experiment that was performed. *E. coli* and *B. subtilis* cells were encapsulated together followed by lysis and whole genome amplification by MDA. Single amplified genomes were debranched by T7 Endonuclease I, followed by end-prep and split-and-pool barcoding. An aliquot (~2000 cells) of SPCs was taken further for the NGS library preparation. The final library was sequenced on an Illumina NextSeq550 instrument.

Encapsulation.

E. coli (MG1655) and B. subtilis (ATCC 6633) cells were inoculated in 5 ml of liquid LB media separately, and incubated at 37° C. overnight. The absorbance was measured at OD600. The samples were centrifuged at 1000×g for 5 min, resuspended in 1×PBS buffer by aiming final density at 2 OD. Shell solution was prepared by mixing 100 µL 20% w/w DexMAB shell polymer with 20 µL 100 mM DTT (Sigma-Aldrich, 43816) and 70 µL nuclease-free water (Invitrogen, AM9932). Core solution was prepared by mixing 100 µL core solution (Droplet Genomics, 20% Dextran 500) with 25 µL of 4% LAP (900889, Merck) with 75 µL diluted E. coli and B. subtilis cells. Cell concentration was aimed at 0.1 occupancy of SPCs. ~200 µL of the working solutions were added into two different 1-mL syringe backfilled with ~300 µL HFE-7500 (Sigma-Aldrich 98-0212-2929-3 and 1 mL of 0.25% DSO (Droplet Genomics, DG-DSO-20) was added into another 1-mL syringe. The run was started for generating SPCs with flow rates of 100 L/hr; 100 µL/hr; 700 µL/hr for shell, core and DSO, respectively in CF-60 microfluidic device (Droplet Genomics). The shell was polymerized by placing the tube of collected emulsion in the 405 nm LED device (Droplet Genomics) and exposed the emulsion to light for 30 s. Excess oil was removed, followed by breaking the emulsion, 20% PFO (Fluorochem, 007128).

Cell Lysis.

Semi-permeable capsules (SPCs) were incubated in 50 U/µL lysozyme mix (VWR, 76081), 0.2 mg/ml Proteinase K, 1 mM EDTA (Invitrogen, 15575020), 10 mM Tris-HCl (Invitrogen, 15575027), 0.1% Triton X-100 (Sigma-Aldrich, T8787-100ML) (Wash buffer, WB), at 37° C. for 30 min, followed by 50° C. for 30 min. Then, SPCs were washed once in 1 mL wash buffer, by vortexing and spinning down, supernatant was removed and discarded, leaving 500 µL of total solution. 2× fresh alkaline lysis reagent (0.8M KOH (Roth, 7949.1), 20 mM EDTA, 200 mM DTT) was prepared and added as 500 µL onto the solution (final concentration of lysis reagents were 0.4M KOH, 10 mM EDTA, 100 mM DTT). Total volume was adjusted up to 1 mL by adding wash buffer (10 mM Tris-HCl, 0.1% Triton X-100) on top. Rotated for 15 min at room temperature. Then samples were washed 5× with 1M Tris-HCl, 0.1% Triton X-100 (Neutralization buffer). Followed by washing 5× with wash buffer (10 mM Tris-HCl, 0.1% Triton X-100).

MDA.

MDA reaction was performed by mixing 1500 µL SPCs with 975 µL nuclease-free water, 375 µL 10× EquiPhi29 Buffer (Thermo Scientific, B39), 375 µL dNTP Mix (Thermo Scientific, R0192), 37.5 µL 0.1M DTT solution, 37.5 µL 10% Triton X-100, 187.5 µL Exo-resistant random primer mix (Thermo Scientific, SO181), 187.5 µL 10 U/µL EquiPhi29 DNA Polymerase (Thermo Scientific, A39391), 75 µL 0.1 U/µL pyrophosphatase (Thermo Scientific, EF0221). The sample was mixed by pipetting and then placed in a thermal cycler and incubated at 45° C. for 1 h followed by enzyme inactivation at 65° C. for 10 min. For imaging; 3 µL of SPCs were mixed with 7 µL 10×SYTO9 green fluorescent nucleic acid stain (Thermo Scientific, S34854) and the suspension was loaded to a hemocytometer and imaged by using a fluorescent microscope with 488 nm filter (FITC).

T7E1 Debranching.

T7E1 Debranching reaction was performed by mixing 690 µL of SPCs with 712.5 µL nuclease-free water, 165 µL 10× NEBuffer 2 (NEB, B7002S) and mixed by pipetting. And then, 82.5 µL 10 U/µL T7 Endonuclease I (NEB, M0302L) was added to the solution avoiding mixing and the sample was placed in thermomixer—C and incubated at 37° C., 1000 rpm, for 1 h. The sample was washed 3× with wash buffer.

End-Prep (A-Tailing).

A-tailing was performed by using NEBNext® Ultra™ II End Repair/dA-Tailing Module (NEB, E7546) reagents. 690 µL of SPCs were suspended in a mix containing 58 µL Ultra-II End-prep reaction buffer and 50 µL Ultra-II End-prep enzyme mix and 92 µL nuclease-free water. The tube was placed in thermomixer—C, and incubated at 20° C. for 30 min and 65° C. for 30 min. The sample was washed 3× with wash buffer.

Split and Pool Barcoding.

Barcode—D Oligo Preparation Prior to barcoding, 16 sets of barcode—D oligos were centrifuged for 1 min at 1000×g, (IDT) were resuspended with 166.7 µL of DS buffer (10 mM Tris-HCl pH 8.0, 0.1 mM EDTA), to the final concentration of 300 µM, vortexed and spun down. Then, 6.25 µL of oligos were aliquoted into 0.2 mL PCR tubes and mixed with 56.25 µL nuclease-free water. The tubes were transferred into a thermal cycler for oligo annealing starting from 95° C. by gradually decreasing the temperature to 20° C., in ~60 min and final hold at 20° C. Master Plate Preparation (300 µM) 96 sets of barcode C, B, and A were received in master plates containing 300 µM of oligos in solution, in 96 well plates. Master plates were transferred into the thermal cycler for oligo annealing starting from 95° C. by gradually decreasing the temperature to 20° C., in ~60 min and final hold at 20° C. Working Plate (30 µM) Preparation from Master Plates (300 µM)

1 µL of oligos from A, B, C master plates were transferred into each well of newly-assigned working plate 9 µL of nuclease-free water was added into each well to reach 30 M oligo concentration. Then, each well was mixed by pipetting and plates centrifuged for 1 min at 1000×g.

Barcode—D Ligation (in PCR Tubes).

Master mix was prepared by mixing 690 µL of SPCs with 225 µL 10× T4 DNA Ligase Buffer, 75 µL 5 U/µL T4 DNA Ligase Enzyme and 510 µL nuclease-free water. 125 µL of master mix was added into each tube containing 62.5 µL (30 µM) barcode—D oligos, to the final concentration of 10 µM in 187.5 µL. The tubes were placed into the thermal cycler, followed by incubation for 15 min at 22° C. 50 µL STOP25 (10 mM Tris-HCl pH 8.0, 0.1% v/v Tween-20, 100 mM KCl, 25 mM EDTA) buffer was added into each tube, and the samples were pooled into a 15 mL tube. After incubation, STOP25 buffer was added up to 7-8 mL, incubated for 5 min @RT. The mix was aliquoted into 1.5 mL tubes, resuspending SPCs by pipetting. SPCs were then washed 5× with wash buffer.

Barcode—C, B and a Ligation in Working Plates.

Master mix was prepared by mixing 690 µL of SPCs with 330 µL T4 DNA ligase buffer, 110 µL T4 DNA ligase enzyme and 1070 µL nuclease-free water. (In case if there were less than 690 µL of SPCs, remaining volume was replaced with nuclease-free water). Next, 20 µL of master mix was added into each well of the working plate. The plate was then placed into the thermal cycler, followed by incubation for 15 min at 22° C. After incubation, 50 µL STOP25 buffer was added into each well, and the samples were pooled into a 15 mL tube. STOP25 buffer was added up to 7-8 mL, incubated for 5 min @RT. The mix was aliquoted into 1.5 mL tubes, resuspending SPCs by pipetting. SPCs were then washed 5× with wash buffer. Earlier described procedure was repeated for two more rounds with barcode B and barcode A containing plates.

Library Preparation for Illumina Sequencing and Sequencing.

An SPC aliquot of 2000 cells was taken from 100k barcoded cells. SPCs were dissolved with 1 µL of Dextranase (Sigma Aldrich), reaction volume adjusted to 100 µL with nuclease free water. DNA was purified with 0.8× AMPure XP beads (Beckman Coulter). Sequencing ready libraries were constructed with The NEBNext© Ultra™ II FS DNA Library Prep Kit (NEB, #E7805S) using 50 ng of DNA as input and sequenced on NextSeq550 (Illumina) Results.

Single *Escherichia coli* and *Bacillus subtilis* cells were counted and encapsulated into SPCs aiming to have lambda of <0.1. After lysis and whole genome amplification single amplified genomes were stained with DNA specific dye and imaged under fluorescent microscope (FIG. 36). Next, DNA was enzymatically fragmented and combinatorically indexed. An SPC aliquot containing ~2000 cells was taken and sequenced on NextSeq550 (Illumina). After sequencing we obtained ~70 mln reads, 79% of reads had correct barcode D sequence used for sample indexing. 79% of reads mapped uniquely to the reference genome. More than 90% of reads were assigned to the highly abundant cell barcodes in the sample (FIG. 37). Cells were identified as either *E. coli* or *B. subtilis* (FIG. 38) if more than 99% of reads mapped to individual genome, otherwise those cells were identified as mixed genomes (<3% of all genomes). In this plot each dot is a cell barcode. Cells are assigned to either *E. coli* or *B. subtilis* if more than 99% of reads associated with that barcode are mapping to individual genome. Otherwise, cell barcodes are identified as mixed genomes. <3% genomes were identified as mixed. Genome coverage is highly dependent on sequencing depth, however up to 75% of genome coverage was achieved with sequencing depth of >6×.

At FIG. 39 one sees a scatter plot illustrating genome coverage vs sequencing depth per single cell. In this plot each dot is a cell barcode.

TABLE 14 demultiplexing statistics

| | Reads | % |
|---|---|---|
| Sequenced | 88002597 | 100 |
| Demultiplexed on bcdD | 70402078 | 80.0 |
| Bcd C + B + A in demultiplexed data | 67884737 | 96.4 |
| Uniquely mapped to the genome | 55669448 | 79.1 |

Example 13: Microcapsule Sonication

This example presents results demonstrating an alternate approach for microcapsule contents release. Methods. Bacteria culture preparation. *E. coli* MG1655 were inoculated into 5 mL of liquid LB media (Sigma-Aldrich, L2542) and cultured for 2-3 hours at 37° C. with shaking at 220 RPM until the culture reached an OD600≈0.5. 1 ml of culture was centrifuged for 10 minutes at 1000 rcf. The resulting pellet was washed with 1 mL 1×PBS, prepared from 10×PBS buffer (Invitrogen, AM9625), by removing the supernatant, resuspending the cells in 1×PBS buffer, centrifuging for 10 minutes at 1000 rcf and removing the supernatant again. The pellet was resuspended once more in 1×PBS buffer and diluted to a final OD600 0.1.

Bacteria encapsulation. 47.5 µL of bacteria culture from previous step was mixed with 50 µL of 2× core solution (20% w/w Dextran 500) and 2.5 4% LAP solution, resulting in 100 µL of Core base. Shell base was prepared by mixing 50 µL 20% w/w DexMAb 10:90 solution (Droplet Genomics) with 10 µL 100 mM DTT solution (Sigma-Aldrich, 646563) and 40 µL 1×PBS solution. 250 µL of 1% Droplet Stabilization Oil (Droplet Genomics) was diluted with 750 µL HFE7500. Core and shell bases were loaded into 1 mL syringes (BD, 309628) pre-filled with 500 µL HFE7500 (Acota, 297730-93-9). 0.25% Droplet stabilization oil was loaded into an empty syringe. Needles (Agani, AN*2716R1) with pre-attached tubing (Adtech, 81925) were mounted on the syringes. For SPC generation, ONYX device (Droplet Genomics) and a CF-60-10 chip (Droplet Genomics) was used. The chip was primed using the following flowrates: DSO—450 µL/hr; Core base—300 µL/hr; Shell base—300 L/hr. Once the chip was primed, the Core base and Shell base flowrates were adjusted to 75 µL/hr. Once the flowrates stabilized, the emulsion collection was started. After 1 hour, the run was stopped, and the emulsion was polymerized under 405 nm light for 40 seconds. The oil under the emulsion was removed by pipetting and the SPCs were released by adding 300 µL of 20% PFO (Fluorochem, 647-42-7) and 300 µL 1×PBS solution. The sample was mixed by inverting the tube several times and the tube was spun down. The bottom oil and upper water layers were removed by pipetting, leaving only the released SPCs in the tube. The SPCs were washed 3 times with 1 mL of 1×PBS, supplemented with 0.1% Pluronic F-68 (Gibco, 24040032).

Bacteria lysis. SPCs were washed with wash buffer (10 mM Tris-HCl pH 7.5 (Invitrogen, 15575027), 1 mM EDTA (Invitrogen, 15575020), 0.1% Triton X-100 (Sigma-Aldrich, T8787)). After the last wash, the supernatant was removed and replaced with 1 mL fresh wash buffer. The sample was supplemented with 50 U/µL Lysozyme solution (VWR, 76081), 200 µg/mL Proteinase K (Thermo Fisher, E00491) and incubated for 30 minutes at 37° C. and 30 minutes at 50° C. The SPCs were then washed 1 time with wash buffer. The supernatant was removed and 500 µL of alkaline lysis solution (0.8 M KOH (Roth, 7949), 20 mM EDTA, 200 mM DTT) was added. The volume was adjusted to 1 mL with wash buffer. The tube was placed into a rotator for 15 minutes at room temperature. The SCPs were then washed 5 times with wash buffer without EDTA.

Multiple Displacement Amplification. MDA reaction was prepared in a 1.5 mL Eppendorf tube by mixing 200 µL SPCs, EquiPhi29 DNA Polymerase (Thermo Fisher Scientific, A39391) to a final concentration of 0.5 U/µL, 50 µL 10× EquiPhi29 buffer (Thermo Fisher Scientific, B39), DTT to a final concentration of 1 mM, Triton X-100 to a final concentration of 0.1%, Exo-resistant random primer (Thermo Scientific, SO181) to a final concentration of 25 µM, dNTPs 10 mM each (Thermo Scientific, R0192), to a final concentration of 1 mM, pyrophosphatase (Thermo Fisher, EF0221) to a final concentration of 0,002 U/µL. Reaction volume was adjusted to 500 µl with nuclease free water. The reaction was incubated for 1 hour at 45° C., followed by enzyme inactivation for 10 minutes at 65°. The SPCs were then washed 3 times with wash buffer.

DNA sonication. Packed SPCs were transferred into 3 2 mL tubes, 50 µL each, and diluted to 500 µL with wash buffer. SPCs were placed in an ice bath and sonicated using a Vibrocell VCX130PB sonicator, in 3 different conditions: 1-20% amplitude, for 2 minutes with 9 second on/off pulses; 2-40% amplitude, for 2 minutes with 9 second on/off pulses; 3-80% amplitude, for 2 minutes with 9 second on/off pulses. Sonicated samples were imaged under a brightfield microscope. Agarose gel electrophoresis. 50 mL agarose gel was prepared by dissolving one tablet of TopVision Agarose (Thermo Fisher, R2801) in 1×TAE buffer (Thermo Fisher, B49). 20 µL of each sonicated sample was mixed with 4 µL TriTrack Loading Dye (Thermo Fisher, R1161). 20 µL unsonicated SPCs were dissolved by adding 1 µL of dextranase (Sigma-Aldrich, D0443). After SPCs were dissolved, the sample was mixed with 4 µL TriTrack Loading Dye. 20 µL of samples were loaded into the agarose gel wells, along with 5 µL of GeneRuler DNA Ladder Mix (Thermo Fisher, SM0331). Electrophoresis was carried out for 30 minutes, with 5V/cm voltage. After the electrophoresis run, the gel was dyed for 10 minutes in SYBR Gold Nucleic Acid Gel Stain (Thermo Fisher, S11494). The gel was imaged using a proBLUEVIEW Dual Color Transilluminator (Cleaver Scientific).

Results. Sonication effects SPC integrity. Microscope images of sonicated samples showed that SPC integrity is compromised under all sonication conditions with a dependence on sonication amplitude, where some intact SPCs and large debris is observed after 20% amplitude sonication (FIG. 44), no intact SPCs and large debris observed after 40% amplitude sonication (FIG. 45) and small debris observed after 80% amplitude sonication (FIG. 46).

MDA product is fragmented by sonication. Agarose gel electrophoresis shows that the MDA product inside SPCs is fragmented by sonication and the level of fragmentation depends on the amplitude of sonication, where some full length MDA product and fragment length distribution between 3000 and 800 base pairs is observed after 20% amplitude sonication (FIG. 47 lane 1). Fragment length distribution between 1200 and 700 base pairs was observed after 40% amplitude sonication (FIG. 47, lane 2). Fragment length distribution between 800 and 600 base pairs was observed after 80% amplitude sonication (FIG. 47, lane 3).

These results indicate that sonication may serve as an alternate approach for release of microcapsule contents, and is particularly suited for products that are below 300 bp in size or are suitable reduced to below 3000 bas pairs in size for subsequent analysis.

Example 14: Arabinoxylan-Based Capsule Shell Polymer Synthesis

This example describes the synthesis of methacryloil-modified arabinoxylan for use as the SPC shell polymer. The modified polymer is referred to as AxylMA10.

Consumables

| Material | CAS no. | Catalogue no. | Lot. No | Amount | Equivalents, mol % |
|---|---|---|---|---|---|
| ArabinoXylan $M_w$ ~323,000 | 9040-27-1 | Megazyme #P-WAXYM | 40601a | 500 mg | 100 |
| Methacrylic acid anhydride | 760-93-0 | Aldrich #276685 | stbj5515 | 51 UL | 11 |
| Dimethylsulfoxide 99.7% (DMSO) | 67-68-5 | sigma #276855 | stbj8063 | 50 mL | n/a |
| 4-Dimethylaminopyridine (DMAP) | 1122-58-3 | Sigma-Aldrich #107700 | mkcm0690 | 94 mg | 25 |
| 1M HCl solution | n/a | n/a | n/a | 0.77 mL | 25 |
| Deionized water | n/a | From in-house system | n/a | n/a | n/a |
| Dialysis hose, MWCO 14 kDa | n/a | Roth 1780.1 | n/a | n/a | n/a |

Procedure. Arabinoxylan (500 mg, 3.1 mmol) and 4-dimethylamino pyridine (94 mg, 0.77 mmol) were suspended in dimethyl sulfoxide (50 mL) and argon bubbled through for 20 minutes. The mixture was left stirring overnight at 40° C. to ensure full dissolution. Next morning, methacrylic acid anhydride (51 uL, 0.34 mmol) was added dropwise and the solution was stirred at 80° C. for 24 hours. The reaction was then cooled down to room temperature, and 1M HCl was added dropwise over 5 minutes, followed by reaction mixture transfer to a dialysis tube. The mixture was dialyzed against deionized water for 72 hours, changing water every 3-4 hours during working hours. After dialysis, the product was freeze-dried to yield 377 mg of off-white highly electrostatic powder. 1H-NMR analysis in D20 confirmed the expected structure.

Result. Methacrylate groups were found by NMR to be present on methacryloyl-arabinoxylan (AxylMA10).

Example 15: SPC Generation Using Methacryloyl-Arabinoxylan as Shell and Different Size Dextrans as Core Polymer SPCs were generated similarly as described in other examples. Briefly, the Working Shell Solution was composed of 1% w/w methacryloyl-arabinoxylan (AxylMA10) in 1×PBS, 100 ul total. The Working Core Solution was composed of 50 ul of 20% w/w Dextran 500k (Sigma-Aldrich, #31392J) in 1×PBS, 12.5 ul of 4% w/w LAP (Sigma-Aldrich, #900889-1G) and 37.5 ul of 1×PBS, mixed well before use. The Working Shell Solution and the Working core solution were injected into a co-flow microfluidic device (CF-60, Droplet Genomics) at 75 ul/h each. The carrier oil (0.25×DSO, DropletGenomics) was injected at 450 ul/h. Droplets~62 um in diameter were generated. After 1 hour, the run was stopped, and the emulsion was polymerized under 405 nm light LED device (Droplet Genomics) for 30 seconds. The oil under emulsion was removed by pipetting. The remained emulsion was broken by adding 1×PBS solution (Invitrogen, #AM9625) and 20% v/v PFO (Fluorochem, #647-42-7) in HFE7500. The sample was mixed by briefly vortexing and then was spun down. The bottom oil and upper water layers were removed by pipetting, leaving only the released SPCs in the tube. The SPCs were washed 3 times with 1 mL of 1×PBS supplemented with 0.1% Pluronic F-68.

The generation of SPCs using AxylMA10 and Dextran 2M was analogous expect that the Working Shell Solution was composed of 175 ul 2% AxylMA10 and 25 ul of 4% LAP, and the Working Core Solution was 15% w/w Dextran 2M.

As shown in FIG. 48, SPCs were formed with both Dextran 500k (average molecular weight 500 kDa) and Dextran 2M (average molecular weight 2 MDa) as core polymer. The figure depicts Bright-field microscopy images of AxylMA10 shell-based SPCs at several stages of their generation, using two different average molecular weight dextrans as core polymers. Scale bar 200 um.

Example 16: Biotin-Modified Shell Polymer Synthesis

This example describes the synthesis of novel carbohydrate-based heteropolymer primarily used in microfluidic applications to form easily dissolvable capsules as a shell reagent. The protocol was adapted from Su et al and the DexMAB synthesis protocols described in previous examples. The biotin-, butyryl- and methacryloyl-modified dextran is referred to as DexBio1MAB1090.
Consumables

| Material | CAS no. | Catalogue no. | Lot. no | Amount | Equivalents, mol % |
|---|---|---|---|---|---|
| Dextran, MW 500K (Dex) | 9005-54-0 | Sigma-Aldrich #31392 | bccf8905 | 1000 mg | 100 |
| Glycidyl methacrylate (GMA) | 106-91-2 | Sigma-Aldrich #151238 | mkcm5823 | 84 uL | 10 |
| R-(—)-Glycidyl butyrate (GB) | 60456-26-0 | Ambeed #290102 | A290102-005 | 776 uL | 90 |
| Dimethylsulfoxide 99.7% (DMSO) | 67-68-5 | sigma #276855 | stbj8063 | 12 mL | |
| 4-Dimethylaminopyridine (DMAP) | 1122-58-3 | Sigma-Aldrich #107700 | mkcm0690 | 151 mg | 20 |
| N,N'-Diisopropylcarbodiimide, (DIC) | 693-13-0 | tci #d0254 | dpopl-gh | 290 uL | 30 |
| Biotin | 58-85-5 | tci #B0463 | T6GQN-hl | 151 mg | 10 |
| 1M HCl solution | n/a | n/a | | 1.23 mL | |
| Deionized water | n/a | From in-house system | n/a | n/a | n/a |
| Dialysis hose, MWCO 14 kDa | n/a | Roth 1780.1 | n/a | n/a | n/a |

Procedure. Biotin (31 mg, 0.12 mmol) and DIC (290 uL, 1.8 mmol) were dissolved in 1 mL DMSO. In a separate flask dextran (1.000 gram, 6.2 mmol) and DMAP (151 mg, 1.2 mmol) were dissolved in 10 mL DMSO. The first solution was added to the second and stirred at 60° C. overnight. The next day, the reaction mixture was cooled down to room temperature, and additional DMAP (124 mg, 0.50 mmol) was added. GMA (84 uL, 0.61 mmol), GB (776 uL, 0.54 mmol), and 1 mL DMSO were mixed in a dropping funnel. This mixture was added to the reaction solution dropwise. The reaction mixture was stirred at 60° C. for 8 hours. The solution was cooled down and neutralized with 1M HCl (1.23 mL, 1.23 mmol), followed by dialysis against deionized water for 72 hours, changing water every 3-4 hours during working hours. After dialysis, the product was freeze-dried to yield 1118 mg of slightly yellowish highly electrostatic powder. The product was analyzed by NMR to determine the observed degree of substitution.

Result. An HNMR spectrum was generated for DexMAB. The spectrum shows presence of acrylate (DS~6%), butyrate (DS~45%) groups and biotin scaffold. The accurate degree of substitution with the latter cannot be determined but is approximately 1%.

Example 17: Generation of Capsules with Biotin-Modified Shell Polymer

The core base was prepared by mixing 50 μL of 20% w/w dextran 500k (Sigma-Aldrich, #31392J) in 1×PBS with 12.5 μL 4% LAP (Sigma-Aldrich, #900889-1G) solution in water and 37.5 μL nuclease free water. Shell base was prepared by mixing 50 μL 20% w/w DexBiolMAB 10:90 solution in 1×PBS or 50 μL 20% w/w DexMAB 10:90 solution in 1×PBS with 10 μL 100 mM DTT (Sigma-Aldrich, #43816) and 40 μL nuclease free water. 0.25% of Droplet stabilization oil solution was prepared by diluting 1% Droplet stabilization oil (Droplet Genomics) with HFE7500 (Acota, #297730-93-9) to a final 1 mL volume. Core and shell bases were loaded into 1-mL syringes (BD, #309628) pre-filled with 500 μL HFE7500 (Acota, #297730-93-9). 0.25% Droplet stabilization oil solution was loaded into an empty syringe. Needles (Agani, #AN*2716R1) with pre-attached tubing (Adtech, #81925) were mounted on the syringes. For SPC generation, the ONYX device (Droplet Genomics) and a CF-60 chip (Droplet Genomics) was used. Used 75 μL/hr, 75 μL/hr and 450 μL/hr flow rates for core, shell and oil, respectively. Once the flow rates stabilized, the emulsion collection was started. After 1 hour, the run was stopped, and the emulsion was polymerized under 405 nm light LED device (Droplet Genomics) for 30 seconds. The oil under emulsion was removed by pipetting. The remained emulsion was broken by adding 1×PBS solution (Invitrogen, #AM9625) and 20% v/v PFO (Fluorochem, #647-42-7) in HFE7500. The sample was mixed by brief vortexing and then spun down. The bottom oil and upper water layers were removed by pipetting, leaving only the released SPCs in the tube. The SPCs were washed 3 times with 1 mL of 1×PBS (Invitrogen, #AM9625).

SPC staining with fluorescent avidin. 15 μL of SPCs (either with or without biotin in the shell) were mixed with 15 ul of FITC-Avidin (2-3.5 mg/ml; Sigma-Aldrich,

A2050) and incubated at room temperature for 2 h on a rotator mixer, followed by 3 washes in 1×PBS.

Fluorescent biotin bridging via avidin. 15 µL of SPCs were mixed with 15 µL of 4 mg/mL avidin (Sigma-Aldrich, #189725). Then sample incubated on a rotator mixer for 15 minutes at room temperature. After incubation, SPCs were washed 3 times with 1 mL of 1×PBS (Invitrogen, #AM9625). The supernatant was removed and 10-fold excess of Atto 520-biotin (Sigma-Aldrich, #01632) was added and incubated on a rotator mixer for 15 minutes at room temperature. SPCs were washed 3 times with 1 mL of 1×PBS and were imaged on a fluorescence microscope.

Results. FIG. 49 presents fluorescent microscopy images of SPCs with (left) or without (center and right) biotin modification of the shell. The center and right images are the same field of view at two different exposure times. As seen in FIG. 49, FITC-avidin stains capsules with biotin-modified shell but not those without the biotin modification.

FIG. 50 presents fluorescent microscopy images of SPCs with (left) and without (right) biotin modification of the shell stained with FITC-biotin via avidin bridging. As seen in FIG. 50, capsules with the biotinylated shell bind FITC-biotin via avidin bridging.

Example 18: 2-Hydroxyethyl Cellulose-Based Capsule Shell Polymer Synthesis

This example describes the synthesis of methacryloyl-modified 2-hydroxyethyl cellulose for use as the SPC shell polymer. The modified polymer is referred to as ITEC-MAX2080.

Consumables

Example 19: Generation and Enzymatic Degradation of SPCs with Shell Polymer Based on Methacryloyl-Modified 2-Hydroxyethyl Cellulose Procedure. SPCs were generated similarly as described in other examples. Briefly, the Working Shell Solution was composed of 2.5% w/w methacryloyl-2-hydroxyethyl cellulose (HECMAX2080) in 1×PBS, 100 ul total. The Working Core Solution was composed of 50 ul of 10% w/w Dextran 500k (Sigma-Aldrich, #31392J) in 1×PBS, 25 ul of 4% w/w LAP (Sigma-Aldrich, #900889-1G) and 125 ul of 1×PBS, mixed well before use. The Working Shell Solution and the Working core solution were injected into a co-flow microfluidic device (CF-60, Droplet Genomics) at 75 ul/h each. The carrier oil (0.25×DSO, DropletGenomics) was injected at 450 ul/h. Droplets~77 um in diameter were generated. After 1 hour, the run was stopped, and the emulsion was polymerized under 405 nm light LED device (Droplet Genomics) for 30 seconds. The oil under emulsion was removed by pipetting. The remained emulsion was broken by adding 1×PBS (Invitrogen, #AM9625) and 20% v/v PFO (Fluorochem, #647-42-7) in HFE7500. The sample was mixed by briefly vortexing and then was spun down. The bottom oil and upper water layers were removed by pipetting, leaving only the released SPCs in the tube. The SPCs were washed 3 times with 1 mL of 1×PBS supplemented with 0.1% Pluronic F-68. SPCs were dissolved by enzymatic shell hydrolysis under acidic conditions: 5 ul of cellulase (Sigma-Aldrich, #C2605-50 ml) and 5 ul of 1M HCl were added to 45 ul of SPCs in 1×PBS, and the suspension was incubated overnight.

| Material | CAS no. | Catalogue no. | Lot. no | Amount | Equivalents, mol % |
|---|---|---|---|---|---|
| 2-Hydroxyethyl cellulose $M_w$ ~380,000 | 9004-62-0 | Sigma-Aldrich #308633 | stbj6333 | 1000 mg | 100 |
| Methacrylic acid anhydride | 760-93-0 | Aldrich #276685 | stbj5515 | 184 uL | 20 |
| Chloroacetic acid | 79-11-8 | Sigma-Aldrich #8.00412.0100 | s7989912108 | 467 mg | 80 |
| Dimethylsulfoxide 99.7% (DMSO) | 67-68-5 | sigma #276855 | stbj8063 | 50 mL | n/a |
| 4-Dimethylamino pyridine (DMAP) | 1122-58-3 | Sigma-Aldrich #107700 | mkcm0690 | 754 mg | 100 |
| Deionized water | n/a | From in-house system | n/a | n/a | n/a |
| Dialysis hose, MWCO 14 kDa | n/a | Roth 1780.1 | n/a | n/a | n/a |

Procedure. 2-Hydroxyethyl cellulose (1000 mg, 6.2 mmol) was suspended in dimethyl sulfoxide (50 mL) and argon bubbled through for approx. 15 minutes. Then, 4-dimethylamino pyridine (754 mg, 6.2 mmol) was added to the suspension and the solution became clear. Methacrylic acid anhydride (184 uL, 1.2 mmol) was added dropwise and the solution was stirred at 80° C. for 16 hours. Then, the reaction mixture cooled down to 0 degrees and chloroacetic acid was added. The mixture was stirred for 30 min at 0° C. and for 6 hours at room temperature. The mixture was dialyzed against deionized water for 72 hours, changing water every 3-4 hours during working hours. After dialysis, the product was freeze-dried to yield 954 mg of white highly electrostatic powder. 1H-NMVR analysis in D20 confirmed the expected structure. 1H-NMR spectrum of HECMAX2080 showed the presence of methacrylate-like protons, as well as other aliphatic group that cannot be determined unambiguously, as well as two highly shielded aliphatic proton signals at 6 ppm 4.24 (s) and 4.33 (s).

Results. FIG. 51 presents appearance and enzymatic dissolution of SPCs with a HEC-based shell. Scale bar in microscopy images—100 um As FIG. 51 indicates, SPCs can be formed using a methacryloyl-modified 2-hydroxyethyl cellulose-based shell. Such SPCs can be dissolved by enzymatic shell digestion with a cellulase, as seen at right in the figure.

Example 20: Modification of Dextran with Acryloyl Moieties

This example describes the synthesis of acryloyl-modified dextran for use as the SPC shell polymer. The synthesis was performed in two stages: 1) first, dextran 500k was modified with butyryl-moieties to obtain butyryl-dextran, referred to as DexB100; 2) second, DexB100 was modified with acryloyl moieties, to obtain acryloyl- and butyryl-modified dextran, referred to as DexAB50100. Consumables for dextran modification with butyryl moieties

| Material | CAS no. | Catalogue no. | Lot. no | Amount | | Equivalents |
|---|---|---|---|---|---|---|
| Dextran Dex500 | 9005-54-0 | Sigma-Aldrich #31392 | bccf8905 | 5000 | Mg | 100 |
| R-(—)-Glycidyl butyrate (GB) | 60456-26-0 | Ambeed #290102 | A290102-005 | 4312 | uL | 100 |
| Dimethylsulfoxide 99.7% (DMSO) | 67-68-5 | sigma #276855 | stbj8063 | 50 | mL | n/a |
| 4-Dimethylamino pyridine (DMAP) | 1122-58-3 | Sigma-Aldrich #107700 | mkcm0690 | 943 | Mg | 25 |
| 1M HCl solution | n/a | n/a | | 7.72 | mL | |
| Deionized water | n/a | From in-house system | | n/a | | n/a |
| Dialysis hose, MWCO 14 kDa | n/a | Roth 1780.1 | | n/a | | n/a |

Procedure for dextran modification with butyryl moieties. Dextran and DNAP were dissolved in DMSO, and GB was added dropwise. The reaction mixture was stirred for 44 h. The reaction was quenched with 1M HCl equimolar to the base, to neutralize DMAP. Then, the reaction mixture was dialyzed against deionized water for three days, changing water every 3-4 hours during workhours. After dialysis, the product was freeze-dried to yield a slightly yellowish highly electrostatic powder. The product was analyzed by 1H-NMR to determine the observed degree of substitution.

Result of Dextran Modification with Butyryl Moieties

1H-NMR spectrum of DexB100 revealed and observed degree of substitution of 45%. The reaction yield was 5.252 g. As in other example, the degree of substitution is defined as the molar ration between butyryl moieties and glucose units.

Consumables for Butyryl-Modified Dextran Modification with Acryloyl Moieties radation and/or rearrangement of butyrate groups, as well as the addition of de-shielded protons which may correspond to acrylate groups that are consistent with reagents. The estimated degree of substitution is ~9% for acrylate and ~42% for butyrate substituents, although the structure is not unambiguously derived.

Example 21 Generation of SPCs with Acryloyl- and Butyryl-Modified Shell

Procedure. SPCs were generated similarly as described in other examples. Briefly, the Working Shell Solution was composed of 10% w/w acryloyl-butyryl-dextran (DexAB50100) in 1×PBS, 100 ul total. The Working Core Solution was composed of 50 ul of 20% w/w Dextran 500k (Sigma-Aldrich, #31392J) in 1×PBS, 12.5 ul of 4% w/w LAP (Sigma-Aldrich, #900889-1G) and 37.5 ul of 1×PBS, mixed well before use. The Working Shell Solution and the

| Material | CAS no. | Catalogue no. | Lot. no | Amount | | Equivalents, mol % |
|---|---|---|---|---|---|---|
| Butyryl-dextran, MW 500K (DexB100) | n/a | n/a | DG-GZ-39 | 1000 | Mg | 100 |
| Acrylic acid | 79-10-7 | Acros #164250010 | A0339102 | 211 | uL | 50 |
| 1,1'-Carbonyldiimidazole, CDI | 530-62-1 | TCI #C0119 | TEM8J-JY | 512 | Mg | 50 |
| Tetrahydrofunran (wet) | 109-99-9 | Fischer Sci #BO1140-1 | 127310 | 10 | mL | n/a |
| Dimethylsulfoxide 99.7% (DMSO) | 67-68-5 | Sigma-Aldrich #276855 | stbj8063 | 40 | mL | |
| Deionized water | n/a | From in-house system | n/a | n/a | | n/a |
| Dialysis hose, MWCO 14 kDa | n/a | Roth 1780.1 | n/a | n/a | | n/a |

Procedure. CDI was suspended in wet THE followed by addition of acrylic acid (211 uL, 3.1 mmol). The reaction mixture was stirred at room temperature for 4 h. The mixture immediately got cloudy and stayed so over the course of reaction. Afterwards, the solvent was removed under reduced pressure. In a separate flask, DexB100 (1000 mg) was dissolved in 20 ml of dry DMSO, and the resulting solution was added dropwise to the main reaction mixture over the course of 10 min. The reaction mixture was stirred for 40 h at room temperature and the solution remained clear throughout the time. Afterwards, the mixture was dialyzed against deionized water for 72 hours, changing water every 3-4 hours during working hours. After dialysis, the product was freeze-dried to yield 786 mg of white highly electrostatic powder. The product was then analyzed by 1H-NMR to determine the observed degree of substitution.

Result of butyryl-modified dextran modification with acryloyl moieties. An H-HMR spectrum shows slight deg- Working Core Solution were injected into a co-flow microfluidic device (CF-60, Droplet Genomics) at 75 ul/h each. The carrier oil (0.25×DSO, DropletGenomics) was injected at 450 ul/h. Droplets~62 um in diameter were generated. After 1 hour, the run was stopped, and the emulsion was polymerized under 405 nm light LED device (Droplet Genomics) for 30 seconds. The oil under emulsion was removed by pipetting. The remained emulsion was broken by adding 1×PBS (Invitrogen, #AM9625) and 20% v/v PFO (Fluorochem, #647-42-7) in HFE7500. The sample was mixed by briefly vortexing and then was spun down. The bottom oil and upper water layers were removed by pipetting, leaving only the released SPCs in the tube. The SPCs were washed 3 times with 1 mL of 1×PBS supplemented with 0.100 Pluronic F-68.

Result. FIG. 52 depicts Bright-field microscopy image of SPCs in 1×PBS. Scale bar—100 um. As shown in FIG. 52, SPCs are formed when using acryloyl- and butyryl-modified dextran as shell polymer. The characteristic shell-core topology is observed.

Example 22: Synthesis of a Dextran Highly Substituted with Methacryloyl Moieties This example describes the synthesis of methacryloyl-modified Dextran 500k. High degrees of substitution were explored. As in other examples, the nomenclature of the modified polysaccharides is [backbone polysaccharide] [substitution] [stoichiometric degree of substitution in %]. Below is described the synthesis of DexMA200: dextran modified with methacryloyl moieties, such that during reaction setup the molar ratio of glucose subunits (in dextran) to methacryloyl moieties was 1:2. An even more substituted version, DexMA250, was insoluble in water after synthesis, and therefore unsuitable for SPC generation.

Consumables

| Material | CAS no. | Catalogue no. | Lot. no | Amount | | Equivalents, mol % |
|---|---|---|---|---|---|---|
| Dextran, MW 500K (Dex) | 9005-54-0 | Sigma-Aldrich #31392 | BCCF8905 | 2.00 | g | 100 |
| Glycidyl methacrylate (GMA) | 106-91-2 | Sigma-Aldrich #338125 | MKCM5823 | 3380 | uL | 200 |
| Dimethylsulfoxide 99.7% (DMSO) | 67-68-5 | Acros #348440010 | STBJ8063 | 25 | mL | n/a |
| 4-Dimethylamino pyridine (DMAP) | 1122-58-3 | Sigma-Aldrich #107700 | MKCM0690 | 396 | mg | 25 |
| 1M HCl solution | n/a | n/a | | 3.25 | mL | |
| Deionized water | n/a | From in-house system | n/a | n/a | | n/a |
| Dialysis hose, MWCO 14 kDa | n/a | Roth 1780.1 | n/a | n/a | | n/a |

Procedure. Dextran (2001 mg, 12.3 mmol) and 4-dimethylamino pyridine (396 mg, 3.25 mmol) were suspended in dimethyl sulfoxide (20 mL) and argon was bubbled through for until dissolved.

In a dropping funnel, GMA (3380 uL, 12.3 mmol) was mixed with 5 mL of DMSO, and the resulting solution was added dropwise to the reaction mixture, over 30 min. The reaction mixture was stirred for 48 h at room temperature and quenched with 1M HCl (3.25 mL, 3.25 mmol), followed by dialysis against deionized water for 72 hours, changing water every 3-4 hours during working hours. After dialysis, the product was freeze-dried to yield 2240 mg of white highly electrostatic powder.

Result. 1H-NMR analysis in D20 confirmed the expected structure with methacrylate substitution of approx. 110%, but it cannot be determined unambiguously due to overlapping 1H signals.

Example 23: Generation of SPCs Using DexMA200 as Shell Polymer

Procedure. SPCs were generated similarly as described in other examples. Briefly, the Working Shell Solution was composed of 5% w/w DexMA200 in 1×PBS, 100 ul total. The Working Core Solution was composed of 50 ul of 10% w/w Dextran 500k (Sigma-Aldrich, #31392J) in 1×PBS, 12.5 ul of 4% w/w LAP (Sigma-Aldrich, #900889-1G) and 37.5 ul of 1×PBS, mixed well before use. The Working Shell Solution and the Working Core Solution were injected into a co-flow microfluidic device (CF-60, Droplet Genomics) at 75 ul/h each. The carrier oil (0.25×DSO, Droplet Genomics) was injected at 450 ul/h. Droplets~62 um in diameter were generated. After 1 hour, the run was stopped, and the emulsion was polymerized under 405 nm light LED device (Droplet Genomics) for 30 seconds. The oil under emulsion was removed by pipetting. The remained emulsion was broken by adding 1×PBS (Invitrogen, #AM9625) and 20% v/v PFO (Fluorochem, #647-42-7) in HFE7500. The sample was mixed by briefly vortexing and then was spun down. The bottom oil and upper water layers were removed by pipetting, leaving only the released SPCs in the tube. The SPCs were washed 3 times with 1 mL of 1×PBS supplemented with 0.1% Pluronic F-68. The results indicate that SPCs can be formed using dextran 500k modified only with methacryloyl-moieties as the shell polymer. In this case, methacryloyl moieties both change the solubility of dextran to encourage ATPS formation with dextran, and enable shell cross-linking.

Example 24: Agarose Electrophoresis Analysis of dsDNA Ladder Retention

Ladder encapsulation and SPC washes. 45 µL of GeneRuler 1 kb Plus DNA Ladder (Thermo Fisher, SM1333) was mixed with 50 µL of 20% w/w Dextran 500k (Sigma-Aldrich, #31392J) in 1×PBS and 5 µL 4% LAP solution (Sigma-Aldrich, #900889-1G), resulting in 100 µL of Core base (the 100 µL was split into two tubes, 50 µL each). Shell base was prepared by mixing 25 µL of 20% w/w DexMAB1090 solution or DexMAB545 solution with 5 µL 100 mM DTT solution (Sigma-Aldrich, 646563) and 25 µL 1×PBS solution. 250 µL of 1% Droplet Stabilization Oil (Droplet Genomics) was diluted with 750 µL HFE7500. Core and shell bases were loaded into 1 mL syringes (BD, 309628) pre-filled with 500 µL HFE7500 (Acota, 297730-93-9). 0.25% Droplet stabilization oil was loaded into two empty syringes, 500 µL of DSO each. Needles (Agani, AN*2716R1) with pre-attached tubing (Adtech, 81925) were mounted on the syringes. For SPC generation, ONYX device (Droplet Genomics) and a CF-60-10 chip (Droplet Genomics) was used. The chip was primed using the following flowrates: DSO—450 µL/hr; Core base—300 µL/hr; Shell base—300 µL/hr. Once the chip was primed, the Core base and Shell base flowrates were adjusted to 75 µL/hr. Once the flowrates stabilized, the emulsion collection was started. 30 minutes, the run was stopped, and the emulsion was polymerized under 405 nm light for 40 seconds. The oil under the emulsion was removed by pipetting and the SPCs were released by adding 300 µL of 20% PFO (Fluorochem, 647-42-7) and 300 µL 1×PBS solution. The samples were mixed by inverting the tubes several times and the tubes were spun down. The bottom oil and upper water layers were removed by pipetting, leaving only the released SPCs in the tube. The SPCs were washed 3 times with 1 mL of 1×PBS, supplemented with 0.1% Pluronic F-68 (Gibco, 24040032). 20 μL of SPCs from each sample were saved before washing, for agarose gel electrophoresis.

Agarose gel electrophoresis including sample preparation. A 1% percent agarose gel was prepared by dissolving 2 tablets of TopVision Agarose (Thermo Fisher, R2801) in 100 mL 1×TAE buffer (Thermo Fisher, B49). 20 μL of each sample was dissolved by adding 1 μL of dextranase (Sigma-Aldrich, D0443). Once the SPCs were dissolved, 4 μL of TriTrack Loading Dye (Thermo Fisher, R1161) were added to each tube. 20 μL of each prepared sample were loaded into agarose gel wells along with 5 μL GeneRuler 1 kb Plus DNA Ladder. Electrophoresis was run with a voltage of 5V/cm. Once the electrophoresis run was completed, the gel was stained in SYBR Gold Nucleic Acid Gel Stain for 30 minutes. The stained gel was then imaged on a Bio-Rad Gel Imaging station.

Result. FIG. 53 shows an electrophoresis analysis of microcapsule contents retention. The ladder is a Generuler 1 kb Plus DNA Ladder. Rg-dsDNA gyration radius calculated as described by Leonaviciene et al. As shown in FIG. 53, dsDNA fragments of 300 bp (gyration radius~25 nm) and above are retained within SPCs for the two shell polymers tested and cannot be removed from SPCs by washes. Visual evaluation of the agarose gels clearly suggests that the SPC shell based on the DexMAB545 polymer is permeable to 200 bp fragments (gyration radius~17 nm). By comparison, DexMAB1090 is less permeable as 200 bp fragments are retained better compared to DexMAB545.

Example 25: Summary of Proteins Confirmed to Diffuse Through the SPC Shell

Table 15 lists enzymes and antibodies that have been confirmed to pass through the shell of SPCs, where the polymer DexMAB 1090 was used as the shell polymer.

TABLE 15

List of proteins confirmed to diffuse through the DexMAB1090 shell.

| Name | Mw, kDa |
|---|---|
| Ready-Lyse lysozyme | 15 |
| Proteinase K | 28.9 |
| DNase I, RNase-free | 39 |
| T7 endonuclease I | 60.3 |
| BSA | 66 |
| T4 DNA Ligase | 68 |
| M-MLV Reverse Transcriptase | 71 |
| Phi29 DNA polymerase | 74.4 |
| Taq DNA Polymerase, recombinant | 94 |
| T4 DNA Polymerase | 108 |
| T4 Polynucleotide Kinase | 115.6 |
| Goat Anti-Mouse IgG, F(ab')$_2$ | 160 |
| KAPA | n/a |
| KAPA U | n/a |
| EquiPhi | n/a |
| Maxima H- | n/a |
| Phusion polymerase | n/a |

These data, in view of the results of Example 24, above, confirm that analytes in microcapsules may be subjected to multiple reactions in series, with buffers and enzymes being iteratively washed out or introduced through the microcapsules without loss of nucleic acid contents above a threshold size that is determined in part by the composition of the microcapsules.

Example 26: SPC Shell Pore Patterning with Magnetic Particles

This example describes the use of particles of defined size to pattern the shell of the SPCs. This way, pores in the um range can be obtained. Here, we describe the use of magnetic particles (2-2.9 um size) and their subsequent mechanical removal by vortexing. Alternatively, enzyme degradable particles, e.g., polylactic acid particles, can be used to pattern the shell and be removed when desired by enzymatic treatment.

Generation of SPCs with patterned shell. SPCs were generated similarly as in previous examples. The Core Solution was composed of 100 ul 20% w/w Dextran 500k, 25 ul of 4% LAP, and 75 ul of 1×PBS. The Shell Solution was composed of 100 ul of 20% w/w DexMAB1090 and 100 uL magnetic particle suspension (manufacturer: Spherotech, catalogue #PMS-20-10, lot #AN01). The Core Solution and the Shell Solution were injected into a co-flow microfluidic device (CF-60, Droplet Genomics) at 75 ul/h each. The carrier oil (0.25×DSO, DropletGenomics) was injected at 450 ul/h. After 1 hour, the run was stopped, and the emulsion was polymerized under 405 nm light LED device (Droplet Genomics) for 30 seconds. The oil under emulsion was removed by pipetting. The remained emulsion was broken by adding 1×PBS solution (Invitrogen, #AM9625) and 20% v/v PFO (Fluorochem, #647-42-7) in HFE7500. The sample was mixed by briefly vortexing and then was spun down. The bottom oil and upper water layers were removed by pipetting, leaving only the released SPCs in the tube. The SPCs were washed 3 times with 1 mL of 1×PBS supplemented with 0.1% Pluronic F-68.

Mechanical removal of magnetic particles from the shell. The SPC suspension was vortex and shaken, centrifuged then inverted a few times and left for 3-4 minutes on a magnetic stand. The unbound aqueous phase with most of the SPCs was transferred to a different tube leaving behind dark brown sediment at the magnet, which included some SPCs too. These steps were repeated 10 times.

Results. FIG. 54 presents bright-field microscopy images of SPCs with the shell pattern with 2-3 um magnetic beads. Left—capsules in 1×PBS right after generation and breaking the water in oil emulsion. Right—capsules after 10 washes that involved vigorous vortexing to remove beads from the shell.

FIG. 54 compares the appearance of SPCs with shell patterned with magnetic beads before (left) and after (right) 10 washes that involved vigorous vortexing. A depletion in the number of magnetic beads in the shell can be appreciated after the procedure. Removal of the particles from the shell results in pores or holes of sizes at least as large as the particles removed.

Example 27: Acetyl-Modified Dextran Synthesis

This example describes the synthesis of acetyl- and methacryloyl-modified dextran. The polymer is referred to as DexMAC21090. The acyl (two carbon atoms long, C2) group serves as the hydrophobicity/hydrophilicity modifying moiety. The C4 butyryl group is used in most of the other examples. Longer chain fatty acid can also be attached to dextran. For example, Su et al describe the modification of dextran with lauroyl (C12) moieties.

Consumables

| Material | CAS no. | Catalogue no. | Lot. no | Amount | | Equivalents, mol % |
|---|---|---|---|---|---|---|
| Dextran $m_w$ = 500k | 9005-54-0 | Sigma-Aldrich #31392 | bccf8905 | 2000 | mg | 100 |
| Methacrylic acid anhydride | 760-93-0 | Sigma-Aldrich #276685 | stbj5515 | 184 | uL | 10 |
| Acetic acid anhydride | | Merck #1.00041.1000 | K317791 41 324 | 1042 | uL | 90 |
| Dimethylsulfoxide 99.7% (DMSO) | 67-68-5 | Sigma-Aldrich #276855 | stbj8063 | 30 | mL | n/a |
| 4-Dimethylamino pyridine (DMAP) | 1122-58-3 | Sigma-Aldrich #107700 | mkcm0690 | 377 | mg | 25 |
| 1M HCl solution | n/a | n/a | n/a | 3.10 | mL | 25 |
| Deionized water | n/a | From in-house system | n/a | n/a | | n/a |
| Dialysis hose, MWCO 14 kDa | n/a | Roth 1780.1 | n/a | n/a | | n/a |

Procedure. Dextran (2001 mg, 12.3 mmol) and 4-dimethylamino pyridine (378 mg, 3.1 mmol) were suspended in dimethyl sulfoxide (30 mL) and argon bubbled through for approx. 10 min. Acetic (1042 uL, 11.0 mmol) and methacrylic (184 uL, 1.2 mmol) acid anhydrides were premixed and added to reaction mixture dropwise over 15 min. The solution was stirred at 80° C. overnight. Then, the reaction was cooled down to room temperature, and the 1M HCl solution added dropwise over 5 minutes, followed by reaction mixture transfer to a dialysis tube. The mixture was dialyzed against deionized water for 72 hours, changing water every 3-4 hours during working hours. After dialysis, the product was freeze-dried to yield 2317 mg of white highly electrostatic powder.

Result. 1H-NMR analysis in D20 confirmed the expected structure, with methacryloyl substitution of approx. 5% and the acetyl substitution possibly near 50% across two different positions.

Example 28: SPC Generation Using Acetyl-Modified Dextran as Shell Polymer

Procedure. SPCs were generated similarly as described in other examples. Briefly, the Working Shell Solution was composed of 10% w/w DexMAC21090 in 1×PBS, 200 ul total. The Working Core Solution was composed of 100 ul of 20% w/w Dextran 500k (Sigma-Aldrich, #31392J) in 1×PBS, 25 ul of 4% w/w LAP (Sigma-Aldrich, #900889-1G) and 75 ul of 1×PBS, mixed well before use. The Working Shell Solution and the Working Core Solution were injected into a co-flow microfluidic device (CF-60, Droplet Genomics) at 75 ul/h each. The carrier oil (0.33×DSO, DropletGenomics) was injected at 450 ul/h. After 1 hour, the run was stopped, and the emulsion was polymerized under 405 nm light LED device (Droplet Genomics) for 30 seconds. The oil under emulsion was removed by pipetting. The remained emulsion was broken by adding 1×PBS solution (Invitrogen, #AM9625) and 20% v/v PFO (Fluorochem, #647-42-7) in HFE7500. The sample was mixed by briefly vortexing and then was spun down. The bottom oil and upper water layers were removed by pipetting, leaving only the released SPCs in the tube. The SPCs were washed 3 times with 1 mL of 1×PBS supplemented with 0.1% Pluronic F-68.

Results. As seen in FIG. 55, SPCs can be generated the DexMAC21090 polymer.

Example 29: Generation of <20 um Diameter Capsules

This example describes the generation of <20 um diameter capsules, as well as the strategy of injecting a mixture of both the shell and core polymer solutions through one inlet of a microfluidic device.

SPC generation and polymerization. The Core-Shell mixture was prepared by combining 100 µL of 20% w/w DexMAB1090 (lot GZ28, Droplet Genomics; shell polymer) in 1×PBS, 50 µL of 4% LAP in water, 100 µL of 20% w/v Dex500 in 1×PBS (core polymer), and 150 µL of 1×PBS solution. The resulting Core-Shell mixture was mixed by pipetting, vortexing and spun down to eliminate bubbles. It was then loaded into a 1-mL syringe (BD, 309628). Carrier oil (1% DSO, Droplet Genomics) was loaded into an empty syringe. Needles (Agani, AN*2325R1) with pre-attached tubing (Adtech, 81925) were mounted on the syringes. The syringe containing the Core-Shell mix was mounted in a horizontal position to reduce gravity separation effects. For SPC generation, Harvard apparatus pumps were used at a constant flow rate. Drop formation on WA4.1 chip (Droplet Genomics R&D 2.6 µm×7 µm H×W nozzle) was observed using a 10× microscope objective and a high-speed camera. The chip was primed using the following flowrates: Carrier oil—500 µL/hr; Core-Shell mix—500 L/hr. Once the chip was primed, the carrier oil flowrate was adjusted to 50 µL/hr, and that of the Core-Shell mix to 30 L/hr. Once the flowrates stabilized (FIG. 56), the emulsion collection was started—the emulsion was collected into a 1.5-mL tube. After 1 hour, the run was stopped, and the emulsion was polymerized by 405 nm illumination through the tube bottom for 30 s. The oil under the emulsion was removed by pipetting and the SPCs were released by adding 500 µL of 20% PFO (Fluorochem, 647-42-7) in HFE-7500 and 500 µL Capsule Wash Solution (10 mM Tris-HCl pH 7.5 with 0.1% Triton X-100). The SPCs were then washed 3 times with 1 mL Capsule Wash Solution. The samples were imaged using 20× magnification on inverted microscope in bright-field (FIG. 57).

Result. Having the solutions of core and shell pre-mixed was deemed suitable for semi-permeable capsule formation. Their size distribution is polydisperse—due to chip surface wetting at these drop formation speeds, and some have inclusions of shell material in the inner volume, however SPCs of down to 14 µm diameter were observed in this instance. Even smaller diameters could be observed on-chip during the drop formation, swelling to final size during the washes.

Example 30: Generation of >100 um Diameter Capsules

This example describes the generation of >100 um diameter capsules, as well as the strategy of injecting a mixture of both the shell and core polymer solutions through one inlet of a microfluidic device.

SPC generation and polymerization. The procedure is analogous to the one for generating <20 um capsules expect that a different chip and different flow rates are used. In this example, a single aqueous flow chip with a nozzle of the dimension 80 um×100 um (H×W) was used. The chip was primed using the following flowrates: Carrier oil—5000 μL/hr; Core-Shell mix—5000 μL/hr. Once the chip was primed, the flow rates were adjusted to 400 ul/h and 200 ul/h, respectively, for stable droplet generation (FIG. 58).

Results. Having the solutions of core and shell pre-mixed was deemed suitable for semi-permeable capsule formation. Their size distribution is polydisperse and some have inclusions of shell material in the inner volume, however SPCs of up to 140 μm diameter were observed in this instance, as shown in FIG. 59.

Example 31: Triple Co-Flow Dispersed Phase Capsule Generation

This example describes the scenario where two aqueous phase inlets are used for the core polymer solution and one is used for the shell polymer solution. Such a microfluidic chip and droplet generation strategy may be attractive when two species of particles or molecules should be encapsulated into SPCs but avoiding the interaction of the two species in the same solution before compartmentalization. For visualization purposes, one of the core polymer phases in this example contains 1 um beads visible using bright-field microscopy.

SPC generation and polymerization. Three aqueous polymers solutions were prepared. SHELL: 130 μL 2× DexMAB1090 (20% w/v in PBS) and 150 μL 1×PBS solution. CORE 1:70 μL of 20% w/w Dextran 500k in 1×PBS, 35 μL of 4% LAP in water, and 35 μL of 1×PBS solution; CORE 2: 70 μL of 20% w/w Dextran 500k in 1×PBS, 10 μL of Dynabeads 10 mg/ml (Invitrogen, 65001), and 60 μL 1×PBS solution.

Each of the three solutions was mixed by pipetting, vortexing and spun down to eliminate bubbles. Each was then loaded into 1-mL syringes (BD, 309628) pre-filled with 300 μL HFE7500 (Acota, 297730-93-9). Carrier oil (1% DSO, Droplet Genomics) was loaded into an empty syringe. Needles (Agani, AN*2325R1) with pre-attached tubing (Adtech, 81925) were mounted on the syringes. All solution syringes were mounted in vertical orientation. For SPC generation, Harvard apparatus pumps were used at a constant flow rate. Drop formation on TCD.1 chip (Droplet Genomics R&D 27 μm×30 μm H×W nozzle) was observed using a 10× microscope objective and a high-speed camera. The chip was primed at 1000 μL/hr flowrates for all 4 inlets. Once the chip was primed, the carrier oil flowrate was adjusted to 500 μL/hr, Core 1 and Core 2 flowrates to 40 μL/hr each, and the Shell flowrate to 80 L/h. Once the flowrates stabilized (FIG. 60 and FIG. 61), the emulsion collection was started—the emulsion was collected into a 1.5-mL tube. At FIG. 60, one sees Bright-field microscopy image of Core solutions 1 and 2 (Top Right and Bottom Right respectively) making a stable flow of required proportions with Shell solution (Far Right). Particle encapsulation can be observed within the drops (Left). At FIG. 61, one sees Bright-field microscopy image montage of one pre-SPC drop traveling along the microfluidic channel just after it has been formed, note the 4 dark particles changing position. Vertical scale bar at 50 μm. Elapsed time is 25 ms start to finish. After 2 hours, the run was stopped, and the emulsion was polymerized by 405 nm illumination through the tube bottom for 30 s. The oil under the emulsion was removed by pipetting and the SPCs were released by adding 500 μL of 20% PFO (Fluorochem, 647-42-7) in HFE-7500 and 500 μL Capsule Wash Buffer (50 mM Tris-HCl pH 7.5, 75 μM KCl, 3 μM MgCl2 with 1% Igepal CA-630-56741-50ML-F SIGMA). The SPCs were then washed 3 times with 1 mL Capsule Wash Buffer. The samples were imaged using 10× magnification on inverted microscope in bright-field. FIG. 62 shows one of these images—a bright-field microscopy image of SPC suspension in aqueous buffer after polymerization. SPCs of approx. 54 μm in diameter are formed. Note dark particles embedded within the capsules.

Results. Having the solutions destined for the core of the capsules separated into two did not hinder capsule formation (FIGS. 60-62). This way sample constituents can be effectively separated prior to the capsule generation step.

Example 32: Different Molecular Weight Dextrans as SPC Core Polymers

This example demonstrates that dextrans in the 10,000 Da-2,000,000 Da molecular weight range can be used as SPC core polymers.

Procedure. SPCs were generated similarly as described in other examples. Briefly, the Working Shell Solution was composed of 50 ul of 20% w/w methacryloyl-butyryl-dextran (DexMAB1090) in 1×PBS, 10 ul of 100 mM DTT, and 40 ul 1×PBS. The Working Core Solution was composed of 50 ul of 2× Stock Core Solution in 1×PBS, 12.5 ul of 4% w/w LAP (Sigma-Aldrich, #900889-1G) and 37.5 ul of 1×PBS, mixed well before use. Three 2× Stock Core solutions were tested: i) 50% w/w dextran 10 kDa; ii) 40% w/w dextran 100 kDa; iii) 15% w/w dextran 2 MDa. The Working Shell Solution and the Working Core Solution were injected into a co-flow microfluidic device (CF-60, Droplet Genomics) at 75 ul/h each. The carrier oil (0.25×DSO, DropletGenomics) was injected at 450 ul/h. Droplets~62 um in diameter were generated. After 1 hour, the run was stopped, and the emulsion was polymerized under 405 nm light LED device (Droplet Genomics) for 30 seconds. The oil under emulsion was removed by pipetting. The remained emulsion was broken by adding 1×PBS (Invitrogen, #AM9625) and 20% v/v PFO (Fluorochem, #647-42-7) in HFE7500. The sample was mixed by briefly vortexing and then spun down. The bottom oil and upper water layers were removed by pipetting, leaving only the released SPCs in the tube. The SPCs were washed 3 times with 1 mL of 1×PBS supplemented with 0.1% Pluronic F-68.

Result. As shown in FIG. 63, SPCs are successfully formed when different dextrans with average molecular weights in the range from 10 kDa to 2 MDa as the core polymer. The characteristic shell-core topology is observed.

Example 33: Generation of SPCs with a Blend of Shell Polymers

This example describes the use of a blend of i) methacryloyl- and butyryl-modified dextran (DexMAB1090, and ii) acryl-oil and butyryl-modified dextran (DexAB50100) for the formation of the shell of SPCs Procedure. SPCs were generated similarly as described in other examples. Briefly, the Working Shell Solution was composed of 25 ul of 10% w/w acryloyl-butyryl-dextran (DexAB50100) in 1×PBS, 75 ul of 15% w/w methacryloyl-butyryl-dextran (DexMAB1090) in 1×PBS, and 50 ul 1×PBS. The Working Core Solution was composed of 50 ul of 20% w/w Dextran 500k (Sigma-Aldrich, #31392J) in 1×PBS, 12.5 ul of 4% w/w LAP (Sigma-Aldrich, #900889-1G) and 37.5 ul of 1×PBS, mixed well before use. The Working Shell Solution and the Working Core Solution were injected into a co-flow microfluidic device (CF-60, Droplet Genomics) at 75 ul/h each. The carrier oil (0.25×DSO, DropletGenomics) was injected at 450 ul/h. Droplets~62 um in diameter were generated. After 1 hour, the run was stopped, and the emulsion was polymerized under 405 nm light LED device (Droplet Genomics) for 30 seconds. The oil under emulsion was removed by pipetting. The remaining emulsion was broken by adding 1×PBS (Invitrogen, #AM9625) and 20% v/v PFO (Fluorochem, #647-42-7) in HFE7500. The sample was mixed by briefly vortexing and then was spun down. The bottom oil and upper water layers were removed by pipetting, leaving only the released SPCs in the tube. The SPCs were washed 3 times with 1 mL of 1×PBS supplemented with 0.1% Pluronic F-68.

Result. As shown in FIG. 64, SPCs are successfully formed when using a blend of DexMAB1090 and DexAB50100 as shell polymer. The characteristic shell-core topology is observed.

The entirety of each patent, patent application, publication and document referenced herein is incorporated by reference. Citation of patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

The technology has been described with reference to specific implementations. The terms and expressions that have been utilized herein to describe the technology are descriptive and not necessarily limiting. Certain modifications made to the disclosed implementations can be considered within the scope of the technology. Certain aspects of the disclosed implementations suitably may be practiced in the presence or absence of certain elements not specifically disclosed herein.

Each of the terms "comprising," "consisting essentially of," and "consisting of" may be replaced with either of the other two terms. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%; e.g., a weight of "about 100 grams" can include a weight between 90 grams and 110 grams). Use of the term "about" at the beginning of a listing of values modifies each of the values (e.g., "about 1, 2 and 3" refers to "about 1, about 2 and about 3"). When a listing of values is described the listing includes all intermediate values and all fractional values thereof (e.g., the listing of values "80%, 85% or 90%" includes the intermediate value 86% and the fractional value 86.4%). When a listing of values is followed by the term "or more," the term "or more" applies to each of the values listed (e.g., the listing of "80%, 90%, 95%, or more" or "80%, 90%, 95% or more" or "80%, 90%, or 95% or more" refers to "80% or more, 90% or more, or 95% or more"). When a listing of values is described, the listing includes all ranges between any two of the values listed (e.g., the listing of "80%, 90% or 95%" includes ranges of "80% to 90%," "80% to 95%" and "90% to 95%").

As used herein, the term "about" in reference to a number represents a range spanning from −10% of that number to +10% of that number. In reference to a range, the term "about" refers to an extended range having a lower limit of 10% less than the stated lower limit, and an upper limit of 10% above the stated upper limit.

We claim:

1. A composition, comprising a plurality of microcapsules each comprising a core surrounded by a shell, wherein:

the shell is a hydrogel comprising a first polymer, wherein the first polymer comprises a polysaccharide modified with a conjugated cross-linking moiety, wherein the cross-linking moiety is selected from the group consisting of acryloyl, methacryloyl, and combinations thereof, and modified with a conjugated hydrophilicity/hydrophobicity-modifying moiety, and molecules of cross-linking moiety of the first polymer are cross-linked in the hydrogel; and the core comprises a second polymer comprising a polysaccharide that does not include the cross-linking moiety and does not include the hydrophilicity/hydrophobicity-modifying moiety of the first polymer, wherein the shell of the microcapsules comprises pores and the microcapsules retain nucleic acid of a size of about 100 base pairs or greater.

2. The composition of claim 1, wherein the first polymer is a major component of the shell and the second polymer is a major component of the core.

3. The composition of claim 2, wherein the polysaccharide of the first polymer is a charge-neutral non-ionic polysaccharide.

4. The composition of claim 3, wherein the polysaccharide is a glucan.

5. The composition of claim 3, wherein the polysaccharide comprises pentose and/or hexose monomers.

6. The composition of claim 3, wherein the polysaccharide comprises glucose and/or fructose monomers.

7. The composition claim 3, wherein the polysaccharide is chosen from dextran and cellulose.

8. The composition of claim 3, wherein the polysaccharide has a molecular mass of about 5,000 g/mole to about 50,000,000 g/mole.

9. The composition of claim 8, wherein the polysaccharide has a molecular mass of about 50,000 g/mole to about 2,000,000 g/mole.

10. The composition of claim 1, wherein the second polymer is not cross-linked.

11. The composition of claim 1, wherein the hydrophilicity/hydrophobicity-modifying moiety comprises a fatty acid acyl group.

12. The composition of claim 11, wherein the fatty acid is a C2-C8 fatty acid.

13. The composition of claim 12, wherein the hydrophilicity/hydrophobicity-modifying moiety comprises a butyryl group.

14. The composition of claim 1, wherein the first polymer further comprises a detectable label.

15. The composition of claim 1, wherein the first polymer further comprises a binding partner moiety to which a binding partner counterpart moiety can bind.

16. The composition of claim 1, wherein the microcapsules remain intact under polymerase chain reaction thermocycling conditions.

17. The composition of claim 1, wherein the microcapsules are microspheroids.

18. The composition of claim 17, wherein the microcapsules are defined by a diameter of about 1 micrometer to about 10,000 micrometers.

19. The composition of claim 17, wherein the diameter of the microcapsules varies by a coefficient of variation of about 30% or less.

20. The composition of claim 17, wherein circularity of the microcapsules in the composition is about 0.8 to about 1.0.

21. The composition of claim 17, wherein concentricity of the microcapsules in the composition is about 75% or greater.

22. The composition of claim 1, wherein the shell of the microcapsules comprises pores and the microcapsules retain nucleic acid of a size of about 500 base pairs or greater.

23. The composition of claim 1, wherein the microcapsule or portion thereof is glycosidase degradable at a pH between about 6 and about 8 and at a temperature of about 40 degrees Celsius or less.

24. The composition of claim 23, wherein the glycosidase is chosen from dextranase, amylase, agarase and cellulase.

25. The composition of claim 1, wherein the microcapsules are lipid-free and organic solvent free.

26. The composition of claim 1, comprising a biological entity encapsulated within the core of the microcapsules.

27. The composition of claim 26, wherein the biological entity is chosen from a eukaryotic cell, prokaryotic cell, unicellular organism, multi-cellular organism, microorganism, bacterium, archaeon, fungus, plant, virus, organelle, liposomal vector, extracellular vesicle, nucleic acid, protein, organic molecule and biological molecule.

* * * * *

SEQUENCE LISTING

```
Sequence total quantity: 81
SEQ ID NO: 1            moltype = DNA  length = 21
FEATURE                 Location/Qualifiers
source                  1..21
                        mol_type = other DNA
                        organism = synthetic construct
SEQUENCE: 1
tgaaacagcg tgctgcactg a                                                   21

SEQ ID NO: 2            moltype = DNA  length = 24
FEATURE                 Location/Qualifiers
source                  1..24
                        mol_type = other DNA
                        organism = synthetic construct
SEQUENCE: 2
cagtctgttg attacctgat ctcc                                                24

SEQ ID NO: 3            moltype = DNA  length = 21
FEATURE                 Location/Qualifiers
source                  1..21
                        mol_type = other DNA
                        organism = synthetic construct
SEQUENCE: 3
cctggatccg aaagacggtt c                                                   21

SEQ ID NO: 4            moltype = DNA  length = 27
FEATURE                 Location/Qualifiers
source                  1..27
                        mol_type = other DNA
                        organism = synthetic construct
SEQUENCE: 4
ttcactctga agtctgacgt tctgttc                                             27
```

```
SEQ ID NO: 5            moltype = DNA  length = 20
FEATURE                 Location/Qualifiers
source                  1..20
                        mol_type = other DNA
                        organism = synthetic construct
SEQUENCE: 5
tgctgagcct gggtgtttcc                                                 20

SEQ ID NO: 6            moltype = DNA  length = 20
FEATURE                 Location/Qualifiers
source                  1..20
                        mol_type = other DNA
                        organism = synthetic construct
SEQUENCE: 6
agtggcactg gctggtttcg                                                 20

SEQ ID NO: 7            moltype = DNA  length = 20
FEATURE                 Location/Qualifiers
source                  1..20
                        mol_type = other DNA
                        organism = synthetic construct
SEQUENCE: 7
cctgcggctg agttacaacg                                                 20

SEQ ID NO: 8            moltype = DNA  length = 30
FEATURE                 Location/Qualifiers
source                  1..30
                        mol_type = other DNA
                        organism = synthetic construct
misc_feature            1..27
                        note = DNA
misc_feature            28..30
                        note = guanosine (ribonucleoside) - RNA
SEQUENCE: 8
aagcagtggt atcaacgcag agtacatggg                                      30

SEQ ID NO: 9            moltype = DNA  length = 22
FEATURE                 Location/Qualifiers
source                  1..22
                        mol_type = other DNA
                        organism = synthetic construct
SEQUENCE: 9
tcagcacggg acaaactctt ct                                              22

SEQ ID NO: 10           moltype = DNA  length = 22
FEATURE                 Location/Qualifiers
source                  1..22
                        mol_type = other DNA
                        organism = synthetic construct
SEQUENCE: 10
gcaggagaca gactcttctc ca                                              22

SEQ ID NO: 11           moltype = DNA  length = 19
FEATURE                 Location/Qualifiers
source                  1..19
                        mol_type = other DNA
                        organism = synthetic construct
SEQUENCE: 11
aactggctgc tcatggtgt                                                  19

SEQ ID NO: 12           moltype = DNA  length = 21
FEATURE                 Location/Qualifiers
source                  1..21
                        mol_type = other DNA
                        organism = synthetic construct
SEQUENCE: 12
tggtgcaagt gtggttgagg t                                               21

SEQ ID NO: 13           moltype = DNA  length = 20
FEATURE                 Location/Qualifiers
source                  1..20
                        mol_type = other DNA
                        organism = synthetic construct
SEQUENCE: 13
tggtcacttg gctggtggtg                                                 20

SEQ ID NO: 14           moltype = DNA  length = 24
FEATURE                 Location/Qualifiers
```

```
source                  1..24
                        mol_type = other DNA
                        organism = synthetic construct
SEQUENCE: 14
cacttggcag gtgaactgtt ttct                                              24

SEQ ID NO: 15           moltype = DNA  length = 23
FEATURE                 Location/Qualifiers
source                  1..23
                        mol_type = other DNA
                        organism = synthetic construct
SEQUENCE: 15
aaccttcaag gatgctcttg gga                                               23

SEQ ID NO: 16           moltype = DNA  length = 21
FEATURE                 Location/Qualifiers
source                  1..21
                        mol_type = other DNA
                        organism = synthetic construct
SEQUENCE: 16
ggacagggat ccagagttcc a                                                 21

SEQ ID NO: 17           moltype = DNA  length = 20
FEATURE                 Location/Qualifiers
source                  1..20
                        mol_type = other DNA
                        organism = synthetic construct
SEQUENCE: 17
aggtgacggt ctgacttggc                                                   20

SEQ ID NO: 18           moltype = DNA  length = 21
FEATURE                 Location/Qualifiers
source                  1..21
                        mol_type = other DNA
                        organism = synthetic construct
SEQUENCE: 18
gctggacagg gctccatagt t                                                 21

SEQ ID NO: 19           moltype = DNA  length = 23
FEATURE                 Location/Qualifiers
source                  1..23
                        mol_type = other DNA
                        organism = synthetic construct
SEQUENCE: 19
ggcaccttgt ccaatcatgt tcc                                               23

SEQ ID NO: 20           moltype = DNA  length = 24
FEATURE                 Location/Qualifiers
source                  1..24
                        mol_type = other DNA
                        organism = synthetic construct
SEQUENCE: 20
atgtcgttca tactcgtcct tggt                                              24

SEQ ID NO: 21           moltype = DNA  length = 22
FEATURE                 Location/Qualifiers
source                  1..22
                        mol_type = other DNA
                        organism = synthetic construct
SEQUENCE: 21
aagcagtggt atcaacgcag ag                                                22

SEQ ID NO: 22           moltype = DNA  length = 28
FEATURE                 Location/Qualifiers
source                  1..28
                        mol_type = other DNA
                        organism = synthetic construct
modified_base           6
                        mod_base = OTHER
                        note = uracil
SEQUENCE: 22
aacgttaagc agtggtatca acgcagag                                          28

SEQ ID NO: 23           moltype = DNA  length = 24
FEATURE                 Location/Qualifiers
source                  1..24
                        mol_type = other DNA
                        organism = synthetic construct
modified_base           7
```

```
                          mod_base = OTHER
                          note = uracil
SEQUENCE: 23
aatgagtccc ttgaccaggc atcc                                          24

SEQ ID NO: 24             moltype = DNA  length = 27
FEATURE                   Location/Qualifiers
source                    1..27
                          mol_type = other DNA
                          organism = synthetic construct
modified_base             7
                          mod_base = OTHER
                          note = uracil
SEQUENCE: 24
actcattgaa gcacacgact gaggcac                                       27

SEQ ID NO: 25             moltype = DNA  length = 20
FEATURE                   Location/Qualifiers
source                    1..20
                          mol_type = other DNA
                          organism = synthetic construct
SEQUENCE: 25
agagtttgat cmtggctcag                                               20

SEQ ID NO: 26             moltype = DNA  length = 29
FEATURE                   Location/Qualifiers
source                    1..29
                          mol_type = other DNA
                          organism = synthetic construct
modified_base             7
                          mod_base = OTHER
                          note = uracil
SEQUENCE: 26
actcatttac ggytaccttg ttaygactt                                     29

SEQ ID NO: 27             moltype = DNA  length = 27
FEATURE                   Location/Qualifiers
source                    1..27
                          mol_type = other DNA
                          organism = synthetic construct
modified_base             7
                          mod_base = OTHER
                          note = uracil
SEQUENCE: 27
acaaggtatg cgtaaaggcg aagagct                                       27

SEQ ID NO: 28             moltype = DNA  length = 23
FEATURE                   Location/Qualifiers
source                    1..23
                          mol_type = other DNA
                          organism = synthetic construct
SEQUENCE: 28
cctggtcatc atttgtacag ttc                                           23

SEQ ID NO: 29             moltype = DNA  length = 27
FEATURE                   Location/Qualifiers
source                    1..27
                          mol_type = other DNA
                          organism = synthetic construct
modified_base             7
                          mod_base = OTHER
                          note = uracil
SEQUENCE: 29
aatgagtgag taaacttggt ctgacag                                       27

SEQ ID NO: 30             moltype = DNA  length = 27
FEATURE                   Location/Qualifiers
source                    1..27
                          mol_type = other DNA
                          organism = synthetic construct
modified_base             7
                          mod_base = OTHER
                          note = uracil
SEQUENCE: 30
accttgtaat ggtttcttag acgtcag                                       27

SEQ ID NO: 31             moltype = DNA  length = 123
FEATURE                   Location/Qualifiers
source                    1..123
```

```
                            mol_type = other DNA
                            organism = synthetic construct
misc_difference             25
                            note = a, c, g, t, unknown or other
misc_difference             26
                            note = a, c, g, t, unknown or other
misc_difference             27
                            note = a, c, g, t, unknown or other
misc_difference             28
                            note = a, c, g, t, unknown or other
misc_difference             29
                            note = a, c, g, t, unknown or other
misc_difference             30
                            note = a, c, g, t, unknown or other
misc_difference             31
                            note = a, c, g, t, unknown or other
misc_difference             32
                            note = a, c, g, t, unknown or other
misc_difference             33
                            note = a, c, g, t, unknown or other
misc_difference             34
                            note = a, c, g, t, unknown or other
misc_difference             35
                            note = a, c, g, t, unknown or other
misc_difference             36
                            note = a, c, g, t, unknown or other
misc_difference             37
                            note = a, c, g, t, unknown or other
misc_difference             38
                            note = a, c, g, t, unknown or other
misc_difference             39
                            note = a, c, g, t, unknown or other
misc_difference             40
                            note = a, c, g, t, unknown or other
misc_difference             41
                            note = a, c, g, t, unknown or other
misc_difference             42
                            note = a, c, g, t, unknown or other
misc_difference             43
                            note = a, c, g, t, unknown or other
misc_difference             44
                            note = a, c, g, t, unknown or other
misc_difference             79..86
                            note = a, c, g, t, unknown or other
misc_difference             91..98
                            note = a, c, g, t, unknown or other
misc_difference             103..110
                            note = a, c, g, t, unknown or other
misc_difference             115..122
                            note = a, c, g, t, unknown or other
SEQUENCE: 31
caagcagaag acggcatacg agatnnnnnn nnnnnnnnnn nnnngtgact ggagttcaga   60
cgtgtgctct tccgatctnn nnnnnnagga nnnnnnnnac tcnnnnnnnn aaggnnnnnn  120
nnt                                                                123

SEQ ID NO: 32               moltype = DNA  length = 68
FEATURE                     Location/Qualifiers
source                      1..68
                            mol_type = other DNA
                            organism = synthetic construct
misc_difference             34..39
                            note = a, c, g, t, unknown, other, or absent
SEQUENCE: 32
agatcggaag agcgtcgtgt agggaaagag tgtnnnnnng tgtagatctc ggtggtcgcc   60
gtatcatt                                                            68

SEQ ID NO: 33               moltype = DNA  length = 126
FEATURE                     Location/Qualifiers
source                      1..126
                            mol_type = other DNA
                            organism = synthetic construct
misc_difference             25..29
                            note = ccata, agatc, ttcgt, tggta, tcaac, atggc, ctgat,
                            aggag, ggagt, gaaac, cagta, gttag, actag, aagca, ctact,
                            agact, gaagg, gcttc, tgacg, ctatc, gtgca, tacgg, aagac,
                            acatg, caaca, tagtc, actca, agcgt, ggcta, gatcg, caagt,
                            accta, tctcg, caatg, cgtta, tccca, catga, tttcc, ttggg,
                            agtac, gcgtt, gacca, acagt, cagag, tggat, aactc, ttgac,
                            taacc, ctgtg, ccaat, ggtca, gctct, agtcg, tcgag, aacga,
```

```
                              tacac, tgttc, acacc, cctaa, gactt, gaact, tgtga, atgct,
                              cacaa, ctagg, cattc, tcact, cggtt, tagct, cgtct, tcctg,
                              gtgtc, cgaac, gcaga, gtcga, tcggt, ttctc, ctgga, tccat,
                              atacg, gtggt, ttccg, aacag, gccaa, agagg, cacct, gagtg,
                              ccttg, gtcac, gatgt, aaggg, cttca, gtatg, gagat, tgcag, or
                              aatcc
misc_difference               32..37
                              note = agtgtg, atgcac, atacgc, tcggaa, cgatca, gccaat,
                              gcgata, gcaaga, attgcc, ccacaa, gtttgc, cacaac, aagcca,
                              atgctg, aacacc, ccaaca, cacgta, tcgatg, cgacat, tgtcgt,
                              cgctaa, tcagct, cgcatt, gcagat, tgatgc, atcagc, gcattg,
                              aaggct, acggtt, cgtcaa, tgctga, tcgaac, aggtgt, atcgct,
                              caacca, tcaacg, tcgaca, ggttgt, gcttca, taaccg, acccat,
                              tgcaag, tgtgga, ttgcag, accgta, ttgctc, aacggt, cattgc,
                              aacgac, acgact, tcgttc, aagtgc, ttggca, tgcgta, ttccca,
                              cgatgt, gaagct, tctcga, cattcg, agcaga, tcgtgt, tgttcg,
                              acgtac, aaagcg, atccga, ctgtgt, tacgtc, attcgg, ttgtgc,
                              ttgtcg, acttcg, tcgctt, tccgtt, acagca, agcatc, acagtg,
                              agcgaa, gctgaa, gtcgat, gcaact, aggcaa, atcacg, actgct,
                              cagctt, agctca, acgatc, aagctc, tgacac, aggctt, tgcaca,
                              tagcgt, accaca, acttgc, tctgca, catgca, or actcgt
misc_difference               40..44
                              note = ccata, agatc, ttcgt, tggta, atctg, tcaac, atggc,
                              ctgat, aggag, ggagt, gaaac, cagta, gttag, actag, aagca,
                              ctact, agact, gaagg, gcttc, tgacg, ctatc, gtgca, tacgg,
                              aagac, acatg, caaca, ctcag, tagtc, actca, agcgt, ggcta,
                              gatcg, caagt, accta, tctcg, caatg, cgtta, tccca, catga,
                              tttcc, ttggg, agtac, gcgtt, gacca, acagt, cagag, tggat,
                              aactc, ttgac, taacc, ctgtg, ccaat, ggtca, gctct, agtcg,
                              tcgag, aacga, tgttc, acacc, cctaa, gactt, gaact, tgtga,
                              atgct, cacaa, ctagg, cattc, tcact, cggtt, tagct, cgtct,
                              tcctg, gtgtc, cgaac, gcaga, gtcga, tcggt, ttctc, tccat,
                              ggcat, atacg, gtggt, ttccg, aacag, gccaa, agagg, cacct,
                              gagtg, ccttg, gatgt, aaggg, cttca, gtatg, gagat, tgcag, or
                              aatcc
misc_difference               79
                              note = a, c, g, t, unknown or other
misc_difference               80
                              note = a, c, g, t, unknown or other
misc_difference               81
                              note = a, c, g, t, unknown or other
misc_difference               82
                              note = a, c, g, t, unknown or other
misc_difference               83
                              note = a, c, g, t, unknown or other
misc_difference               84
                              note = a, c, g, t, unknown or other
misc_difference               85
                              note = a, c, g, t, unknown or other
misc_difference               86
                              note = a, c, g, t, unknown or other
misc_difference               87
                              note = a, c, g, t, unknown or other
misc_difference               88
                              note = a, c, g, t, unknown or other
misc_difference               89..94
                              note = agtgtg, atgcac, atacgc, cgatca, gcgata, attgcc,
                              gtttgc, atgctg, cacgta, tcgatg, cgacat, tgtcgt, tcagct,
                              cgcatt, gcagat, or tgatgc
misc_difference               126
                              note = a, c, g, t, unknown or other
SEQUENCE: 33
caagcagaag acggcatacg agatnnnnna cnnnnnncan nnnngtgact ggagttcaga   60
cgtgtgctct tccgatctnn nnnnnnnnnn nnnnttttt ttttttttttt tttttttttt  120
ttttvn                                                             126

SEQ ID NO: 34                 moltype = DNA  length = 42
FEATURE                       Location/Qualifiers
source                        1..42
                              mol_type = other DNA
                              organism = synthetic construct
misc_difference               35..42
                              note = a, c, g, t, unknown or other
SEQUENCE: 34
gtgactggag ttcagacgtg tgctcttccg atctnnnnnn nn                      42

SEQ ID NO: 35                 moltype = DNA  length = 37
FEATURE                       Location/Qualifiers
source                        1..37
```

-continued

```
                        mol_type = other DNA
                        organism = synthetic construct
modified_base           1
                        mod_base = OTHER
                        note = 5' phosphate modified nucleotide
misc_difference         5..12
                        note = a, c, g, t, unknown or other
misc_difference         17..24
                        note = a, c, g, t, unknown or other
misc_difference         29..36
                        note = a, c, g, t, unknown or other
SEQUENCE: 35
aggannnnnn nnactcnnnn nnnnaaggnn nnnnnnt                              37

SEQ ID NO: 36           moltype = DNA   length = 22
FEATURE                 Location/Qualifiers
source                  1..22
                        mol_type = other DNA
                        organism = synthetic construct
modified_base           1
                        mod_base = OTHER
                        note = 5' phosphate modified nucleotide
misc_difference         5..12
                        note = a, c, g, t, unknown or other
SEQUENCE: 36
tcctnnnnnn nnagatcgga ag                                              22

SEQ ID NO: 37           moltype = DNA   length = 14
FEATURE                 Location/Qualifiers
source                  1..14
                        mol_type = other DNA
                        organism = synthetic construct
SEQUENCE: 37
catcacagga agtc                                                       14

SEQ ID NO: 38           moltype = DNA   length = 79
FEATURE                 Location/Qualifiers
source                  1..79
                        mol_type = other DNA
                        organism = synthetic construct
misc_difference         35..42
                        note = a, c, g, t, unknown or other
misc_difference         47..54
                        note = a, c, g, t, unknown or other
misc_difference         59..66
                        note = a, c, g, t, unknown or other
misc_difference         71..78
                        note = a, c, g, t, unknown or other
SEQUENCE: 38
gtgactggag ttcagacgtg tgctcttccg atctnnnnnn nnaggannnn nnnnactcnn      60
nnnnnnaagg nnnnnnnnt                                                  79

SEQ ID NO: 39           moltype = DNA   length = 54
FEATURE                 Location/Qualifiers
source                  1..54
                        mol_type = other DNA
                        organism = synthetic construct
modified_base           1
                        mod_base = OTHER
                        note = 5' phosphate modified nucleotide
misc_difference         1..8
                        note = a, c, g, t, unknown or other
misc_difference         13..20
                        note = a, c, g, t, unknown or other
misc_difference         25..32
                        note = a, c, g, t, unknown or other
misc_difference         37..44
                        note = a, c, g, t, unknown or other
SEQUENCE: 39
nnnnnnnncc ttnnnnnnnn gagtnnnnnn nntcctnnnn nnnnagatcg aag             54

SEQ ID NO: 40           moltype = DNA   length = 65
FEATURE                 Location/Qualifiers
source                  1..65
                        mol_type = other DNA
                        organism = synthetic construct
misc_difference         25
                        note = a, c, g, t, unknown or other
misc_difference         26
```

US 11,958,947 B2

139                                                                                                             140

-continued

```
                                note = a, c, g, t, unknown or other
misc_difference                 27
                                note = a, c, g, t, unknown or other
misc_difference                 28
                                note = a, c, g, t, unknown or other
misc_difference                 29
                                note = a, c, g, t, unknown or other
misc_difference                 30
                                note = a, c, g, t, unknown or other
misc_difference                 31
                                note = a, c, g, t, unknown or other
misc_difference                 32
                                note = a, c, g, t, unknown or other
misc_difference                 33
                                note = a, c, g, t, unknown or other
misc_difference                 34
                                note = a, c, g, t, unknown or other
misc_difference                 35
                                note = a, c, g, t, unknown or other
misc_difference                 36
                                note = a, c, g, t, unknown or other
misc_difference                 37
                                note = a, c, g, t, unknown or other
misc_difference                 38
                                note = a, c, g, t, unknown or other
misc_difference                 39
                                note = a, c, g, t, unknown or other
misc_difference                 40
                                note = a, c, g, t, unknown or other
misc_difference                 41
                                note = a, c, g, t, unknown or other
misc_difference                 42
                                note = a, c, g, t, unknown or other
misc_difference                 43
                                note = a, c, g, t, unknown or other
misc_difference                 44
                                note = a, c, g, t, unknown or other
SEQUENCE: 40
caagcagaag acggcatacg agatnnnnnn nnnnnnnnnn nnngtgact ggagttcaga         60
cgtgt                                                                    65

SEQ ID NO: 41           moltype = DNA  length = 55
FEATURE                 Location/Qualifiers
source                  1..55
                        mol_type = other DNA
                        organism = synthetic construct
misc_difference         30
                        note = a, c, g, t, unknown or other
misc_difference         31
                        note = a, c, g, t, unknown or other
misc_difference         32
                        note = a, c, g, t, unknown or other
misc_difference         33
                        note = a, c, g, t, unknown or other
misc_difference         34
                        note = a, c, g, t, unknown or other
misc_difference         35
                        note = a, c, g, t, unknown or other
SEQUENCE: 41
aatgatacgg cgaccaccga gatctacacn nnnnnacact ctttccctac acgac            55

SEQ ID NO: 42           moltype = DNA  length = 33
FEATURE                 Location/Qualifiers
source                  1..33
                        mol_type = other DNA
                        organism = synthetic construct
modified_base           32
                        mod_base = OTHER
                        note = Nucleotide with phosphorothioate linkage
SEQUENCE: 42
agatcggaag agcgtcgtgt agggaaagag tgt                                    33

SEQ ID NO: 43           moltype = DNA  length = 55
FEATURE                 Location/Qualifiers
source                  1..55
                        mol_type = other DNA
                        organism = synthetic construct
misc_difference         2..9
                        note = a, c, g, t, unknown or other
```

| | |
|---|---|
| misc_difference | 14..21 |
| | note = a, c, g, t, unknown or other |
| misc_difference | 26..33 |
| | note = a, c, g, t, unknown or other |
| misc_difference | 38..45 |
| | note = a, c, g, t, unknown or other |
| SEQUENCE: 43 | | annnnnnnnc cttnnnnnnn ngagtnnnnn nnnacctnnn nnnnnagatc ggaag  55

| | |
|---|---|
| SEQ ID NO: 44 | moltype = DNA  length = 13 |
| FEATURE | Location/Qualifiers |
| source | 1..13 |
| | mol_type = other DNA |
| | organism = synthetic construct |
| modified_base | 1 |
| | mod_base = OTHER |
| | note = 5' Amino modifier C6 modified nucleotide |
| SEQUENCE: 44 | | gctcttccga tct  13

| | |
|---|---|
| SEQ ID NO: 45 | moltype = DNA  length = 68 |
| FEATURE | Location/Qualifiers |
| source | 1..68 |
| | mol_type = other DNA |
| | organism = synthetic construct |
| misc_difference | 34 |
| | note = a, c, g, t, unknown or other |
| misc_difference | 35 |
| | note = a, c, g, t, unknown or other |
| misc_difference | 36 |
| | note = a, c, g, t, unknown or other |
| misc_difference | 37 |
| | note = a, c, g, t, unknown or other |
| misc_difference | 38 |
| | note = a, c, g, t, unknown or other |
| misc_difference | 39 |
| | note = a, c, g, t, unknown or other |
| SEQUENCE: 45 | | agatcggaag agcgtcgtgt agggaaagag tgtnnnnnng tgtagatctc ggtggtcgcc  60
gtatcatt  68

| | |
|---|---|
| SEQ ID NO: 46 | moltype = DNA  length = 123 |
| FEATURE | Location/Qualifiers |
| source | 1..123 |
| | mol_type = other DNA |
| | organism = synthetic construct |
| misc_difference | 2..9 |
| | note = a, c, g, t, unknown or other |
| misc_difference | 14..21 |
| | note = a, c, g, t, unknown or other |
| misc_difference | 26..33 |
| | note = a, c, g, t, unknown or other |
| misc_difference | 38..45 |
| | note = a, c, g, t, unknown or other |
| misc_difference | 80 |
| | note = a, c, g, t, unknown or other |
| misc_difference | 81 |
| | note = a, c, g, t, unknown or other |
| misc_difference | 82 |
| | note = a, c, g, t, unknown or other |
| misc_difference | 83 |
| | note = a, c, g, t, unknown or other |
| misc_difference | 84 |
| | note = a, c, g, t, unknown or other |
| misc_difference | 85 |
| | note = a, c, g, t, unknown or other |
| misc_difference | 86 |
| | note = a, c, g, t, unknown or other |
| misc_difference | 87 |
| | note = a, c, g, t, unknown or other |
| misc_difference | 88 |
| | note = a, c, g, t, unknown or other |
| misc_difference | 89 |
| | note = a, c, g, t, unknown or other |
| misc_difference | 90 |
| | note = a, c, g, t, unknown or other |
| misc_difference | 91 |
| | note = a, c, g, t, unknown or other |
| misc_difference | 92 |

-continued

|                   |                                              |
|-------------------|----------------------------------------------|
| misc_difference   | 93                                           |
|                   | note = a, c, g, t, unknown or other          |
| misc_difference   | 94                                           |
|                   | note = a, c, g, t, unknown or other          |
| misc_difference   | 95                                           |
|                   | note = a, c, g, t, unknown or other          |
| misc_difference   | 96                                           |
|                   | note = a, c, g, t, unknown or other          |
| misc_difference   | 97                                           |
|                   | note = a, c, g, t, unknown or other          |
| misc_difference   | 98                                           |
|                   | note = a, c, g, t, unknown or other          |
| misc_difference   | 99                                           |
|                   | note = a, c, g, t, unknown or other          |

SEQUENCE: 46
annnnnnnnc cttnnnnnnn ngagtnnnnn nnnacctnnn nnnnnagatc ggaagagcac 60
acgtctgaac tccagtcacn nnnnnnnnnn nnnnnnnnna tctcgtatgc cgtcttctgc 120
ttg                                                              123

| SEQ ID NO: 47     | moltype = DNA   length = 68                  |
| FEATURE           | Location/Qualifiers                          |
| source            | 1..68                                        |
|                   | mol_type = other DNA                         |
|                   | organism = synthetic construct               |
| misc_difference   | 30                                           |
|                   | note = a, c, g, t, unknown or other          |
| misc_difference   | 31                                           |
|                   | note = a, c, g, t, unknown or other          |
| misc_difference   | 32                                           |
|                   | note = a, c, g, t, unknown or other          |
| misc_difference   | 33                                           |
|                   | note = a, c, g, t, unknown or other          |
| misc_difference   | 34                                           |
|                   | note = a, c, g, t, unknown or other          |
| misc_difference   | 35                                           |
|                   | note = a, c, g, t, unknown or other          |

SEQUENCE: 47
aatgatacgg cgaccaccga gatctacacn nnnnnacact ctttccctac acgacgctct 60
tccgatct                                                         68

| SEQ ID NO: 48     | moltype = DNA   length = 70                  |
| FEATURE           | Location/Qualifiers                          |
| source            | 1..70                                        |
|                   | mol_type = other DNA                         |
|                   | organism = synthetic construct               |
| misc_difference   | 23                                           |
|                   | note = a, c, g, t, unknown or other          |
| misc_difference   | 24                                           |
|                   | note = a, c, g, t, unknown or other          |
| misc_difference   | 25                                           |
|                   | note = a, c, g, t, unknown or other          |
| misc_difference   | 26                                           |
|                   | note = a, c, g, t, unknown or other          |
| misc_difference   | 27                                           |
|                   | note = a, c, g, t, unknown or other          |
| misc_difference   | 28                                           |
|                   | note = a, c, g, t, unknown or other          |
| misc_difference   | 29                                           |
|                   | note = a, c, g, t, unknown or other          |
| misc_difference   | 30                                           |
|                   | note = a, c, g, t, unknown or other          |
| misc_difference   | 31                                           |
|                   | note = a, c, g, t, unknown or other          |
| misc_difference   | 32                                           |
|                   | note = a, c, g, t, unknown or other          |
| misc_difference   | 33..38                                       |
|                   | note = a, c, g, t, unknown or other          |
| misc_difference   | 70                                           |
|                   | note = a, c, g, t, unknown or other          |

SEQUENCE: 48
cagacgtgtg ctcttccgat ctnnnnnnnn nnnnnnnntt tttttttttt tttttttttt 60
tttttttvn                                                        70

| SEQ ID NO: 49     | moltype = DNA   length = 30                  |
| FEATURE           | Location/Qualifiers                          |
| source            | 1..30                                        |
|                   | mol_type = other DNA                         |
|                   | organism = synthetic construct               |

```
SEQUENCE: 49
aagcagtggt atcaacgcag agtacatggg                                              30

SEQ ID NO: 50          moltype = DNA  length = 25
FEATURE                Location/Qualifiers
source                 1..25
                       mol_type = other DNA
                       organism = synthetic construct
modified_base          4
                       mod_base = OTHER
                       note = Uracil
SEQUENCE: 50
agttcagacg tgtgctcttc cgatc                                                   25

SEQ ID NO: 51          moltype = DNA  length = 30
FEATURE                Location/Qualifiers
source                 1..30
                       mol_type = other DNA
                       organism = synthetic construct
SEQUENCE: 51
cccatgtact ctgcgttgat accactgctt                                              30

SEQ ID NO: 52          moltype = DNA  length = 22
FEATURE                Location/Qualifiers
source                 1..22
                       mol_type = other DNA
                       organism = synthetic construct
modified_base          1
                       mod_base = OTHER
                       note = 5' Amino modifier C6 modified nucleotide
SEQUENCE: 52
aagcagtggt atcaacgcag ag                                                      22

SEQ ID NO: 53          moltype = DNA  length = 74
FEATURE                Location/Qualifiers
source                 1..74
                       mol_type = other DNA
                       organism = synthetic construct
modified_base          4
                       mod_base = OTHER
                       note = Uracil
misc_difference        27
                       note = a, c, g, t, unknown or other
misc_difference        28
                       note = a, c, g, t, unknown or other
misc_difference        29
                       note = a, c, g, t, unknown or other
misc_difference        30
                       note = a, c, g, t, unknown or other
misc_difference        31
                       note = a, c, g, t, unknown or other
misc_difference        32
                       note = a, c, g, t, unknown or other
misc_difference        33
                       note = a, c, g, t, unknown or other
misc_difference        34
                       note = a, c, g, t, unknown or other
misc_difference        35
                       note = a, c, g, t, unknown or other
misc_difference        36
                       note = a, c, g, t, unknown or other
misc_difference        37..42
                       note = a, c, g, t, unknown or other
misc_difference        74
                       note = a, c, g, t, unknown or other
SEQUENCE: 53
agttcagacg tgtgctcttc cgatctnnnn nnnnnnnnnn nntttttttt tttttttttt             60
tttttttttt ttvn                                                               74

SEQ ID NO: 54          moltype = DNA  length = 31
FEATURE                Location/Qualifiers
source                 1..31
                       mol_type = other DNA
                       organism = synthetic construct
SEQUENCE: 54
cccatgtact ctgcgttgat accactgctt a                                            31

SEQ ID NO: 55          moltype = DNA  length = 74
FEATURE                Location/Qualifiers
```

```
source                  1..74
                        mol_type = other DNA
                        organism = synthetic construct
misc_difference         1
                        note = a, c, g, t, unknown or other
misc_difference         33..38
                        note = a, c, g, t, unknown or other
misc_difference         39
                        note = a, c, g, t, unknown or other
misc_difference         40
                        note = a, c, g, t, unknown or other
misc_difference         41
                        note = a, c, g, t, unknown or other
misc_difference         42
                        note = a, c, g, t, unknown or other
misc_difference         43
                        note = a, c, g, t, unknown or other
misc_difference         44
                        note = a, c, g, t, unknown or other
misc_difference         45
                        note = a, c, g, t, unknown or other
misc_difference         46
                        note = a, c, g, t, unknown or other
misc_difference         47
                        note = a, c, g, t, unknown or other
misc_difference         48
                        note = a, c, g, t, unknown or other
SEQUENCE: 55
nvttttttttt tttttttttt tttttttttt ttnnnnnnnn nnnnnnnnag atcggaagag    60
cacacgtctg aact                                                      74

SEQ ID NO: 56           moltype = DNA  length = 30
FEATURE                 Location/Qualifiers
source                  1..30
                        mol_type = other DNA
                        organism = synthetic construct
modified_base           1
                        mod_base = OTHER
                        note = 5' Amino modifier C6 modified nucleotide
SEQUENCE: 56
aagcagtggt atcaacgcag agtacatggg                                     30

SEQ ID NO: 57           moltype = DNA  length = 19
FEATURE                 Location/Qualifiers
source                  1..19
                        mol_type = other DNA
                        organism = synthetic construct
modified_base           1
                        mod_base = OTHER
                        note = 5' phosphate modified nucleotide
misc_difference         3..7
                        note = a, c, g, t, unknown or other
SEQUENCE: 57
cannnnngtg actggagtt                                                 19

SEQ ID NO: 58           moltype = DNA  length = 70
FEATURE                 Location/Qualifiers
source                  1..70
                        mol_type = other DNA
                        organism = synthetic construct
modified_base           1
                        mod_base = OTHER
                        note = 5' phosphate modified nucleotide
misc_difference         23
                        note = a, c, g, t, unknown or other
misc_difference         24
                        note = a, c, g, t, unknown or other
misc_difference         25
                        note = a, c, g, t, unknown or other
misc_difference         26
                        note = a, c, g, t, unknown or other
misc_difference         27
                        note = a, c, g, t, unknown or other
misc_difference         28
                        note = a, c, g, t, unknown or other
misc_difference         29
                        note = a, c, g, t, unknown or other
misc_difference         30
                        note = a, c, g, t, unknown or other
```

```
misc_difference        31
                       note = a, c, g, t, unknown or other
misc_difference        32
                       note = a, c, g, t, unknown or other
misc_difference        33..38
                       note = a, c, g, t, unknown or other
misc_difference        70
                       note = a, c, g, t, unknown or other
SEQUENCE: 58
cagacgtgtg ctcttccgat ctnnnnnnnn nnnnnnnntt tttttttttt tttttttttt    60
tttttttvn                                                            70

SEQ ID NO: 59          moltype = DNA  length = 89
FEATURE                Location/Qualifiers
source                 1..89
                       mol_type = other DNA
                       organism = synthetic construct
modified_base          1
                       mod_base = OTHER
                       note = 5' phosphate modified nucleotide
misc_difference        3..7
                       note = a, c, g, t, unknown or other
misc_difference        42
                       note = a, c, g, t, unknown or other
misc_difference        43
                       note = a, c, g, t, unknown or other
misc_difference        44
                       note = a, c, g, t, unknown or other
misc_difference        45
                       note = a, c, g, t, unknown or other
misc_difference        46
                       note = a, c, g, t, unknown or other
misc_difference        47
                       note = a, c, g, t, unknown or other
misc_difference        48
                       note = a, c, g, t, unknown or other
misc_difference        49
                       note = a, c, g, t, unknown or other
misc_difference        50
                       note = a, c, g, t, unknown or other
misc_difference        51
                       note = a, c, g, t, unknown or other
misc_difference        52..57
                       note = a, c, g, t, unknown or other
misc_difference        89
                       note = a, c, g, t, unknown or other
SEQUENCE: 59
cannnnngtg actggagttc agacgtgtgc tcttccgatc tnnnnnnnnn nnnnnnntt    60
tttttttttt tttttttttt tttttttvn                                     89

SEQ ID NO: 60          moltype = DNA  length = 87
FEATURE                Location/Qualifiers
source                 1..87
                       mol_type = other DNA
                       organism = synthetic construct
misc_difference        1
                       note = a, c, g, t, unknown or other
misc_difference        33..38
                       note = a, c, g, t, unknown or other
misc_difference        39
                       note = a, c, g, t, unknown or other
misc_difference        40
                       note = a, c, g, t, unknown or other
misc_difference        41
                       note = a, c, g, t, unknown or other
misc_difference        42
                       note = a, c, g, t, unknown or other
misc_difference        43
                       note = a, c, g, t, unknown or other
misc_difference        44
                       note = a, c, g, t, unknown or other
misc_difference        45
                       note = a, c, g, t, unknown or other
misc_difference        46
                       note = a, c, g, t, unknown or other
misc_difference        47
                       note = a, c, g, t, unknown or other
misc_difference        48
                       note = a, c, g, t, unknown or other
```

```
misc_difference         83..87
                        note = a, c, g, t, unknown or other
SEQUENCE: 60
nvtttttttt tttttttttt tttttttttt ttnnnnnnnn nnnnnnnnag atcggaagag    60
cacacgtctg aactccagtc acnnnnn                                        87

SEQ ID NO: 61           moltype = DNA  length = 29
FEATURE                 Location/Qualifiers
source                  1..29
                        mol_type = other DNA
                        organism = synthetic construct
misc_difference         25..29
                        note = a, c, g, t, unknown or other
SEQUENCE: 61
caagcagaag acggcatacg agatnnnnn                                      29

SEQ ID NO: 62           moltype = DNA  length = 96
FEATURE                 Location/Qualifiers
source                  1..96
                        mol_type = other DNA
                        organism = synthetic construct
modified_base           1
                        mod_base = OTHER
                        note = 5' phosphate modified nucleotide
misc_difference         3..7
                        note = a, c, g, t, unknown or other
misc_difference         10..14
                        note = a, c, g, t, unknown or other
misc_difference         49
                        note = a, c, g, t, unknown or other
misc_difference         50
                        note = a, c, g, t, unknown or other
misc_difference         51
                        note = a, c, g, t, unknown or other
misc_difference         52
                        note = a, c, g, t, unknown or other
misc_difference         53
                        note = a, c, g, t, unknown or other
misc_difference         54
                        note = a, c, g, t, unknown or other
misc_difference         55
                        note = a, c, g, t, unknown or other
misc_difference         56
                        note = a, c, g, t, unknown or other
misc_difference         57
                        note = a, c, g, t, unknown or other
misc_difference         58
                        note = a, c, g, t, unknown or other
misc_difference         59..64
                        note = a, c, g, t, unknown or other
misc_difference         96
                        note = a, c, g, t, unknown or other
SEQUENCE: 62
acnnnnncan nnnngtgact ggagttcaga cgtgtgctct tccgatctnn nnnnnnnnn     60
nnnntttttt tttttttttt tttttttttt ttttvn                              96

SEQ ID NO: 63           moltype = DNA  length = 18
FEATURE                 Location/Qualifiers
source                  1..18
                        mol_type = other DNA
                        organism = synthetic construct
modified_base           1
                        mod_base = OTHER
                        note = 5' phosphate modified nucleotide
misc_difference         3..7
                        note = a, c, g, t, unknown or other
SEQUENCE: 63
gtnnnnnatc tcgtatgc                                                  18

SEQ ID NO: 64           moltype = DNA  length = 95
FEATURE                 Location/Qualifiers
source                  1..95
                        mol_type = other DNA
                        organism = synthetic construct
misc_difference         1
                        note = a, c, g, t, unknown or other
misc_difference         33..38
                        note = a, c, g, t, unknown or other
misc_difference         39
```

|                  |                                              |
|------------------|----------------------------------------------|
| misc_difference  | 40                                           |
|                  | note = a, c, g, t, unknown or other          |
| misc_difference  | 41                                           |
|                  | note = a, c, g, t, unknown or other          |
| misc_difference  | 42                                           |
|                  | note = a, c, g, t, unknown or other          |
| misc_difference  | 43                                           |
|                  | note = a, c, g, t, unknown or other          |
| misc_difference  | 44                                           |
|                  | note = a, c, g, t, unknown or other          |
| misc_difference  | 45                                           |
|                  | note = a, c, g, t, unknown or other          |
| misc_difference  | 46                                           |
|                  | note = a, c, g, t, unknown or other          |
| misc_difference  | 47                                           |
|                  | note = a, c, g, t, unknown or other          |
| misc_difference  | 48                                           |
|                  | note = a, c, g, t, unknown or other          |
| misc_difference  | 83..87                                       |
|                  | note = a, c, g, t, unknown or other          |
| misc_difference  | 90..95                                       |
|                  | note = a, c, g, t, unknown or other          |

SEQUENCE: 64
nvttttttttt tttttttttt tttttttttt ttnnnnnnnn nnnnnnnnag atcggaagag 60
cacacgtctg aactccagtc acnnnnntgn nnnnn                             95

| SEQ ID NO: 65   | moltype = DNA  length = 112        |
|-----------------|------------------------------------|
| FEATURE         | Location/Qualifiers                |
| source          | 1..112                             |
|                 | mol_type = other DNA               |
|                 | organism = synthetic construct     |
| misc_difference | 1                                  |
|                 | note = a, c, g, t, unknown or other |
| misc_difference | 33..38                             |
|                 | note = a, c, g, t, unknown or other |
| misc_difference | 39                                 |
|                 | note = a, c, g, t, unknown or other |
| misc_difference | 40                                 |
|                 | note = a, c, g, t, unknown or other |
| misc_difference | 41                                 |
|                 | note = a, c, g, t, unknown or other |
| misc_difference | 42                                 |
|                 | note = a, c, g, t, unknown or other |
| misc_difference | 43                                 |
|                 | note = a, c, g, t, unknown or other |
| misc_difference | 44                                 |
|                 | note = a, c, g, t, unknown or other |
| misc_difference | 45                                 |
|                 | note = a, c, g, t, unknown or other |
| misc_difference | 46                                 |
|                 | note = a, c, g, t, unknown or other |
| misc_difference | 47                                 |
|                 | note = a, c, g, t, unknown or other |
| misc_difference | 82..86                             |
|                 | note = a, c, g, t, unknown or other |
| misc_difference | 89..94                             |
|                 | note = a, c, g, t, unknown or other |
| misc_difference | 97..101                            |
|                 | note = a, c, g, t, unknown or other |

SEQUENCE: 65
nvttttttttt tttttttttt tttttttttt ttnnnnnnnn nnnnnnnaga tcggaagagc 60
acacgtctga actccagtca cnnnnntgnn nnnngtnnnn natctcgtat gc          112

| SEQ ID NO: 66  | moltype = DNA  length = 32                         |
|----------------|----------------------------------------------------|
| FEATURE        | Location/Qualifiers                                |
| source         | 1..32                                              |
|                | mol_type = other DNA                               |
|                | organism = synthetic construct                     |
| modified_base  | 1                                                  |
|                | mod_base = OTHER                                   |
|                | note = 5' phosphate modified nucleotide            |
| modified_base  | 31                                                 |
|                | mod_base = OTHER                                   |
|                | note = Nucleotide with phosphorothioate linkage    |

SEQUENCE: 66
gatcggaaga gcgtcgtgta gggaaagagt gt                                32

SEQ ID NO: 67        moltype = DNA  length = 112

```
FEATURE              Location/Qualifiers
source               1..112
                     mol_type = other DNA
                     organism = synthetic construct
misc_difference      1
                     note = a, c, g, t, unknown or other
misc_difference      33..38
                     note = a, c, g, t, unknown or other
misc_difference      39
                     note = a, c, g, t, unknown or other
misc_difference      40
                     note = a, c, g, t, unknown or other
misc_difference      41
                     note = a, c, g, t, unknown or other
misc_difference      42
                     note = a, c, g, t, unknown or other
misc_difference      43
                     note = a, c, g, t, unknown or other
misc_difference      44
                     note = a, c, g, t, unknown or other
misc_difference      45
                     note = a, c, g, t, unknown or other
misc_difference      46
                     note = a, c, g, t, unknown or other
misc_difference      47
                     note = a, c, g, t, unknown or other
misc_difference      48
                     note = a, c, g, t, unknown or other
misc_difference      82..86
                     note = a, c, g, t, unknown or other
misc_difference      89..94
                     note = a, c, g, t, unknown or other
misc_difference      97..101
                     note = a, c, g, t, unknown or other
SEQUENCE: 67
nvttttttttt ttttttttt tttttttttt ttnnnnnnnn nnnnnnnnag atcggaagag    60
cacacgtctg aactcagtca cnnnnntgnn nnnngtnnnn natctcgtat gc            112

SEQ ID NO: 68        moltype = DNA   length = 14
FEATURE              Location/Qualifiers
source               1..14
                     mol_type = other DNA
                     organism = synthetic construct
SEQUENCE: 68
gcactaagga agtc                                                     14

SEQ ID NO: 69        moltype = DNA   length = 24
FEATURE              Location/Qualifiers
source               1..24
                     mol_type = other DNA
                     organism = synthetic construct
SEQUENCE: 69
caagcagaag acggcatacg agat                                          24

SEQ ID NO: 70        moltype = DNA   length = 55
FEATURE              Location/Qualifiers
source               1..55
                     mol_type = other DNA
                     organism = synthetic construct
misc_difference      30..35
                     note = a, c, g, t, unknown, other, or absent
SEQUENCE: 70
aatgatacgg cgaccaccga gatctacacn nnnnnacact ctttccctac acgac        55

SEQ ID NO: 71        moltype = DNA   length = 33
FEATURE              Location/Qualifiers
source               1..33
                     mol_type = other DNA
                     organism = synthetic construct
modified_base        32
                     mod_base = OTHER
                     note = Nucleotide with phosphorothioate linkage
SEQUENCE: 71
agatcggaag agcgtcgtgt agggaaagag tgt                                33

SEQ ID NO: 72        moltype = DNA   length = 113
FEATURE              Location/Qualifiers
source               1..113
                     mol_type = other DNA
```

|                  | organism = synthetic construct |
| --- | --- |
| misc_difference  | 1 |
|                  | note = a, c, g, t, unknown or other |
| misc_difference  | 33..38 |
|                  | note = a, c, g, t, unknown or other |
| misc_difference  | 39 |
|                  | note = a, c, g, t, unknown or other |
| misc_difference  | 40 |
|                  | note = a, c, g, t, unknown or other |
| misc_difference  | 41 |
|                  | note = a, c, g, t, unknown or other |
| misc_difference  | 42 |
|                  | note = a, c, g, t, unknown or other |
| misc_difference  | 43 |
|                  | note = a, c, g, t, unknown or other |
| misc_difference  | 44 |
|                  | note = a, c, g, t, unknown or other |
| misc_difference  | 45 |
|                  | note = a, c, g, t, unknown or other |
| misc_difference  | 46 |
|                  | note = a, c, g, t, unknown or other |
| misc_difference  | 47 |
|                  | note = a, c, g, t, unknown or other |
| misc_difference  | 48 |
|                  | note = a, c, g, t, unknown or other |
| misc_difference  | 83..87 |
|                  | note = a, c, g, t, unknown or other |
| misc_difference  | 90..95 |
|                  | note = a, c, g, t, unknown or other |
| misc_difference  | 98..102 |
|                  | note = a, c, g, t, unknown or other |

SEQUENCE: 72
nvttttttttt tttttttttt tttttttttt ttnnnnnnnn nnnnnnnnag atcggaagag    60
cacacgtctg aactccagtc acnnnnntgn nnnnngtnnn nnatctcgta tgc            113

| SEQ ID NO: 73   | moltype = DNA   length = 126 |
| --- | --- |
| FEATURE          | Location/Qualifiers |
| source           | 1..126 |
|                  | mol_type = other DNA |
|                  | organism = synthetic construct |
| misc_difference  | 1 |
|                  | note = a, c, g, t, unknown or other |
| misc_difference  | 33..38 |
|                  | note = a, c, g, t, unknown or other |
| misc_difference  | 39 |
|                  | note = a, c, g, t, unknown or other |
| misc_difference  | 40 |
|                  | note = a, c, g, t, unknown or other |
| misc_difference  | 41 |
|                  | note = a, c, g, t, unknown or other |
| misc_difference  | 42 |
|                  | note = a, c, g, t, unknown or other |
| misc_difference  | 43 |
|                  | note = a, c, g, t, unknown or other |
| misc_difference  | 44 |
|                  | note = a, c, g, t, unknown or other |
| misc_difference  | 45 |
|                  | note = a, c, g, t, unknown or other |
| misc_difference  | 46 |
|                  | note = a, c, g, t, unknown or other |
| misc_difference  | 47 |
|                  | note = a, c, g, t, unknown or other |
| misc_difference  | 48 |
|                  | note = a, c, g, t, unknown or other |
| misc_difference  | 83..87 |
|                  | note = a, c, g, t, unknown or other |
| misc_difference  | 90..95 |
|                  | note = a, c, g, t, unknown or other |
| misc_difference  | 98..102 |
|                  | note = a, c, g, t, unknown or other |

SEQUENCE: 73
nvttttttttt tttttttttt tttttttttt ttnnnnnnnn nnnnnnnnag atcggaagag    60
cacacgtctg aactccagtc acnnnnntgn nnnnngtnnn nnatctcgta tgccgtcttc   120
tgcttg                                                              126

| SEQ ID NO: 74   | moltype = DNA   length = 68 |
| --- | --- |
| FEATURE          | Location/Qualifiers |
| source           | 1..68 |
|                  | mol_type = other DNA |

```
                        organism = synthetic construct
misc_difference         30..35
                        note = a, c, g, t, unknown, other, or absent
SEQUENCE: 74
attgatacgg cgaccaccga gatctacacn nnnnnacact ctttccctac acgacgctct    60
tccgatct                                                             68

SEQ ID NO: 75           moltype = DNA  length = 14
FEATURE                 Location/Qualifiers
source                  1..14
                        mol_type = other DNA
                        organism = synthetic construct
SEQUENCE: 75
atcggctcat ggtc                                                      14

SEQ ID NO: 76           moltype = DNA  length = 14
FEATURE                 Location/Qualifiers
source                  1..14
                        mol_type = other DNA
                        organism = synthetic construct
SEQUENCE: 76
acataatcat ggtc                                                      14

SEQ ID NO: 77           moltype = DNA  length = 14
FEATURE                 Location/Qualifiers
source                  1..14
                        mol_type = other DNA
                        organism = synthetic construct
SEQUENCE: 77
gtcggacgat ggtc                                                      14

SEQ ID NO: 78           moltype = DNA  length = 14
FEATURE                 Location/Qualifiers
source                  1..14
                        mol_type = other DNA
                        organism = synthetic construct
SEQUENCE: 78
caggtcggtc agtc                                                      14

SEQ ID NO: 79           moltype = DNA  length = 14
FEATURE                 Location/Qualifiers
source                  1..14
                        mol_type = other DNA
                        organism = synthetic construct
SEQUENCE: 79
cggacatctc agtc                                                      14

SEQ ID NO: 80           moltype = DNA  length = 14
FEATURE                 Location/Qualifiers
source                  1..14
                        mol_type = other DNA
                        organism = synthetic construct
SEQUENCE: 80
tcagcacgtc agtc                                                      14

SEQ ID NO: 81           moltype = DNA  length = 14
FEATURE                 Location/Qualifiers
source                  1..14
                        mol_type = other DNA
                        organism = synthetic construct
SEQUENCE: 81
cggacatcga agtc                                                      14
```